(12) United States Patent
Nikiforov

(10) Patent No.: US 11,542,549 B2
(45) Date of Patent: *Jan. 3, 2023

(54) LABELED ENZYME COMPOSITIONS, METHODS AND SYSTEMS

(71) Applicant: LIFE TECHNOLOGIES CORPORATION, Carlsbad, CA (US)

(72) Inventor: Theo Nikiforov, Carlsbad, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/907,845

(22) Filed: Feb. 28, 2018

(65) Prior Publication Data

US 2018/0258415 A1   Sep. 13, 2018

Related U.S. Application Data

(60) Division of application No. 15/401,757, filed on Jan. 9, 2017, now Pat. No. 9,932,573, which is a division of application No. 14/284,187, filed on May 21, 2014, now Pat. No. 9,567,629, which is a division of application No. 13/594,532, filed on Aug. 24, 2012, now Pat. No. 8,741,618, which is a continuation of application No. 12/748,314, filed on Mar. 26, 2010, now abandoned.

(60) Provisional application No. 61/307,356, filed on Feb. 23, 2010, provisional application No. 61/299,917, filed on Jan. 29, 2010, provisional application No. 61/299,919, filed on Jan. 29, 2010, provisional application No. 61/293,616, filed on Jan. 8, 2010, provisional application No. 61/293,618, filed on Jan. 8, 2010, provisional application No. 61/289,388, filed on Dec. 22, 2009, provisional application No. 61/263,974, filed on Nov. 24, 2009, provisional application No. 61/245,457, filed on Sep. 24, 2009, provisional application No. 61/242,771, filed on Sep. 15, 2009, provisional application No. 61/184,770, filed on Jun. 5, 2009, provisional application No. 61/164,324, filed on Mar. 27, 2009.

(51) Int. Cl.

| | |
|---|---|
| C12N 9/12 | (2006.01) |
| C12Q 1/6869 | (2018.01) |
| C07H 19/20 | (2006.01) |
| C12N 9/96 | (2006.01) |
| C12Q 1/6818 | (2018.01) |
| G01N 33/58 | (2006.01) |
| G01N 21/64 | (2006.01) |

(52) U.S. Cl.
CPC .......... *C12Q 1/6869* (2013.01); *C07H 19/20* (2013.01); *C12N 9/1241* (2013.01); *C12N 9/1252* (2013.01); *C12N 9/96* (2013.01); *C12Q 1/6818* (2013.01); *C12Y 207/07007* (2013.01); *G01N 21/6428* (2013.01); *G01N 33/582* (2013.01); *C12Y 207/07* (2013.01); *G01N 2021/6432* (2013.01)

(58) Field of Classification Search
None
See application file for complete search history.

(56) References Cited

U.S. PATENT DOCUMENTS

| | | |
|---|---|---|
| 4,658,649 A | 4/1987 | Brook |
| 5,001,050 A | 3/1991 | Blanco et al. |
| 5,151,507 A | 9/1992 | Hobbs et al. |
| 5,188,934 A | 2/1993 | Menchen et al. |
| 5,198,543 A | 3/1993 | Blanco et al. |
| 5,322,785 A | 6/1994 | Comb et al. |
| 5,473,060 A | 12/1995 | Gryaznov et al. |
| 5,510,270 A | 4/1996 | Fodor et al. |
| 5,558,991 A | 9/1996 | Trainor |
| 5,576,204 A | 11/1996 | Blanco et al. |
| 5,599,695 A | 2/1997 | Pease et al. |
| 5,707,804 A | 1/1998 | Mathies et al. |
| 5,723,584 A | 3/1998 | Schatz |
| 5,831,070 A | 11/1998 | Pease et al. |

(Continued)

FOREIGN PATENT DOCUMENTS

| | | |
|---|---|---|
| EP | 0272007 | 6/1988 |
| EP | 0272007 | 3/1992 |

(Continued)

OTHER PUBLICATIONS

Agard, N et al., "A Strain-Promoted [3+2]Azide-Alkyne Cycloaddition for Covalent Modification of Biomolecules in Living Systems", *J. Am. Chem Soc*, vol. 126(46), 2004, pp. 15046-15047.

(Continued)

*Primary Examiner* — Richard G Hutson
(74) *Attorney, Agent, or Firm* — Klarquist Sparkman, LLP

(57) ABSTRACT

Disclosed herein are conjugates comprising a biomolecule linked to a label that have biological activity and are useful in a wide variety of biological applications. For example, provided herein are labeled polymerase conjugates including a polymerase linked to one or more labels, wherein the conjugate has polymerase activity. Such conjugates can exhibit enhanced biological activity and/or superior detectability as compared to conventional labeled polymerases. Also disclosed herein are improved methods for preparing such conjugates, and methods and systems for using such conjugates in biological applications such as nucleotide incorporation, primer extension and single molecule sequencing.

11 Claims, 26 Drawing Sheets

Specification includes a Sequence Listing.

(56) References Cited

U.S. PATENT DOCUMENTS

| | | |
|---|---|---|
| 5,874,239 A | 2/1999 | Schatz |
| 5,932,433 A | 8/1999 | Schatz |
| 6,087,095 A | 7/2000 | Rosenthal et al. |
| 6,207,229 B1 | 3/2001 | Bawendi et al. |
| 6,221,592 B1 | 4/2001 | Schwartz et al. |
| 6,255,083 B1 | 7/2001 | Williams |
| 6,294,136 B1 | 9/2001 | Schwartz |
| 6,316,230 B1 | 11/2001 | Egholm et al. |
| 6,322,901 B1 | 11/2001 | Bawendi et al. |
| 6,399,304 B1 | 6/2002 | Kilger et al. |
| 6,399,335 B1 | 6/2002 | Kao et al. |
| 6,423,551 B1 | 7/2002 | Weiss et al. |
| 6,524,829 B1 | 2/2003 | Seeger |
| 6,627,424 B1 | 9/2003 | Wang |
| 6,635,163 B1 | 10/2003 | Han et al. |
| 6,664,079 B2 | 12/2003 | Ju et al. |
| 6,815,064 B2 | 11/2004 | Treadway et al. |
| 6,818,395 B1 | 11/2004 | Quake et al. |
| 6,849,411 B2 | 2/2005 | Knapp et al. |
| 6,864,626 B1 | 3/2005 | Weiss et al. |
| 6,911,345 B2 | 6/2005 | Quake et al. |
| 6,955,855 B2 | 10/2005 | Naasani |
| 6,960,437 B2 | 11/2005 | Enzelberger et al. |
| 6,982,146 B1 | 1/2006 | Schneider et al. |
| 7,033,762 B2 | 4/2006 | Nelson et al. |
| 7,033,764 B2 | 4/2006 | Korlach et al. |
| 7,041,812 B2 | 5/2006 | Kumar et al. |
| 7,052,839 B2 | 5/2006 | Nelson et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,078,499 B2 | 7/2006 | Odedra et al. |
| 7,125,671 B2 | 10/2006 | Sood et al. |
| 7,198,847 B2 | 4/2007 | Naasani |
| 7,205,048 B2 | 4/2007 | Naasani |
| 7,211,414 B2 | 5/2007 | Hardin et al. |
| 7,214,428 B2 | 5/2007 | Naasani |
| 7,217,562 B2 | 5/2007 | Cao et al. |
| 7,223,541 B2 | 5/2007 | Fuller et al. |
| 7,223,568 B2 | 5/2007 | Kondow et al. |
| 7,229,799 B2 | 6/2007 | Williams |
| 7,244,566 B2 | 7/2007 | Sood et al. |
| 7,244,602 B2 | 7/2007 | Frey et al. |
| 7,256,019 B2 | 8/2007 | Sood et al. |
| 7,264,934 B2 | 9/2007 | Fuller |
| 7,270,951 B1 | 9/2007 | Stemple et al. |
| 7,276,720 B2 | 10/2007 | Ulmer |
| 7,329,492 B2 | 2/2008 | Hardin et al. |
| 7,345,159 B2 | 3/2008 | Ju et al. |
| 7,361,466 B2 | 4/2008 | Korlach et al. |
| 7,368,086 B2 | 5/2008 | Naasani |
| 7,393,640 B2 | 7/2008 | Kumar et al. |
| 7,405,281 B2 | 7/2008 | Xu et al. |
| 7,416,844 B2 | 8/2008 | Korlach et al. |
| 7,427,673 B2 | 9/2008 | Balasubramanian et al. |
| 7,452,698 B2 | 11/2008 | Sood et al. |
| 7,456,954 B2 | 11/2008 | Weiss et al. |
| 7,485,424 B2 | 2/2009 | Korlach et al. |
| 7,501,245 B2 | 3/2009 | Quake et al. |
| 7,521,541 B2 | 4/2009 | Eigenbrot et al. |
| 7,541,444 B2 | 6/2009 | Milton et al. |
| 7,553,949 B2 | 6/2009 | Lee et al. |
| 7,599,059 B2 | 10/2009 | Laurence et al. |
| 7,611,907 B2 | 11/2009 | Dickson et al. |
| 7,668,697 B2 | 2/2010 | Volkov et al. |
| 7,670,770 B2 | 3/2010 | Chou et al. |
| 7,745,116 B2 | 6/2010 | Williams |
| 7,928,038 B2 | 4/2011 | Menchen et al. |
| 8,058,414 B2 | 11/2011 | Menchen et al. |
| 8,603,792 B2 | 12/2013 | Nikiforov et al. |
| 8,999,674 B2 | 4/2015 | Beechem et al. |
| 9,695,471 B2 | 7/2017 | Beechem et al. |
| 2002/0115092 A1 | 8/2002 | Rebek, Jr. et al. |
| 2002/0132259 A1 | 9/2002 | Wagner et al. |
| 2002/0197611 A1 | 12/2002 | Chagovetz |
| 2003/0044781 A1 | 3/2003 | Korlach et al. |
| 2003/0064366 A1 | 4/2003 | Hardin et al. |
| 2003/0087300 A1 | 5/2003 | Knapp et al. |
| 2003/0092005 A1 | 5/2003 | Levene et al. |
| 2004/0048300 A1 | 3/2004 | Sood et al. |
| 2004/0152119 A1 | 8/2004 | Sood et al. |
| 2004/0197800 A1 | 10/2004 | Borns |
| 2004/0197843 A1 | 10/2004 | Chou et al. |
| 2004/0244827 A1 | 12/2004 | Hatsukaiwa et al. |
| 2005/0003464 A1 | 1/2005 | Tibbe et al. |
| 2005/0042633 A1 | 2/2005 | Williams |
| 2005/0164255 A1 | 7/2005 | Korlach et al. |
| 2005/0244827 A1 | 11/2005 | Olsson et al. |
| 2005/0266424 A1 | 12/2005 | Hardin et al. |
| 2006/0003383 A1 | 1/2006 | Graham |
| 2006/0057565 A1 | 3/2006 | Ju et al. |
| 2006/0063264 A1 | 3/2006 | Turner et al. |
| 2006/0078937 A1 | 4/2006 | Korlach |
| 2006/0176479 A1 | 8/2006 | Laurence et al. |
| 2006/0177495 A1 | 8/2006 | Allen et al. |
| 2006/0275806 A1 | 12/2006 | Schwartz et al. |
| 2007/0009980 A1 | 1/2007 | Graham |
| 2007/0020772 A1 | 1/2007 | Cao et al. |
| 2007/0054337 A1 | 3/2007 | Ferning et al. |
| 2007/0072196 A1 | 3/2007 | Xu et al. |
| 2007/0109536 A1 | 5/2007 | Weiss et al. |
| 2007/0111350 A1 | 5/2007 | Weiss et al. |
| 2007/0116868 A1 | 5/2007 | Weiss et al. |
| 2007/0128133 A1 | 6/2007 | Eid et al. |
| 2007/0161028 A1 | 7/2007 | Schwartz et al. |
| 2007/0172819 A1 | 7/2007 | Hardin et al. |
| 2007/0172858 A1 | 7/2007 | Hardin et al. |
| 2007/0172859 A1 | 7/2007 | Hardin et al. |
| 2007/0172860 A1 | 7/2007 | Hardin et al. |
| 2007/0172861 A1 | 7/2007 | Hardin et al. |
| 2007/0172862 A1 | 7/2007 | Hardin et al. |
| 2007/0172863 A1 | 7/2007 | Hardin et al. |
| 2007/0172864 A1 | 7/2007 | Gao et al. |
| 2007/0172865 A1 | 7/2007 | Hardin et al. |
| 2007/0172866 A1 | 7/2007 | Hardin et al. |
| 2007/0172867 A1 | 7/2007 | Hardin et al. |
| 2007/0172868 A1 | 7/2007 | Hardin et al. |
| 2007/0172869 A1 | 7/2007 | Hardin et al. |
| 2007/0184475 A1 | 8/2007 | Hardin et al. |
| 2007/0196846 A1 | 8/2007 | Hanzel et al. |
| 2007/0250274 A1 | 10/2007 | Volkov et al. |
| 2007/0275395 A1 | 11/2007 | Hardin et al. |
| 2007/0292679 A1 | 12/2007 | Pellerite et al. |
| 2007/0292867 A1 | 12/2007 | Hardin et al. |
| 2008/0009100 A1 | 1/2008 | Davison |
| 2008/0091005 A1 | 4/2008 | Wang et al. |
| 2008/0108082 A1 | 5/2008 | Rank et al. |
| 2008/0131952 A1 | 6/2008 | Wu et al. |
| 2008/0132692 A1 | 6/2008 | Wu et al. |
| 2008/0176316 A1 | 7/2008 | Eid et al. |
| 2008/0176761 A1 | 7/2008 | Menchen et al. |
| 2008/0213910 A1 | 9/2008 | Jogikalmath |
| 2008/0219888 A1 | 9/2008 | Lawson et al. |
| 2008/0219890 A1 | 9/2008 | Lawson et al. |
| 2008/0261833 A1 | 10/2008 | Stemmer et al. |
| 2008/0274905 A1 | 11/2008 | Greene |
| 2008/0293071 A1 | 11/2008 | Gelfand et al. |
| 2009/0024331 A1 | 1/2009 | Tomaney et al. |
| 2009/0029385 A1 | 1/2009 | Christians et al. |
| 2009/0047699 A1 | 2/2009 | Graham |
| 2009/0061447 A1 | 3/2009 | Schneider |
| 2009/0081686 A1 | 3/2009 | Wu et al. |
| 2009/0176233 A1 | 7/2009 | Clark et al. |
| 2009/0275036 A1 | 11/2009 | Hardin et al. |
| 2009/0286245 A1 | 11/2009 | Bjornson et al. |
| 2009/0298075 A1 | 12/2009 | Travers et al. |
| 2009/0305248 A1 | 12/2009 | Lander et al. |
| 2009/0305278 A1 | 12/2009 | Hardin et al. |
| 2010/0093555 A1 | 4/2010 | Bjornson et al. |
| 2010/0216122 A1 | 8/2010 | Hardin et al. |
| 2010/0255463 A1 | 10/2010 | Hardin et al. |
| 2010/0255464 A1 | 10/2010 | Hardin et al. |
| 2010/0255487 A1 | 10/2010 | Beechem et al. |
| 2010/0261185 A1 | 10/2010 | Nikiforov |

(56) References Cited

U.S. PATENT DOCUMENTS

| | | |
|---|---|---|
| 2010/0304367 A1 | 12/2010 | Hardin et al. |
| 2010/0317005 A1 | 12/2010 | Hardin et al. |
| 2010/0330570 A1 | 12/2010 | Vander Horn et al. |
| 2011/0003343 A1 | 1/2011 | Nikiforov et al. |
| 2011/0014604 A1 | 1/2011 | Hardin et al. |
| 2011/0014612 A1 | 1/2011 | Hendricks et al. |
| 2011/0021383 A1 | 1/2011 | Hardin et al. |
| 2011/0059436 A1 | 3/2011 | Hardin et al. |
| 2011/0184163 A1 | 7/2011 | Hardin et al. |
| 2011/0220844 A1 | 9/2011 | Tulsky et al. |
| 2011/0226995 A1 | 9/2011 | Tulsky et al. |
| 2011/0281740 A1 | 11/2011 | Beechem et al. |
| 2011/0306079 A1 | 12/2011 | Tulsky et al. |
| 2012/0322057 A1 | 12/2012 | Hendricks et al. |
| 2012/0329042 A1 | 12/2012 | Beechem et al. |
| 2013/0005020 A1 | 1/2013 | Peris et al. |
| 2013/0040363 A1 | 2/2013 | Nikiforov et al. |
| 2013/0102050 A1 | 4/2013 | Hardin et al. |

FOREIGN PATENT DOCUMENTS

| | | | |
|---|---|---|---|
| EP | 1681356 | 7/2006 | |
| WO | WO-1990/007576 | 7/1990 | |
| WO | WO-1991/001087 | 2/1991 | |
| WO | WO-91/05060 | 4/1991 | |
| WO | WO-91/06678 | 5/1991 | |
| WO | WO-1998/022615 | 5/1998 | |
| WO | WO-98/31834 | 7/1998 | |
| WO | WO-1999/053034 | 12/1999 | |
| WO | WO-00/17330 | 3/2000 | |
| WO | WO-2000/036152 | 6/2000 | |
| WO | WO-2000036151 | 6/2000 | |
| WO | WO-2000/067698 | 11/2000 | |
| WO | WO-2000/070073 | 11/2000 | |
| WO | WO-2002/004680 | 1/2002 | |
| WO | WO-2002/044425 | 6/2002 | |
| WO | WO-2007/070642 | 6/2007 | |
| WO | WO-2008/030115 | 3/2008 | |
| WO | WO-2008/069973 | 6/2008 | |
| WO | WO-2008/154317 | 12/2008 | |
| WO | WO-2009/017678 | 2/2009 | |
| WO | WO-2009/091847 | 7/2009 | |
| WO | WO-2010/002939 | 1/2010 | |
| WO | WO-2010/039897 | 4/2010 | |
| WO | WO-2010/040111 | 4/2010 | |
| WO | WO-2010/048580 | 4/2010 | |
| WO | WO-2010/048581 | 4/2010 | |
| WO | WO-2010068884 A2 * | 6/2010 | ........... C12Q 1/6869 |
| WO | WO-2010/096084 | 8/2010 | |
| WO | WO-2010/111674 | 9/2010 | |
| WO | WO-2010/111686 | 9/2010 | |
| WO | WO-2010/111690 | 9/2010 | |
| WO | WO-2010/111691 | 9/2010 | |
| WO | WO-2010/151714 | 12/2010 | |
| WO | WO-2010111691 A9 | 1/2011 | |
| WO | WO-2011/038158 | 3/2011 | |
| WO | WO-2010111690 A3 | 3/2011 | |
| WO | WO-2010111686 A3 | 5/2011 | |
| WO | WO-2011/078897 | 6/2011 | |

OTHER PUBLICATIONS

Ahn, Jinwoo et al., "DNA Polymerase Beta: Structure-Fidelity Relationship from Pre-Steady-State Kinetic Analyses of All Possible Correct and Incorrect Base Pairs for Wild Type and R283A Mutant", *Biochemistry*, 36, 1997, 1100-1107.

Akerman, Maria E. et al., "Nanocrystal targeting in vivo", *Proceedings of the National Academy of Sciences (PNAS)*, vol. 99, No. 20, Oct. 1, 2002, 12617-12621.

Arenkov, Pavel et al., "Protein Microchips: Use for Immunoassay and Enzymatic Reactions", *Analytical Biochemistry*, vol. 278, 2000, 123-131.

Arion, Dominique et al., "HIV resistance to zidovudine: the role of pyrophosphorolysis", *Drug Resistance Updates*, vol. 2, No. 2, Apr. 1999, 91-95.

Arkin, A. P. et al., "An algorithm for protein engineering: Simulations of recursive ensemble mutagenesis", *PNAS USA;* vol. 89, 1992, pp. 7811-7815.

Arzumanov, Andrey A. et al., "γ-Phosphate-substituted 2'-Deoxynucleoside 5'-Triphosphates as Substrates for DNA Polymerases", *J. Biol. Chem.*, vol. 271(40), 1996, pp. 24389-24394.

Bakhtina, Marina et al., "Contribution of the Reverse Rate of the Conformational Step to Polymerase B Fidelity", *Biochem.*, vol. 48, 2009, 3197-3208.

Barone, A. D. et al., "Novel Nucleoside Triphosphate Analogs for the Enzymatic Labeling of Nucleic Acids", *Nucleosides, Nucleotides & Nucleic Acids*, 20(4-7), 2001, 1141-1145.

Barone, Anthony D. et al., "Photolithographic Synthesis of High-Density Oligonucleotide Probe Arrays", *Nucleosides, Nucleotides & Nucleic Acids*, vol. 20, Nos. 4-7, 2001, 525-531.

Beattie, W. G. et al., "Hybridization of DNA targets to glass-tethered oligonucleotide probes", *Mol. Biotechnology*, vol. 4(3), 1995, pp. 213-225.

Berman, Andrea J. et al., "Structures of phi29 DNA polymerase complexed with substrate: the mechanism of translocation in B-family polymerases", *The EMBO Journal*, vol. 26, 2007, 3494-3505.

Bernad, Antonio et al., "Structural and functional relationships between prokaryotic and eukaryotic DNA polymerases", *The EMBO Journal*, vol. 6 No. 13, 1987, 4219-4225.

Blanco, L. et al., "A general structure for DNA-dependent DNA polymerases", *Gene*, vol. 100, Elsevier Science Publishers B.V., 1991, 27-38.

Blasco, M. A. et al., "Phi29 D A polymerase active site. Residue ASP249 of co nserved amino acid motif "Dx2SLYP" is critical for synthetic activities", *The Journal of Biological Chemistry.* vol. 268 No. 32, Nov. 15, 1993, pp. 24106-24113.

Blasco, M. A. , "Phi29 DNA polymerase active site. Mutants in conserved residues Tyr254 and Tyr390 are affected in dNTP binding", *The Journal of Biological Chemistry.* vol. 267 No. 27, Sep. 25, 1992, pp. 19427-19434.

Blasco, M. A. et al., "Primer terminus stabi l izat ion at the phi29 DNA polymer ase active site. Mutational analysis of conserved motif KXY", *The Journal of Biological Chemistry.* vol. 270 No. 6, Feb. 10, 1995, pp. 2735-2740.

Blasco, Maria et al., "Phi29 DNA Polymerase Active Site", *The Journal of Biological Chemistry*, vol. 268, No. 22,, 1993, 16763-16770.

Bouizar, et al., "Purification and Characterization of Calcitonin Receptors in Rat Kidney Membranes by Covalent Cross-Linking Techniques.", *European Journal of Biochemistry*, vol. 155, No. 1, 1986, 141-147.

Bowers, Jayson et al., "Virtual terminator nucleotides for next-generation DNA sequencing", *Nature Methods*, vol. 6, No. 8, 2009, 593-595.

Braslavsky, Ido et al., "Sequence information can be obtained from single DNA molecules", *Proc. Natl. Acad. Sci.*, vol. 100( 7), 2003, pp. 3960-3964.

Brinkley, , "A Brief Survey of Methods for Preparing Protein Conjugates with Dyes, Haptens, and Cross-Linking Reagents", *Bioconjugate Chemistry*, vol. 3, No. 1, 1992, 2-13.

Browning, et al., "Studies on the Differing Effects of the Tumor Necrosis Factor and Lymphotoxin on the Growth of Several Human Tumor Lines", *Journal of Immunology*, vol. 143, No. 6, 1989, 1859-1867.

Brustad, Eric et al., "A General and Efficient Method for the Site-Specific Dual-Labeling of Proteins for Single Molecule Fluorescence Resonance Energy Transfer", *J. Am. Chem. Soc.*, 130, 2008, 17664-17665.

Calogero, S. et al., "In vivo recombination and the production of hybrid genes", *FEMS Microbiology Letters*, vol. 97, 1992, pp. 41-44.

Campbell, A. K. et al., "A homogeneous immunoassay for cyclic nucleotides based on chemiluminescence energy transfer", *Biochem. J.*, vol. 216, 1983, pp. 185-194.

(56) References Cited

OTHER PUBLICATIONS

Caren, R. et al., "Efficient Sampling of Protein Sequence Space for Multiple Mutants", *Bio/Technology*, vol. 12, 1994, pp. 517-520.

Caspar, J. et al., "Photochemistry of Ru(bpy)3 2+. Solvent Effects", *J. Am. Chem. Soc.*, 105, 1983, 5583.

Caspar, Jonathan V. et al., "Application of the Energy Gap Law to Nonradiative, Excited-State Decay", *J. Phys. Chem.*, vol. 87, No. 6, 1983, pp. 952-957.

Castro, Christian et al., "Nucleic acid polymerases use a general acid for nucleotidyl transfer", *Nature Structural & Molecular Biology*, vol. 16 No. 2, 2009, 212-218.

Cha, Taewoon et al., "Enzymatic activity on a chip: The critical role of protein orientation", *Proteomics*, vol. 5, 2005, 416-419.

Cha, Taewoon et al., "Immobilization of oriented protein molecules on poly(ethylene glycol)-coated Si(111)", *Proteomics*, vol. 4, 2004, 1965-1976.

Choi, H. S. et al. "Nature Biotechnology", vol. 25, No. 10, Oct. 2007, pp. 1165-1170.

Chrisey, Linda A. et al., "Covalent attachment of synthetic DNA to self-assembled monolayer films", *Nucleic Acid Research*, vol. 24, No. 15, 1996, pp. 3031-3039.

Clapp, A.R. et al., "Fluorescence Resonance Energy Transfer Between Quantum Dot Donars and Dye-Labeled Protein Acceptors", J. Am. Chem. Soc., 126, 2004, 301-310.

Clapp, Aaron et al., "Capping of CdSe—ZnS quantum dots with DHLA and subsequent conjugation with proteins", *Nature Protocols*, vol. 1 No. 3, 2006, 1258-1266.

Cull, Millard G. et al., "Screening for receptor ligands using large libraries of peptides linked to the C terminus of the lac repressor", *Proc. Natl. Acad. Sci. USA*, vol. 89, 1992, pp. 1865-1869.

Cwirla, Steven E. et al., "Peptides on phage: A vast library of peptides for identifying ligands", *PNAS*, vol. 87, 1990, pp. 6378-6382.

Dafni, H. et al., "Overexpression of Vascular Endothelial Growth Factor 165 Drives Peritumor Interstitial Convection and Induces Lymphatic Drain: Magnetic Resonance Imaging, Confocal Microscopy, and Histological Tracking of Triple-labeled Albumin", *Cancer Research*. vol. 62, No. 15, Nov. 15, 2002, pp. 6731-6739.

Dawson, Philip et al., "Synthesis of Native Proteins by Chemical Ligation", *Annu. Rev. Biochem.*, 69:, 2000, 923-960.

Dawson, Philip E. et al., "Synthesis of Proteins by Native Chemical Ligation", *Science*, vol. 266, 1994, pp. 776-779.

De Graaf, Albert et al., "Nonnatural Amino Acids for Site-Specific Protein Conjugation", *Bioconjugate Chem.*, vol. 20, No. 7, 2009, 1281-1295.

De Vega, Miguel et al., "Primer-terminus stabilization at the 3'-5' exonuclease active site of Phi29 DNA polymerase. Involvement of two amino acid residues highly conserved in proofreading DNA polymerases", *The EMBO Journal*, vol. 15 No. 5, 1996, 1182-1192.

Decher, G. et al., "Buildup of ultrathin multilayer films by a self-assembly process: III. Consecutively alternating adsorption of anionic and cationic polyelectrolytes on charged surfaces", *Thin Solid Films*, vol. 210-211, Part 2, 1992, pp. 831-835.

Delagrave, Simon et al., "Recursive ensemble mutagenesis", *Protein Engineering*, vol. 6, No. 3, 1993, 327-331.

Delagrave, Simon et al., "Searching Sequence Space to Engineer Proteins: Exponential Ensemble Mutagenesis", *Bio/Technology*, vol. 11, 1993, pp. 1548-1552.

Derfus, A. M. et al.. "Nano Letters.", vol. 4. No. I, Dec. 10, 2003, pp. 11-18.

Deuschle, Karen et al., "Construction and optimization of a family of genetically encoded metabolite sensors by semirational protein engineering", *Protein Science*, vol. 14, Iss. 9, 14, 2005, 2304-2314.

Dilgimen, Aydan Salman et al., "Water-soluble covalent conjugates of bovine serum albumin with anionic poly(N-isopropyl-acrylamide) and their immunogenicity", *Biomaterials*, 22, 2001, 2383-2392.

Dos Remedios, Cristobal G. et al., "Fluorescence Resonance Energy Transfer Spectroscopy is a Reliable "Ruler" for Measuring Structural Changes in Proteins", *Journal of Structural Biology*, vol. 115, 1995, pp. 175-185.

Drosopoulos, W. et al., "Virtues of being faithful: Can we limit the genetic variation in Human Immunodeficiency Virus", *J. Molecular Medicine*, vol. 76 (9), Aug. 1998, pp. 604-612.

Dryden, D.T.F. et al., "Nucleoside triphosphate-dependent restriction enzymes", *Nucleic Acids Research*, vol. 29, No. 18, 2001, 3728-3741.

Eigen, Manfred et al., "The fifth Paul Ehrlich lecture virus strains as models of molecular evolution", *Medicinal Research Reviews*, vol. 13, No. 4 (XP000430626), Jul. 1993, 385-398.

Eschenmoser, Albert , "Chemical Etiology of Nucleic Acid Structure", *Science*, vol. 284, 1999, 2118-2124.

Fasman, Gerald D. , "UV Spectral Characteristics and Acidic Dissociation Constants of 280 Alkyl Bases. Nucleosides and Nucleotides", *Practical Handbook of Biochemistry and Molecular Biology*, CRC Press, Boca Raton, FL, 1989, pp. 385-394.

Fazio, Teresa et al., "DNA Curtains and Nanoscale Curtain Rods: High-Throughput Tools for Single Molecule Imaging", *Langmuir*, vol. 24, 2008, 10524-10531.

Ferrero, Miguel et al., "Biocatalytic Selective Modifications of Conventional Nucleosides, Carbocyclic Nucleosides, and C-Nucleosides", *Chem. Rev.*, vol. 100, No. 12, 2000, 4319-4348.

Flemer, Stevenson et al., "Strategies for the Solid-Phase Diversification of Poly-L-proline-Type II Peptide Mimic Scaffolds and Peptide Scaffolds Through Guanidinylation", *J. Org. Chem.*, vol. 73, 2008, 7593-7602.

Forster, T. , "Intermolecular energy migration and fluorescence", *Annalen der Physik*, vol. 437(1-2), 1948, 55-75.

Fu, Dong-Jing et al., "Sequencing double-stranded DNA by strand displacement", *Nucleic Acids Research*, vol. 25 (3), Feb. 1997, pp. 677-679.

Furey, W. S. et al., "Use of Fluorescence Resonance Energy Transfer to Investigate the Conformation of DNA Substrates Bound to the Klenow Fragment", *Biochemistry*, vol. 37, No. 9, 1998, 2979-2990.

Ge, Hui , "UPA, a universal protein array system for quantitative detection of protein-protein, protein-DNA, protein-RNA and protein-ligand interaction", *Nucleic Acids Research*, vol. 28(2), 2000, pp. i-vii.

Ghadessy, Farid J. et al., "Generic expansion of the substrate spectrum of a DNA polymerase by directed evolution", *Nature Biotech.*, vol. 22, No. 6, 2004, 755-759.

Gheorghe, Alexandru et al., "Combination of Perfluoroalkyl and Triazole Moieties: A New Recovery Strategy for TEMPT", *Organic Letters*, vol. 10, No. 19, 2008, 4171-4174.

Givens, R. et al., "New Photoactivated Protecting Groups", *J. Am. Chem. Soc.*, vol. 119, 1997, pp. 8369-8370.

Goldman, E. et al., "An Algorithmically Optimized Combinatorial Library Screened by Digital Imaging Spectroscopy", *Bio/Technology*, vol. 10, 1992, pp. 1557-1561.

Goldman, E. R. et al., "Luminescent Quantum Dot-Adaptor Protein-Antibody Conjugates for Use in Fluoroimmunoassays", *phys. stat. sol. (b)*, 229, No. 1, 2002, 407-414.

Goldman, Ellen et al., "Avidin: A Natural Bridge for Quantum Dot-Antibody Conjugates", *J. Am. Chem. Soc.*, 124, 2002, 6378-6382.

Goldman, Ellen et al., "Conjugation of Luminescent Quantum Dots with Antibodies Using an Engineered Adaptor Protein to Provide New Reagents for Fluoroimmunoassays", *Anal. Chem.*, 74, 2002, 841-847.

Goldman, Ellen et al., "Self-assembled luminescent CdSe—ZnS quantum dot bioconjugates prepared using engineered poly-histidine terminated proteins", *Analytica Chimica Acta*, 534, 2005, 63-67.

Gram, Hermann et al., "In vitro selection and affinity maturation of antibodies from a naive combinatorial immunoglobulin library", *PNAS*, vol. 89, 1992, pp. 3576-3580.

Guo, Zhen et al., "Direct fluorescence analysis of genetic polymorphisms by hybridization with oligonucleotide arrays on glass supports", *Nucleic Acids Research*, vol. 22, No. 24, 1994, 5456-5465.

(56) References Cited

OTHER PUBLICATIONS

Ha, Taekjip et al., "Initiation and re-initiation of DNA unwinding by the *Escherichia coli* Rep helicase", *Nature*, vol. 419, 2002, 638-641.
Haab, Brian B. et al., "Protein microarrays for highly parallel detection and quantitation of specific proteins and antibodies in complex solutions", *Genome Biology*, vol. 2, No. 2, 2001, 1-13.
Hainfeld, James F et al., "Ni-NTA-Gold Clusters Target His-Tagged Proteins", *Journal of Structural Biology*, 127, 1999, 185-198.
Han, M. et al., "Quantum-dot-tagged Microbeads for Multiplexed Optical Coding of Biomolecules,", *Nature Biotechnology*, vol. 19, Jul. 2001, 631-635.
Harris, Timothy D. et al., "Single-Molecule DNA Sequencing of a Viral Genome", *Science*, vol. 320, 2008, 106-109.
Hermes, J, et al., "Searching sequence space by definably random mutagenesis: Improving the catalytic potency of an enzyme", *PNAS*, vol. 87, 1990, pp. 696-700.
Howarth, Mark et al., "Targeting quantum dots to surface proteins in living cells with biotin ligase", *PNAS*, vol. 102, No. 21, 2005, 7583-7588.
Jaiswal, Jyoti et al., "Use of quantum dots for live cell imaging", *Nature Methods*, vol. 1, No. 1, 2004, 71-78.
Jares-Erijman, Elizabeth A. et al., "FRET imaging", *Nature Biotechnology*, vol. 21, No. 11, 2003, 1387-1395.
Jauffred, Liselotte et al., "Three-Dimensional Optical Control of Individual Quantum Dots", *Nano Letter*, vol. 8, No. 10, 2008, 3376-3380.
Jeong, Lak S. et al., "Structure-activity relationships of .beta.-D-(2S,5R)- and .alpha.-D-(2S,5S)-1,3-oxathiolanyl nucleosides as potential anti-HIV agents", *J. Med. Chem.*, vol. 36, 1993, pp. 2627-2638.
Jewett, John et al., "Rapid Cu-Free Click Chemistry with Readily Synthesized Biarylazacyclooctynones", *J. Am. Chem. Soc.*, 132, 2010, 3688-3690.
Johnson, Erik et al., "Insights into the Mechanism and Catalysis of the Native Chemical Ligation Reaction", *J. Am. Chem. Soc.*, 128, 2006, 6640-6646.
Johnson, K. , "Rapid kinetic analysis of mechanochemical adenosinetriphosphatases", *Methods Enzymol.*, vol. 134, 1986, pp. 677-705.
Joos, Beda et al., "Covalent Attachment of Hybridizable Oligonucleotides to Glass Supports", *Analytical Biochem.*, vol. 247(1), 1997, pp. 96-101.
Joshi, et al., "ATP Synthase Complex from Bovine Heart Mitochondria", *Journal of Biological Chemistry*, vol. 265, No. 24, 1990, 14518-14525.
Jung, et al., "Crosslinking of platelet glycoprotein lb by N-succinimidyl(4-azidophenyldithio)propionate and 3,3'-dithiobis(sulfosuccinimidyl propionate)", *Biochimica et Biophysica Acta*, vol. 761, No. 2, 1983, 152-162.
Kamiya, Mako et al., "Extension of the Applicable Range of Fluorescein: A Fluorescein-Based Probe for Western Blot Analysis", *Angew. Chem. Int. Ed.*, vol. 44, 2005, 5439-5441.
Kamtekar, Satwik et al., "The phi29 DNA polymerase:protein-primer structure suggests a model for the initiation to elongation transition", *EMBO Journal*, vol. 25, No. 6, 2006, 1335-1343.
Kim, Hea O. et al., "1,3-Dioxolanylpurine nucleosides (2R,4R) and (2R,4S) with selective anti-HIV-1 activity in human lymphocytes", *J. Med. Chem.*, vol. 36, No. 1, 1993, 30-37.
Kiyonaka, Shigeki et al., "Semi-wet peptide/protein array using supramolecular hydrogel", *Nature Materials*, vol. 3, 2004, 58-64.
Kumar, Amarendra et al., "Inhibition of T7 Rna Polymerase: Transcription Initiation and Transition from Initiation to Elongation Are Inhibited by T7 Lysozyme via a Ternary Complex with RNA Polymerase and Promoter DNA", *Biochemistry*, vol. 36, No. 45, 1997, pp. 13954-13962.
Kumar, Shiv et al., "Terminal Phosphate Labeled Nucleotides: Synthesis, Applications, and Linker Effect on Incorporation by DNA Polymerases", *Nucleosides, Nucleotides and Nucleic Acids*, vol. 24, Nos. 5-7, 2005, 401-408.
Kunkel, Thomas A. , "DNA replication fidelity", *Journal of Biological Chemistry*, vol. 267, No. 26, Sep. 15, 1992, 18251-18254.
Laitala, Ville et al., "Homogeneous Assay Based on Anti-Stokes' Shift Time-Resolved Fluorescence Resonance Energy-Transfer Measurement", *Analytical Chem.*, vol. 77, 2005, 1483-1487.
Lakowicz, J. R. , "Energy Transfer", *Principles of Fluorescence Spectroscopy, 2nd Ed.* Plenum Publishing Corp., New York, NY, 1999, 367-394.
Lamture, J. et al., "Direct detection of nucleic acid hybridization on the surface of a charge coupled device", *Nucleic Acids Research*, vol. 22(11), 1994, pp. 2121-2125.
Liu, Wenshe et al., "Genetic incorporation of unnatural amino acids into proteins in mammalian cells", *Nature Methods*, vol. 4, No. 3, 2007, 239-244.
Lundberg, Kelly S. et al., "High-fidelity amplification using a thermostabile DNA polymerase isolated from Pyrococcus furiosus", *Gene*, vol. 108, Elsevier Science Publishers B.V.,, 1991, 1-6.
Mac Beath, Gavin et al., "Printing Proteins as Microarrays for High-Throughput Function Determination", *Science*, vol. 289, 2000, 1760-1763.
Marshall, P. N. , "Rules for the visible absorption spectra of halogenated Fluorescein dyes", *Histochemical Journal*, vol. 7, 1975, pp. 299-303.
Martinez, Carlos I. et al., "Acyclic nucleoside triphosphate analogs as terminators in biocatalytic DNA replication", *Bioorganic & Medicinal Chemistry Letters*, vol. 7(23), 1997, pp. 3013-3016.
Martinez, Carlos I. et al., "An allylic/acyclic adenosine nucleoside triphosphate for termination of DNA synthesis by DNA template-dependent polymerases", *Nucleic Acids Research*, vol. 27, No. 5, 1999, 1271-1274.
Matayoshi, et al., "Novel Fluoregenic Substrates for Assaying Retroviral Proteases by Resonance Energy Transfer", *Science*, vol. 247, Feb. 23, 1990, pp. 954-958.
Mathis, G. , "Probing molecular interactions with homogeneous techniques based on rare earth cryptates and fluorescence energy transfer", *Clin. Chem.*, vol. 41, No. 9, 1995, pp. 1391-1397.
Matsumoto, et al., "Genbank Accession No. M33144", 1993.
Mattoussi, H. et al., "Bioconjugation of Highly Luminescent Colloidal CdSe—ZnS Quantum Dots with an Engineered Two-Domain Recombinant Protein", *Phys. Status Solido B-Basic Res.*, 224, No. 1, 2001, 277-283.
Mattoussi, H. et al., "Self-Assembly of CdSe—ZnS Quantum Dot Bioconjugates Using an Engineered Recombinant Protein", *J Am Chem Soc.*, vol. 122, No. 49, Nov. 22, 2000, 12142-12150.
McCafferty, J. et al., "Phage antibodies: filamentous phage displaying antibody variable domains", *Nature*, vol. 348, Dec. 6, 1990, 552-554.
Medintz, et al., "A fluorescence resonance energy transfer-derived structure of a quantum dot-protein bioconjugate nanoassembly", *Proceedings of the National Academy of Sciences (PNAS)*, 101 (26), 2004, 9612-9617.
Medintz, Igor L. et al., "Self-assembled nanoscale biosensors based on quantum dot FRET donors", *Nature Materials*, vol. 2, 2003, 630-638.
Megiatto, Jackson D. et al., "General Method for Synthesis of Functionalized Macrocycles and Catenanes Utilizing "Click" Chemistry", *J. Am. Chem. Soc.*, vol. 130, 2008, 12872-12873.
Meijer, Wilfried et al., "Phi29 Family of Phages", *Microbiology and Molecular Biology Reviews*, vol. 65, No. 2, 2001, 261-287.
Meisel, Andreas et al., "Type III restriction enzymes need two inversely oriented recognition sites for DNA cleavage", *Nature*, vol. 355, 1992, 467-469.
Moll, Jonathan R. et al., "Designed heterodimerizing leucine zippers with a ranger of pls and stabilities up to 10-15 M", *Protein Science*, vol. 10, 2001, 649-655.
Motre, Aurelie et al., "Enhancing helicase-dependent amplification by fusing the helicase with the DNA polymerase", *Gene*, 420:, 2008, 17-22.
Murray, Noreen E. , "Type I Restriction Systems: Sophisticated Molecular Machines (a Legacy of Bertani and Weigle)", *Microbiology and Molecular Biology Reviews*, vol. 64, No. 2, 2000, 412-434.

(56) References Cited

OTHER PUBLICATIONS

Nakaji-Hirabayashi, Tadashi et al., "Oriented immobilization of epidermal growth factor onto culture substrates for the selective expansion of neural stem cells", *Biomaterials*, vol. 28, No. 24, 2007, 3517-3529.
Nakanishi, Kazuhiro et al., "Recent Advances in Controlled Immobilization of Proteins onto the Surface of the Solid Substrate and Its Possible Application to Proteomics", *Current Proteomics*, vol. 5, 2008, 161-175.
Ngo, et al., "The Protein Folding Problem and Tertiary Structure Predict ion", Merz et al. (ed .), *Birkhauser, Boston, MA*, 1994, pp. 433 and 492-495.
Oliphant, Arnold R. et al., "Cloning of random-sequence oligodeoxynucleotides", *Gene*, vol. 44, Iss. 2-3, 1986, 177-183.
Park, et al., "Characterization of the Cell Surface Receptor for a Multi-Lineage Colony-Stimulating Factor (CSF-2alpha)*", *Journal of Biological Chemistry*, vol. 261, No. 1, 1986, 205-210.
Park, Chan-Ho et al., "New Photoactivated Protecting Groups. 6. p-Hydroxyphenacyl: A Phototrigger for Chemical and Biochemical Probes1,2", *J. Am. Chem. Soc.*, vol. 119, No. 10, 1997, 2453-2463.
Patel, Smita et al., "Pre-Steady-State Kinetic Analysis of Processive DNA Replication Including Complete Characterization of an Exonuclease-Deficient Mutant", *Biochemistry*, 30, 1991, 511-525.
PCT/US01/21811, , "International Search Report", dated May 12, 2003, 6 Pages.
PCT/US01/45819, , "International Search Report", dated Jun. 2, 2003, 6 Pages.
PCT/US2010/028952, , "International Search Report and Written Opinion", dated Mar. 23, 2011, 11 Pages.
PCT/US2010/028967, , "International Search Report and Written Opinion", dated Mar. 18, 2011, 10 Pages.
PCT/US2010/028972, , "International Search Report and Written Opinion", dated Jan. 21, 2011, 13 Pages.
PCT/US2010/028974, , "International Search Report and Written Opinion Received", dated Jan. 26, 2011, 13 Pages.
PCT/US2010/050406, , "International Search Report and Written Opinion", dated Feb. 21, 2011, 14 Pages.
Pease, Ann C. et al., "Light-Generated Oligonucleotide Arrays for Rapid DNA Sequence Analysis", *Proc. Natl. Acad. Sci.*, vol. 91, May 1994, 5022-5026.
Pecenkova, et al., "DNA Polymerase (Early Protein GP2)", *UniProt Accession Q37882*, Dec. 1998, 1-2.
Pecenkova, Tamara et al., "Bacteriophage B103: complete DNA sequence of its genome and relationship to other Bacillus phages", *Gene*, 199, 1997, 157-163.
Pingoud, Alfred et al., "Structure and function of type II restriction endonucleases", *Nucleic Acids Research*, vol. 29, No. 18, 2001, 3705-3727.
Piston, David W. et al., "Fluorescent protein FRET: the good, the bad and the ugly", *Trends Biochem. Sci.,*, vol. 32, No. 9, 2007, 407-414.
Qu, Lianhua et al., "Alternative Routes Toward High Quality CdSe Nanocrystals", *Nano Letters*, vol. 1, No. 6, 2001, 333-337.
Rao, et al., "Oriented Immobilization of Proteins", *Mikrochim. Acta*, vol. 128, 1998, 127-143.
Richard, Jean-Alexandre et al., "7-Hydroxycoumarin-Hemicyanine Hybrids: A New Class of Far-Red Emitting Fluorogenic Dyes", *Organic Letters*, vol. 10, 2008, 4175-4178.
Rienitz, Axel et al., "On the fidelity of DNA polymerase alpha: the influence of alpha-thio dNTPs, Mn2+ and mismatch repair", *Nucleic Acids Research*, vol. 13, No. 15, 1985, 5685-5695.
Roettger, Michelle P. et al., "Mismatched and Matched dNTP Incorporation by DNA Polymerase # Proceed via Analogous Kinetic Pathways", *Biochemistry*, vol. 47, No. 37, 2008, 9718-9727.
Rogers, Yu-Hui et al., "Immobilization of Oligonucleotides onto a Glass Support via Disulfide Bonds: A Method for Preparation of DNA Microarrays", *Analytical Biochemistry*, vol. 266, 1999, 23-30.
Ronaghi, M. et al., "Real-time DNA Sequencing Using Detection of Pyrophosphate Release", *Anal Biochem*, vol. 242(1), 1996, pp. 84-89.
Rothwell, Paul J. et al., "Structure and Mechanism of DNA Polymerases", *Advances in Protein Chemistry*, vol. 71, 2005, 401-440.
Sapsford, Kim E. et al., "Materials for Fluorescence Resonance Energy Transfer Analysis: Beyond Traditional Donor-Acceptor Combinations", *Angew. Chem. Int. Ed.*, vol. 45, 2006, 4562-4588.
Sarkez, A. et al., "A Fluorescence-based Assay for Analysis of Biotinylated Proteins and Nucleic Acids", *Biophysical Society 48th Annual Meeting*, Feb. 14, 2004, 1-6.
Schlageck, Joseph G. et al., "Spectroscopic techniques for study of phosphodiester bond formation by *Escherichia coli* RNA polymerase", *Journal of Biological Chemistry*, vol. 254, No. 23, Dec. 10, 1979, 12074-12077.
Schmitt, Christophe et al., "Kinetics of Formation and Functional Properties of Conjugates Prepared by Dry-State Incubation of Beta-Lactoglobulin/Acacia Gum Electrostatic Complexes", *J. Agric. Food Chem.*, 53, 2005, 9089-9099.
Schwartz, David C. et al., "Separation of Yeast Chromosome-Sized DNAs by Pulsed Field Gradient Gel Electrophoresis", *Cell*, vol. 37, 1984, 67-75.
Scott, Jamie K. et al., "Searching for Peptide Ligands with an Epitope Library", *Science*, vol. 249, 1990, 386-390.
Selvin, , "Fluorescence Resonance Energy Transfer", *Methods in Enzymology*, vol. 246, 1995, 300-334.
Shao, Jun et al., "Unprotected Peptides as Building Blocks for the Synthesis of Peptide Dendrimers with Oxime, Hydrazone, and Thiazolidine Linkages", *J. Am. Chem. Soc.*, vol. 117, No. 14, 1995, 3893-3899.
Smith, J. J. et al., "Orthogonal Site-Specific Protein Modification by Engineering Reversible Thiol Protection Mechanisms", *Protein Science*, vol. 14, 2005, 64-73.
Soengas, Maria et al., "Site-directed mutagenesis at the Exo III motif of Phi29 DNA polymerase; overlapping structural domains for the 3'-5' exonuclease and strand-displacement activities", *The EMBO Journal*, vol. 1 1 No. 1 1, 1992, 4227-4237.
Sood, Anup et al., "Terminal Phosphate-Labeled Nucleotides with Improved Substrate Properties for Homogeneous Nucleic Acid Assays", *J. Am. Chem. Soc.*, vol. 127, No. 8, 2005, 2394-2395.
Steitz, Thomas , "DNA Polymerases: Structural Diversity and Common Mechanisms", *The Journal of Biological Chemistry*, vol. 274, No. 25, 1999, 17395-17398.
Stryer, , "Fluorescence Energy Transfer as a Spectroscopic Ruler", *Annual Review of Biochemistry*, vol. 47, Jul. 1978, 819-846.
Sun, Lan et al., "Surface-Enhanced Raman Scattering Based Nonfluorescent Probe for Multiplex Detection", *Analytical Chemistry*, vol. 79, No. 11, 2007, 3981-3988.
Tolbert, Thomas et al., "Conjugation of Glycopeptide Thioesters to Expressed Protein Fragments", *Methods in Molecular Biology, Bioconjugation Protocols: Strategies and Methods*, vol. 283, 2004, 255-266.
Tominaga, Jo et al., "An enzymatic strategy for site-specific immobilization of functional proteins using microbial transglutaminase", *Enzyme and Microbial Technology*, vol. 35, Iss. 6-7, 2004, 613-618.
Truniger, V. et al., "Phi29 DNA polymerase residue Leu384 , highly conserved in motif B of eukaryotic type DNA replicases, is involved in nucleotide insert ion fidelity", *The Journal of Biological Chemistry*. vol. 278 No. 35, Jun. 12, 2003, pp. 33482-33491.
Truniger, V. et al., "Two positively charged residues of phi29 DNA polymerase conserved in protein-primed DNA polymerases, are involved in stabil isation of the incoming nucleotide", *Journal of Molecular Biology*. vol. 335 No. 2, Jan. 9, 2004, pp. 481-494.
Tsai, Yu-Chih et al., "A New Paradigm for DNA Polymerase Specificity", *Biochemistry*, vol. 45, No. 32, 2006, 9675-9687.
Tsang, Shui Y. et al., "Copper-1,10-phenanthroline induces internucleosomal DNA fragmentation in HepG2 cells, resulting from direct oxidation by the hydroxyl radical", *Biochem. J.*, vol. 317, 1996, 13-16.
Tyagi, Sanjay et al., "Multicolor molecular beacons for allele discrimination", *Nature Biotechnology*, vol. 16, 1998, 49-53.
Tyagi, Sanjay , "Taking DNA probes into a protein world", *Nature Biotechnology*, vol. 14, 1996, 947-948.

(56) References Cited

OTHER PUBLICATIONS

Vallina-Garcia, Romina et al., "Oriented immobilisation of anti-pneumolysin Fab through a histidine tag for electrochemical immunosensors", *Biosensors and Bioelectronics*, vol. 23, Iss. 2, 2007, 210-217.
Watkins, Lucas P. et al., "Detection of Intensity Change Points in Time-Resolved Single-Molecule Measurements", *J. Phys. Chem. B.*, vol. 109(1), 2005, 617-628.
Werts, Michel P., "Mechanically Linked Polyrotaxanes: A Stepwise Approach", *Macromolecules*, vol. 36, Iss. 19, 2003, 7004-7013.
Wetmur, J. G., "DNA probes: applications of the principles of nucleic acid hybridization", *Crit. Rev. Biochem. Mol. Biol.*, vol. 26, Nos. 3-4, 1991, 227-259.
Williams, J. G. et al., "An artificial processivity clamp made with streptavidin facilitates oriented attachment of polymerase-DNA complexes to surfaces", *Nucleic Acid Research*. vol. 36. No. 18., Aug. 22, 2008, pp. e121.
Wong, Isaac et al., "An induced-fit kinetic mechanism for DNA replication fidelity: direct measurement by single-turnover kinetics", *Biochemistry*, vol 30, No. 2, Jan. 1991, 526-537.
Wu, Felicia et al., "Synthesis and Properties of Adenosine-5'-triphosphoro-gamma-1-(5-sulfonic acid)naphthyl Ethylamidate: A Fluorescent Nucleotide Substrate for DNA-Dependent RNA Polymerase from *Escherichia coli*", *Archives of Biochemistry and Biophysics*, vol. 246, No. 2,, 1986, 564-571.
Wu, P. et al., "Resonance Energy Transfer: Methods and Applications", *Anal. Biochem.*, vol. 218(1), 1994, pp. 1-13.
Xia, Jie et al., "Photolabile 'Caged' Fatty Acids Containing A 1-(2'-Nitrophenyl)-1,2-Ethanediol Moiety", *Bioorganic & Medicinal Chemistry Letters*, vol. 7, Iss. 10, 1997, 1243-1248.
Xu, Yao et al., "Imaging protein interactions with bioluminescence resonance energy transfer (BRET) in plant and mammalian cells and tissues", *Proc. Natl. Acad. Sci.*, vol. 96, 1999, 151-156.
Yarbrough, L. R. et al., "Synthesis and properties of fluorescent nucleotide substrates for DNA-dependent RNA polymerases", *Journal of Biological Chemistry*, vol. 254, No. 23, Dec. 10, 1979, 12069-12073.
Yarbrough, Lynwood R., "Synthesis and Properties of a New Fluorescent Analog of ATP: Adenosine-5'-Triphosphoro-y-1-(5-Sulfonic Acid) Napthylamidate", *Biochemical and Biophysical Research Communications*, vol. 81, No. 1, Mar. 15, 1978, 35-41.
Yeo, Sanghak et al., "The patterned hydrophilic surfaces of glass slides to be applicable for the construction of protein chips", *Current Applied Physics*, vol. 6, 2006, 267-270.
Zarling, et al., "Mapping of Lymphocyte Surface Polypeptide Antigens by Chemical Cross-Linking with BSOCOES", *Journal of Immunology*, vol. 124, No. 2, 1980, 913-920.
Zhang, Kechun et al., "Artificial Polypeptide Scaffold for Protein Immobilization", *J. Am. Chem. Soc.*, vol. 127, No. 29, 2005, 10136-10137.
Zhu, Heng et al., "Analysis of Yeast Protein Kinases Using Protein Chips", *Nature Genetics*, vol. 26, 2000, 283-289.
Zhu, Heng et al., "Protein Chip Technology", *Curr. Opin. Chem. Biol.*, vol. 7, No. 1, 2003, 55-63.
U.S. Appl. No. 11/007,794, filed Dec. 8, 2004, Hardin et al.
U.S. Appl. No. 12/321,343, filed Jan. 16, 2009, Hardin, Susan et al.
U.S. Appl. No. 13/291,070, filed Nov. 7, 2011, Hardin, Susan et al.
Xu, Y. et al., "A bioluminescence resonance energy transfer (BRET) system: application to interacting circadian proteins", Proceedings of the National Academy of Sciences (PNAS) vol. 96 1999, 151-156.
Gentle et al., "Direct Production of Proteins with N-Terminal Cysteine for Site-Specific Conjugation", Bioconjugate Chem. 15, pp. 658-663. (Year: 2004).

\* cited by examiner

SEQUENCE LISTING

<160> NUMBER OF SEQ ID NOS: 62

<210> SEQ ID NO 1
<211> LENGTH: 928
<212> TYPE: PRT
<213> ORGANISM: Escherichia coli

<400> SEQUENCE: 1

Met Val Gln Ile Pro Gln Asn Pro Leu Ile Leu Val Asp Gly Ser Ser
1               5                   10                  15

Tyr Leu Tyr Arg Ala Tyr His Ala Phe Pro Pro Leu Thr Asn Ser Ala
            20                  25                  30

Gly Glu Pro Thr Gly Ala Met Tyr Gly Val Leu Asn Met Leu Arg Ser
        35                  40                  45

Leu Ile Met Gln Tyr Lys Pro Thr His Ala Ala Val Val Phe Asp Ala
    50                  55                  60

Lys Gly Lys Thr Phe Arg Asp Glu Leu Phe Glu His Tyr Lys Ser His
65                  70                  75                  80

Arg Pro Pro Met Pro Asp Asp Leu Arg Ala Gln Ile Glu Pro Leu His
                85                  90                  95

Ala Met Val Lys Ala Met Gly Leu Pro Leu Leu Ala Val Ser Gly Val
            100                 105                 110

Glu Ala Asp Asp Val Ile Gly Thr Leu Ala Arg Glu Ala Glu Lys Ala
        115                 120                 125

Gly Arg Pro Val Leu Ile Ser Thr Gly Asp Lys Asp Met Ala Gln Leu
    130                 135                 140

Val Thr Pro Asn Ile Thr Leu Ile Asn Thr Met Thr Asn Thr Ile Leu
145                 150                 155                 160

Gly Pro Glu Glu Val Val Asn Lys Tyr Gly Val Pro Pro Glu Leu Ile
                165                 170                 175

Ile Asp Phe Leu Ala Leu Met Gly Asp Ser Ser Asp Asn Ile Pro Gly
            180                 185                 190

```
Val Pro Gly Val Gly Glu Lys Thr Ala Gln Ala Leu Leu Gln Gly Leu
        195                 200                 205

Gly Gly Leu Asp Thr Leu Tyr Ala Glu Pro Glu Lys Ile Ala Gly Leu
    210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
                245                 250                 255

Glu Leu Glu Leu Thr Cys Glu Gln Leu Glu Val Gln Gln Pro Ala Ala
                260                 265                 270

Glu Glu Leu Leu Gly Leu Phe Lys Lys Tyr Glu Phe Lys Arg Trp Thr
                275                 280                 285

Ala Asp Val Glu Ala Gly Lys Trp Leu Gln Ala Lys Gly Ala Lys Pro
                290                 295                 300

Ala Ala Lys Pro Gln Glu Thr Ser Val Ala Asp Glu Ala Pro Glu Val
305                 310                 315                 320

Thr Ala Thr Val Ile Ser Tyr Asp Asn Tyr Val Thr Ile Leu Asp Glu
                325                 330                 335

Glu Thr Leu Lys Ala Trp Ile Ala Lys Leu Glu Lys Ala Pro Val Phe
                340                 345                 350

Ala Phe Asp Thr Glu Thr Asp Ser Leu Asp Asn Ile Ser Ala Asn Leu
                355                 360                 365

Val Gly Leu Ser Phe Ala Ile Glu Pro Gly Val Ala Ala Tyr Ile Pro
                370                 375                 380

Val Ala His Asp Tyr Leu Asp Ala Pro Asp Gln Ile Ser Arg Glu Arg
385                 390                 395                 400

Ala Leu Glu Leu Leu Lys Pro Leu Leu Glu Asp Glu Lys Ala Leu Lys
                405                 410                 415

Val Gly Gln Asn Leu Lys Tyr Asp Arg Gly Ile Leu Ala Asn Tyr Gly
                420                 425                 430

Ile Glu Leu Arg Gly Ile Ala Phe Asp Thr Met Leu Glu Ser Tyr Ile
                435                 440                 445

Leu Asn Ser Val Ala Gly Arg His Asp Met Asp Ser Leu Ala Glu Arg
                450                 455                 460

Trp Leu Lys His Lys Thr Ile Thr Phe Glu Glu Ile Ala Gly Lys Gly
465                 470                 475                 480

Lys Asn Gln Leu Thr Phe Asn Gln Ile Ala Leu Glu Glu Ala Gly Arg
                485                 490                 495

Tyr Ala Ala Glu Asp Ala Asp Val Thr Leu Gln Leu His Leu Lys Met
                500                 505                 510

Trp Pro Asp Leu Gln Lys His Lys Gly Pro Leu Asn Val Phe Glu Asn
                515                 520                 525

Ile Glu Met Pro Leu Val Pro Val Leu Ser Arg Ile Glu Arg Asn Gly
                530                 535                 540

Val Lys Ile Asp Pro Lys Val Leu His Asn His Ser Glu Glu Leu Thr
545                 550                 555                 560

Leu Arg Leu Ala Glu Leu Glu Lys Lys Ala His Glu Ile Ala Gly Glu
                565                 570                 575

Glu Phe Asn Leu Ser Ser Thr Lys Gln Leu Gln Thr Ile Leu Phe Glu
                580                 585                 590

Lys Gln Gly Ile Lys Pro Leu Lys Lys Thr Pro Gly Gly Ala Pro Ser
                595                 600                 605
```

```
Thr Ser Glu Glu Val Leu Glu Leu Ala Leu Asp Tyr Pro Leu Pro
    610                 615                 620

Lys Val Ile Leu Glu Tyr Arg Gly Leu Ala Lys Leu Lys Ser Thr Tyr
625                 630                 635                 640

Thr Asp Lys Leu Pro Leu Met Ile Asn Pro Lys Thr Gly Arg Val His
                645                 650                 655

Thr Ser Tyr His Gln Ala Val Thr Ala Thr Gly Arg Leu Ser Ser Thr
                660                 665                 670

Asp Pro Asn Leu Gln Asn Ile Pro Val Arg Asn Glu Glu Gly Arg Arg
            675                 680                 685

Ile Arg Gln Ala Phe Ile Ala Pro Glu Asp Tyr Val Ile Val Ser Ala
690                 695                 700

Asp Tyr Ser Gln Ile Glu Leu Arg Ile Met Ala His Leu Ser Arg Asp
705                 710                 715                 720

Lys Gly Leu Leu Thr Ala Phe Ala Glu Gly Lys Asp Ile His Arg Ala
                725                 730                 735

Thr Ala Ala Glu Val Phe Gly Leu Pro Leu Glu Thr Val Thr Ser Glu
                740                 745                 750

Gln Arg Arg Ser Ala Lys Ala Ile Asn Phe Gly Leu Ile Tyr Gly Met
            755                 760                 765

Ser Ala Phe Gly Leu Ala Arg Gln Leu Asn Ile Pro Arg Lys Glu Ala
770                 775                 780

Gln Lys Tyr Met Asp Leu Tyr Phe Glu Arg Tyr Pro Gly Val Leu Glu
785                 790                 795                 800

Tyr Met Glu Arg Thr Arg Ala Gln Ala Lys Glu Gln Gly Tyr Val Glu
                805                 810                 815

Thr Leu Asp Gly Arg Arg Leu Tyr Leu Pro Asp Ile Lys Ser Ser Asn
                820                 825                 830

Gly Ala Arg Arg Ala Ala Ala Glu Arg Ala Ala Ile Asn Ala Pro Met
            835                 840                 845

Gln Gly Thr Ala Ala Asp Ile Ile Lys Arg Ala Met Ile Ala Val Asp
850                 855                 860

Ala Trp Leu Gln Ala Glu Gln Pro Arg Val Arg Met Ile Met Gln Val
865                 870                 875                 880

His Asp Glu Leu Val Phe Glu Val His Lys Asp Asp Val Asp Ala Val
                885                 890                 895

Ala Lys Gln Ile His Gln Leu Met Glu Asn Cys Thr Arg Leu Asp Val
                900                 905                 910

Pro Leu Leu Val Glu Val Gly Ser Gly Glu Asn Trp Asp Gln Ala His
            915                 920                 925

<210> SEQ ID NO 2
<211> LENGTH: 606
<212> TYPE: PRT
<213> ORGANISM: Escherichia coli

<400> SEQUENCE: 2

Met Val Ile Ser Tyr Asp Asn Tyr Val Thr Ile Leu Asp Glu Glu Thr
1               5                   10                  15

Leu Lys Ala Trp Ile Ala Lys Leu Glu Lys Ala Pro Val Phe Ala Phe
                20                  25                  30

Asp Thr Glu Thr Asp Ser Leu Asp Asn Ile Ser Ala Asn Leu Val Gly
            35                  40                  45

Leu Ser Phe Ala Ile Glu Pro Gly Val Ala Ala Tyr Ile Pro Val Ala
50                  55                  60
```

```
His Asp Tyr Leu Asp Ala Pro Asp Gln Ile Ser Arg Glu Arg Ala Leu
 65                  70                  75                  80

Glu Leu Leu Lys Pro Leu Leu Glu Asp Glu Lys Ala Leu Lys Val Gly
                 85                  90                  95

Gln Asn Leu Lys Tyr Asp Arg Gly Ile Leu Ala Asn Tyr Gly Ile Glu
                100                 105                 110

Leu Arg Gly Ile Ala Phe Asp Thr Met Leu Glu Ser Tyr Ile Leu Asn
            115                 120                 125

Ser Val Ala Gly Arg His Asp Met Asp Ser Leu Ala Glu Arg Trp Leu
        130                 135                 140

Lys His Lys Thr Ile Thr Phe Glu Glu Ile Ala Gly Lys Gly Lys Asn
145                 150                 155                 160

Gln Leu Thr Phe Asn Gln Ile Ala Leu Glu Glu Ala Gly Arg Tyr Ala
                165                 170                 175

Ala Glu Asp Ala Asp Val Thr Leu Gln Leu His Leu Lys Met Trp Pro
            180                 185                 190

Asp Leu Gln Lys His Lys Gly Pro Leu Asn Val Phe Glu Asn Ile Glu
        195                 200                 205

Met Pro Leu Val Pro Val Leu Ser Arg Ile Glu Arg Asn Gly Val Lys
    210                 215                 220

Ile Asp Pro Lys Val Leu His Asn His Ser Glu Glu Leu Thr Leu Arg
225                 230                 235                 240

Leu Ala Glu Leu Glu Lys Lys Ala His Glu Ile Ala Gly Glu Glu Phe
                245                 250                 255

Asn Leu Ser Ser Thr Lys Gln Leu Gln Thr Ile Leu Phe Glu Lys Gln
            260                 265                 270

Gly Ile Lys Pro Leu Lys Lys Thr Pro Gly Gly Ala Pro Ser Thr Ser
        275                 280                 285

Glu Glu Val Leu Glu Glu Leu Ala Leu Asp Tyr Pro Leu Pro Lys Val
    290                 295                 300

Ile Leu Glu Tyr Arg Gly Leu Ala Lys Leu Lys Ser Thr Tyr Thr Asp
305                 310                 315                 320

Lys Leu Pro Leu Met Ile Asn Pro Lys Thr Gly Arg Val His Thr Ser
                325                 330                 335

Tyr His Gln Ala Val Thr Ala Thr Gly Arg Leu Ser Ser Thr Asp Pro
            340                 345                 350

Asn Leu Gln Asn Ile Pro Val Arg Asn Glu Glu Gly Arg Arg Ile Arg
        355                 360                 365

Gln Ala Phe Ile Ala Pro Glu Asp Tyr Val Ile Val Ser Ala Asp Tyr
    370                 375                 380

Ser Gln Ile Glu Leu Arg Ile Met Ala His Leu Ser Arg Asp Lys Gly
385                 390                 395                 400

Leu Leu Thr Ala Phe Ala Glu Gly Lys Asp Ile His Arg Ala Thr Ala
                405                 410                 415

Ala Glu Val Phe Gly Leu Pro Leu Glu Thr Val Thr Ser Glu Gln Arg
            420                 425                 430

Arg Ser Ala Lys Ala Ile Asn Phe Gly Leu Ile Tyr Gly Met Ser Ala
        435                 440                 445

Phe Gly Leu Ala Arg Gln Leu Asn Ile Pro Arg Lys Glu Ala Gln Lys
    450                 455                 460

Tyr Met Asp Leu Tyr Phe Glu Arg Tyr Pro Gly Val Leu Glu Tyr Met
465                 470                 475                 480
```

-continued

```
Glu Arg Thr Arg Ala Gln Ala Lys Glu Gln Gly Tyr Val Glu Thr Leu
                485                 490                 495

Asp Gly Arg Arg Leu Tyr Leu Pro Asp Ile Lys Ser Ser Asn Gly Ala
            500                 505                 510

Arg Arg Ala Ala Ala Glu Arg Ala Ala Ile Asn Ala Pro Met Gln Gly
        515                 520                 525

Thr Ala Ala Asp Ile Ile Lys Arg Ala Met Ile Ala Val Asp Ala Trp
    530                 535                 540

Leu Gln Ala Glu Gln Pro Arg Val Arg Met Ile Met Gln Val His Asp
545                 550                 555                 560

Glu Leu Val Phe Glu Val His Lys Asp Val Asp Ala Val Ala Lys
                565                 570                 575

Gln Ile His Gln Leu Met Glu Asn Cys Thr Arg Leu Asp Val Pro Leu
                580                 585                 590

Leu Val Glu Val Gly Ser Gly Glu Asn Trp Asp Gln Ala His
                595                 600                 605

<210> SEQ ID NO 3
<211> LENGTH: 575
<212> TYPE: PRT
<213> ORGANISM: Bacillus sp.
<220> FEATURE:
<223> OTHER INFORMATION: Phage Phi-29

<400> SEQUENCE: 3

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
        50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
        130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Tyr
        210                 215                 220

Ala Tyr Arg Gly Gly Phe Thr Trp Leu Asn Asp Arg Phe Lys Glu Lys
225                 230                 235                 240
```

-continued

```
Glu Ile Gly Glu Gly Met Val Phe Asp Val Asn Ser Leu Tyr Pro Ala
            245                 250                 255

Gln Met Tyr Ser Arg Leu Leu Pro Tyr Gly Pro Ile Val Phe Glu
        260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
        420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
            485                 490                 495

Gln Lys Thr Tyr Ile Gln Asp Ile Tyr Met Lys Glu Val Asp Gly Lys
        500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
        530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
            565                 570                 575

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Leu Gly Ala Ala Lys Gly Ala Ala Lys Gly Ser Ala Ala
1               5                   10                  15

<210> SEQ ID NO 5
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Leu Gly Gly Gly Ser Gly Gly Gly Ser Ala Ala Ala Gly
1               5                   10                  15

Ser Ala Ala

<210> SEQ ID NO 6
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Cys Cys Cys Cys Cys Cys Cys Cys Cys Cys Leu Leu Gly
1               5                   10                  15

Gly Gly Gly Ser Gly Gly Gly Ser Ala Ala Ala Gly Ser Ala Ala
                20                  25                  30

Arg Lys Met Tyr Ser Cys Asp Phe Glu Thr Thr Lys Val Glu Asp
            35                  40                  45

Cys Arg Val Trp Ala Tyr Gly Tyr Met Asn Ile Glu Asp His Ser Glu
        50                  55                  60

Tyr Lys Ile Gly Asn Ser Leu Asp Glu Phe Met Ala Trp Val Leu Lys
65                  70                  75                  80

Val Gln Ala Asp Leu Tyr Phe His Asn Leu Lys Phe Asp Gly Ala Phe
                85                  90                  95

Ile Ile Asn Trp Leu Glu Arg Asn Gly Phe Lys Trp Ser Ala Asp Gly
            100                 105                 110

Leu Pro Asn Thr Tyr Asn Thr Ile Ile Ser Arg Met Gly Gln Trp Tyr
        115                 120                 125

Met Ile Asp Ile Cys Leu Gly Tyr Lys Gly Lys Arg Lys Ile His Thr
130                 135                 140

Val Ile Tyr Asp Ser Leu Lys Lys Leu Pro Phe Pro Val Lys Lys Ile
145                 150                 155                 160

Ala Lys Asp Phe Lys Leu Thr Val Leu Lys Gly Asp Ile Asp Tyr His
                165                 170                 175

Lys Glu Arg Pro Val Gly Tyr Lys Ile Thr Pro Glu Glu Tyr Ala Tyr
            180                 185                 190

Ile Lys Asn Asp Ile Gln Ile Ile Ala Glu Ala Leu Leu Ile Gln Phe
        195                 200                 205

Lys Gln Gly Leu Asp Arg Met Thr Ala Gly Ser Asp Ser Leu Lys Gly
210                 215                 220

Phe Lys Asp Ile Ile Thr Thr Lys Lys Phe Lys Lys Val Phe Pro Thr
225                 230                 235                 240

Leu Ser Leu Gly Leu Asp Lys Glu Val Arg Tyr Ala Tyr Arg Gly Gly
                245                 250                 255

Phe Thr Trp Leu Asn Asp Arg Phe Lys Glu Lys Glu Ile Gly Glu Gly
            260                 265                 270

Met Val Phe Asp Val Asn Ser Leu Tyr Pro Ala Gln Met Tyr Ser Arg
        275                 280                 285
```

-continued

```
Leu Leu Pro Tyr Gly Glu Pro Ile Val Phe Glu Gly Lys Tyr Val Trp
            290                 295                 300

Asp Glu Asp Tyr Pro Leu His Ile Gln His Ile Arg Cys Glu Phe Glu
305                 310                 315                 320

Leu Lys Glu Gly Tyr Ile Pro Thr Ile Gln Ile Lys Arg Ser Arg Phe
                325                 330                 335

Tyr Lys Gly Asn Glu Tyr Leu Lys Ser Ser Gly Gly Glu Ile Ala Asp
            340                 345                 350

Leu Trp Leu Ser Asn Val Asp Leu Glu Leu Met Lys Glu His Tyr Asp
        355                 360                 365

Leu Tyr Asn Val Glu Tyr Ile Ser Gly Leu Lys Phe Lys Ala Thr Thr
370                 375                 380

Gly Leu Phe Lys Asp Phe Ile Asp Lys Trp Thr Tyr Ile Lys Thr Thr
385                 390                 395                 400

Ser Glu Gly Ala Ile Lys Gln Leu Ala Lys Leu Met Leu Asn Ser Leu
                405                 410                 415

Tyr Gly Lys Phe Ala Ser Asn Pro Asp Val Thr Gly Lys Val Pro Tyr
            420                 425                 430

Leu Lys Glu Asn Gly Ala Leu Gly Phe Arg Leu Gly Glu Glu Glu Thr
        435                 440                 445

Lys Asp Pro Val Tyr Thr Pro Met Gly Val Phe Ile Thr Ala Trp Ala
450                 455                 460

Arg Tyr Thr Thr Ile Thr Ala Ala Gln Ala Cys Tyr Asp Arg Ile Ile
465                 470                 475                 480

Tyr Cys Asp Thr Asp Ser Ile His Leu Thr Gly Thr Glu Ile Pro Asp
                485                 490                 495

Val Ile Lys Asp Ile Val Asp Pro Lys Lys Leu Gly Tyr Trp Ala His
            500                 505                 510

Glu Ser Thr Phe Lys Arg Ala Lys Tyr Leu Arg Gln Lys Thr Tyr Ile
        515                 520                 525

Gln Asp Ile Tyr Met Lys Glu Val Asp Gly Lys Leu Val Glu Gly Ser
530                 535                 540

Pro Asp Asp Tyr Thr Asp Ile Lys Phe Ser Val Lys Cys Ala Gly Met
545                 550                 555                 560

Thr Asp Lys Ile Lys Lys Glu Val Thr Phe Glu Asn Phe Lys Val Gly
                565                 570                 575

Phe Ser Arg Lys Met Lys Pro Lys Pro Val Gln Val Pro Gly Gly Val
            580                 585                 590

Val Leu Val Asp Asp Thr Phe Thr Ile Lys
        595                 600

<210> SEQ ID NO 7
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Lys Lys Lys Lys Lys Lys Lys Lys Lys Lys Lys Leu Leu Gly
1               5                   10                  15

Gly Gly Gly Ser Gly Gly Gly Ser Ala Ala Ala Gly Ser Ala Ala
            20                  25                  30

Arg Lys Met Tyr Ser Cys Asp Phe Glu Thr Thr Thr Lys Val Glu Asp
        35                  40                  45
```

-continued

```
Cys Arg Val Trp Ala Tyr Gly Tyr Met Asn Ile Glu Asp His Ser Glu
     50                  55                  60
Tyr Lys Ile Gly Asn Ser Leu Asp Glu Phe Met Ala Trp Val Leu Lys
 65                  70                  75                  80
Val Gln Ala Asp Leu Tyr Phe His Asn Leu Lys Phe Asp Gly Ala Phe
                 85                  90                  95
Ile Ile Asn Trp Leu Glu Arg Asn Gly Phe Lys Trp Ser Ala Asp Gly
                100                 105                 110
Leu Pro Asn Thr Tyr Asn Thr Ile Ile Ser Arg Met Gly Gln Trp Tyr
                115                 120                 125
Met Ile Asp Ile Cys Leu Gly Tyr Lys Gly Lys Arg Lys Ile His Thr
            130                 135                 140
Val Ile Tyr Asp Ser Leu Lys Lys Leu Pro Phe Pro Val Lys Lys Ile
145                 150                 155                 160
Ala Lys Asp Phe Lys Leu Thr Val Leu Lys Gly Asp Ile Asp Tyr His
                165                 170                 175
Lys Glu Arg Pro Val Gly Tyr Lys Ile Thr Pro Glu Glu Tyr Ala Tyr
                180                 185                 190
Ile Lys Asn Asp Ile Gln Ile Ala Glu Ala Leu Leu Ile Gln Phe
                195                 200                 205
Lys Gln Gly Leu Asp Arg Met Thr Ala Gly Ser Asp Ser Leu Lys Gly
            210                 215                 220
Phe Lys Asp Ile Ile Thr Thr Lys Lys Phe Lys Lys Val Phe Pro Thr
225                 230                 235                 240
Leu Ser Leu Gly Leu Asp Lys Glu Val Arg Tyr Ala Tyr Arg Gly Gly
                245                 250                 255
Phe Thr Trp Leu Asn Asp Arg Phe Lys Glu Lys Glu Ile Gly Glu Gly
                260                 265                 270
Met Val Phe Asp Val Asn Ser Leu Tyr Pro Ala Gln Met Tyr Ser Arg
            275                 280                 285
Leu Leu Pro Tyr Gly Glu Pro Ile Val Phe Glu Gly Lys Tyr Val Trp
            290                 295                 300
Asp Glu Asp Tyr Pro Leu His Ile Gln His Ile Arg Cys Glu Phe Glu
305                 310                 315                 320
Leu Lys Glu Gly Tyr Ile Pro Thr Ile Gln Ile Lys Arg Ser Arg Phe
                325                 330                 335
Tyr Lys Gly Asn Glu Tyr Leu Lys Ser Ser Gly Gly Glu Ile Ala Asp
                340                 345                 350
Leu Trp Leu Ser Asn Val Asp Leu Glu Leu Met Lys Glu His Tyr Asp
            355                 360                 365
Leu Tyr Asn Val Glu Tyr Ile Ser Gly Leu Lys Phe Lys Ala Thr Thr
            370                 375                 380
Gly Leu Phe Lys Asp Phe Ile Asp Lys Trp Thr Tyr Ile Lys Thr Thr
385                 390                 395                 400
Ser Glu Gly Ala Ile Lys Gln Leu Ala Lys Leu Met Leu Asn Ser Leu
                405                 410                 415
Tyr Gly Lys Phe Ala Ser Asn Pro Asp Val Thr Gly Lys Val Pro Tyr
                420                 425                 430
Leu Lys Glu Asn Gly Ala Leu Gly Phe Arg Leu Gly Glu Glu Glu Thr
                435                 440                 445
Lys Asp Pro Val Tyr Thr Pro Met Gly Val Phe Ile Thr Ala Trp Ala
450                 455                 460
```

```
Arg Tyr Thr Thr Ile Thr Ala Ala Gln Ala Cys Tyr Asp Arg Ile Ile
465                 470                 475                 480

Tyr Cys Asp Thr Asp Ser Ile His Leu Thr Gly Thr Glu Ile Pro Asp
            485                 490                 495

Val Ile Lys Asp Ile Val Asp Pro Lys Lys Leu Gly Tyr Trp Ala His
            500                 505                 510

Glu Ser Thr Phe Lys Arg Ala Lys Tyr Leu Arg Gln Lys Thr Tyr Ile
            515                 520                 525

Gln Asp Ile Tyr Met Lys Glu Val Asp Gly Lys Leu Val Glu Gly Ser
            530                 535                 540

Pro Asp Asp Tyr Thr Asp Ile Lys Phe Ser Val Lys Cys Ala Gly Met
545                 550                 555                 560

Thr Asp Lys Ile Lys Lys Glu Val Thr Phe Glu Asn Phe Lys Val Gly
            565                 570                 575

Phe Ser Arg Lys Met Lys Pro Lys Pro Val Gln Val Pro Gly Gly Val
            580                 585                 590

Val Leu Val Asp Asp Thr Phe Thr Ile Lys
            595                 600

<210> SEQ ID NO 8
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met His His His His His Leu Leu Gly Gly Gly Ser Gly Gly
1               5                   10                  15

Gly Gly Ser Ala Ala Ala Pro Lys Pro Gln Gln Phe Ser Ala Ala
            20                  25                  30

Arg Lys Met Tyr Ser Cys Asp Phe Glu Thr Thr Thr Lys Val Glu Asp
            35                  40                  45

Cys Arg Val Trp Ala Tyr Gly Tyr Met Asn Ile Glu Asp His Ser Glu
50                  55                  60

Tyr Lys Ile Gly Asn Ser Leu Asp Glu Phe Met Ala Trp Val Leu Lys
65                  70                  75                  80

Val Gln Ala Asp Leu Tyr Phe His Asn Leu Lys Phe Asp Gly Ala Phe
            85                  90                  95

Ile Ile Asn Trp Leu Glu Arg Asn Gly Phe Lys Trp Ser Ala Asp Gly
            100                 105                 110

Leu Pro Asn Thr Tyr Asn Thr Ile Ile Ser Arg Met Gly Gln Trp Tyr
            115                 120                 125

Met Ile Asp Ile Cys Leu Gly Tyr Lys Gly Lys Arg Lys Ile His Thr
130                 135                 140

Val Ile Tyr Asp Ser Leu Lys Lys Leu Pro Phe Pro Val Lys Lys Ile
145                 150                 155                 160

Ala Lys Asp Phe Lys Leu Thr Val Leu Lys Gly Asp Ile Asp Tyr His
            165                 170                 175

Lys Glu Arg Pro Val Gly Tyr Lys Ile Thr Pro Glu Gly Tyr Ala Tyr
            180                 185                 190

Ile Lys Asn Asp Ile Gln Ile Ile Ala Glu Ala Leu Leu Ile Gln Phe
            195                 200                 205

Lys Gln Gly Leu Asp Arg Met Thr Ala Gly Ser Asp Ser Leu Lys Gly
            210                 215                 220
```

Phe Lys Asp Ile Ile Thr Thr Lys Lys Phe Lys Val Phe Pro Thr
225                 230                 235                 240

Leu Ser Leu Gly Leu Asp Lys Glu Val Arg Tyr Ala Tyr Arg Gly Gly
            245                 250                 255

Phe Thr Trp Leu Asn Asp Arg Phe Lys Glu Lys Glu Ile Gly Glu Gly
        260                 265                 270

Met Val Phe Asp Val Asn Ser Leu Tyr Pro Ala Gln Met Tyr Ser Arg
        275                 280                 285

Leu Leu Pro Tyr Gly Glu Pro Ile Val Phe Glu Gly Lys Tyr Val Trp
        290                 295                 300

Asp Glu Asp Tyr Pro Leu His Ile Gln His Ile Arg Cys Glu Phe Glu
305                 310                 315                 320

Leu Lys Glu Gly Tyr Ile Pro Thr Ile Gln Ile Lys Arg Ser Arg Phe
                325                 330                 335

Tyr Lys Gly Asn Glu Tyr Leu Lys Ser Ser Gly Gly Glu Ile Ala Asp
            340                 345                 350

Leu Trp Leu Ser Asn Val Asp Leu Glu Leu Met Lys Glu His Tyr Asp
        355                 360                 365

Leu Tyr Asn Val Glu Tyr Ile Ser Gly Leu Lys Phe Lys Ala Thr Thr
370                 375                 380

Gly Leu Phe Lys Asp Phe Ile Asp Lys Trp Thr Tyr Ile Lys Thr Thr
385                 390                 395                 400

Ser Glu Gly Ala Ile Lys Gln Leu Ala Lys Leu Met Leu Asn Ser Leu
                405                 410                 415

Tyr Gly Lys Phe Ala Ser Asn Pro Asp Val Thr Gly Lys Val Pro Tyr
            420                 425                 430

Leu Lys Glu Asn Gly Ala Leu Gly Phe Arg Leu Gly Glu Glu Glu Thr
        435                 440                 445

Lys Asp Pro Val Tyr Thr Pro Met Gly Val Phe Ile Thr Ala Trp Ala
        450                 455                 460

Arg Tyr Thr Thr Ile Thr Ala Ala Gln Ala Cys Tyr Asp Arg Ile Ile
465                 470                 475                 480

Tyr Cys Asp Thr Asp Ser Ile His Leu Thr Gly Thr Glu Ile Pro Asp
                485                 490                 495

Val Ile Lys Asp Ile Val Asp Pro Lys Lys Leu Gly Tyr Trp Ala His
            500                 505                 510

Glu Ser Thr Phe Lys Arg Ala Lys Tyr Leu Arg Gln Lys Thr Tyr Ile
        515                 520                 525

Gln Asp Ile Tyr Met Lys Glu Val Asp Gly Lys Leu Val Glu Gly Ser
        530                 535                 540

Pro Asp Asp Tyr Thr Asp Ile Lys Phe Ser Val Lys Cys Ala Gly Met
545                 550                 555                 560

Thr Asp Lys Ile Lys Lys Glu Val Thr Phe Glu Asn Phe Lys Val Gly
                565                 570                 575

Phe Ser Arg Lys Met Lys Pro Lys Pro Val Gln Val Pro Gly Gly Val
            580                 585                 590

Val Leu Val Asp Asp Thr Phe Thr Ile Lys
        595                 600

<210> SEQ ID NO 9
<211> LENGTH: 599
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 9

```
Met Gly Leu Arg Arg Ala Ser Leu His His Leu Leu Gly Gly Gly
1               5                   10                  15

Ser Gly Gly Gly Gly Ser Ala Ala Gly Ser Ala Ala Arg Lys Met
            20                  25                  30

Tyr Ser Cys Asp Phe Glu Thr Thr Thr Lys Val Glu Asp Cys Arg Val
        35                  40                  45

Trp Ala Tyr Gly Tyr Met Asn Ile Glu Asp His Ser Glu Tyr Lys Ile
    50                  55                  60

Gly Asn Ser Leu Asp Glu Phe Met Ala Trp Val Leu Lys Val Gln Ala
65                  70                  75                  80

Asp Leu Tyr Phe His Asn Leu Lys Phe Asp Gly Ala Phe Ile Ile Asn
                85                  90                  95

Trp Leu Glu Arg Asn Gly Phe Lys Trp Ser Ala Asp Gly Leu Pro Asn
            100                 105                 110

Thr Tyr Asn Thr Ile Ile Ser Arg Met Gly Gln Trp Tyr Met Ile Asp
        115                 120                 125

Ile Cys Leu Gly Tyr Lys Gly Lys Arg Lys Ile His Thr Val Ile Tyr
130                 135                 140

Asp Ser Leu Lys Lys Leu Pro Phe Pro Val Lys Lys Ile Ala Lys Asp
145                 150                 155                 160

Phe Lys Leu Thr Val Leu Lys Gly Asp Ile Asp Tyr His Lys Glu Arg
                165                 170                 175

Pro Val Gly Tyr Lys Ile Thr Pro Glu Glu Tyr Ala Tyr Ile Lys Asn
            180                 185                 190

Asp Ile Gln Ile Ile Ala Glu Ala Leu Leu Ile Gln Phe Lys Gln Gly
        195                 200                 205

Leu Asp Arg Met Thr Ala Gly Ser Asp Ser Leu Lys Gly Phe Lys Asp
210                 215                 220

Ile Ile Thr Thr Lys Lys Phe Lys Lys Val Phe Pro Thr Leu Ser Leu
225                 230                 235                 240

Gly Leu Asp Lys Glu Val Arg Tyr Ala Tyr Arg Gly Phe Thr Trp
                245                 250                 255

Leu Asn Asp Arg Phe Lys Glu Lys Glu Ile Gly Glu Gly Met Val Phe
            260                 265                 270

Asp Val Asn Ser Leu Tyr Pro Ala Gln Met Tyr Ser Arg Leu Leu Pro
        275                 280                 285

Tyr Gly Glu Pro Ile Val Phe Glu Gly Lys Tyr Val Trp Asp Glu Asp
290                 295                 300

Tyr Pro Leu His Ile Gln His Ile Arg Cys Glu Phe Glu Leu Lys Glu
305                 310                 315                 320

Gly Tyr Ile Pro Thr Ile Gln Ile Lys Arg Ser Arg Phe Tyr Lys Gly
                325                 330                 335

Asn Glu Tyr Leu Lys Ser Ser Gly Gly Glu Ile Ala Asp Leu Trp Leu
            340                 345                 350

Ser Asn Val Asp Leu Glu Leu Met Lys Glu His Tyr Asp Leu Tyr Asn
        355                 360                 365

Val Glu Tyr Ile Ser Gly Leu Lys Phe Lys Ala Thr Thr Gly Leu Phe
370                 375                 380

Lys Asp Phe Ile Asp Lys Trp Thr Tyr Ile Lys Thr Thr Ser Glu Gly
385                 390                 395                 400
```

-continued

```
Ala Ile Lys Gln Leu Ala Lys Leu Met Leu Asn Ser Leu Tyr Gly Lys
            405                 410                 415

Phe Ala Ser Asn Pro Asp Val Thr Gly Lys Val Pro Tyr Leu Lys Glu
        420                 425                 430

Asn Gly Ala Leu Gly Phe Arg Leu Gly Glu Glu Thr Lys Asp Pro
    435                 440                 445

Val Tyr Thr Pro Met Gly Val Phe Ile Thr Ala Trp Ala Arg Tyr Thr
450                 455                 460

Thr Ile Thr Ala Ala Gln Ala Cys Tyr Asp Arg Ile Ile Tyr Cys Asp
465                 470                 475                 480

Thr Asp Ser Ile His Leu Thr Gly Thr Glu Ile Pro Asp Val Ile Lys
                485                 490                 495

Asp Ile Val Asp Pro Lys Lys Leu Gly Tyr Trp Ala His Glu Ser Thr
            500                 505                 510

Phe Lys Arg Ala Lys Tyr Leu Arg Gln Lys Thr Tyr Ile Gln Asp Ile
        515                 520                 525

Tyr Met Lys Glu Val Asp Gly Lys Leu Val Glu Gly Ser Pro Asp Asp
    530                 535                 540

Tyr Thr Asp Ile Lys Phe Ser Val Lys Cys Ala Gly Met Thr Asp Lys
545                 550                 555                 560

Ile Lys Lys Glu Val Thr Phe Glu Asn Phe Lys Val Gly Phe Ser Arg
                565                 570                 575

Lys Met Lys Pro Lys Pro Val Gln Val Pro Gly Gly Val Val Leu Val
            580                 585                 590

Asp Asp Thr Phe Thr Ile Lys
        595

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Leu Asn Asp Ile Phe Glu Ala Gln Lys Ile Glu Trp His Glu
1               5                   10                  15

<210> SEQ ID NO 11
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ser His His His His His His Ser Met Ser Gly Leu Asn Asp Ile
1               5                   10                  15

Phe Glu Ala Gln Lys Ile Glu Trp His Glu Gly Ala Pro Gly Ala Arg
            20                  25                  30

Gly Ser Lys His Met Pro Arg Lys Met Tyr Ser Cys Ala Phe Glu Thr
        35                  40                  45

Thr Thr Lys Val Glu Asp Cys Arg Val Trp Ala Tyr Gly Tyr Met Asn
    50                  55                  60

Ile Glu Asp His Ser Glu Tyr Lys Ile Gly Asn Ser Leu Asp Glu Phe
65                  70                  75                  80
```

```
Met Ala Trp Val Leu Lys Val Gln Ala Asp Leu Tyr Phe His Asn Leu
                85                  90                  95

Lys Phe Ala Gly Ala Phe Ile Ile Asn Trp Leu Glu Arg Asn Gly Phe
            100                 105                 110

Lys Trp Ser Ala Asp Gly Leu Pro Asn Thr Tyr Asn Thr Ile Ile Ser
        115                 120                 125

Arg Met Gly Gln Trp Tyr Met Ile Asp Ile Cys Leu Gly Tyr Lys Gly
    130                 135                 140

Lys Arg Lys Ile His Thr Val Ile Tyr Asp Ser Leu Lys Lys Leu Pro
145                 150                 155                 160

Phe Pro Val Lys Lys Ile Ala Lys Asp Phe Lys Leu Thr Val Leu Lys
                165                 170                 175

Gly Asp Ile Asp Tyr His Lys Glu Arg Pro Val Gly Tyr Lys Ile Thr
            180                 185                 190

Pro Glu Glu Tyr Ala Tyr Ile Lys Asn Asp Ile Gln Ile Ile Ala Glu
        195                 200                 205

Ala Leu Leu Ile Gln Phe Lys Gln Gly Leu Asp Arg Met Thr Ala Gly
    210                 215                 220

Ser Asp Ser Leu Lys Gly Phe Asp Ile Ile Thr Thr Lys Lys Phe
225                 230                 235                 240

Lys Lys Val Phe Pro Thr Leu Ser Leu Gly Leu Asp Lys Glu Val Arg
                245                 250                 255

Tyr Ala Tyr Arg Gly Gly Phe Thr Trp Leu Asn Asp Arg Phe Lys Glu
            260                 265                 270

Lys Glu Ile Gly Glu Gly Met Val Phe Asp Val Asn Ser Leu Tyr Pro
        275                 280                 285

Ala Gln Met Tyr Ser Arg Leu Leu Pro Tyr Gly Glu Pro Ile Val Phe
    290                 295                 300

Glu Gly Lys Tyr Val Trp Asp Glu Asp Tyr Pro Leu His Ile Gln His
305                 310                 315                 320

Ile Arg Cys Glu Phe Glu Leu Lys Glu Gly Tyr Ile Pro Thr Ile Gln
                325                 330                 335

Ile Lys Arg Ser Arg Phe Tyr Lys Gly Asn Glu Tyr Leu Lys Ser Ser
            340                 345                 350

Gly Gly Glu Ile Ala Asp Leu Trp Leu Ser Asn Val Asp Leu Glu Leu
        355                 360                 365

Met Lys Glu His Tyr Asp Leu Tyr Asn Val Glu Tyr Ile Ser Gly Leu
    370                 375                 380

Lys Phe Lys Ala Thr Thr Gly Leu Phe Lys Asp Phe Ile Asp Lys Trp
385                 390                 395                 400

Thr Tyr Ile Lys Thr Thr Ser Glu Gly Ala Ile Lys Gln Leu Ala Lys
                405                 410                 415

Leu Met Leu Asn Ser Leu Tyr Gly Lys Phe Ala Ser Asn Pro Asp Val
            420                 425                 430

Thr Gly Lys Val Pro Tyr Leu Lys Glu Asn Gly Ala Leu Gly Phe Arg
        435                 440                 445

Leu Gly Glu Glu Glu Thr Lys Asp Pro Val Tyr Thr Pro Met Gly Val
    450                 455                 460

Phe Ile Thr Ala Trp Ala Arg Tyr Thr Thr Ile Thr Ala Ala Gln Ala
465                 470                 475                 480

Cys Tyr Asp Arg Ile Ile Tyr Cys Asp Thr Asp Ser Ile His Leu Thr
                485                 490                 495
```

-continued

```
Gly Thr Glu Ile Pro Asp Val Ile Lys Asp Ile Val Asp Pro Lys Lys
            500                 505                 510

Leu Gly Tyr Trp Ala His Glu Ser Thr Phe Lys Arg Ala Lys Tyr Leu
        515                 520                 525

Arg Gln Lys Thr Tyr Ile Gln Asp Ile Tyr Met Lys Glu Val Asp Gly
    530                 535                 540

Lys Leu Val Glu Gly Ser Pro Asp Asp Tyr Thr Asp Ile Lys Phe Ser
545                 550                 555                 560

Val Lys Cys Ala Gly Met Thr Asp Lys Ile Lys Lys Glu Val Thr Phe
                565                 570                 575

Glu Asn Phe Lys Val Gly Phe Ser Arg Lys Met Lys Pro Lys Pro Val
            580                 585                 590

Gln Val Pro Gly Gly Val Val Leu Val Asp Asp Thr Phe Thr Ile Lys
        595                 600                 605

<210> SEQ ID NO 12
<211> LENGTH: 593
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met His His His His His Leu Leu Gly Ala Ala Ala Lys Gly Ala
1               5                   10                  15

Ala Ala Lys Gly Ser Ala Ala Arg Lys Met Tyr Ser Cys Asp Phe Glu
            20                  25                  30

Thr Thr Thr Lys Val Glu Asp Cys Arg Val Trp Ala Tyr Gly Tyr Met
        35                  40                  45

Asn Ile Glu Asp His Ser Glu Tyr Lys Ile Gly Asn Ser Leu Asp Glu
    50                  55                  60

Phe Met Ala Trp Val Leu Lys Val Gln Ala Asp Leu Tyr Phe His Asn
65                  70                  75                  80

Leu Lys Phe Asp Gly Ala Phe Ile Ile Asn Trp Leu Glu Arg Asn Gly
                85                  90                  95

Phe Lys Trp Ser Ala Asp Gly Leu Pro Asn Thr Tyr Asn Thr Ile Ile
            100                 105                 110

Ser Arg Met Gly Gln Trp Tyr Met Ile Asp Ile Cys Leu Gly Tyr Lys
        115                 120                 125

Gly Lys Arg Lys Ile His Thr Val Ile Tyr Asp Ser Leu Lys Lys Leu
    130                 135                 140

Pro Phe Pro Val Lys Lys Ile Ala Lys Asp Phe Lys Leu Thr Val Leu
145                 150                 155                 160

Lys Gly Asp Ile Asp Tyr His Lys Glu Arg Pro Val Gly Tyr Lys Ile
                165                 170                 175

Thr Pro Glu Glu Tyr Ala Tyr Ile Lys Asn Ala Ile Gln Ile Ile Ala
            180                 185                 190

Glu Ala Leu Leu Ile Gln Phe Lys Gln Gly Leu Asp Arg Met Thr Ala
        195                 200                 205

Gly Ser Asp Ser Leu Lys Gly Phe Lys Asp Ile Ile Thr Thr Lys Lys
    210                 215                 220

Phe Lys Lys Val Phe Pro Thr Leu Ser Leu Gly Leu Asp Lys Glu Val
225                 230                 235                 240

Arg Tyr Ala Tyr Arg Gly Gly Phe Thr Trp Leu Asn Asp Arg Phe Lys
                245                 250                 255
```

Glu Lys Glu Ile Gly Glu Gly Met Val Phe Asp Val Asn Ser Leu Tyr
                260                 265                 270

Pro Ala Gln Met Tyr Ser Arg Leu Pro Tyr Gly Glu Pro Ile Val
            275                 280                 285

Phe Glu Gly Lys Tyr Val Trp Asp Glu Asp Tyr Pro Leu His Ile Gln
290                 295                 300

His Ile Arg Cys Glu Phe Glu Leu Lys Glu Gly Tyr Ile Pro Thr Ile
305                 310                 315                 320

Gln Ile Lys Arg Ser Arg Phe Tyr Lys Gly Asn Glu Tyr Leu Lys Ser
                325                 330                 335

Ser Gly Gly Glu Ile Ala Asp Leu Trp Leu Ser Asn Val Asp Leu Glu
            340                 345                 350

Leu Met Lys Glu His Tyr Asp Leu Tyr Asn Val Glu Tyr Ile Ser Gly
        355                 360                 365

Leu Lys Phe Lys Ala Thr Thr Gly Leu Phe Lys Asp Phe Ile Asp Lys
    370                 375                 380

Trp Thr Tyr Ile Lys Thr Thr Ser Glu Gly Ala Ile Lys Gln Leu Ala
385                 390                 395                 400

Lys Leu Met Leu Asn Ser Leu Tyr Gly Lys Phe Ala Ser Asn Pro Asp
                405                 410                 415

Val Thr Gly Lys Val Pro Tyr Leu Lys Glu Asn Gly Ala Leu Gly Phe
            420                 425                 430

Arg Leu Gly Glu Glu Glu Thr Lys Asp Pro Val Tyr Thr Pro Met Gly
        435                 440                 445

Val Phe Ile Thr Ala Trp Ala Arg Tyr Thr Thr Ile Thr Ala Ala Gln
    450                 455                 460

Ala Cys Tyr Asp Arg Ile Ile Tyr Cys Asp Thr Asp Ser Ile His Leu
465                 470                 475                 480

Thr Gly Thr Glu Ile Pro Asp Val Ile Lys Asp Ile Val Asp Pro Lys
                485                 490                 495

Lys Leu Gly Tyr Trp Ala His Glu Ser Thr Phe Lys Arg Ala Lys Tyr
            500                 505                 510

Leu Arg Gln Lys Thr Tyr Ile Gln Asp Ile Tyr Met Lys Glu Val Asp
        515                 520                 525

Gly Lys Leu Val Glu Gly Ser Pro Asp Asp Tyr Thr Asp Ile Lys Phe
    530                 535                 540

Ser Val Lys Cys Ala Gly Met Thr Asp Lys Ile Lys Lys Glu Val Thr
545                 550                 555                 560

Phe Glu Asn Phe Lys Val Gly Phe Ser Arg Lys Met Lys Pro Lys Pro
                565                 570                 575

Val Gln Val Pro Gly Gly Val Val Leu Val Asp Asp Thr Phe Thr Ile
            580                 585                 590

Lys

<210> SEQ ID NO 13
<211> LENGTH: 596
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met His His His His His Leu Leu Gly Gly Gly Gly Ser Gly Gly
1               5                   10                  15

```
Gly Gly Ser Ala Ala Ala Gly Ser Ala Ala Arg Lys Met Tyr Ser Cys
            20                  25                  30

Asp Phe Glu Thr Thr Thr Lys Val Glu Asp Cys Arg Val Trp Ala Tyr
            35                  40                  45

Gly Tyr Met Asn Ile Glu Asp His Ser Glu Tyr Lys Ile Gly Asn Ser
 50                  55                  60

Leu Asp Glu Phe Met Ala Trp Val Leu Lys Val Gln Ala Asp Leu Tyr
 65                  70                  75                  80

Phe His Asn Leu Lys Phe Asp Gly Ala Phe Ile Ile Asn Trp Leu Glu
                85                  90                  95

Arg Asn Gly Phe Lys Trp Ser Ala Asp Gly Leu Pro Asn Thr Tyr Asn
            100                 105                 110

Thr Ile Ile Ser Arg Met Gly Gln Trp Tyr Met Ile Asp Ile Cys Leu
            115                 120                 125

Gly Tyr Lys Gly Lys Arg Lys Ile His Thr Val Ile Tyr Asp Ser Leu
130                 135                 140

Lys Lys Leu Pro Phe Pro Val Lys Lys Ile Ala Lys Asp Phe Lys Leu
145                 150                 155                 160

Thr Val Leu Lys Gly Asp Ile Asp Tyr His Lys Glu Arg Pro Val Gly
            165                 170                 175

Tyr Lys Ile Thr Pro Glu Glu Tyr Ala Tyr Ile Lys Asn Ala Ile Gln
            180                 185                 190

Ile Ile Ala Glu Ala Leu Leu Ile Gln Phe Lys Gln Gly Leu Asp Arg
            195                 200                 205

Met Thr Ala Gly Ser Asp Ser Leu Lys Gly Phe Lys Asp Ile Ile Thr
            210                 215                 220

Thr Lys Lys Phe Lys Lys Val Phe Pro Thr Leu Ser Leu Gly Leu Asp
225                 230                 235                 240

Lys Glu Val Arg Tyr Ala Tyr Arg Gly Gly Phe Thr Trp Leu Asn Asp
            245                 250                 255

Arg Phe Lys Glu Lys Glu Ile Gly Glu Gly Met Val Phe Asp Val Asn
            260                 265                 270

Ser Leu Tyr Pro Ala Gln Met Tyr Ser Arg Leu Leu Pro Tyr Gly Glu
            275                 280                 285

Pro Ile Val Phe Glu Gly Lys Tyr Val Trp Asp Glu Asp Tyr Pro Leu
            290                 295                 300

His Ile Gln His Ile Arg Cys Glu Phe Glu Leu Lys Glu Gly Tyr Ile
305                 310                 315                 320

Pro Thr Ile Gln Ile Lys Arg Ser Arg Phe Tyr Lys Gly Asn Glu Tyr
            325                 330                 335

Leu Lys Ser Ser Gly Gly Glu Ile Ala Asp Leu Trp Leu Ser Asn Val
            340                 345                 350

Asp Leu Glu Leu Met Lys Glu His Tyr Asp Leu Tyr Asn Val Glu Tyr
            355                 360                 365

Ile Ser Gly Leu Lys Phe Lys Ala Thr Thr Gly Leu Phe Lys Asp Phe
            370                 375                 380

Ile Asp Lys Trp Thr Tyr Ile Lys Thr Thr Ser Glu Gly Ala Ile Lys
385                 390                 395                 400

Gln Leu Ala Lys Leu Met Leu Asn Ser Leu Tyr Gly Lys Phe Ala Ser
            405                 410                 415

Asn Pro Asp Val Thr Gly Lys Val Pro Tyr Leu Lys Glu Asn Gly Ala
            420                 425                 430
```

```
Leu Gly Phe Arg Leu Gly Glu Glu Thr Lys Asp Pro Val Tyr Thr
            435                 440                 445

Pro Met Gly Val Phe Ile Thr Ala Trp Ala Arg Tyr Thr Thr Ile Thr
450                 455                 460

Ala Ala Gln Ala Cys Tyr Asp Arg Ile Ile Tyr Cys Asp Thr Asp Ser
465                 470                 475                 480

Ile His Leu Thr Gly Thr Glu Ile Pro Asp Val Ile Lys Asp Ile Val
                485                 490                 495

Asp Pro Lys Lys Leu Gly Tyr Trp Ala His Glu Ser Thr Phe Lys Arg
            500                 505                 510

Ala Lys Tyr Leu Arg Gln Lys Thr Tyr Ile Gln Asp Ile Tyr Met Lys
            515                 520                 525

Glu Val Asp Gly Lys Leu Val Glu Gly Ser Pro Asp Asp Tyr Thr Asp
530                 535                 540

Ile Lys Phe Ser Val Lys Cys Ala Gly Met Thr Asp Lys Ile Lys Lys
545                 550                 555                 560

Glu Val Thr Phe Glu Asn Phe Lys Val Gly Phe Ser Arg Lys Met Lys
                565                 570                 575

Pro Lys Pro Val Gln Val Pro Gly Gly Val Val Leu Val Asp Asp Thr
            580                 585                 590

Phe Thr Ile Lys
        595

<210> SEQ ID NO 14
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Asn His Leu Val His His His His His Ile Glu Gly Arg His
1               5                   10                  15

Met Glu Leu Gly Thr Leu Glu Gly Ser Met Lys His Met Pro Arg Lys
            20                  25                  30

Met Tyr Ser Cys Ala Phe Glu Thr Thr Thr Lys Val Glu Asp Cys Arg
        35                  40                  45

Val Trp Ala Tyr Gly Tyr Met Asn Ile Glu Asp His Ser Glu Tyr Lys
    50                  55                  60

Ile Gly Asn Ser Leu Asp Glu Phe Met Ala Trp Val Leu Lys Val Gln
65                  70                  75                  80

Ala Asp Leu Tyr Phe His Asn Leu Lys Phe Ala Gly Ala Phe Ile Ile
                85                  90                  95

Asn Trp Leu Glu Arg Asn Gly Phe Lys Trp Ser Ala Asp Gly Leu Pro
            100                 105                 110

Asn Thr Tyr Asn Thr Ile Ile Ser Arg Met Gly Gln Trp Tyr Met Ile
        115                 120                 125

Asp Ile Cys Leu Gly Tyr Lys Gly Lys Arg Lys Ile His Thr Val Ile
    130                 135                 140

Tyr Asp Ser Leu Lys Lys Leu Pro Phe Pro Val Lys Lys Ile Ala Lys
145                 150                 155                 160

Asp Phe Lys Leu Thr Val Leu Lys Gly Asp Ile Asp Tyr His Lys Glu
                165                 170                 175

Arg Pro Val Gly Tyr Lys Ile Thr Pro Glu Glu Tyr Ala Tyr Ile Lys
            180                 185                 190
```

```
Asn Asp Ile Gln Ile Ile Ala Glu Ala Leu Leu Ile Gln Phe Lys Gln
            195                 200                 205

Gly Leu Asp Arg Met Thr Ala Gly Ser Asp Ser Leu Lys Gly Phe Lys
        210                 215                 220

Asp Ile Ile Thr Thr Lys Lys Phe Lys Val Phe Pro Thr Leu Ser
225                 230                 235                 240

Leu Gly Leu Asp Lys Glu Val Arg Tyr Ala Tyr Arg Gly Gly Phe Thr
                245                 250                 255

Trp Leu Asn Asp Arg Phe Lys Glu Lys Glu Ile Gly Glu Gly Met Val
                260                 265                 270

Phe Asp Val Asn Ser Leu Tyr Pro Ala Gln Met Tyr Ser Arg Leu Leu
            275                 280                 285

Pro Tyr Gly Glu Pro Ile Val Phe Glu Gly Lys Tyr Val Trp Asp Glu
        290                 295                 300

Asp Tyr Pro Leu His Ile Gln His Ile Arg Cys Glu Phe Glu Leu Lys
305                 310                 315                 320

Glu Gly Tyr Ile Pro Thr Ile Gln Ile Lys Arg Ser Arg Phe Tyr Lys
                325                 330                 335

Gly Asn Glu Tyr Leu Lys Ser Ser Gly Gly Glu Ile Ala Asp Leu Trp
            340                 345                 350

Leu Ser Asn Val Asp Leu Glu Leu Met Lys Glu His Tyr Asp Leu Tyr
        355                 360                 365

Asn Val Glu Tyr Ile Ser Gly Leu Lys Phe Lys Ala Thr Thr Gly Leu
370                 375                 380

Phe Lys Asp Phe Ile Asp Lys Trp Thr Tyr Ile Lys Thr Thr Ser Glu
385                 390                 395                 400

Gly Ala Ile Lys Gln Leu Ala Lys Leu Met Leu Asn Ser Leu Tyr Gly
                405                 410                 415

Lys Phe Ala Ser Asn Pro Asp Val Thr Gly Lys Val Pro Tyr Leu Lys
            420                 425                 430

Glu Asn Gly Ala Leu Gly Phe Arg Leu Gly Glu Glu Thr Lys Asp
        435                 440                 445

Pro Val Tyr Thr Pro Met Gly Val Phe Ile Thr Ala Trp Ala Arg Tyr
450                 455                 460

Thr Thr Ile Thr Ala Ala Gln Ala Cys Tyr Asp Arg Ile Ile Tyr Cys
465                 470                 475                 480

Asp Thr Asp Ser Ile His Leu Thr Gly Thr Glu Ile Pro Asp Val Ile
                485                 490                 495

Lys Asp Ile Val Asp Pro Lys Lys Leu Gly Tyr Trp Ala His Glu Ser
            500                 505                 510

Thr Phe Lys Arg Ala Lys Tyr Leu Arg Gln Lys Thr Tyr Ile Gln Asp
        515                 520                 525

Ile Tyr Met Lys Glu Val Asp Gly Lys Leu Val Glu Gly Ser Pro Asp
530                 535                 540

Asp Tyr Thr Asp Ile Lys Phe Ser Val Lys Cys Ala Gly Met Thr Asp
545                 550                 555                 560

Lys Ile Lys Lys Glu Val Thr Phe Glu Asn Phe Lys Val Gly Phe Ser
                565                 570                 575

Arg Lys Met Lys Pro Lys Pro Val Gln Val Pro Gly Gly Val Val Leu
            580                 585                 590

Val Asp Asp Thr Phe Thr Ile Lys
        595                 600
```

-continued

```
<210> SEQ ID NO 15
<211> LENGTH: 586
<212> TYPE: PRT
<213> ORGANISM: Unknown
<220> FEATURE:
<223> OTHER INFORMATION: Description of Unknown: Cyanophage S-CBP1
      polypeptide

<400> SEQUENCE: 15
```

Met Thr Leu Ile Phe Asp Ile Glu Thr Asp Gly Leu Tyr Asn Asp Ala
1               5                   10                  15

Ser Cys Ile His Cys Ile Gly Ile His Asp Leu Asn Ala Gly Glu Thr
            20                  25                  30

Tyr Val Phe Asn Asp Val Gly Thr Gln Gln Pro Ile Thr Lys Gly Ile
        35                  40                  45

Gln Leu Leu Glu Asp Ala Asp Leu Ile Val Gly His Asn Ile Ile Gly
    50                  55                  60

Tyr Asp Ile Pro Val Ile Ser Lys Leu Phe Pro Trp Phe Ser Arg Thr
65                  70                  75                  80

Asn Gly Val Leu Asp Thr Leu Val Leu Ser Arg Leu Tyr His Thr Asp
                85                  90                  95

Leu Leu Asp Ile Asp Gln Lys Arg Lys Trp Lys His Met Pro Leu Gln
            100                 105                 110

Leu Tyr Gly Arg His Ser Leu Glu Ala Tyr Gly Tyr Arg Leu Gly Glu
        115                 120                 125

Tyr Lys Gly Ser Phe Gly Lys Thr Ala Asp Trp Lys Glu Trp Ser Gln
    130                 135                 140

Asp Met Glu Asp Tyr Met Ile Gln Asp Val Asn Val Thr Arg Lys Leu
145                 150                 155                 160

Trp Lys His Phe Pro Gln Ile Pro Glu Trp Val Gln Leu Glu His Arg
                165                 170                 175

Val Ala Gln Ile Leu Thr Glu Gln Glu Ile Tyr Gly Trp Tyr Phe Asp
            180                 185                 190

Glu Asn Ala Ala Arg Glu Leu Ala Gln Thr Leu Tyr Thr Glu Leu Asp
        195                 200                 205

Asp Leu Lys Gly Val Leu Arg Lys Arg Tyr Pro Tyr Val Ala Gly Arg
    210                 215                 220

Glu Phe Thr Pro Lys Arg Val Asn Arg Ser Leu Gly Tyr Val Glu Gly
225                 230                 235                 240

Ala Thr Cys Thr Lys Leu Val Glu Phe Ser Pro Thr Ser Arg Asp His
                245                 250                 255

Ile Ala Trp Val Met Lys Asn Leu His Gly Trp Lys Pro Asp Lys Lys
            260                 265                 270

Thr Lys Ala Gly Lys Thr Ala Ile Asp Glu Ile Val Leu Lys Glu Ile
        275                 280                 285

Gly Thr Glu Glu Ala Leu Gln Phe Phe Arg Cys Leu Glu Ile Thr Lys
    290                 295                 300

Gln Leu Gly Met Leu Ser Glu Gly Lys Asn Ala Trp Leu Lys Leu Ser
305                 310                 315                 320

Arg Lys Asp Arg Val His His Cys Ser Val Ala Thr Val Thr His
                325                 330                 335

Arg Cys Ala His Arg Asn Pro Asn Leu Ala Gln Val Pro Ser Asp Leu
            340                 345                 350

Asn Phe Arg Arg Leu Phe Cys Ala Ser Pro Gly His Ile Met Val Gly
        355                 360                 365

-continued

Ala Asp Leu Ser Gly Ile Glu Leu Arg Met Leu Ala His Tyr Leu Ala
    370                 375                 380

Arg Tyr Asp Asp Gly Arg Tyr Gly Asp Ile Leu Leu His Gly Asp Ile
385                 390                 395                 400

His Gln Glu Asn Ala Asp Lys Ile Gly Ile Ser Arg Arg Leu Val Lys
            405                 410                 415

Thr Val Thr Tyr Ala Phe Leu Tyr Gly Ala Gly Asp Gln Lys Ile Gly
        420                 425                 430

Leu Ser Tyr Asp Gln Gly Leu Ser Pro Asp Lys Ala Lys Gln Lys Gly
    435                 440                 445

Lys Glu Ile Arg Gln Ala Tyr Met Asp Ala Ile Pro Gly Leu Glu Lys
450                 455                 460

Leu Val Glu Ala Thr Lys Lys Ala Ala Asp Arg Gly Phe Ile Arg Ser
465                 470                 475                 480

Ile Asp Gly Arg His Ile Asn Val Asp Ser Ser His Lys Ala Leu Asn
            485                 490                 495

Met Leu Leu Gln Ser Ser Ala Gly Cys Ile Ala Lys Arg Trp Met Val
        500                 505                 510

Ile Ala Asn Asp Asn Phe Pro Thr Ile Asp Asn Glu Tyr Leu Ala His
    515                 520                 525

Thr His Gln Leu Ala Phe Ile His Asp Glu Leu Gln Phe Glu Cys Leu
530                 535                 540

Pro Leu Tyr Ala Glu Asp Leu Lys Thr His Leu Glu Leu Cys Ala Glu
545                 550                 555                 560

Leu Ala Gly Glu Tyr Tyr Asn Leu Arg Ile Pro Ile Ala Ala Glu Gly
            565                 570                 575

Lys Ile Gly Ser Thr Trp Ala Asp Val His
        580                 585

<210> SEQ ID NO 16
<211> LENGTH: 588
<212> TYPE: PRT
<213> ORGANISM: Unknown
<220> FEATURE:
<223> OTHER INFORMATION: Description of Unknown: Cyanophage S-CBP2
    polypeptide

<400> SEQUENCE: 16

Met Lys Leu Val Phe Asp Ile Glu Thr Asp Gly Phe Leu Arg Lys Leu
1               5                   10                  15

Thr Thr Val His Cys Val Val Ala Lys Asp Ile Glu Thr Gly Glu Val
            20                  25                  30

Phe Lys Phe Asp Asp Ser Gly Arg His Gln Ser Val Ser Ser Gly Leu
        35                  40                  45

Thr Leu Leu Met Glu Ala Glu Leu Trp Gly His Asn Ile Ile Gly
    50                  55                  60

Phe Asp Val Pro Ala Ile Gln Glu Ile Tyr Pro Phe Phe Gln Pro Trp
65                  70                  75                  80

Glu Ser Thr Tyr Tyr Asp Thr Leu Ile Leu Ser Arg Leu Phe Phe Thr
            85                  90                  95

Asp Met Leu Asp Arg Asp Leu Arg Ser Lys Pro Ala Asn Met Pro Gly
        100                 105                 110

Asn Leu Tyr Gly Arg His Ser Leu Glu Ala Trp Gly Tyr Arg Leu Gly
    115                 120                 125

Val Leu Lys Ser Glu Tyr Gly Lys Gln Leu His Gly Asp Trp Ala Thr

```
            130                 135                 140
Tyr Thr Pro Glu Met Leu Glu Tyr Cys Glu Gln Asp Val Glu Ala Asn
145                 150                 155                 160

Leu Pro Ile Val Lys Leu Phe Gln Pro Lys Leu Glu Gln Tyr Ala Asp
                165                 170                 175

Ala Ile Lys Thr Glu His Asp Cys Ala Leu Val Met Thr Arg Gln Glu
            180                 185                 190

Gln Ala Gly Phe Pro Phe Asp Ile Asp Lys Ala Arg Ala Leu Glu Ser
                195                 200                 205

Lys Leu Arg Ser Glu Leu Glu Thr Leu Ser Asp Glu Met Arg Ala Thr
210                 215                 220

Phe Thr Phe Val Ala Gly Lys Glu Phe Thr Pro Ala Arg Asn Asn Ala
225                 230                 235                 240

Thr Arg Gly Tyr Ile Thr Gly Cys Pro Phe Thr Lys Leu Thr Glu Phe
                245                 250                 255

Ser Pro Thr Ser Arg Asp His Ile Ala Trp Ala Phe Gln Gln His Arg
                260                 265                 270

Gly Trp Glu Pro Ile Glu Met Thr Asp Thr Gly Lys Pro Lys Ile Asp
                275                 280                 285

Glu Glu Val Leu Asn Ala Ile Gly Thr Glu Glu Ala Lys Lys Phe Gly
                290                 295                 300

Arg Ile Leu Glu Leu Gln Lys His Val Gly Met Leu Ser Glu Gly Lys
305                 310                 315                 320

Asn Ser Trp Leu Gln Met Val Glu Lys Asp Gly Arg Ile His Ser
                325                 330                 335

Cys Val Leu Asn Thr Ala Thr Gly Arg Asn Ala His Met Arg Pro Asn
                340                 345                 350

Leu Ala Gln Val Pro Ser Gly His Glu Phe Arg Glu Leu Phe Thr Pro
                355                 360                 365

Gly Glu Gly Tyr Val Gln Val Gly Ala Asp Ala Ser Gly Leu Glu Leu
                370                 375                 380

Arg Cys Leu Ala His Tyr Leu Ala Arg Phe Asp Gly Gly Lys Phe Gly
385                 390                 395                 400

Lys Val Leu Leu Glu Gly Asp Ile His Thr Asp Leu Ala Asn Ile Tyr
                405                 410                 415

Gly Thr Asp Arg Lys Thr Gly Lys Thr Val Thr Tyr Cys Leu Ile Tyr
                420                 425                 430

Gly Gly Gly Asp Thr Lys Leu Gly Leu Ser Ala Gly Glu Pro Lys Lys
                435                 440                 445

Ser Ala Ala Ser Arg Gly Lys Lys Ile Arg Gln Ala Ile Met Lys Asp
450                 455                 460

Leu Asp Gly Phe Ala Gln Leu Ile Thr Ala Val Gln Glu Arg Ala Gln
465                 470                 475                 480

Ser Gly Val Ile Thr Gly Ile Asp Gly Arg Pro Ile Arg Met Arg Lys
                485                 490                 495

Ala His Ala Ala Leu Asn Tyr Leu Leu Gln Ser Cys Gly Ala Val Ile
                500                 505                 510

Cys Lys Lys Trp Val Val Arg Ser Asn Glu Leu Leu Thr Glu Ala Gly
                515                 520                 525

Ile Asp Tyr Thr Pro Leu Ala Phe Val His Asp Glu Gln Gln Leu Ala
                530                 535                 540

Val Arg Pro Asp Gln Val Glu Met Ala Ser Thr Leu Ile Ser Leu Ala
545                 550                 555                 560
```

Met Lys Asp Val Glu His Ala Ile Lys Phe Arg Val Pro Leu Asp Cys
            565                 570                 575

Asp Val Gln Ser Gly Ala Asn Trp Gly Asp Thr His
            580                 585

<210> SEQ ID NO 17
<211> LENGTH: 582
<212> TYPE: PRT
<213> ORGANISM: Unknown
<220> FEATURE:
<223> OTHER INFORMATION: Description of Unknown: Cyanophage S-CBP3
      polypeptide

<400> SEQUENCE: 17

Met Thr Leu Ile Phe Asp Ile Glu Thr Asp Gly Leu Tyr Asn Asp Val
1               5                   10                  15

Thr Cys Ile His Cys Ile Gly Ile His Asp Leu Asn Thr Lys Glu Thr
            20                  25                  30

Tyr Val Phe Asn Asp Val Gly Thr Gln Gln Pro Ile Thr Lys Gly Ile
        35                  40                  45

Gln Leu Leu Glu Asp Ala Asp Ile Ile Val Gly His Asn Ile Ile Gly
    50                  55                  60

Tyr Asp Leu Pro Val Ile Arg Lys Leu Tyr Pro Trp Phe Ser Asn Val
65                  70                  75                  80

Gly Arg Val Leu Asp Thr Leu Val Leu Ser Arg Leu Tyr His Ala Asp
                85                  90                  95

Leu Leu Lys Thr Asp Gln Lys Arg Asn Trp Lys His Met Pro Val Gln
            100                 105                 110

Leu Trp Gly Arg His Ser Leu Glu Ala Tyr Gly Tyr Arg Leu Gly Glu
        115                 120                 125

Tyr Lys Gly Cys Phe Gly Lys Thr Thr Asp Trp Lys Asp Trp Ser Gln
    130                 135                 140

Glu Met Glu Asp Tyr Met Val Gln Asp Val Asn Ile Thr Arg Lys Leu
145                 150                 155                 160

Trp Lys Asp Phe Pro Glu Ile Pro Glu Trp Val Gln Leu Glu His Arg
                165                 170                 175

Val Ala Gln Ile Leu Thr Glu Gln Glu Ile His Gly Trp Tyr Phe Asp
            180                 185                 190

Glu Pro Ala Ala Trp Glu Leu Glu Ser Thr Leu Arg Arg Glu Leu Glu
        195                 200                 205

Ser Leu Lys Ala Val Leu Arg Asn Arg His Pro Phe Ile Leu Gly Glu
    210                 215                 220

Glu Phe Thr Pro Lys Arg Pro Asn Ser Thr Gln Gly Tyr Phe Thr Gly
225                 230                 235                 240

Ala Thr Phe Thr Arg Leu Lys Glu Met Asn Pro Thr Ser Arg Asp His
                245                 250                 255

Ile Ala Tyr Ile Leu Gln Lys Phe Tyr Asp Trp Glu Pro Thr Glu Arg
            260                 265                 270

Thr Glu Lys Gly Lys Pro Val Val Asp Glu Ile Val Leu Lys Asp Ile
        275                 280                 285

Gly Ser Glu Ile Ala Leu Gln Phe Phe Arg Cys Leu Glu Leu Thr Lys
    290                 295                 300

Gln Ile Gly Met Leu Thr Glu Gly Val Asn Ala Trp Leu Lys Leu Val
305                 310                 315                 320

Arg Asn Asp Arg Ile His His His Cys Ser Val Ala Thr Asn Thr His

```
            325                 330                 335
Arg Cys Ala His Arg Lys Pro Asn Leu Ala Gln Val Pro Ala Glu Ala
            340                 345                 350

Glu Phe Arg Lys Leu Phe Arg Ala Thr Pro Gly Met Val Met Val Gly
            355                 360                 365

Ala Asp Leu Ala Gly Ile Glu Leu Arg Met Leu Ala His Tyr Leu Ala
            370                 375                 380

Gln Trp Asp Gly Gly Arg Tyr Gly Asp Val Leu Leu Asn Gly Asp Ile
385                 390                 395                 400

His Gln Glu Asn Ala Asp Lys Ile Gly Ile Ser Arg Arg Leu Val Lys
                405                 410                 415

Thr Val Thr Tyr Ala Phe Leu Tyr Gly Ala Gly Asn Gln Lys Ile Gly
            420                 425                 430

Leu Ser Tyr Asp Gln Ser Leu Ser Pro Asp Lys Ala Lys Lys Lys Gly
            435                 440                 445

Gln Glu Ile Arg Gln Ala Tyr Met Asp Ala Ile Pro Gly Leu Arg Lys
            450                 455                 460

Leu Val Glu Ala Thr Lys Lys Ala Ala Asn Arg Gly Tyr Ile Arg Ala
465                 470                 475                 480

Ile Asp Gly Arg His Ile Ser Val Asp Ser Pro His Lys Ser Leu Asn
                485                 490                 495

Tyr Leu Leu Gln Ser Ser Ala Gly Val Ile Ala Lys Arg Trp Leu Ala
            500                 505                 510

Leu Thr His Glu Ala Ile Ile Arg Ala Asp Ile Lys Ala His Gln Leu
            515                 520                 525

Ala Phe Ile His Asp Glu Leu Gln Phe Glu Thr Thr Pro Glu His Val
            530                 535                 540

Glu Asp Leu Lys Phe Ala Leu Leu Trp Gly Ala Ala Ser Ala Gly Glu
545                 550                 555                 560

Tyr Tyr Asn Leu Arg Ile Pro Ile Ala Ala Asp Ala Lys Ser Gly Asn
                565                 570                 575

Asp Trp Ser Glu Val His
            580

<210> SEQ ID NO 18
<211> LENGTH: 583
<212> TYPE: PRT
<213> ORGANISM: Unknown
<220> FEATURE:
<223> OTHER INFORMATION: Description of Unknown: Cyanophage Syn5
      polypeptide

<400> SEQUENCE: 18

Met Arg Leu Val Phe Asp Ile Glu Thr Asp Gly Leu Leu Arg Gly Leu
1               5                   10                  15

Ser Val Ile His Cys Ile Val Ala Arg Asp Leu Asp Thr Asn Glu Glu
                20                  25                  30

His Arg Phe Glu Pro His Gln Thr Lys Ala Gly Leu Gln Leu Leu Lys
            35                  40                  45

Glu Ala Asp Glu Leu Trp Gly His Asn Ile Val Gly Tyr Asp Ile Glu
            50                  55                  60

Ala Ile Lys Glu Leu Tyr Pro Lys Trp Thr Thr Lys Ala Lys Leu Tyr
65                  70                  75                  80

Asp Thr Leu Ile Leu Ser Arg Leu Phe Phe Thr Asp Leu Leu Asp Arg
                85                  90                  95
```

```
Asp Phe Arg Ser Lys Pro Ala Asn Met Pro Gly Asn Leu Tyr Gly Arg
            100                 105                 110

His Ser Leu Glu Ala Trp Gly His Arg Leu Gly Val His Lys Ser Glu
        115                 120                 125

Phe Gly Lys Gln Leu Asp Gly Asp Trp Ser Thr Tyr Ser Pro Glu Met
    130                 135                 140

Leu Glu Tyr Cys Ala Gln Asp Val Thr Val Ser Val Gln Val Ala Gln
145                 150                 155                 160

Met Phe Glu Pro Lys Leu Glu Gln Tyr Ala Asp Cys Ile Asp Thr Glu
                165                 170                 175

His Arg Leu Ala Thr Ile Met Ala Trp Gln Glu Arg Glu Gly Phe Pro
            180                 185                 190

Phe Asp Val Thr Ala Ala Gln Gln Leu Glu Ser Arg Leu Arg Thr Glu
        195                 200                 205

Leu Asp Ala Leu Ser Asp Gln Met Arg Ser Thr Phe Leu Phe Val Asp
    210                 215                 220

Gly Gly Thr Phe Thr Pro Arg Arg Asn Asn Lys Pro Gln Gly Tyr Ile
225                 230                 235                 240

Ala Asp Ala Pro Met Cys Lys Leu Lys Glu Phe Asn Pro Thr Ser Arg
                245                 250                 255

His His Ile Ala Trp Ala Phe Gln Gln Phe Arg Asn Trp Glu Pro Lys
            260                 265                 270

Glu Phe Thr Asp Ser Gly Lys Pro Lys Ile Asp Glu Pro Thr Leu Thr
        275                 280                 285

Ala Ile Gly Thr Asp Glu Ala Lys Ala Phe Ala Arg Ile Leu Glu Leu
    290                 295                 300

Gln Lys His Leu Gly Gln Leu Ala Glu Gly Lys Asn Ala Trp Leu Lys
305                 310                 315                 320

Leu Glu Ser Lys Gly Arg Val His Ser Cys Val Leu Asn Thr Asn
                325                 330                 335

Thr Gly Arg Gln Ala His Met Arg Pro Asn Leu Ala Gln Val Pro Ser
            340                 345                 350

Ala Ser Glu Tyr Arg Ala Leu Phe Gly Pro Gly Asp Ser Arg Val Gln
        355                 360                 365

Val Gly Ala Asp Ala Ser Gly Leu Glu Leu Arg Cys Leu Ala His Tyr
    370                 375                 380

Leu Ala Pro Phe Asp Asn Gly Ser Phe Ala Glu Thr Val Val Asn Gly
385                 390                 395                 400

Asp Ile His Thr Glu Leu Ala Ser Ile Tyr Gly Thr Asp Arg Lys Ser
                405                 410                 415

Gly Lys Gly Val Thr Tyr Cys Leu Ile Tyr Gly Gly Gly Asp His Lys
            420                 425                 430

Leu Gly Ser Thr Ala Gly Ala Ser Lys Ala Gln Ala Ser Lys Lys Gly
        435                 440                 445

Lys Glu Ile Arg Gly Arg Ile Met Arg Asp Leu Asp Gly Phe Ala Ala
    450                 455                 460

Leu Ser Asp Ala Val Ser Arg Ala Arg Thr Gly Val Leu Arg Gly
465                 470                 475                 480

Leu Asp Gly Arg Pro Ile Arg Leu Gln Gly Lys Ser His Ala Ala Leu
                485                 490                 495

Asn Tyr Leu Leu Gln Ser Ala Gly Ala Val Ile Cys Lys Gln Trp Leu
            500                 505                 510

Leu Arg Ser Tyr Glu Leu Leu Asp Glu Ala Asn Ile Asp Tyr Trp Pro
```

```
                515                 520                 525
Leu Ala Phe Val His Asp Glu Leu Gln Ile Ser Val Ala Pro Ser Gln
            530                 535                 540

Ala Glu Met Ala Thr Leu Leu Ile Thr Ala Met Lys Asp Val Gln
545                 550                 555                 560

His Asn Leu Lys Phe Arg Cys Glu Leu Asp Ser Glu Ala Gln Thr Gly
                565                 570                 575

Asn Ser Trp Ala Asp Cys His
                580

<210> SEQ ID NO 19
<211> LENGTH: 588
<212> TYPE: PRT
<213> ORGANISM: Unknown
<220> FEATURE:
<223> OTHER INFORMATION: Description of Unknown: Cyanophage S-CBP42
      polypeptide

<400> SEQUENCE: 19

Met Arg Leu Ala Phe Asp Ile Glu Thr Asp Gly Leu Leu Arg Asn Leu
1               5                   10                  15

Thr Lys Ile His Cys Ile Val Ala Gln Asp Leu Asp Thr Asn Glu Val
            20                  25                  30

Tyr Lys Phe Asp Gly Thr Gly Asp His Pro Ser Ile Arg Glu Gly Leu
        35                  40                  45

Ala Leu Leu Lys Asp Ala Asp Glu Leu Trp Gly His Asn Ile Ile Gly
    50                  55                  60

Tyr Asp Phe Glu Ala Ile Lys Glu Val Phe Pro Arg Trp Asn Tyr Ser
65                  70                  75                  80

Ser Thr Val Tyr Asp Thr Leu Ile Leu Ser Arg Leu Phe Phe Thr Asp
                85                  90                  95

Leu Leu Asp Arg Asp Phe Arg Ser Arg Pro Ala Asn Met Pro Ala Gln
            100                 105                 110

Leu Tyr Gly Arg His Ser Leu Glu Ala Trp Gly His Arg Leu Ser Val
        115                 120                 125

His Lys Ser Glu Phe Gly Lys Ser Leu Ser Gly Asp Trp Ser Thr Tyr
    130                 135                 140

Ser Pro Glu Met Leu Asp Tyr Cys Ala Arg Asp Val Val Ser Val
145                 150                 155                 160

Ser Leu Ala Arg Leu Phe Thr Ala Lys Val Ala Glu Tyr Arg Asp Cys
                165                 170                 175

Ile Ser Thr Glu His Arg Leu Ala Thr Ile Met Ala Trp Gln Glu Ser
            180                 185                 190

Glu Gly Phe Pro Phe Asp Val Ala Lys Ala Glu Arg Leu Glu Gly Gln
        195                 200                 205

Leu Arg Ser Glu Leu Leu Lys Leu Ser Glu Gln Met Arg Glu Thr Phe
    210                 215                 220

Pro Tyr Val Asp Gly Gly Ser Phe Thr Pro Arg Thr Asn Asn Gly Pro
225                 230                 235                 240

Arg Gly Tyr Val Lys Gly Ala Ala Met Cys Arg Leu Lys Glu Phe Asn
                245                 250                 255

Pro Thr Ser Arg Gln His Ile Ala Trp Ala Phe Ala Thr Phe Arg Asp
            260                 265                 270

Trp Glu Pro Lys Glu Leu Thr Asp Thr Gly Lys Pro Lys Ile Asp Glu
        275                 280                 285
```

```
Thr Thr Leu Leu Glu Tyr Gly Thr Asp Glu Ala Lys Thr Phe Ala Arg
    290                 295                 300

Ile Leu Glu Leu Gln Lys His Leu Gly Gln Leu Ser Glu Gly Ala Asn
305                 310                 315                 320

Ala Trp Leu Lys Lys Val Glu Ser Asp Gly Arg Ile His His Ser Cys
                325                 330                 335

Val Leu Asn Thr Asn Thr Gly Arg Gln Ala His Met Lys Pro Asn Leu
            340                 345                 350

Ala Gln Val Pro Ser Gly His Glu Tyr Arg Glu Leu Phe His Pro Gly
        355                 360                 365

Ala Asn Arg Ser Gln Val Gly Ala Asp Ala Ser Gly Leu Glu Leu Arg
370                 375                 380

Cys Leu Gly His Tyr Leu Ala Arg Phe Asp Gly Gly Lys Phe Ala Lys
385                 390                 395                 400

Glu Val Val Gln Gly Asp Ile His Thr Ala Leu Ala Glu Ile Tyr Gly
                405                 410                 415

Thr Asp Arg Lys Ser Gly Lys Gly Val Thr Tyr Cys Leu Ile Tyr Gly
            420                 425                 430

Gly Gly Asp Ser Lys Leu Gly Leu Thr Ala Gly Ala Ser Lys Ala Gln
        435                 440                 445

Ala Val Lys Lys Gly Lys Glu Ile Arg Ser Arg Ile Met Ala Asn Leu
450                 455                 460

Asp Gly Phe Ala Ala Leu Asn Ala Ala Val Gln Glu Arg Ala Lys Ser
465                 470                 475                 480

Gly Val Leu Lys Gly Leu Asp Gly Arg Pro Ile Arg Leu Gln Gly Lys
                485                 490                 495

Asn His Ala Ala Leu Asn Tyr Leu Leu Gln Ser Ala Gly Ala Val Ile
            500                 505                 510

Cys Lys Leu Trp Leu Leu Arg Ser Tyr Glu Leu Leu Asp Glu Ala Gly
        515                 520                 525

Ile Asp Tyr Phe Pro Met Ala Phe Val His Asp Glu Val His Ile Ser
530                 535                 540

Val Ala Pro Ser Gln Ala Glu Gln Ala Gly Gln Leu Ile Gln Ile Ala
545                 550                 555                 560

Met Lys Asp Val Glu His Gln Ile Lys Phe Arg Cys Ala Leu Asp Ser
                565                 570                 575

Glu Tyr Gln Ile Gly Asn Ser Trp Ala Asp Cys His
            580                 585

<210> SEQ ID NO 20
<211> LENGTH: 587
<212> TYPE: PRT
<213> ORGANISM: Synechococcus sp.
<220> FEATURE:
<223> OTHER INFORMATION: Phage P60

<400> SEQUENCE: 20

Met Lys Leu Ala Phe Asp Ile Glu Thr Asp Gly Leu Ile Pro Asp Leu
1               5                   10                  15

Thr Ile Ile His Cys Ile Val Ala Arg Asp Ile Asp Thr Asp Glu Glu
            20                  25                  30

Phe Arg Phe Asp Gly Thr Gly Asp Tyr Pro Ser Ile Lys Glu Gly Leu
        35                  40                  45

Glu Leu Leu Ser Lys Ala Asp Glu Leu Trp Gly His Asn Ile Val Asn
50                  55                  60
```

Tyr Asp Tyr Pro Ala Ile Gln Lys Leu His Pro Asp Trp Thr Pro Pro
 65                  70                  75                  80

Ser Cys Thr Arg Asp Thr Leu Ile Leu Ser Arg Leu Phe Phe Thr Asp
                 85                  90                  95

Leu Leu Asp Arg Asp Phe Arg Ser Arg Pro Ala Leu Met Pro Gly Asn
            100                 105                 110

Leu Tyr Gly Arg His Ser Leu Glu Ala Trp Gly His Arg Leu Gly His
        115                 120                 125

His Lys Ser Glu Phe Gly Lys Ser Leu Glu Gly Asp Trp Ser Thr Tyr
    130                 135                 140

Ser Pro Glu Met Leu Glu Tyr Cys Ala Arg Asp Val Glu Val Ser Val
145                 150                 155                 160

Ala Leu Ala Lys Thr Phe Val Pro Lys Ile Pro Glu Tyr Gln Trp Ser
                165                 170                 175

Val Asp Thr Glu His Glu Ile Ala Arg Ile Met Ser Trp Gln Glu Gln
            180                 185                 190

Met Gly Phe Pro Phe Asp Val Arg Ala Ala Gln Ala Leu Glu Gly Lys
        195                 200                 205

Leu Arg Leu Glu Leu Asp Thr Leu Ser Asp Asp Met Arg Glu Thr Phe
    210                 215                 220

His Phe Val Asp Gly Gly Val Met Thr Pro Lys Arg Ser Asn Lys Val
225                 230                 235                 240

Arg His Tyr Phe Glu Asn Ala Pro Phe Cys Lys Leu Arg Glu Phe Asn
                245                 250                 255

Pro Thr Ser Arg His His Ile Ala Trp Ala Phe Glu His His Arg Gly
            260                 265                 270

Trp Glu Pro Lys Glu Arg Thr Ala Gly Gly Gln Pro Lys Ile Asp Asp
        275                 280                 285

Glu Ile Leu Arg Glu Ile Asn Thr Lys Glu Ser Leu Ala Phe Ala Arg
    290                 295                 300

Ile Leu Glu Leu Gln Lys His Leu Gly Gln Leu Ser Glu Gly Lys Asn
305                 310                 315                 320

Ala Trp Leu Lys Leu Glu Arg Lys Gly Arg Leu His His Ser Cys Val
                325                 330                 335

Leu Asn Thr Asn Thr Gly Arg Gln Ala His Met Arg Pro Asn Leu Ala
            340                 345                 350

Gln Val Pro Ser Ala His Glu Tyr Arg Ser Leu Phe Lys Pro Ser Asp
        355                 360                 365

Asn His Leu Gln Val Gly Ser Asp Ala Ser Gly Leu Glu Leu Arg Cys
    370                 375                 380

Leu Gly His Tyr Leu Ser Arg Tyr Asp Gly Gly Lys Phe Ala Glu Glu
385                 390                 395                 400

Val Val Asn Gly Asp Ile His Thr Ala Leu Ala Glu Ile Tyr Gly Thr
                405                 410                 415

Asp Arg Lys Ser Gly Lys Gly Val Thr Tyr Cys Leu Ile Tyr Gly Gly
            420                 425                 430

Gly Asn His Lys Leu Gly Leu Thr Ala Gly Ala Ser Lys Ser Ser Ala
        435                 440                 445

Ser Arg Lys Gly Gln Glu Ile Arg Gly Lys Ile Met Gln Gly Leu Ser
    450                 455                 460

Gly Phe Ala Asp Leu Asn Ala Ala Ile Gln Glu Arg Ala Lys Ser Gly
465                 470                 475                 480

Val Leu Lys Gly Leu Asp Gly Arg Pro Ile Arg Leu Gln Gly Lys Asn

-continued

```
                485                 490                 495

His Ala Ala Leu Asn Tyr Leu Leu Gln Ser Ala Gly Ala Ile Ile Cys
                500                 505                 510

Lys Leu Trp Val Ile Arg Thr His Glu Leu Leu Gln Glu Ala Gly Ile
                515                 520                 525

Asp Tyr Tyr Pro Leu Ala Phe Val His Asp Glu Gln Gln Leu Ser Val
                530                 535                 540

Arg Ala Asp Gln Ala Glu Met Ala Ala Gln Leu Thr Thr Leu Ala Met
545                 550                 555                 560

Lys Asp Val Glu His Gln Val Lys Phe Arg Cys Ala Leu Asp Ser Glu
                565                 570                 575

Tyr Gln Ile Gly Asn Ser Trp Ala Asp Cys His
                580                 585

<210> SEQ ID NO 21
<211> LENGTH: 580
<212> TYPE: PRT
<213> ORGANISM: Roseobacter sp.
<220> FEATURE:
<223> OTHER INFORMATION: Phage SIO1

<400> SEQUENCE: 21

Met Glu Val Val Phe Asp Ile Glu Thr Asp Ala Leu Asp Ala Thr Val
1               5                   10                  15

Ile His Val Leu Val Ala Lys Arg Val Gly Gln Lys Gly Phe Tyr Val
                20                  25                  30

Val Arg Asp Ala Glu Thr Phe Lys Arg Leu Ala Lys Gln Val Thr Leu
            35                  40                  45

Trp Ile Gly His Asn Val Ile Gly Phe Asp Ile Pro Gln Ile Lys Lys
        50                  55                  60

Leu Trp Gly Tyr Gly Ile Pro Leu Lys Asp Val Ala Asp Thr Leu Val
65                  70                  75                  80

Met Ser Arg Leu Leu Asp Pro Thr Arg Lys Gly Gly His Ser Leu Asp
                85                  90                  95

Ala Leu Ser Gly Asn Glu Lys Ile Asp Phe His Asp Phe Ser Thr Tyr
                100                 105                 110

Thr Pro Glu Met Leu Ala Tyr Cys Lys Gln Asp Val Ala Ile Asn Glu
            115                 120                 125

Lys Val Tyr Leu Gln Leu Lys Glu Glu Leu Ser Asn Phe Gly Lys Ala
        130                 135                 140

Ser Ile Gln Leu Glu His Gln Met Gln Ala Ile Val Cys Glu Gln Glu
145                 150                 155                 160

Lys Asn Gly Phe Met Leu Asp Thr Asp Ile Ala Glu Glu Ile Tyr Thr
                165                 170                 175

Thr Cys Leu Arg Glu Thr Asn Arg Ile Glu Ala Glu Ile Lys Glu Phe
                180                 185                 190

Met Val Pro Ile Ala Val Pro Val Lys Glu Val Ile Ile Lys Arg Lys
            195                 200                 205

Lys Asp Gly Ser Ile Tyr Ser Asn Gln Leu Leu Glu Gly Cys Asn Val
        210                 215                 220

Gln Gly Asp Tyr Thr Lys Ile Ala Trp Glu Glu Phe Asn Leu Gly Ser
225                 230                 235                 240

Pro Ala Gln Val Asn Lys Arg Leu Asp Arg Leu Gly Trp Lys Pro Thr
                245                 250                 255

Val Lys Thr Lys Ser Gly Asn Ser Tyr Lys Ile Cys Pro Glu Asn Leu
```

-continued

```
                260                 265                 270
Ala Thr Ile Pro Asp Thr Ala Pro Glu Ala Val Lys Gly Leu Lys Ala
                275                 280                 285

Trp Lys Val Leu Glu Thr Arg Trp Lys Leu Ala Gln Glu Trp Leu Gln
        290                 295                 300

Lys Ser Gln Glu Thr Gly Arg Val His Gly Arg Val Ile Leu Thr Gly
305                 310                 315                 320

Ala Val Thr His Arg Ala Ala His Gln Gly Pro Asn Met Ala Asn Ile
                325                 330                 335

Pro Ser Val Pro His Gly Lys Asp Gly Ile Leu Trp Lys Met Glu Gly
            340                 345                 350

Met Tyr Gly Ala Glu Cys Arg Gln Ala Phe Lys Val Pro Glu Gly Lys
        355                 360                 365

Leu Leu Val Gly Thr Asp Ala Ala Gly Ile Gln Leu Arg Val Leu Ala
    370                 375                 380

His Tyr Met Asn Asp Pro Ile Tyr Thr Glu Gln Val Ile Asp Gly Asp
385                 390                 395                 400

Ile His Thr Phe Asn Lys Glu Ala Leu Gly Arg Tyr Cys Lys Asp Arg
                405                 410                 415

Pro Thr Ala Lys Thr Phe Ile Tyr Ala Phe Leu Leu Gly Ala Gly Thr
            420                 425                 430

Gly Met Ile Ala Ser Ile Leu Gly Cys Asn Asn Arg Gln Ala Asn Glu
        435                 440                 445

Ala Met Ala Asn Phe Tyr Glu Ala Ile Pro Ser Leu Lys Lys Leu Lys
    450                 455                 460

Ser Gln Ala Ser Gln Ala Ala Ser Met Gly Trp Met Lys Gly Leu Asp
465                 470                 475                 480

Gly Arg Val Leu Arg Ile Gly Ser Asp His Leu Ala Leu Ser Val Tyr
                485                 490                 495

Leu Gln Gly Gly Glu Thr Val Ile Met Arg Leu Ala Asn Val Phe Trp
            500                 505                 510

Gln Arg Gln Ala Lys Lys Glu Gly Ile Asn Phe Lys Gln Cys Ala Trp
        515                 520                 525

Val His Asp Glu Trp Gln Thr Glu Val Asp Glu Gln Ala Gln Arg
    530                 535                 540

Leu Gly Glu Ile Gln Val Gln Ala Ile Lys Asp Ala Gly Thr Phe Phe
545                 550                 555                 560

Lys Leu Asn Cys Pro Met Asp Gly Glu Ala Lys Ile Gly Lys Asn Trp
                565                 570                 575

Leu Glu Thr His
            580

<210> SEQ ID NO 22
<211> LENGTH: 538
<212> TYPE: PRT
<213> ORGANISM: Oedogonium cardiacum

<400> SEQUENCE: 22

Met Ile Glu Phe Tyr Ala Ser Phe Asp Lys Asp Lys Glu Ile Glu Ile
1               5                   10                  15

Asn Lys Glu Asp Ser Glu Met Asn Lys Glu Asp Ile Glu Met Asn Lys
            20                  25                  30

Glu Asp Ile Glu Ile Asp Leu Asp Glu Val Asn Glu Glu Glu Arg Phe
        35                  40                  45
```

```
Asp Val Asn Arg Glu Met Leu Gln Thr Asn Tyr Phe Val Lys Arg Phe
    50                  55                  60

Lys Asn Ile Leu Phe Pro Ile Ala Ala Ser Phe Tyr Thr Ser Glu Gly
 65                  70                  75                  80

Asn Lys Asn Val Ser Lys Thr Phe Ser Leu Thr Ser Asn Ile Phe Asp
                 85                  90                  95

Lys Lys Ile Pro Ser Thr Ile Asn Ile Leu Lys Glu Ser Gln Ile Met
                100                 105                 110

Met Gln Glu Phe Leu Ile Glu Leu Ile Ser Leu Ala Glu Asp Leu Leu
            115                 120                 125

Lys Lys Arg Asn Pro Thr Asn Ser Leu Phe Tyr Gly Asp Asp Lys Val
    130                 135                 140

Ile Ile Tyr Met His Asn Leu Ser Ser Phe Asp Gly Phe Phe Ile Leu
145                 150                 155                 160

Gln Thr Leu Leu Lys Ser Arg Ile Leu Asn Tyr Thr Phe Asn Leu Asn
                165                 170                 175

Lys Lys Leu Lys Val Thr Ser Tyr Glu Gly Leu Ile Tyr Arg Ile Lys
            180                 185                 190

Ile Gly Asn Leu Cys Phe Gln Asp Ser Tyr Arg Val Ile Pro Met Ser
        195                 200                 205

Leu Asn Lys Leu Ser Phe Leu Leu Asn Lys Gln Lys Lys Asp Phe
210                 215                 220

Asp Val Glu Asn Ile Asn Ser Gln Lys Leu Gln His Ile Phe Lys Asn
225                 230                 235                 240

Lys Glu Ile Leu Glu Lys Met Leu Glu Tyr Cys Leu Tyr Asp Ser Ile
                245                 250                 255

Leu Leu Tyr Glu Ser Met Ile Leu Ile Gln Lys Thr Phe Trp Asp Glu
            260                 265                 270

Leu Lys Phe Asp Ile Thr Ser Glu Ser Thr Ile Ser Asn Thr Ala Ile
        275                 280                 285

Asn Phe Phe Ser Lys Tyr Tyr Glu Phe Pro Thr Gln Tyr Tyr Trp
290                 295                 300

His Thr Thr Thr Lys Lys Asp Gly Leu Ser Ala Lys Leu Lys Tyr Asp
305                 310                 315                 320

Asn Lys Arg Val Thr Val Ser Thr His His Asn Ala Ile Phe Tyr Thr
                325                 330                 335

Lys Pro Phe Leu Asp Gln Gln Leu Arg Ser Ala Tyr Phe Gly Gly Arg
            340                 345                 350

Thr Glu Leu Tyr Lys Pro Gln Thr Ser Asn Gly Tyr Val Phe Asp Ile
        355                 360                 365

Asn Ser Leu Tyr Ala Phe Ala Leu Met Tyr Asp Met Pro Tyr Gly Ser
    370                 375                 380

Pro Ile Tyr Glu Asn Glu Tyr Lys Asn Trp Thr Thr Asn Glu Phe Glu
385                 390                 395                 400

Ser Phe Phe Gly Phe Leu Lys Ile Ile Phe Ile Thr Pro Pro Asn Tyr
                405                 410                 415

Asp Ile Leu Pro Val Leu Pro Arg Arg Tyr Pro Pro Ile Ser His
            420                 425                 430

Asn Val Tyr Cys Leu Gly Ile Gly Glu Gly Trp Tyr Phe Ser Glu Glu
        435                 440                 445

Ile Lys Leu Ala Arg Gln Lys Gly Tyr Lys Leu Lys Ile Leu Glu Ser
    450                 455                 460

Ile Lys Phe Thr Pro His Lys Gly Phe Glu Lys Phe Val Arg Asp Phe
```

```
465                 470                 475                 480
Phe Ser Ile Arg Gln Gln Tyr Pro Lys Gly His Pro Leu Asn Leu Leu
                    485                 490                 495

Ala Lys Leu Ile Leu Asn Ser Thr Tyr Gly Arg Phe Gly Ile Ala Leu
                500                 505                 510

Thr Thr His Lys Gln Met Lys Thr Phe Asn Gln Ile Lys Leu Lys Glu
                515                 520                 525

Lys Lys Asn Lys Lys Ile Asn Ile Asn Ile
                530                 535

<210> SEQ ID NO 23
<211> LENGTH: 717
<212> TYPE: PRT
<213> ORGANISM: Salterprovirus His1

<400> SEQUENCE: 23

Met Ala Lys Cys Asp Lys Ser Leu Glu Ala Ile Asp Leu Asp Arg Ala
1               5                   10                  15

Tyr Thr Ala Pro Arg Lys Ala Lys Trp Ala Glu Asn Lys Arg Ile Asn
            20                  25                  30

Gly Leu Asp Thr Glu Thr Ser Asp Gly Asp Ile Phe Cys Ile Ser Val
        35                  40                  45

Cys Trp Glu Gly Glu Lys Pro Met Val Gln His Asn Asp Arg Glu Lys
    50                  55                  60

Leu Thr Ser Lys Gln Val Trp Gln Val Leu Thr Asp His Lys Ala Arg
65                  70                  75                  80

Ser Ser Leu Asn Met Trp Tyr Asn Leu Asp Phe Asp Ala Asn Val Val
                85                  90                  95

Leu Asn His Val Cys Ser Glu Glu Gln Leu Ala Glu Leu Val Val Ser
            100                 105                 110

Gly Thr Thr Leu Ala Asn Ser Asp Arg Thr Tyr Arg Gln Tyr Met Asp
        115                 120                 125

Thr Asp Lys Glu Leu Arg Lys Gly Glu Tyr Leu Ile Thr Tyr Ile Gln
    130                 135                 140

Ser Lys Phe Leu Glu Ile Lys Asp His Asn Ser His Ile Tyr Thr His
145                 150                 155                 160

Tyr Asp Ala Ser Gln Phe Phe Tyr Thr Ser Leu Glu Asn Ala Val Thr
                165                 170                 175

Glu Trp Leu Gly Glu Ser Lys Ala Asn Asp Gly Leu Glu Ala Gly Leu
            180                 185                 190

Phe Gly Ser Gln Thr Pro Asn Gln Leu Arg Glu Thr Val Ala Glu Ser
        195                 200                 205

Asp Cys Val Thr Trp Thr Asn Leu Ser Leu Thr Tyr Asn Val Ser Lys
    210                 215                 220

Gly Asp Lys Trp Thr Ile His Asn Ala Lys Ser Tyr Ile Ser Lys Asn
225                 230                 235                 240

Trp Ser Asp Ile Leu Lys Tyr Ala Gln Ile Asp Ala Glu Leu Val Arg
                245                 250                 255

Asp Leu Trp Gln Glu Ala Val Asn Val Gly Glu Glu Leu Asp Ile Pro
            260                 265                 270

Met Gly Arg Pro Phe Ser Thr Gly Tyr Leu Ala Glu Ser Tyr Leu Asp
        275                 280                 285

Asn Arg Leu Arg Glu Lys Pro Gly Leu Gly Pro Met Pro Met Ala Lys
    290                 295                 300
```

```
Met Ala Trp Glu Ser Tyr Ala Gly Gly Arg Phe Glu Val Leu Lys Arg
305                 310                 315                 320

Gly Asn Val Gly Arg Val Ala Gly Pro Asp Ile Asn Ser Ala Tyr Pro
                325                 330                 335

Ala Val Leu Ala Glu Leu Pro Asp Pro Lys Thr Leu Arg Trp Lys Arg
                340                 345                 350

Ala Lys His Ala Ser Ile Ser Glu Ile Glu Thr Ala Asp Tyr Gly Phe
            355                 360                 365

Met Thr Val Lys Val Ser Thr Asp Pro Thr Arg Glu Ile Gln Pro Phe
        370                 375                 380

Ala Val Lys Asp Glu Lys Gln Asp Lys Leu Val Tyr Pro Ser Pro Gln
385                 390                 395                 400

Asn Thr Glu Ile Thr Val Val Lys Asp Ile Phe Ile His Ala Tyr Asn
                405                 410                 415

Gln Gly Tyr Val Thr Asp Tyr Glu Val Ile Asp Cys Trp Leu Gly Tyr
                420                 425                 430

Lys Thr Glu Gly Thr Thr Phe Pro Phe Asp Phe Ile Pro Glu Leu Tyr
            435                 440                 445

Asp Asn Arg Lys Thr Ala Glu Ala Asn Gly Leu Glu Lys Arg Gly Leu
450                 455                 460

Leu Leu Lys Ile Val Leu Asn Ser Met Tyr Gly Lys Thr Cys Gln Thr
465                 470                 475                 480

Thr Pro Lys Arg Arg Glu Leu Ala Glu Ser Thr Glu Leu Glu Leu His
                485                 490                 495

Glu Ser Tyr Val Pro Asp Met Ser Leu Pro Lys Met Ile Arg Glu Lys
                500                 505                 510

Tyr Ser Glu Gly Phe Ile Glu Ser Leu Thr Ala Gly Ala Trp Phe Asn
            515                 520                 525

Pro Phe Leu Ala Ser Tyr Ile Thr Gly Leu Thr Arg Leu Glu Leu His
530                 535                 540

Lys Gln Ile Cys Lys His Asp Leu Glu Glu Asn Thr Val Met Leu Ala
545                 550                 555                 560

Thr Asp Cys Val Met Ile Glu Glu Lys Pro Phe Glu Glu Ser Asn Phe
                565                 570                 575

Val Glu Asn Leu Val Gln Asp Gly Leu Gly Tyr Trp Asp Met Glu Tyr
            580                 585                 590

Lys Gly Asp Ala Phe Val Leu Gly Ala Val Tyr Gln Ile Asp Phe
            595                 600                 605

Asp Thr Cys Gln Lys Gly Cys Lys Asp Asn Cys Asn Lys Phe Ser His
610                 615                 620

Lys His Lys Val Lys Thr Arg Gly Phe Ser Glu Ala Asp Leu Glu Lys
625                 630                 635                 640

Gly Leu Val Asn Ala Ala Glu Lys Ala Asn Gly His Ile Glu Ile Glu
                645                 650                 655

Ser Thr Arg Pro Gln Thr Ile Ser Glu Ile Ile Trp Ser Asn Glu Glu
                660                 665                 670

Leu Ser Gln Val Gly Asn Phe Leu Glu Gln Glu Arg Lys Ile Lys Pro
            675                 680                 685

Glu Met Asp Thr Lys Arg Lys Trp Ser Glu Asn Thr Asp Phe Lys Lys
            690                 695                 700

Leu Leu Ser Thr Cys Glu Thr Ser Leu Pro Leu Lys Ile
705                 710                 715
```

<210> SEQ ID NO 24
<211> LENGTH: 720
<212> TYPE: PRT
<213> ORGANISM: Salterprovirus His2

<400> SEQUENCE: 24

```
Met Ala Lys Ser Asp Arg Asn Leu Asp Glu Val Asn Leu Tyr Pro Ala
1               5                   10                  15

Tyr Gln Asp Gln Tyr Ser Ala Thr Phe Val Asp Gly Lys Leu Ile Asn
            20                  25                  30

Ala Phe Asp Thr Glu Thr Ser Ser Gly Thr Val Phe Met Leu Thr Ser
        35                  40                  45

Ala Tyr Gly Asp Lys Thr Gln Ala Tyr Tyr Asn Arg Asp Val Ser Glu
    50                  55                  60

Leu Asp Ala Glu Thr Ile Met Asp Ala Leu Thr Asp Tyr Lys Thr Arg
65                  70                  75                  80

Ser Asn Ile Asn Ile Trp Tyr Asn Leu Asp Phe Asp Ala Asn Ala Ile
                85                  90                  95

Leu Ser Gly Ile Leu Ser Gln Lys Glu Met Ser Glu Leu Val Val Thr
            100                 105                 110

Asn Glu Thr Thr Thr Thr Val Ala Gly Ile Glu Tyr Glu Ile Phe Tyr
        115                 120                 125

Ile Lys Gly Lys Met Leu Arg Ile Val Asp Glu Asn Gly Asn Ile Ser
    130                 135                 140

Pro His Tyr Asp Ile Ala Gln Phe Phe Tyr Thr Ser Leu Asp Asn Ala
145                 150                 155                 160

Ala Glu Glu Trp Leu Gly Glu Asn Lys Lys Gly Ile Asp Thr Ser
                165                 170                 175

Lys Phe Asp Asp Lys Glu Tyr Ile Lys Asp Asn Phe Asp Glu Ile Leu
            180                 185                 190

Lys Tyr Ala Lys Lys Asp Ala Ser Leu Thr Gln Asp Leu Ala Ile Glu
        195                 200                 205

Leu Thr Asn Glu Ala Glu Asn Leu Asp Ile Pro Met Gly Arg Pro Ile
    210                 215                 220

Ser Thr Gly Tyr Leu Ser Ala Glu Tyr Leu Arg Ala Asn Thr Glu Glu
225                 230                 235                 240

Lys Pro Ser Leu Gly Asn Glu Ala Met Gln Asn Leu Phe Trp Glu Ser
                245                 250                 255

Tyr Tyr Gly Gly Arg Phe Glu Val Phe Gln Arg Gly Asn Val Gly Glu
            260                 265                 270

Val Val Ala Pro Asp Ile Asn Ser Ala Tyr Pro Ala Ile Met Lys Asp
        275                 280                 285

Leu Pro Asp Pro Thr Thr Leu Asn Trp Asn His Tyr Leu Asn Glu Val
    290                 295                 300

Ser Asp Lys Glu Pro Phe Ser His Ser Ile Asn Lys Phe Gly Tyr Glu
305                 310                 315                 320

Glu Ile Glu Asn Gly His Tyr Gly Val Val Lys Ala Arg Val Thr Thr
                325                 330                 335

Asp Ser Ser Arg Met Ile Gln Pro Phe Ala Cys Lys Ile Asp Gly Lys
            340                 345                 350

Val Lys Phe Pro Ala Met Thr Asn Lys Val Val Thr Val Ile Lys Pro
        355                 360                 365

Ile Phe Glu Phe Ala Val Asn Asn Gly Leu Val Thr Asp Phe Glu Leu
    370                 375                 380
```

```
Ile Glu Ala Trp Ile Gly Asn Ile Thr Asp Arg Thr Ser Lys Pro Phe
385                 390                 395                 400

Glu Phe Ile Gly Asp Met Tyr Ala Glu Arg Lys Val Phe Glu Gln Leu
            405                 410                 415

Lys Asn Lys Pro Lys Lys Gly Gln Leu Leu Lys Ile Val Leu Asn Ser
        420                 425                 430

Ser Tyr Gly Lys Thr Cys Gln Thr Thr Glu Lys Arg His Lys His Asp
    435                 440                 445

Leu Asp Lys Asp Gly Lys Lys Ile Met Gln Ala His Glu Thr Gln Tyr
450                 455                 460

Pro Arg Phe Tyr Leu Ser Lys Lys Gln Arg Glu Ala Leu Gly Asp Asp
465                 470                 475                 480

Glu Ile Ile Ile Thr Glu Leu Glu Ala Gly Lys Arg Phe Asn Pro Phe
                485                 490                 495

Phe Ala Ser Tyr Ile Thr Gly Leu Thr Arg Leu Glu Leu His Lys Gln
            500                 505                 510

Val Val Glu His Asp Ile Glu Asp Ser Thr Val Met Phe Ala Thr Asp
        515                 520                 525

Cys Leu Met Val Glu Lys Glu Ala Tyr Glu Asn Ser Ser Phe Asp Glu
    530                 535                 540

Gln Ile His Val Pro Asp Asp Ser Leu Pro Glu Ser Glu Phe Arg Lys
545                 550                 555                 560

Glu Ala Thr Arg Ser Leu Gly Ala Trp Asp Phe Asp Tyr Glu Gly Ser
                565                 570                 575

Ala Phe Ile Val Gly Ser Gly Val Tyr Glu Val Asp Thr Ile Gln Gly
            580                 585                 590

Lys Thr Lys Thr Lys Thr Arg Gly Phe Ile Glu Ser Asn Leu Gly Asp
        595                 600                 605

Thr Leu Lys Gly Leu Ala Lys Lys His Lys Glu Ala Ile Pro Leu Asp
610                 615                 620

Asn Glu Arg Pro Leu Thr Met Ala Glu Val Leu Ile Asn Thr Glu Arg
625                 630                 635                 640

Gly Ser Val Ser Glu Phe Val Glu Asn Ser Lys Lys Leu Lys Pro Asp
                645                 650                 655

Phe Asp Asp Lys Arg Asn Trp Asn Arg Glu Asn Pro Asn Phe His Asp
            660                 665                 670

Leu Leu Asn Asp Lys Glu Tyr Ser Lys Pro Ile Asp Leu Gln Glu Gln
        675                 680                 685

Lys Glu Glu Met Ile Gln Glu Gln Met Asp Ile Asn Glu Lys Met Ile
690                 695                 700

Gly Asp Ala Thr Pro Asn Gly Asn Glu Thr Val Val Lys Asp Asp
705                 710                 715                 720
```

<210> SEQ ID NO 25
<211> LENGTH: 957
<212> TYPE: PRT
<213> ORGANISM: Ostreococcus tauri

<400> SEQUENCE: 25

```
Met Val Val Phe Gln Ala Leu Thr Trp Glu Ser Arg Asp Thr Asp Asp
1               5                   10                  15

Glu His Leu Ile Ser Ile Phe Gly Lys Thr Glu Glu Gly Lys Ser Val
            20                  25                  30

Cys Leu Thr Thr Ala Phe Thr Pro Tyr Phe Phe Ile Lys Leu Pro Glu
        35                  40                  45
```

```
Lys Ile Asp Ala Gly Lys Ile Arg Arg Ile Tyr Asn Ile Leu Asp Glu
 50                  55                  60

Lys Cys Lys Asp Ser Leu Val Ala Tyr Ser Val Met Lys Ser Lys Asp
 65              70                  75                  80

Val Trp Gly Phe Gln Asn Asn Glu Glu Phe Val Phe Met Lys Val Asn
                 85                  90                  95

Phe Lys His Leu Gln Ala Arg Arg Leu Val Asp Ser Phe Leu Arg Lys
            100                 105                 110

Pro Leu Asp Arg Thr Pro Glu Leu Phe Asn Ile Phe Gly Val Arg Asn
        115                 120                 125

Val Lys Val Tyr Glu Ser Asn Leu Asp Pro Val Leu Arg Leu Met His
    130                 135                 140

Arg Thr Gly Ile Gln Ser Thr Gly Trp Leu Asp Thr Gly Asp Lys Cys
145                 150                 155                 160

Ile Arg Ser His Leu Ala Arg Val Asp Leu Asp Leu Phe Cys Asn Asp
                165                 170                 175

Trp Thr Thr Leu Lys Pro Val Ala Arg Asp Asp Ile Ala Pro Phe Val
            180                 185                 190

Val Ala Ser Val Asp Ile Glu Cys Asn Ser Ser Thr Gly Lys Phe Pro
        195                 200                 205

Asp Ala Asp Val Thr Gly Asp Ala Cys Phe Gln Ile Ala Ile Ser Leu
    210                 215                 220

Cys Lys Phe Gly Ser Asp Glu Pro Tyr Asp Lys Thr Cys Leu Cys Tyr
225                 230                 235                 240

Lys Lys Thr Asp Pro Asn Leu Glu Gly Ser Thr Ile Arg Ser Tyr Glu
                245                 250                 255

Thr Glu Arg Glu Met Leu Glu Ala Phe Gln Lys Tyr Leu His Thr Lys
            260                 265                 270

Asp Val Asp Ile Ile Thr Gly Trp Asn Ile Phe Gly Phe Asp Met Glu
        275                 280                 285

Tyr Ile Tyr Lys Arg Ala Gln Val Asn Arg Cys His Tyr Glu Phe Phe
    290                 295                 300

Asn Leu Gly Lys Leu Arg Asp Thr Glu Ser Glu Leu Val Ile Lys Lys
305                 310                 315                 320

Leu Ser Ser Ser Ala Leu Gly Asp Asn Leu Leu Lys Leu Leu Pro Met
                325                 330                 335

Pro Gly Arg Phe Ile Phe Asp Met Phe His Glu Val Lys Lys Gly Tyr
            340                 345                 350

Lys Leu Asp Ser Tyr Lys Leu Asp Asn Val Ser Lys Leu Tyr Leu Gly
        355                 360                 365

Asp Gln Lys Ile Asp Met Ala Pro Lys Glu Met Phe Ala Arg Tyr Arg
    370                 375                 380

Glu Glu Asp Pro Val Lys Leu Arg Glu Val Ala Glu Tyr Cys Ile Lys
385                 390                 395                 400

Asp Thr Leu Leu Pro His Arg Leu Met Lys Lys Leu Cys Thr Leu Leu
                405                 410                 415

Asn Met Val Glu Met Ala Lys Ala Thr Trp Val Pro Ala Asn Phe Leu
            420                 425                 430

Val Glu Arg Gly Gln Gln Ile Lys Val Phe Ser Gln Leu Thr Lys Lys
        435                 440                 445

Ala Arg Glu Leu Gly Phe Met Val Pro Thr Ile Arg Tyr Gly Ala Ile
    450                 455                 460
```

-continued

Pro Glu Glu Pro Tyr Glu Gly Ala Thr Val Leu Glu Ala Gln Lys Gly
465                 470                 475                 480

Ala Tyr Tyr Thr Pro Ile Thr Ala Leu Asp Phe Glu Ala Leu Tyr Pro
            485                 490                 495

Ser Ile Met Met Ala His Asn Leu Cys Tyr Ser Ser Tyr Val Met Asp
            500                 505                 510

Glu Lys Arg Tyr Gly Ser Val Pro Gly Ile Thr Tyr Glu Thr Phe Asn
            515                 520                 525

Ile Gly Asp Arg Thr Tyr Lys Phe Ala Gln Asp Val Pro Ser Leu Leu
            530                 535                 540

Pro Ala Ile Leu Ala Glu Leu Lys Gln Phe Arg Lys Gln Ala Lys Arg
545                 550                 555                 560

Asp Met Ala Ala Ala Thr Gly Phe Met Lys Glu Val Tyr Asn Gly Lys
                565                 570                 575

Gln Leu Ala Tyr Lys Val Ser Met Asn Ser Val Tyr Gly Phe Thr Gly
            580                 585                 590

Ala Gly Lys Gly Ile Leu Pro Cys Val Pro Ile Ala Ser Thr Thr Thr
            595                 600                 605

Ser Lys Gly Arg Ser Met Ile Glu Glu Thr Lys Asn Tyr Val Glu Lys
            610                 615                 620

Asn Phe Pro Gly Ala Lys Val Arg Tyr Gly Asp Thr Asp Ser Val Met
625                 630                 635                 640

Val Glu Phe Asp Val Gly Asp Arg Lys Gly Glu Ala Ile Ala Tyr
                645                 650                 655

Ser Trp Glu Val Gly Glu Arg Ala Ala Glu Glu Cys Ser Ala Leu Phe
            660                 665                 670

Lys Lys Pro Asn Asn Leu Glu Leu Glu Lys Val Tyr Trp Pro Tyr Phe
            675                 680                 685

Leu Tyr Ser Lys Lys Arg Tyr Ala Ala Lys Leu Trp Thr Lys Gly Lys
            690                 695                 700

Asp Gly Lys Met His Met Asp Tyr Ile Asp Ile Lys Gly Leu Gln Val
705                 710                 715                 720

Val Arg Arg Asp Asn Thr Pro His Val Arg Glu Val Cys Lys Glu Leu
                725                 730                 735

Leu Asp Val Ile Leu Thr Ser Ser Asp Pro Gly Pro Lys Glu Leu
            740                 745                 750

Ala Lys Glu Arg Ala Ile Glu Leu Leu Ser Gly Asp Val Pro Asn Asp
            755                 760                 765

Lys Leu Ile Leu Ser Gln Gly Leu Ser Asp Thr Tyr Lys Val Gly Gly
770                 775                 780

Lys Asn Val Ser Val Thr Ser Ala Asp Ser Val Asn Ile Asn Gln Ser
785                 790                 795                 800

His Val Gln Val Val Thr Lys Met Arg Gln Arg Lys Pro Gly Ser Glu
            805                 810                 815

Pro Gln Ser Gly Asp Arg Val Pro Tyr Leu Leu Thr Lys Thr Gln Asp
            820                 825                 830

Pro Lys Ala Lys Ala Tyr Glu Lys Ala Glu Asp Pro Lys Tyr Val Glu
            835                 840                 845

Glu His Gly Val Pro Val Asp Tyr His Tyr Tyr Phe Leu Asn Lys Phe
            850                 855                 860

Leu Asn Pro Val Cys Asp Leu Leu Asp Pro Leu Tyr Glu Asn Val Lys
865                 870                 875                 880

Glu Asp Ile Phe Gly Glu Ile Ile Asn Ala His Lys Pro Val Lys Pro

```
                885                 890                 895
Pro Lys Leu Pro Ser Leu Ser Gly Met Lys Lys Asp Asp Leu Ile Ala
            900                 905                 910

Glu Cys Gln Arg Leu Gly Leu Glu Glu Thr Gly Thr Leu Ala Ile Leu
        915                 920                 925

Arg Ala Arg Leu Lys Asp Ala Arg His Gly Ser Val Glu Asp Leu Phe
    930                 935                 940

Lys Asn Tyr Glu Leu Thr Gln Ser Lys Asp Glu Ser Ser
945                 950                 955

<210> SEQ ID NO 26
<211> LENGTH: 1046
<212> TYPE: PRT
<213> ORGANISM: Ectocarpus siliculosus virus 1

<400> SEQUENCE: 26

Met Glu Leu Tyr Leu His Asp Ile Arg Asp Asn Ser Gly Ser Phe Gln
1               5                   10                  15

Asn Pro Thr Met Gln Leu Phe Ala Met Glu Glu Asp Gly Thr Asn Val
            20                  25                  30

Phe Val Ser Val Lys Asn Phe Lys Thr Tyr Leu Tyr Val Gly Phe Asp
        35                  40                  45

Leu Asp Ile Ser Glu Asp Ser Val Arg Ser Asn Tyr Leu Glu Lys Phe
    50                  55                  60

Lys Gln Glu Lys Trp Glu Arg Asn Val Tyr Lys Met Ser Val Val Lys
65                  70                  75                  80

Arg Lys Arg Leu Ile Gly Phe Ser Asn Gly Asp Leu Phe Pro Tyr Ile
                85                  90                  95

Leu Met Glu Phe Thr Gly Thr Ile Ser Phe Tyr Ile Val Arg Lys His
            100                 105                 110

Leu His Glu Leu Cys Gly Glu Arg Asp Pro Gly Pro Asn Thr Phe Val
        115                 120                 125

Asp Leu Asn Lys Tyr Pro Gly Met Cys Val Tyr Glu Ser Lys Ser Val
    130                 135                 140

Asp Ser Ile Leu Lys Phe Phe His Ala Ser Gly Val Arg Pro Ser Ser
145                 150                 155                 160

Tyr Phe Arg Met Glu Asn Tyr Val Arg Val Ala Asp Lys Ala Arg Lys
                165                 170                 175

Thr His Cys Ala Lys Glu Phe Ile Val Asp Phe Val Asn Val Arg Pro
            180                 185                 190

Val Gly Glu Glu Val Val Asp Arg Lys Pro Pro Met Thr Ile Cys
        195                 200                 205

Ser Tyr Asp Leu Glu Thr Ser Gly Leu Asn Thr Asn Glu Asp Tyr Ile
    210                 215                 220

Phe Gln Ala Ser Met Ile Phe Ser Arg Leu Gly Asp Pro Cys Pro Asp
225                 230                 235                 240

Ser Glu Gly Ser Ala Thr Gly His Ala Val Asp Ser Tyr Thr Asp Gly
                245                 250                 255

Val Val Ile Cys Val Gly Asp Thr Glu Ser Val Asp Gly Thr Pro Leu
            260                 265                 270

Leu Ile Val Glu Asn Glu Leu Gln Leu Leu Asp Lys Phe Arg Glu Ile
        275                 280                 285

Leu Val Glu Arg Gly Cys Asn Ile Leu Cys Gly Tyr Asn Thr Phe Lys
    290                 295                 300
```

-continued

Phe Asp Ser Ala Phe Leu Tyr Lys Arg Ala Glu Arg Tyr Gly Phe Asp
305                 310                 315                 320

Gly Phe Lys Lys Leu Ser Phe Ile Lys Asp Leu Ala Cys Asp Leu Glu
            325                 330                 335

Val Lys Thr Leu Gln Ser Ala Ala Leu Gly Lys Asn Glu Leu Lys Gln
        340                 345                 350

Ile Ile Ile Pro Gly Arg Val Glu Ile Asp Leu Phe Met Val Met Arg
            355                 360                 365

Arg Ser Gln Lys Leu Ser Ser Tyr Lys Leu Asn Ala Val Cys Asp Lys
        370                 375                 380

Phe Phe Gly Gly Lys Lys Asp Val Thr Tyr Ala Asp Ile Leu Gln
385                 390                 395                 400

Ala Cys Thr Ser Lys Asp Pro Lys Lys Leu Gly Val Ile Ala Lys Tyr
                405                 410                 415

Cys Tyr Gln Asp Ser Gly Leu Val Leu Lys Leu Leu Asp Lys Ile Lys
            420                 425                 430

Glu Val Tyr Asp Ala Thr Glu Met Ala Lys Leu Cys Thr Val Pro Leu
        435                 440                 445

Thr Tyr Ile Val Gly Arg Gly Gln Gln Ile Lys Cys Met Ser Leu Ile
    450                 455                 460

Leu Asn Arg Ile His Gly Glu Tyr Val Cys Asn Tyr Ala Ala Ala Lys
465                 470                 475                 480

Lys Lys Met Ala Ala Asp Gly Lys Gln Val Leu Asn Glu Gly Tyr Lys
                485                 490                 495

Gly Ala Ser Val Ile Asp Ala Lys Lys Gly Phe Tyr Gly Lys Asp Pro
            500                 505                 510

Ile Val Thr Met Asp Phe Ala Ser Leu Tyr Pro Ser Ile Met Arg Leu
        515                 520                 525

Lys Gln Leu Cys Tyr Thr Thr Ile Val Arg Asp Val Lys Tyr Arg Gly
    530                 535                 540

Ile Glu Gly Val Asn Tyr Glu Asp His Gln Ile Ser Asp Gly Val Ser
545                 550                 555                 560

Val Thr Phe Ala His Arg Pro Gly Ser Arg Ser Ile Leu Cys Glu Leu
                565                 570                 575

Glu Glu Met Leu Gly Glu Glu Arg Lys Ala Thr Lys Lys Leu Met Lys
            580                 585                 590

Ser Glu Lys Asp Pro Phe Ala Tyr Ser Leu Leu Asp Ser Lys Gln Lys
        595                 600                 605

Ala Gln Lys Val Thr Met Asn Ser Ile Tyr Gly Phe Thr Gly Thr Val
    610                 615                 620

Asn Asn Gly Met Leu Pro Leu Val Glu Ile Ala Ala Val Thr Ser
625                 630                 635                 640

Thr Gly Arg Asp Met Ile Lys Arg Thr Lys Glu Tyr Ala Glu Lys Glu
                645                 650                 655

His Gly Cys Asn Val Ile Tyr Gly Asp Thr Asp Ser Val Met Val Ile
            660                 665                 670

Phe Pro Glu His Arg Asn Ile Glu Asn Leu Gly Asp Lys Met Arg Tyr
        675                 680                 685

Cys Phe Asp Met Gly Thr Lys Val Ser Lys Glu Ile Ser Glu Met Phe
    690                 695                 700

Gly His Pro Ile Leu Leu Glu Phe Glu Asn Ile Tyr Phe Lys Tyr Leu
705                 710                 715                 720

Leu Val Ser Lys Lys Arg Tyr Ala Gly Leu Ser Trp Glu Thr Val Glu

```
                    725                 730                 735
Gly Pro Pro Thr Met Thr Met Lys Gly Leu Val Thr Val Arg Arg Asp
                740                 745                 750

Asn Ala Pro Phe Val Gly Arg Cys Ala Ser Glu Ala Ile His Met Leu
            755                 760                 765

Met Asp Val Asp Val Thr Asp Gly Arg Gly Ala Val Lys Lys His Leu
        770                 775                 780

Thr Glu Thr Leu Leu Arg Leu Glu Arg Gly Gln Ile Ser Ile Glu Asp
785                 790                 795                 800

Leu Thr Ile Arg Lys Glu Leu Lys Gln Trp Val Tyr Lys Thr Pro Ser
                805                 810                 815

Pro His Ala Thr Leu Ala Leu Lys Ile Leu Glu Arg Thr Lys Glu Gln
            820                 825                 830

Ala Val Phe Arg Glu Phe Ile Lys Pro Ala Tyr Glu Thr Ile Gly Gly
        835                 840                 845

Tyr Asp Asp Ser Leu Leu Ser Ser Val Trp Thr Lys Met Thr Asn Leu
850                 855                 860

Lys Ser Tyr Leu Ser Val Arg Ala Lys Arg Glu Ile Ala Met Ser Asp
865                 870                 875                 880

Met Val Glu Ser Ile Arg Gly Asp Thr Thr Ser Pro Phe Lys Ala Glu
                885                 890                 895

Ala Tyr Ala Val Val Ala Leu Arg Gln Leu Tyr Asp Asp Val His Ser
        900                 905                 910

Val Leu Val Gly Glu Ser Phe Ala Arg Val Val Gly Leu Val Met Ala
        915                 920                 925

Gly Ile Gly Asp Val His Lys Leu Gly Glu Arg Tyr Met Ala Phe Val
        930                 935                 940

Arg Tyr Asn Ile Val Asp Trp Asp Pro Pro Thr Leu Gly Glu Arg Ile
945                 950                 955                 960

Pro Tyr Val Ile Thr Thr Gly Lys Gly Asp Ile Ser Ser Arg Ala Glu
                965                 970                 975

Asp Pro Arg Met Val Asn Val Gly Arg Cys Arg Pro Asp Phe Leu Tyr
            980                 985                 990

Tyr Ile Asp His Gln Leu Arg Asn Pro Met Val Asp Leu Leu Gln His
        995                 1000                1005

Val Ile Glu Ser Pro Ser Ser Leu Phe Val Glu Ser Gln Arg Arg
        1010                1015                1020

Met Ser Asn Leu Asn His Gly Arg Lys Glu Ile Thr Thr Phe Phe
        1025                1030                1035

Lys Lys Arg Lys Val Thr Glu Gly
        1040                1045

<210> SEQ ID NO 27
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Asn His Leu Val His His His His His Ile Glu Gly Arg His
1               5                   10                  15

Met Glu Leu Gly Thr Leu Glu Gly Ser Met Lys His Met Pro Arg Lys
            20                  25                  30
```

-continued

```
Met Tyr Ser Cys Ala Phe Glu Thr Thr Lys Val Glu Asp Cys Arg
            35                  40                  45
Val Trp Ala Tyr Gly Tyr Met Asn Ile Glu Asp His Ser Glu Tyr Lys
 50                  55                  60
Ile Gly Asn Ser Leu Asp Glu Phe Met Ala Trp Val Leu Lys Val Gln
 65                  70                  75                  80
Ala Asp Leu Tyr Phe His Asn Leu Lys Phe Ala Gly Ala Phe Ile Ile
                     85                  90                  95
Asn Trp Leu Glu Arg Asn Gly Phe Lys Trp Ser Ala Asp Gly Leu Pro
                100                 105                 110
Asn Thr Tyr Asn Thr Ile Ile Ser Arg Met Gly Gln Trp Tyr Met Ile
                115                 120                 125
Asp Ile Cys Leu Gly Tyr Lys Gly Lys Arg Lys Ile His Thr Val Ile
                130                 135                 140
Tyr Asp Ser Leu Lys Lys Leu Pro Phe Pro Val Lys Lys Ile Ala Lys
145                 150                 155                 160
Asp Phe Lys Leu Thr Val Leu Lys Gly Asp Ile Asp Tyr His Lys Glu
                165                 170                 175
Arg Pro Val Gly Tyr Lys Ile Thr Pro Glu Glu Tyr Ala Tyr Ile Lys
                180                 185                 190
Asn Asp Ile Gln Ile Ile Ala Glu Ala Leu Leu Ile Gln Phe Lys Gln
                195                 200                 205
Gly Leu Asp Arg Met Thr Ala Gly Ser Asp Ser Leu Lys Gly Phe Lys
                210                 215                 220
Asp Ile Ile Thr Thr Lys Lys Phe Lys Lys Val Phe Pro Thr Leu Ser
225                 230                 235                 240
Leu Gly Leu Asp Lys Glu Val Arg Tyr Ala Tyr Arg Gly Gly Phe Thr
                245                 250                 255
Trp Leu Asn Asp Arg Phe Lys Glu Lys Glu Ile Gly Glu Gly Met Val
                260                 265                 270
Phe Asp Val Asn Ser Leu Tyr Pro Ala Gln Met Tyr Ser Arg Leu Leu
                275                 280                 285
Pro Tyr Gly Glu Pro Ile Val Phe Glu Gly Lys Tyr Val Trp Asp Glu
                290                 295                 300
Asp Tyr Pro Leu His Ile Gln His Ile Arg Cys Glu Phe Glu Leu Lys
305                 310                 315                 320
Glu Gly Tyr Ile Pro Thr Ile Gln Ile Lys Arg Ser Arg Phe Tyr Lys
                325                 330                 335
Gly Asn Glu Tyr Leu Lys Ser Ser Gly Gly Glu Ile Ala Asp Leu Trp
                340                 345                 350
Leu Ser Asn Val Asp Leu Glu Leu Met Lys Glu His Tyr Asp Leu Tyr
                355                 360                 365
Asn Val Glu Tyr Ile Ser Gly Leu Lys Phe Lys Ala Thr Thr Gly Leu
                370                 375                 380
Phe Lys Asp Phe Ile Asp Lys Trp Thr Tyr Ile Lys Thr Thr Ser Glu
385                 390                 395                 400
Gly Ala Ile Lys Ala Leu Ala Lys Leu Met Leu Asn Ser Leu Tyr Gly
                405                 410                 415
Lys Phe Ala Ser Asn Pro Asp Val Thr Gly Lys Val Pro Tyr Leu Lys
                420                 425                 430
Glu Asn Gly Ala Leu Gly Phe Arg Leu Gly Glu Glu Thr Lys Asp
                435                 440                 445
Pro Val Tyr Thr Pro Met Gly Val Phe Ile Thr Ala Trp Ala Arg Tyr
```

```
                450                 455                 460
Thr Thr Ile Thr Ala Ala Gln Ala Cys Tyr Asp Arg Ile Ile Tyr Cys
465                 470                 475                 480

Asp Thr Asp Ser Ile His Leu Thr Gly Thr Glu Ile Pro Asp Val Ile
                485                 490                 495

Lys Asp Ile Val Asp Pro Lys Lys Leu Gly Tyr Trp Ala His Glu Ser
                500                 505                 510

Thr Phe Lys Arg Ala Lys Tyr Leu Arg Gln Lys Thr Tyr Ile Gln Asp
                515                 520                 525

Ile Tyr Met Lys Glu Val Asp Gly Lys Leu Val Glu Gly Ser Pro Asp
                530                 535                 540

Asp Tyr Thr Asp Ile Lys Phe Ser Val Lys Cys Ala Gly Met Thr Asp
545                 550                 555                 560

Lys Ile Lys Lys Glu Val Thr Phe Glu Asn Phe Lys Val Gly Phe Ser
                565                 570                 575

Arg Lys Met Lys Pro Lys Pro Val Gln Val Pro Gly Gly Val Val Leu
                580                 585                 590

Val Asp Asp Thr Phe Thr Ile Lys
                595                 600

<210> SEQ ID NO 28
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Asn His Leu Val His His His His His Ile Glu Gly Arg His
1               5                   10                  15

Met Glu Leu Gly Thr Leu Glu Gly Ser Met Lys His Met Pro Arg Lys
                20                  25                  30

Met Tyr Ser Cys Ala Phe Glu Thr Thr Thr Lys Val Glu Asp Cys Arg
                35                  40                  45

Val Trp Ala Tyr Gly Tyr Met Asn Ile Glu Asp His Ser Glu Tyr Lys
                50                  55                  60

Ile Gly Asn Ser Leu Asp Glu Phe Met Ala Trp Val Leu Lys Val Gln
65                  70                  75                  80

Ala Asp Leu Tyr Phe His Asn Leu Lys Phe Ala Gly Ala Phe Ile Ile
                85                  90                  95

Asn Trp Leu Glu Arg Asn Gly Phe Lys Trp Ser Ala Asp Gly Leu Pro
                100                 105                 110

Asn Thr Tyr Asn Thr Ile Ile Ser Arg Met Gly Gln Trp Tyr Met Ile
                115                 120                 125

Asp Ile Cys Leu Gly Tyr Lys Gly Lys Arg Lys Ile His Thr Val Ile
                130                 135                 140

Tyr Asp Ser Leu Lys Lys Leu Pro Phe Pro Val Lys Lys Ile Ala Lys
145                 150                 155                 160

Asp Phe Lys Leu Thr Val Leu Lys Gly Asp Ile Asp Tyr His Lys Glu
                165                 170                 175

Arg Pro Val Gly Tyr Lys Ile Thr Pro Glu Glu Tyr Ala Tyr Ile Lys
                180                 185                 190

Asn Asp Ile Gln Ile Ile Ala Glu Ala Leu Leu Ile Gln Phe Lys Gln
                195                 200                 205
```

-continued

```
Gly Leu Asp Arg Met Thr Ala Gly Ser Asp Ser Leu Lys Gly Phe Lys
    210                 215                 220

Asp Ile Ile Thr Thr Lys Lys Phe Lys Val Phe Pro Thr Leu Ser
225                 230                 235                 240

Leu Gly Leu Asp Lys Glu Val Arg Tyr Ala Tyr Arg Gly Gly Phe Thr
                245                 250                 255

Trp Leu Asn Asp Arg Phe Lys Glu Lys Glu Ile Gly Glu Gly Met Val
            260                 265                 270

Phe Asp Val Asn Ser Leu Tyr Pro Ala Gln Met Tyr Ser Arg Leu Leu
        275                 280                 285

Pro Tyr Gly Glu Pro Ile Val Phe Glu Gly Lys Tyr Val Trp Asp Glu
    290                 295                 300

Asp Tyr Pro Leu His Ile Gln His Ile Arg Cys Glu Phe Glu Leu Lys
305                 310                 315                 320

Glu Gly Tyr Ile Pro Thr Ile Gln Ile Lys Arg Ser Arg Phe Tyr Lys
                325                 330                 335

Gly Asn Glu Tyr Leu Lys Ser Ser Gly Gly Glu Ile Ala Asp Leu Trp
            340                 345                 350

Leu Ser Asn Val Asp Leu Glu Leu Met Lys Glu His Tyr Asp Leu Tyr
        355                 360                 365

Asn Val Glu Tyr Ile Ser Gly Leu Lys Phe Lys Ala Thr Thr Gly Leu
    370                 375                 380

Phe Lys Asp Phe Ile Asp Lys Trp Thr Tyr Ile Lys Thr Thr Ser Glu
385                 390                 395                 400

Gly Ala Ile Lys Gln Leu Ala Lys Leu Met Leu Asn Gly Leu Tyr Gly
                405                 410                 415

Lys Phe Ala Ser Asn Pro Asp Val Thr Gly Lys Val Pro Tyr Leu Lys
            420                 425                 430

Glu Asn Gly Ala Leu Gly Phe Arg Leu Gly Glu Glu Thr Lys Asp
        435                 440                 445

Pro Val Tyr Thr Pro Met Gly Val Phe Ile Thr Ala Trp Ala Arg Tyr
    450                 455                 460

Thr Thr Ile Thr Ala Ala Gln Ala Cys Tyr Asp Arg Ile Ile Tyr Cys
465                 470                 475                 480

Asp Thr Asp Ser Ile His Leu Thr Gly Thr Glu Ile Pro Asp Val Ile
                485                 490                 495

Lys Asp Ile Val Asp Pro Lys Lys Leu Gly Tyr Trp Ala His Glu Ser
            500                 505                 510

Thr Phe Lys Arg Ala Lys Tyr Leu Arg Gln Lys Thr Tyr Ile Gln Asp
        515                 520                 525

Ile Tyr Met Lys Glu Val Asp Gly Lys Leu Val Glu Gly Ser Pro Asp
    530                 535                 540

Asp Tyr Thr Asp Ile Lys Phe Ser Val Lys Cys Ala Gly Met Thr Asp
545                 550                 555                 560

Lys Ile Lys Lys Glu Val Thr Phe Glu Asn Phe Lys Val Gly Phe Ser
                565                 570                 575

Arg Lys Met Lys Pro Lys Pro Val Gln Val Pro Gly Gly Val Val Leu
            580                 585                 590

Val Asp Asp Thr Phe Thr Ile Lys
        595                 600
```

<210> SEQ ID NO 29
<211> LENGTH: 912
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 29

Met His His His His His Lys His Met Lys Glu Phe Tyr Leu Thr
1               5                   10                  15

Val Glu Gln Ile Gly Asp Ser Ile Phe Glu Arg Tyr Ile Asp Ser Asn
            20                  25                  30

Gly Arg Glu Arg Thr Arg Glu Val Glu Tyr Lys Pro Ser Leu Phe Ala
        35                  40                  45

His Cys Pro Glu Ser Gln Ala Thr Lys Tyr Phe Asp Ile Tyr Gly Lys
    50                  55                  60

Pro Cys Thr Arg Lys Leu Phe Ala Asn Met Arg Asp Ala Ser Gln Trp
65                  70                  75                  80

Ile Lys Arg Met Glu Asp Ile Gly Leu Glu Ala Leu Gly Met Asp Asp
                85                  90                  95

Phe Lys Leu Ala Tyr Leu Ser Asp Thr Tyr Asn Tyr Glu Ile Lys Tyr
            100                 105                 110

Asp His Thr Lys Ile Arg Val Ala Asn Phe Asp Ile Glu Val Thr Ser
        115                 120                 125

Pro Asp Gly Phe Pro Glu Pro Ser Gln Ala Lys His Pro Ile Asp Ala
    130                 135                 140

Ile Thr His Tyr Asp Ser Ile Asp Asp Arg Phe Tyr Val Phe Asp Leu
145                 150                 155                 160

Leu Asn Ser Pro Tyr Gly Asn Val Glu Glu Trp Ser Ile Glu Ile Ala
                165                 170                 175

Ala Lys Leu Gln Glu Gln Gly Gly Asp Glu Val Pro Ser Glu Ile Ile
            180                 185                 190

Asp Lys Ile Ile Tyr Met Pro Phe Asp Asn Glu Lys Glu Leu Leu Met
        195                 200                 205

Glu Tyr Leu Asn Phe Trp Gln Gln Lys Thr Pro Val Ile Leu Thr Gly
    210                 215                 220

Trp Asn Val Glu Ser Phe Asp Ile Pro Tyr Val Tyr Asn Arg Ile Lys
225                 230                 235                 240

Asn Ile Phe Gly Glu Ser Thr Ala Lys Arg Leu Ser Pro His Arg Lys
                245                 250                 255

Thr Arg Val Lys Val Ile Glu Asn Met Tyr Gly Ser Arg Glu Ile Ile
            260                 265                 270

Thr Leu Phe Gly Ile Ser Val Leu Asp Tyr Ile Asp Leu Tyr Lys Lys
        275                 280                 285

Phe Ser Phe Thr Asn Gln Pro Ser Tyr Ser Leu Asp Tyr Ile Ser Glu
    290                 295                 300

Phe Glu Leu Asn Val Gly Lys Leu Lys Tyr Asp Gly Pro Ile Ser Lys
305                 310                 315                 320

Leu Arg Glu Ser Asn His Gln Arg Tyr Ile Ser Tyr Asn Ile Ile Asp
                325                 330                 335

Val Tyr Arg Val Leu Gln Ile Asp Ala Lys Arg Gln Phe Ile Asn Leu
            340                 345                 350

Ser Leu Asp Met Gly Tyr Tyr Ala Lys Ile Gln Ile Gln Ser Val Phe
        355                 360                 365

Ser Pro Ile Lys Thr Trp Asp Ala Ile Ile Phe Asn Ser Leu Lys Glu
    370                 375                 380

-continued

Gln Asn Lys Val Ile Pro Gln Gly Arg Ser His Pro Val Gln Pro Tyr
385                 390                 395                 400

Pro Gly Ala Phe Val Lys Glu Pro Ile Pro Asn Arg Tyr Lys Tyr Val
            405                 410                 415

Met Ser Phe Asp Leu Thr Ser Leu Tyr Pro Ser Ile Ile Arg Gln Val
        420                 425                 430

Asn Ile Ser Pro Glu Thr Ile Ala Gly Thr Phe Lys Val Ala Pro Leu
    435                 440                 445

His Asp Tyr Ile Asn Ala Val Ala Glu Arg Pro Ser Asp Val Tyr Ser
450                 455                 460

Cys Ser Pro Asn Gly Met Met Tyr Tyr Lys Asp Arg Asp Gly Val Val
465                 470                 475                 480

Pro Thr Glu Ile Thr Lys Val Phe Asn Gln Arg Lys Glu His Lys Gly
            485                 490                 495

Tyr Met Leu Ala Ala Gln Arg Asn Gly Glu Ile Ile Lys Glu Ala Leu
        500                 505                 510

His Asn Pro Asn Leu Ser Val Asp Glu Pro Leu Asp Val Asp Tyr Arg
    515                 520                 525

Phe Asp Phe Ser Asp Glu Ile Lys Glu Lys Ile Lys Lys Leu Ser Ala
530                 535                 540

Lys Ser Leu Asn Glu Met Leu Phe Arg Ala Gln Arg Thr Glu Val Ala
545                 550                 555                 560

Gly Met Thr Ala Gln Ile Asn Arg Lys Leu Leu Ile Asn Ser Leu Tyr
            565                 570                 575

Gly Ala Leu Gly Asn Val Trp Phe Arg Tyr Tyr Asp Leu Arg Asn Ala
        580                 585                 590

Thr Ala Ile Thr Thr Phe Gly Gln Met Ala Leu Gln Trp Ile Glu Arg
    595                 600                 605

Lys Val Asn Glu Tyr Leu Asn Glu Val Cys Gly Thr Glu Gly Glu Ala
610                 615                 620

Phe Val Leu Tyr Gly Asp Thr Asp Ser Ile Tyr Val Ser Ala Asp Lys
625                 630                 635                 640

Ile Ile Asp Lys Val Gly Glu Ser Lys Phe Arg Asp Thr Asn His Trp
            645                 650                 655

Val Asp Phe Leu Asp Lys Phe Ala Arg Glu Arg Met Glu Pro Ala Ile
        660                 665                 670

Asp Arg Gly Phe Arg Glu Met Cys Glu Tyr Met Asn Asn Lys Gln His
    675                 680                 685

Leu Met Phe Met Asp Arg Glu Ala Ile Ala Gly Pro Pro Leu Gly Ser
690                 695                 700

Lys Gly Ile Gly Gly Phe Trp Thr Gly Lys Lys Arg Tyr Ala Leu Asn
705                 710                 715                 720

Val Trp Asp Met Glu Gly Thr Arg Tyr Ala Glu Pro Lys Leu Lys Ile
            725                 730                 735

Met Gly Leu Glu Thr Gln Lys Ser Ser Thr Pro Lys Ala Val Gln Lys
        740                 745                 750

Ala Leu Lys Glu Cys Ile Arg Arg Met Leu Gln Glu Gly Glu Glu Ser
    755                 760                 765

Leu Gln Glu Tyr Phe Lys Glu Phe Glu Lys Glu Phe Arg Gln Leu Asn
770                 775                 780

Tyr Ile Ser Ile Ala Ser Val Ser Ser Ala Asn Asn Ile Ala Lys Tyr
785                 790                 795                 800

Asp Val Gly Gly Phe Pro Gly Pro Lys Cys Pro Phe His Ile Arg Gly

```
                        805                 810                 815

Ile Leu Thr Tyr Asn Arg Ala Ile Lys Gly Asn Ile Asp Ala Pro Gln
                820                 825                 830

Val Val Glu Gly Glu Lys Val Tyr Val Leu Pro Leu Arg Glu Gly Asn
                835                 840                 845

Pro Phe Gly Asp Lys Cys Ile Ala Trp Pro Ser Gly Thr Glu Ile Thr
            850                 855                 860

Asp Leu Ile Lys Asp Asp Val Leu His Trp Met Asp Tyr Thr Val Leu
865                 870                 875                 880

Leu Glu Lys Thr Phe Ile Lys Pro Leu Glu Gly Phe Thr Ser Ala Ala
                885                 890                 895

Lys Leu Asp Tyr Glu Lys Lys Ala Ser Leu Phe Asp Met Phe Asp Phe
                900                 905                 910

<210> SEQ ID NO 30
<211> LENGTH: 587
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met His His His His His Lys His Met Ala Arg Ser Val Tyr Val
1               5                   10                  15

Cys Asp Phe Glu Thr Thr Thr Asp Pro Glu Asp Cys Arg Leu Trp Ala
                20                  25                  30

Trp Gly Trp Met Asp Ile Tyr Asn Thr Asp Lys Trp Ser Tyr Gly Glu
            35                  40                  45

Asp Ile Asp Ser Phe Met Glu Trp Ala Leu Asn Ser Asn Ser Asp Ile
        50                  55                  60

Tyr Phe His Asn Leu Lys Phe Asp Gly Ser Phe Ile Leu Pro Trp Trp
65                  70                  75                  80

Leu Arg Asn Gly Tyr Val His Thr Glu Glu Asp Arg Thr Asn Thr Pro
                85                  90                  95

Lys Glu Phe Thr Thr Thr Ile Ser Gly Met Gly Gln Trp Tyr Ala Val
                100                 105                 110

Asp Val Cys Ile Asn Thr Arg Gly Lys Asn Lys Asn His Val Val Phe
            115                 120                 125

Tyr Asp Ser Leu Lys Lys Leu Pro Phe Lys Val Glu Gln Ile Ala Lys
        130                 135                 140

Gly Phe Gly Leu Pro Val Leu Lys Gly Asp Ile Asp Tyr Lys Lys Tyr
145                 150                 155                 160

Arg Pro Val Gly Tyr Val Met Asp Asp Asn Glu Ile Glu Tyr Leu Lys
                165                 170                 175

His Asp Leu Leu Ile Val Ala Leu Ala Leu Arg Ser Met Phe Asp Asn
                180                 185                 190

Asp Phe Thr Ser Met Thr Val Gly Ser Asp Ala Leu Asn Thr Tyr Lys
            195                 200                 205

Glu Met Leu Gly Val Lys Gln Trp Glu Lys Tyr Phe Pro Val Leu Ser
        210                 215                 220

Leu Lys Val Asn Ser Glu Ile Arg Lys Ala Tyr Lys Gly Gly Phe Thr
225                 230                 235                 240

Trp Val Asn Pro Lys Tyr Gln Gly Glu Thr Val Tyr Gly Gly Met Val
                245                 250                 255
```

Phe Asp Val Asn Ser Met Tyr Pro Ala Met Met Lys Asn Lys Leu Leu
                260                 265                 270

Pro Tyr Gly Glu Pro Val Met Phe Lys Gly Glu Tyr Lys Lys Asn Val
            275                 280                 285

Glu Tyr Pro Leu Tyr Ile Gln Gln Val Arg Cys Phe Phe Glu Leu Lys
        290                 295                 300

Lys Asp Lys Ile Pro Cys Ile Gln Ile Lys Gly Asn Ala Arg Phe Gly
305                 310                 315                 320

Gln Asn Glu Tyr Leu Ser Thr Ser Gly Asp Glu Tyr Val Asp Leu Tyr
                325                 330                 335

Val Thr Asn Val Asp Trp Glu Leu Ile Lys Lys His Tyr Asp Ile Phe
            340                 345                 350

Glu Glu Glu Phe Ile Gly Gly Phe Met Phe Lys Gly Phe Ile Gly Phe
        355                 360                 365

Phe Asp Glu Tyr Ile Asp Arg Phe Met Glu Ile Lys Asn Ser Pro Asp
    370                 375                 380

Ser Ser Ala Glu Gln Ser Leu Gln Ala Lys Leu Met Leu Asn Ser Leu
385                 390                 395                 400

Tyr Gly Lys Phe Ala Thr Asn Pro Asp Ile Thr Gly Lys Val Pro Tyr
                405                 410                 415

Leu Asp Glu Asn Gly Val Leu Lys Phe Arg Lys Gly Glu Leu Lys Glu
            420                 425                 430

Arg Asp Pro Val Tyr Thr Pro Met Gly Cys Phe Ile Thr Ala Tyr Ala
        435                 440                 445

Arg Glu Asn Ile Leu Ser Asn Ala Gln Lys Leu Tyr Pro Arg Phe Ile
    450                 455                 460

Tyr Ala Asp Thr Asp Ser Ile His Val Glu Gly Leu Gly Glu Val Asp
465                 470                 475                 480

Ala Ile Lys Asp Val Ile Asp Pro Lys Lys Leu Gly Tyr Trp Asp His
                485                 490                 495

Glu Ala Thr Phe Gln Arg Ala Arg Tyr Val Arg Gln Lys Thr Tyr Phe
            500                 505                 510

Ile Glu Thr Thr Trp Lys Glu Asn Asp Lys Gly Lys Leu Val Val Cys
        515                 520                 525

Glu Pro Gln Asp Ala Thr Lys Val Lys Pro Lys Ile Ala Cys Ala Gly
    530                 535                 540

Met Ser Asp Ala Ile Lys Glu Arg Ile Arg Phe Asn Glu Phe Lys Ile
545                 550                 555                 560

Gly Tyr Ser Thr His Gly Ser Leu Lys Pro Lys Asn Val Leu Gly Gly
                565                 570                 575

Val Val Leu Met Asp Tyr Pro Phe Ala Ile Lys
            580                 585

<210> SEQ ID NO 31
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met His His His His His Lys His Met Pro Arg Lys Met Phe Ser
1               5                   10                  15

Cys Asp Phe Glu Thr Thr Thr Lys Leu Asp Asp Cys Arg Val Trp Ala
            20                  25                  30

```
Tyr Gly Tyr Met Glu Ile Gly Asn Leu Asp Asn Tyr Lys Ile Gly Asn
         35                  40                  45

Ser Leu Asp Glu Phe Met Gln Trp Val Met Glu Ile Gln Ala Asp Leu
 50                  55                  60

Tyr Phe His Asn Leu Lys Phe Asp Gly Ala Phe Ile Val Asn Trp Leu
 65                  70                  75                  80

Glu His His Gly Phe Lys Trp Ser Asn Glu Gly Leu Pro Asn Thr Tyr
                     85                  90                  95

Asn Thr Ile Ile Ser Lys Met Gly Gln Trp Tyr Met Ile Asp Ile Cys
                 100                 105                 110

Phe Gly Tyr Lys Gly Lys Arg Lys Leu His Thr Val Ile Tyr Asp Ser
             115                 120                 125

Leu Lys Lys Leu Pro Phe Pro Val Lys Ile Ala Lys Asp Phe Gln
130                 135                 140

Leu Pro Leu Leu Lys Gly Asp Ile Asp Tyr His Ala Glu Arg Pro Val
145                 150                 155                 160

Gly His Glu Ile Thr Pro Glu Glu Tyr Glu Tyr Ile Lys Asn Asp Ile
                 165                 170                 175

Glu Ile Ile Ala Arg Ala Leu Asp Ile Gln Phe Lys Gln Gly Leu Asp
             180                 185                 190

Arg Met Thr Ala Gly Ser Asp Ser Leu Lys Gly Phe Lys Asp Ile Leu
         195                 200                 205

Ser Thr Lys Lys Phe Asn Lys Val Phe Pro Lys Leu Ser Leu Pro Met
         210                 215                 220

Asp Lys Glu Ile Arg Arg Ala Tyr Arg Gly Gly Phe Thr Trp Leu Asn
225                 230                 235                 240

Asp Lys Tyr Lys Glu Lys Glu Ile Gly Glu Gly Met Val Phe Asp Val
             245                 250                 255

Asn Ser Leu Tyr Pro Ser Gln Met Tyr Ser Arg Pro Leu Pro Tyr Gly
             260                 265                 270

Ala Pro Ile Val Phe Gln Gly Lys Tyr Glu Lys Asp Glu Gln Tyr Pro
         275                 280                 285

Leu Tyr Ile Gln Arg Ile Arg Phe Glu Phe Glu Leu Lys Glu Gly Tyr
     290                 295                 300

Ile Pro Thr Ile Gln Ile Lys Lys Asn Pro Phe Phe Lys Gly Asn Glu
305                 310                 315                 320

Tyr Leu Lys Asn Ser Gly Ala Glu Pro Val Glu Leu Tyr Leu Thr Asn
             325                 330                 335

Val Asp Leu Glu Leu Ile Gln Glu His Tyr Glu Met Tyr Asn Val Glu
         340                 345                 350

Tyr Ile Asp Gly Phe Lys Phe Arg Glu Lys Thr Gly Leu Phe Lys Glu
     355                 360                 365

Phe Ile Asp Lys Trp Thr Tyr Val Lys Thr His Glu Lys Gly Ala Lys
370                 375                 380

Lys Gln Leu Ala Lys Leu Met Phe Asp Ser Leu Tyr Gly Lys Phe Ala
385                 390                 395                 400

Ser Asn Pro Asp Val Thr Gly Lys Val Pro Tyr Leu Lys Glu Asp Gly
             405                 410                 415

Ser Leu Gly Phe Arg Val Gly Asp Glu Glu Tyr Lys Asp Pro Val Tyr
         420                 425                 430

Thr Pro Met Gly Val Phe Ile Thr Ala Trp Ala Arg Phe Thr Thr Ile
     435                 440                 445
```

Thr Ala Ala Gln Ala Cys Tyr Asp Arg Ile Ile Tyr Cys Asp Thr Asp
    450                 455                 460

Ser Ile His Leu Thr Gly Thr Glu Val Pro Glu Ile Ile Lys Asp Ile
465                 470                 475                 480

Val Asp Pro Lys Leu Gly Tyr Trp Ala His Glu Ser Thr Phe Lys
            485                 490                 495

Arg Ala Lys Tyr Leu Arg Gln Lys Thr Tyr Ile Gln Asp Ile Tyr Ala
            500                 505                 510

Lys Glu Val Asp Gly Lys Leu Ile Glu Cys Ser Pro Asp Glu Ala Thr
            515                 520                 525

Thr Thr Lys Phe Ser Val Lys Cys Ala Gly Met Thr Asp Thr Ile Lys
530                 535                 540

Lys Lys Val Thr Phe Asp Asn Phe Arg Val Gly Phe Ser Ser Thr Gly
545                 550                 555                 560

Lys Pro Lys Pro Val Gln Val Asn Gly Gly Val Val Leu Val Asp Ser
            565                 570                 575

Val Phe Thr Ile Lys
            580

<210> SEQ ID NO 32
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Ala Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Arg Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
            245                 250                 255

Ser Arg Pro Leu Pro Tyr Gly Ala Pro Ile Val Phe Gln Gly Lys Tyr
        260                 265                 270

Glu Lys Asp Glu Gln Tyr Pro Leu Tyr Ile Gln Arg Ile Arg Phe Glu
    275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
            325                 330                 335

Tyr Glu Met Tyr Asn Val Glu Tyr Ile Asp Gly Phe Lys Phe Arg Glu
        340                 345                 350

Lys Thr Gly Leu Phe Lys Glu Phe Ile Asp Lys Trp Thr Tyr Val Lys
    355                 360                 365

Thr His Glu Lys Gly Ala Lys Lys Gln Leu Ala Lys Leu Met Phe Asp
370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
            405                 410                 415

Glu Tyr Lys Asp Pro Val Tyr Thr Pro Met Gly Val Phe Ile Thr Ala
        420                 425                 430

Trp Ala Arg Phe Thr Thr Ile Thr Ala Ala Gln Ala Cys Tyr Asp Arg
    435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
            485                 490                 495

Tyr Ile Gln Asp Ile Tyr Ala Lys Glu Val Asp Gly Lys Leu Ile Glu
        500                 505                 510

Cys Ser Pro Asp Glu Ala Thr Thr Thr Lys Phe Ser Val Lys Cys Ala
    515                 520                 525

Gly Met Thr Asp Thr Ile Lys Lys Lys Val Thr Phe Asp Asn Phe Arg
530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
            565                 570

<210> SEQ ID NO 33
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Pro Arg Lys Met Phe Ser Cys Asp Phe Glu Thr Thr Thr Lys Leu

|     |     |     |     |     |     |     |     |     |     |     |     |     |     |     |
|---|---|---|---|---|---|---|---|---|---|---|---|---|---|---|
| 1   |     |     |     | 5   |     |     |     |     | 10  |     |     |     |     | 15  |
| Asp | Asp | Cys | Arg | Val | Trp | Ala | Tyr | Gly | Tyr | Met | Glu | Ile | Gly | Asn | Leu |
|     |     |     | 20  |     |     |     |     | 25  |     |     |     |     | 30  |     |     |
| Asp | Asn | Tyr | Lys | Ile | Gly | Asn | Ser | Leu | Asp | Glu | Phe | Met | Gln | Trp | Val |
|     |     | 35  |     |     |     |     | 40  |     |     |     |     | 45  |     |     |     |
| Met | Glu | Ile | Gln | Ala | Asp | Leu | Tyr | Phe | His | Asn | Leu | Lys | Phe | Asp | Gly |
|     | 50  |     |     |     |     | 55  |     |     |     |     | 60  |     |     |     |     |
| Ala | Phe | Ile | Val | Asn | Trp | Leu | Glu | His | Gly | Phe | Lys | Trp | Ser | Asn |
| 65  |     |     |     |     | 70  |     |     |     |     | 75  |     |     |     |     | 80 |
| Glu | Gly | Leu | Pro | Asn | Thr | Tyr | Asn | Thr | Ile | Ile | Ser | Lys | Met | Gly | Gln |
|     |     |     |     | 85  |     |     |     |     | 90  |     |     |     |     | 95  |     |
| Trp | Tyr | Met | Ile | Asp | Ile | Cys | Phe | Gly | Tyr | Lys | Gly | Lys | Arg | Lys | Leu |
|     |     |     | 100 |     |     |     |     | 105 |     |     |     |     | 110 |     |     |
| His | Thr | Val | Ile | Tyr | Asp | Ser | Leu | Lys | Lys | Leu | Pro | Phe | Pro | Val | Lys |
|     |     |     | 115 |     |     |     |     | 120 |     |     |     |     | 125 |     |     |
| Lys | Ile | Ala | Lys | Asp | Phe | Gln | Leu | Pro | Leu | Leu | Lys | Gly | Asp | Ile | Asp |
|     |     |     | 130 |     |     |     |     | 135 |     |     |     |     | 140 |     |     |
| Tyr | His | Ala | Glu | Arg | Pro | Val | Gly | His | Glu | Ile | Thr | Pro | Glu | Glu | Tyr |
| 145 |     |     |     |     | 150 |     |     |     |     | 155 |     |     |     |     | 160 |
| Glu | Tyr | Ile | Lys | Asn | Asp | Ile | Glu | Ile | Ile | Ala | Arg | Ala | Leu | Asp | Ile |
|     |     |     |     | 165 |     |     |     |     | 170 |     |     |     |     | 175 |     |
| Gln | Phe | Lys | Gln | Gly | Leu | Asp | Arg | Met | Thr | Ala | Gly | Ser | Asp | Ser | Leu |
|     |     |     | 180 |     |     |     |     | 185 |     |     |     |     | 190 |     |     |
| Lys | Gly | Phe | Lys | Asp | Ile | Leu | Ser | Thr | Lys | Lys | Phe | Asn | Lys | Val | Phe |
|     |     |     | 195 |     |     |     |     | 200 |     |     |     |     | 205 |     |     |
| Pro | Lys | Leu | Ser | Leu | Pro | Met | Asp | Lys | Glu | Ile | Arg | Arg | Ala | Tyr | Arg |
|     |     |     | 210 |     |     |     |     | 215 |     |     |     |     | 220 |     |     |
| Gly | Gly | Phe | Thr | Trp | Leu | Asn | Asp | Lys | Tyr | Lys | Glu | Lys | Glu | Ile | Gly |
| 225 |     |     |     |     | 230 |     |     |     |     | 235 |     |     |     |     | 240 |
| Glu | Gly | Met | Val | Phe | Asp | Val | Asn | Ser | Leu | Tyr | Pro | Ser | Gln | Met | Tyr |
|     |     |     |     | 245 |     |     |     |     | 250 |     |     |     |     | 255 |     |
| Ser | Arg | Pro | Leu | Pro | Tyr | Gly | Ala | Pro | Ile | Val | Phe | Gln | Gly | Lys | Tyr |
|     |     |     |     | 260 |     |     |     |     | 265 |     |     |     |     | 270 |     |
| Glu | Lys | Asp | Glu | Gln | Tyr | Pro | Leu | Tyr | Ile | Gln | Arg | Ile | Arg | Phe | Glu |
|     |     |     | 275 |     |     |     |     | 280 |     |     |     |     | 285 |     |     |
| Phe | Glu | Leu | Lys | Glu | Gly | Tyr | Ile | Pro | Thr | Ile | Gln | Ile | Lys | Lys | Asn |
|     |     |     | 290 |     |     |     |     | 295 |     |     |     |     | 300 |     |     |
| Pro | Phe | Phe | Lys | Gly | Asn | Glu | Tyr | Leu | Lys | Asn | Ser | Gly | Ala | Glu | Pro |
| 305 |     |     |     |     | 310 |     |     |     |     | 315 |     |     |     |     | 320 |
| Val | Glu | Leu | Tyr | Leu | Thr | Asn | Val | Asp | Leu | Glu | Leu | Ile | Gln | Glu | His |
|     |     |     |     | 325 |     |     |     |     | 330 |     |     |     |     | 335 |     |
| Tyr | Glu | Met | Tyr | Asn | Val | Glu | Tyr | Ile | Asp | Gly | Phe | Lys | Phe | Arg | Glu |
|     |     |     | 340 |     |     |     |     | 345 |     |     |     |     | 350 |     |     |
| Lys | Thr | Gly | Leu | Phe | Lys | Glu | Phe | Ile | Asp | Lys | Trp | Thr | Tyr | Val | Lys |
|     |     |     | 355 |     |     |     |     | 360 |     |     |     |     | 365 |     |     |
| Thr | His | Glu | Lys | Gly | Ala | Lys | Lys | Gln | Leu | Ala | Lys | Leu | Met | Leu | Asn |
|     |     |     | 370 |     |     |     |     | 375 |     |     |     |     | 380 |     |     |
| Ser | Leu | Tyr | Gly | Lys | Phe | Ala | Ser | Asn | Pro | Asp | Val | Thr | Gly | Lys | Val |
| 385 |     |     |     |     | 390 |     |     |     |     | 395 |     |     |     |     | 400 |
| Pro | Tyr | Leu | Lys | Glu | Asp | Gly | Ser | Leu | Gly | Phe | Arg | Val | Gly | Asp | Glu |
|     |     |     |     | 405 |     |     |     |     | 410 |     |     |     |     | 415 |     |
| Glu | Tyr | Lys | Asp | Pro | Val | Tyr | Thr | Pro | Met | Gly | Val | Phe | Ile | Thr | Ala |
|     |     |     | 420 |     |     |     |     | 425 |     |     |     |     | 430 |     |     |

```
Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
                500                 505                 510

Cys Ser Pro Asp Glu Ala Thr Thr Thr Lys Phe Ser Val Lys Cys Ala
                515                 520                 525

Gly Met Thr Asp Thr Ile Lys Lys Lys Val Thr Phe Asp Asn Phe Arg
                530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 34
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
                35                  40                  45

Met Glu Ile Gln Ala Asp Leu Tyr Phe His Asn Leu Lys Phe Asp Gly
50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ser Lys Met Gly Gln
                85                  90                  95

Trp Tyr Met Ile Asp Ile Cys Phe Gly Tyr Lys Gly Lys Arg Lys Leu
                100                 105                 110

His Thr Val Ile Tyr Asp Ser Leu Lys Lys Leu Pro Phe Pro Val Lys
                115                 120                 125

Lys Ile Ala Lys Asp Phe Gln Leu Pro Leu Leu Lys Gly Asp Ile Asp
                130                 135                 140

Tyr His Ala Glu Arg Pro Val Gly His Glu Ile Thr Pro Glu Glu Tyr
145                 150                 155                 160

Glu Tyr Ile Lys Asn Ala Ile Glu Ile Ile Ala Arg Ala Leu Asp Ile
                165                 170                 175

Gln Phe Lys Gln Gly Leu Asp Arg Met Thr Ala Gly Ser Asp Ser Leu
                180                 185                 190

Lys Gly Phe Lys Asp Ile Leu Ser Thr Lys Lys Phe Asn Lys Val Phe
                195                 200                 205

Pro Lys Leu Ser Leu Pro Met Asp Lys Glu Ile Arg Arg Ala Tyr Arg
```

```
                210                 215                 220
Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
            245                 250                 255

Ser Arg Pro Leu Pro Tyr Gly Ala Pro Ile Val Phe Gln Gly Lys Tyr
        260                 265                 270

Glu Lys Asp Glu Gln Tyr Pro Leu Tyr Ile Gln Arg Ile Arg Phe Glu
    275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
            325                 330                 335

Tyr Glu Met Tyr Asn Val Glu Tyr Ile Asp Gly Phe Lys Phe Arg Glu
        340                 345                 350

Lys Thr Gly Leu Phe Lys Glu Phe Ile Asp Lys Trp Thr Tyr Val Lys
    355                 360                 365

Thr His Glu Lys Gly Ala Lys Lys Gln Leu Ala Lys Leu Met Leu Asn
370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
            405                 410                 415

Glu Tyr Lys Asp Pro Val Tyr Thr Pro Met Gly Val Phe Ile Thr Ala
        420                 425                 430

Trp Ala Arg Phe Thr Thr Ile Thr Ala Ala Gln Ala Cys Tyr Asp Arg
    435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
            485                 490                 495

Tyr Ile Gln Asp Ile Tyr Ala Lys Glu Val Asp Gly Lys Leu Ile Glu
        500                 505                 510

Cys Ser Pro Asp Glu Ala Thr Thr Lys Phe Ser Val Lys Cys Ala
    515                 520                 525

Gly Met Thr Asp Thr Ile Lys Lys Lys Val Thr Phe Asp Asn Phe Arg
530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
            565                 570

<210> SEQ ID NO 35
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35
```

```
Met Ser Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu Gln His Gly Phe Lys Trp Ser Asn
65                  70                  75                  80

Glu Gly Leu Pro Asn Thr Tyr Asn Thr Ile Ser Lys Met Gly Gln
                85                  90                  95

Trp Tyr Met Ile Asp Ile Cys Phe Gly Tyr Lys Gly Lys Arg Lys Leu
                100                 105                 110

His Thr Val Ile Tyr Asp Ser Leu Lys Lys Leu Pro Phe Pro Val Lys
            115                 120                 125

Lys Ile Ala Lys Asp Phe Gln Leu Pro Leu Lys Gly Asp Ile Asp
        130                 135                 140

Tyr His Thr Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
            195                 200                 205

Pro Lys Leu Ser Leu Pro Met Asp Lys Glu Ile Arg Lys Ala Tyr Arg
        210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
            245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
        290                 295                 300

Pro Phe Phe Lys Gly Asn Glu Tyr Leu Lys Asn Ser Gly Val Glu Pro
305                 310                 315                 320

Val Glu Leu Tyr Leu Thr Asn Val Asp Leu Glu Leu Ile Gln Glu His
            325                 330                 335

Tyr Glu Leu Tyr Asn Val Glu Tyr Ile Asp Gly Phe Lys Phe Arg Glu
            340                 345                 350

Lys Thr Gly Leu Phe Lys Asp Phe Ile Asp Lys Trp Thr Tyr Val Lys
        355                 360                 365

Thr His Glu Glu Gly Ala Lys Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Asp Asp Gly Ser Leu Gly Phe Arg Val Gly Asp Glu
            405                 410                 415

Glu Tyr Lys Asp Pro Val Tyr Thr Pro Met Gly Val Phe Ile Thr Ala
```

```
                     420                 425                 430
Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Val Lys Glu Val Asp Gly Lys Leu Lys Glu
            500                 505                 510

Cys Ser Pro Asp Glu Ala Thr Thr Thr Lys Phe Ser Val Lys Cys Ala
        515                 520                 525

Gly Met Thr Asp Thr Ile Lys Lys Lys Val Thr Phe Asp Asn Phe Ala
    530                 535                 540

Val Gly Phe Ser Ser Met Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 36
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Ser Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu Gln His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Arg Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Thr Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205
```

```
Pro Lys Leu Ser Leu Pro Met Asp Lys Glu Ile Arg Lys Ala Tyr Arg
            210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Val Glu Pro
305                 310                 315                 320

Val Glu Leu Tyr Leu Thr Asn Val Asp Leu Glu Leu Ile Gln Glu His
                325                 330                 335

Tyr Glu Leu Tyr Asn Val Glu Tyr Ile Asp Gly Phe Lys Phe Arg Glu
            340                 345                 350

Lys Thr Gly Leu Phe Lys Asp Phe Ile Asp Lys Trp Thr Tyr Val Lys
            355                 360                 365

Thr His Glu Glu Gly Ala Lys Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Asp Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
        450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Val Lys Glu Val Asp Gly Lys Leu Lys Glu
            500                 505                 510

Cys Ser Pro Asp Glu Ala Thr Thr Lys Phe Ser Val Lys Cys Ala
            515                 520                 525

Gly Met Thr Asp Thr Ile Lys Lys Lys Val Thr Phe Asp Asn Phe Ala
530                 535                 540

Val Gly Phe Ser Ser Met Gly Lys Pro Lys Pro Val Gln Val Asn Gly
545                 550                 555                 560

Gly Val Val Leu Val Asp Ser Val Phe Thr Ile Lys
                565                 570
```

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

```
Glu Asn Leu Tyr Phe Gln
1               5

<210> SEQ ID NO 38
<211> LENGTH: 606
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Asn His Lys Val His His His His His Ile Glu Gly Arg Glu
1               5                   10                  15

Asn Leu Tyr Phe Gln Cys Met Glu Leu Gly Thr Leu Glu Gly Ser Met
                20                  25                  30

Lys His Met Pro Arg Lys Met Tyr Ser Cys Ala Phe Glu Thr Thr Thr
            35                  40                  45

Lys Val Glu Asp Cys Arg Val Trp Ala Tyr Gly Tyr Met Asn Ile Glu
    50                  55                  60

Asp His Ser Glu Tyr Lys Ile Gly Asn Ser Leu Asp Glu Phe Met Ala
65                  70                  75                  80

Trp Val Leu Lys Val Gln Ala Asp Leu Tyr Phe His Asn Leu Lys Phe
                85                  90                  95

Ala Gly Ala Phe Ile Ile Asn Trp Leu Glu Arg Asn Gly Phe Lys Trp
            100                 105                 110

Ser Ala Asp Gly Leu Pro Asn Thr Tyr Asn Thr Ile Ile Ser Arg Met
        115                 120                 125

Gly Gln Trp Tyr Met Ile Asp Ile Cys Leu Gly Tyr Lys Gly Lys Arg
    130                 135                 140

Lys Ile His Thr Val Ile Tyr Asp Ser Leu Lys Lys Leu Pro Phe Pro
145                 150                 155                 160

Val Lys Lys Ile Ala Lys Asp Phe Lys Leu Thr Val Leu Lys Gly Asp
                165                 170                 175

Ile Asp Tyr His Lys Glu Arg Pro Val Gly Tyr Lys Ile Thr Pro Glu
            180                 185                 190

Glu Tyr Ala Tyr Ile Lys Asn Asp Ile Gln Ile Ile Ala Glu Ala Leu
        195                 200                 205

Leu Ile Gln Phe Lys Gln Gly Leu Asp Arg Met Thr Ala Gly Ser Asp
    210                 215                 220

Ser Leu Lys Gly Phe Lys Asp Ile Ile Thr Thr Lys Lys Phe Lys Lys
225                 230                 235                 240

Val Phe Pro Thr Leu Ser Leu Gly Leu Asp Lys Glu Val Arg Tyr Ala
                245                 250                 255

Tyr Arg Gly Gly Phe Thr Trp Leu Asn Asp Arg Phe Lys Glu Lys Glu
            260                 265                 270

Ile Gly Glu Gly Met Val Phe Asp Val Asn Ser Leu Tyr Pro Ala Gln
        275                 280                 285

Met Tyr Ser Arg Leu Leu Pro Tyr Gly Glu Pro Ile Val Phe Glu Gly
    290                 295                 300

Lys Tyr Val Trp Asp Glu Asp Tyr Pro Leu His Ile Gln His Ile Arg
305                 310                 315                 320

Cys Glu Phe Glu Leu Lys Glu Gly Tyr Ile Pro Thr Ile Gln Ile Lys
                325                 330                 335

Arg Ser Arg Phe Tyr Lys Gly Asn Glu Tyr Leu Lys Ser Ser Gly Gly
```

```
            340                 345                 350
Glu Ile Ala Asp Leu Trp Leu Ser Asn Val Asp Leu Glu Leu Met Lys
        355                 360                 365

Glu His Tyr Asp Leu Tyr Asn Val Glu Tyr Ile Ser Gly Leu Lys Phe
    370                 375                 380

Lys Ala Thr Thr Gly Leu Phe Lys Asp Phe Ile Asp Lys Trp Thr Tyr
385                 390                 395                 400

Ile Lys Thr Thr Ser Glu Gly Ala Ile Lys Gln Leu Ala Lys Leu Met
                405                 410                 415

Leu Asn Ser Leu Tyr Gly Lys Phe Ala Ser Asn Pro Asp Val Thr Gly
            420                 425                 430

Lys Val Pro Tyr Leu Lys Glu Asn Gly Ala Leu Gly Phe Arg Leu Gly
        435                 440                 445

Glu Glu Glu Thr Lys Asp Pro Val Tyr Thr Pro Met Gly Val Phe Ile
    450                 455                 460

Thr Ala Trp Ala Arg Tyr Thr Thr Ile Thr Ala Ala Gln Ala Cys Tyr
465                 470                 475                 480

Asp Arg Ile Ile Tyr Cys Asp Thr Asp Ser Ile His Leu Thr Gly Thr
                485                 490                 495

Glu Ile Pro Asp Val Ile Lys Asp Ile Val Asp Pro Lys Lys Leu Gly
            500                 505                 510

Tyr Trp Ala His Glu Ser Thr Phe Lys Arg Ala Lys Tyr Leu Arg Gln
        515                 520                 525

Lys Thr Tyr Ile Gln Asp Ile Tyr Met Lys Glu Val Asp Gly Lys Leu
    530                 535                 540

Val Glu Gly Ser Pro Asp Asp Tyr Thr Asp Ile Lys Phe Ser Val Lys
545                 550                 555                 560

Cys Ala Gly Met Thr Asp Lys Ile Lys Lys Glu Val Thr Phe Glu Asn
                565                 570                 575

Phe Lys Val Gly Phe Ser Arg Lys Met Lys Pro Lys Pro Val Gln Val
            580                 585                 590

Pro Gly Gly Val Val Leu Val Asp Asp Thr Phe Thr Ile Lys
        595                 600                 605

<210> SEQ ID NO 39
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met His His His His His Leu Leu Gly Gly Gly Glu Asn Leu
1               5                   10                  15

Tyr Phe Gln Cys Gly Gly Gly Ser Ala Ala Gly Ser Ala Ala
                20                  25                  30

Arg Lys Met Phe Ser Cys Asp Phe Glu Thr Thr Thr Lys Leu Asp Asp
        35                  40                  45

Cys Arg Val Trp Ala Tyr Gly Tyr Met Glu Ile Gly Asn Leu Asp Asn
    50                  55                  60

Tyr Lys Ile Gly Asn Ser Leu Asp Glu Phe Met Gln Trp Val Met Glu
65                  70                  75                  80

Ile Gln Ala Asp Leu Tyr Phe His Asn Leu Lys Phe Asp Gly Ala Phe
                85                  90                  95
```

Ile Val Asn Trp Leu Glu His His Gly Phe Lys Trp Ser Asn Glu Gly
                100                 105                 110

Leu Pro Asn Thr Tyr Asn Thr Ile Ile Ser Lys Met Gly Gln Trp Tyr
            115                 120                 125

Met Ile Asp Ile Cys Phe Gly Tyr Lys Gly Lys Arg Lys Leu His Thr
        130                 135                 140

Val Ile Tyr Asp Ser Leu Lys Lys Leu Pro Phe Pro Val Lys Lys Ile
145                 150                 155                 160

Ala Lys Asp Phe Gln Leu Pro Leu Leu Lys Gly Asp Ile Asp Tyr His
                165                 170                 175

Ala Glu Arg Pro Val Gly His Glu Ile Thr Pro Glu Glu Tyr Glu Tyr
            180                 185                 190

Ile Lys Asn Ala Ile Glu Ile Ile Ala Arg Ala Leu Asp Ile Gln Phe
        195                 200                 205

Lys Gln Gly Leu Asp Arg Met Thr Ala Gly Ser Asp Ser Leu Lys Gly
        210                 215                 220

Phe Lys Asp Ile Leu Ser Thr Lys Lys Phe Asn Lys Val Phe Pro Lys
225                 230                 235                 240

Leu Ser Leu Pro Met Asp Lys Glu Ile Arg Arg Ala Tyr Arg Gly Gly
                245                 250                 255

Phe Thr Trp Leu Asn Asp Lys Tyr Lys Glu Lys Glu Ile Gly Glu Gly
            260                 265                 270

Met Val Phe Asp Val Asn Ser Leu Tyr Pro Ser Gln Met Tyr Ser Arg
        275                 280                 285

Pro Leu Pro Tyr Gly Ala Pro Ile Val Phe Gln Gly Lys Tyr Glu Lys
            290                 295                 300

Asp Glu Gln Tyr Pro Leu Tyr Ile Gln Arg Ile Arg Phe Glu Phe Glu
305                 310                 315                 320

Leu Lys Glu Gly Tyr Ile Pro Thr Ile Gln Ile Lys Lys Asn Pro Phe
                325                 330                 335

Phe Lys Gly Asn Glu Tyr Leu Lys Asn Ser Gly Ala Glu Pro Val Glu
            340                 345                 350

Leu Tyr Leu Thr Asn Val Asp Leu Glu Leu Ile Gln Glu His Tyr Glu
        355                 360                 365

Met Tyr Asn Val Glu Tyr Ile Asp Gly Phe Lys Phe Arg Glu Lys Thr
        370                 375                 380

Gly Leu Phe Lys Glu Phe Ile Asp Lys Trp Thr Tyr Val Lys Thr His
385                 390                 395                 400

Glu Lys Gly Ala Lys Lys Gln Leu Ala Lys Leu Met Leu Asn Ser Leu
                405                 410                 415

Tyr Gly Lys Phe Ala Ser Asn Pro Asp Val Thr Gly Lys Val Pro Tyr
            420                 425                 430

Leu Lys Glu Asp Gly Ser Leu Gly Phe Arg Val Gly Asp Glu Glu Tyr
        435                 440                 445

Lys Asp Pro Val Tyr Thr Pro Met Gly Val Phe Ile Thr Ala Trp Ala
        450                 455                 460

Arg Phe Thr Thr Ile Thr Ala Ala Gln Ala Cys Tyr Asp Arg Ile Ile
465                 470                 475                 480

Tyr Cys Asp Thr Asp Ser Ile His Leu Thr Gly Thr Glu Val Pro Glu
                485                 490                 495

Ile Ile Lys Asp Ile Val Asp Pro Lys Lys Leu Gly Tyr Trp Ala His
            500                 505                 510

Glu Ser Thr Phe Lys Arg Ala Lys Tyr Leu Arg Gln Lys Thr Tyr Ile

```
            515                 520                 525
Gln Asp Ile Tyr Ala Lys Glu Val Asp Gly Lys Leu Ile Glu Cys Ser
        530                 535                 540

Pro Asp Glu Ala Thr Thr Thr Lys Phe Ser Val Lys Cys Ala Gly Met
545                 550                 555                 560

Thr Asp Thr Ile Lys Lys Lys Val Thr Phe Asp Asn Phe Arg Val Gly
                565                 570                 575

Phe Ser Ser Thr Gly Lys Pro Lys Pro Val Gln Val Asn Gly Gly Val
            580                 585                 590

Val Leu Val Asp Ser Val Phe Thr
            595                 600

<210> SEQ ID NO 40
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Ser His His His His His His Ser Met Ser Gly Leu Asn Asp Ile
1               5                   10                  15

Phe Glu Ala Gln Lys Ile Glu Trp His Glu Gly Ala Pro Gly Ala Arg
            20                  25                  30

Gly Ser Lys His Met Pro Arg Lys Met Phe Ser Cys Asp Phe Glu Thr
        35                  40                  45

Thr Thr Lys Leu Asp Asp Cys Arg Val Trp Ala Tyr Gly Tyr Met Glu
50                  55                  60

Ile Gly Asn Leu Asp Asn Tyr Lys Ile Gly Asn Ser Leu Asp Glu Phe
65                  70                  75                  80

Met Gln Trp Val Met Glu Ile Gln Ala Asp Leu Tyr Phe His Asn Leu
                85                  90                  95

Lys Phe Asp Gly Ala Phe Ile Val Asn Trp Leu Glu His His Gly Phe
            100                 105                 110

Lys Trp Ser Asn Glu Gly Leu Pro Asn Thr Tyr Asn Thr Ile Ile Ser
        115                 120                 125

Lys Met Gly Gln Trp Tyr Met Ile Asp Ile Cys Phe Gly Tyr Lys Gly
130                 135                 140

Lys Arg Lys Leu His Thr Val Ile Tyr Asp Ser Leu Lys Lys Leu Pro
145                 150                 155                 160

Phe Pro Val Lys Lys Ile Ala Lys Asp Phe Gln Leu Pro Leu Leu Lys
                165                 170                 175

Gly Asp Ile Asp Tyr His Ala Glu Arg Pro Val Gly His Glu Ile Thr
            180                 185                 190

Pro Glu Glu Tyr Glu Tyr Ile Lys Asn Ala Ile Glu Ile Ala Arg
        195                 200                 205

Ala Leu Asp Ile Gln Phe Lys Gln Gly Leu Asp Arg Met Thr Ala Gly
        210                 215                 220

Ser Asp Ser Leu Lys Gly Phe Lys Asp Ile Leu Ser Thr Lys Lys Phe
225                 230                 235                 240

Asn Lys Val Phe Pro Lys Leu Ser Leu Pro Met Asp Lys Glu Ile Arg
                245                 250                 255

Arg Ala Tyr Arg Gly Gly Phe Thr Trp Leu Asn Asp Lys Tyr Lys Glu
            260                 265                 270
```

```
Lys Glu Ile Gly Glu Gly Met Val Phe Asp Val Asn Ser Leu Tyr Pro
                275                 280                 285
Ser Gln Met Tyr Ser Arg Pro Leu Pro Tyr Gly Ala Pro Ile Val Phe
        290                 295                 300
Gln Gly Lys Tyr Glu Lys Asp Glu Gln Tyr Pro Leu Tyr Ile Gln Arg
305                 310                 315                 320
Ile Arg Phe Glu Phe Glu Leu Lys Glu Gly Tyr Ile Pro Thr Ile Gln
                325                 330                 335
Ile Lys Lys Asn Pro Phe Phe Lys Gly Asn Glu Tyr Leu Lys Asn Ser
        340                 345                 350
Gly Ala Glu Pro Val Glu Leu Tyr Leu Thr Asn Val Asp Leu Glu Leu
            355                 360                 365
Ile Gln Glu His Tyr Glu Met Tyr Asn Val Gly Tyr Ile Asp Gly Phe
        370                 375                 380
Lys Phe Arg Glu Lys Thr Gly Leu Phe Lys Glu Phe Ile Asp Lys Trp
385                 390                 395                 400
Thr Tyr Val Lys Thr Arg Glu Lys Gly Ala Lys Lys Gln Leu Ala Lys
                405                 410                 415
Leu Met Leu Asn Ser Leu Tyr Gly Lys Phe Ala Ser Asn Pro Asp Val
        420                 425                 430
Thr Gly Lys Val Pro Tyr Leu Lys Glu Asp Gly Ser Leu Gly Phe Arg
            435                 440                 445
Val Gly Asp Glu Glu Tyr Lys Asp Pro Val Tyr Thr Pro Met Gly Val
        450                 455                 460
Phe Ile Thr Ala Trp Ala Arg Phe Thr Thr Ile Thr Ala Ala Gln Ala
465                 470                 475                 480
Cys Tyr Asp Arg Ile Ile Tyr Cys Asp Thr Asp Ser Ile His Leu Thr
                485                 490                 495
Gly Thr Glu Val Pro Glu Ile Ile Lys Asp Ile Val Asp Pro Lys Lys
        500                 505                 510
Leu Gly Tyr Trp Ala His Glu Ser Thr Phe Lys Arg Ala Lys Tyr Leu
            515                 520                 525
Arg Gln Lys Thr Tyr Ile Gln Asp Ile Tyr Ala Lys Glu Val Asp Gly
530                 535                 540
Lys Leu Ile Glu Cys Ser Pro Asp Glu Ala Thr Thr Thr Lys Phe Ser
545                 550                 555                 560
Val Lys Cys Ala Gly Met Thr Asp Thr Ile Lys Lys Val Thr Phe
                565                 570                 575
Asp Asn Phe Arg Val Gly Phe Ser Ser Thr Gly Lys Pro Lys Pro Val
        580                 585                 590
Gln Val Asn Gly Gly Val Val Leu Val Asp Ser Val Phe Thr Ile Lys
            595                 600                 605

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttatctttgt gggtgacagg ttttcctgt caccc                               35

<210> SEQ ID NO 42
<211> LENGTH: 39
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42 ttttttttgcc cccagggtga caggttttc ctgtcaccc                           39

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43 ttttttttgca ggtgacaggt ttttcctgtc acctgc                             36

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cgttaaccgc ccgctccttt gcaac                                          25

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gttgcaaagg agcgggcg                                                  18

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cagtaacgga gttggttgga cggctgcgag gc                                  32

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcctcgcagc cgtccaacca actcc                                          25

<210> SEQ ID NO 48
<211> LENGTH: 26
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 48 tttttttttac ccccgggtga caggtt                                            26

<210> SEQ ID NO 49
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tttttccccg acgatgcctc cccgacacgg aggttctatc atcgtcatcg tcatcgtcat        60
cgt                                                                     63

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tgatagaacc tccgtgtc                                                      18

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggggaggcat cgtcgggaaa a                                                  21

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Arg Arg Ala Ser Leu Gly
1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Lys Pro Gln Gln Phe
1               5
```

```
<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 54

His His His His His His
1               5

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: misc_feature
<222> LOCATION: (1)..(12)
<223> OTHER INFORMATION: This sequence may encompass 3-12 "His" residues
<220> FEATURE:
<223> OTHER INFORMATION: See specification as filed for detailed
      description of substitutions and preferred embodiments

<400> SEQUENCE: 55

His His His His His His His His His His His His
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      polycysteine tag
<220> FEATURE:
<221> NAME/KEY: misc_feature
<222> LOCATION: (1)..(12)
<223> OTHER INFORMATION: This sequence may encompass 6-12 "Cys" residues
<220> FEATURE:
<223> OTHER INFORMATION: See specification as filed for detailed
      description of substitutions and preferred embodiments

<400> SEQUENCE: 56

Cys Cys Cys Cys Cys Cys Cys Cys Cys Cys Cys Cys
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      polylysine tag
<220> FEATURE:
<221> NAME/KEY: misc_feature
<222> LOCATION: (1)..(12)
<223> OTHER INFORMATION: This sequence may encompass 6-12 "Lys" residues
<220> FEATURE:
<223> OTHER INFORMATION: See specification as filed for detailed
      description of substitutions and preferred embodiments

<400> SEQUENCE: 57

Lys Lys Lys Lys Lys Lys Lys Lys Lys Lys Lys Lys
1               5                   10
```

```
<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Arg Arg Ala Ser Leu
1               5

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Ile Glu Thr
1

<210> SEQ ID NO 60
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ttcctgtcac cc                                                          12

<210> SEQ ID NO 61
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gggggaaaaa aaa                                                         13

<210> SEQ ID NO 62
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gggggtaaaa aaaa                                                        14
```

LABELED ENZYME COMPOSITIONS, METHODS AND SYSTEMS

CROSS-REFERENCE TO RELATED APPLICATIONS

This application is a divisional of U.S. Non-Provisional application Ser. No. 15/401,757 filed Jan. 9, 2017, which is a divisional of U.S. Non-Provisional application Ser. No. 14/284,187 filed May 21, 2014, now U.S. Pat. No. 9,567,629 issued on Feb. 14, 2017, which is a divisional of U.S. Non-Provisional application Ser. No. 13/594,532, filed on Aug. 24, 2012, now U.S. Pat. No. 8,741,618 issued on Jun. 3, 2014, which is a continuation of U.S. Non-Provisional application Ser. No. 12/748,314, filed on Mar. 26, 2010, now abandoned, which claims the filing date benefit of U.S. Provisional Application No. 61/307,356, filed on Feb. 23, 2010; 61/299,917, filed on Jan. 29, 2010; 61/299,919, filed on Jan. 29, 2010; 61/293,616, filed on Jan. 8, 2010; 61/293,618, filed on Jan. 8, 2010; 61/289,388; filed on Dec. 22, 2009; 61/263,974, filed on Nov. 24, 2009; 61/245,457, filed on Sep. 24, 2009; 61/242,771, filed on Sep. 15, 2009; 61/184,770, filed on Jun. 5, 2009; and 61/164,324, filed on Mar. 27, 2009. The contents of each of the foregoing patent applications are incorporated by reference in their entirety.

SEQUENCE LISTING

The instant application contains a Sequence Listing which has been submitted via EFS-Web and is hereby incorporated by reference in its entirety. Said ASCII copy, created on Jun. 17, 2010, is named LT00053.txt, and is 207,218 bytes in size.

FIELD

The present disclosure relates generally to conjugates comprising a biomolecule linked to a label, for use in a variety of biological applications. More particularly, disclosed herein are labeled polymerase conjugates comprising a polymerase linked to a label, wherein the conjugate has polymerase activity.

BACKGROUND

Labeling of biomolecules is frequently performed in biological assays. Such labeling studies have been widely used to elucidate structural and/or functional properties of various biomolecules, including carbohydrates, lipids, nucleic acids, nucleotides and proteins. Enzymes are of particular interest because they catalyze fundamental biochemical reactions within living organisms. For example, DNA and RNA polymerases assist in genomic replication and transcription by catalyzing the polymerization of nucleotides into nucleic acids.

Conventional labeling techniques generally involve the attachment of one or few organic labels comprising fluorescent small molecules, e.g., dyes, to the biomolecule of interest. However, such labeled conjugates are generally not suitable for use in single molecule assays due the toxicity effect of the label on the biomolecule, and/or the poor detectability (as characterized, for example, by low signal/noise ratio, brightness, e.g., quantum yield, signal lifetime, etc) and photostability of such conjugates. There is therefore a need in the art for labeled biomolecule conjugates that emit stronger and more stable signals than is feasible with conjugates produced by conventional labeling methods, and that retain sufficient biological activity for use in single molecule assays.

Disclosed herein are improved labeled biomolecule conjugates, as well as novel methods of making and using such conjugates. Such conjugates comprise labeled biomolecules exhibiting improved biological activity, detectability and/or photostability and that are suitable for use in single molecule assays. In some embodiments, the conjugates comprise a biomolecule linked to multiple dye labels that retain sufficient biological activity for use in single molecule assays.

The superior detectability of the conjugates of the present disclosure permits a wide range of powerful new approaches not hitherto feasible using conventional labeling methods, including, for example, extended imaging of biological samples over an extended period of time, real time in situ visualization of biomolecules or biomolecular activity in vivo or in vitro, optical coding of biomolecules, physical manipulation of biomolecules and/or biomolecular sorting, all of which can optionally be performed in high-throughput format.

For example, disclosed herein are labeled polymerase conjugates comprising a polymerase linked to a label that emit signals of superior intensities and durations, thus improving their performance in single molecule sequencing applications. In some embodiments, the labeled polymerase conjugates include multiple dyes (typically three or more) linked in tandem to a single polymerase without significant loss of polymerase activity. In other embodiments, the labeled polymerase conjugates comprise a nanoparticle label that typically emits stronger and more stable signals relative to conventional organic dyes.

The labeled polymerase conjugates provided herein can undergo FRET with an acceptor-labeled nucleotide bound to the active site in such a manner that the resulting FRET-based signal is readily detectable in a single molecule system, and also emit signals of sufficient duration to permit longer "reads" from a single nucleic acid molecule, thus permitting single molecule reads of increased length and accuracy. Such conjugates also retain high levels of polymerase activity, thus increasing the efficiency of single molecule sequencing systems using such conjugates.

The production of such improved conjugates is associated with several technical challenges. For example, biomolecules labeled with nanoparticles frequently exhibit a high degree of aggregation; it can also be difficult to precisely control the ratios at which the biomolecule will attach to the nanoparticle, a problem compounded by the difficulty of determining the stochiometric composition (i.e., ratio of biomolecule to nanoparticle) of the resulting conjugates. Similarly, while the detectability of conjugates comprising organic dye labels can be improved by increasing the number of dye labels linked to the biomolecule, such increased dye loading is typically accompanied by a reduction or loss in activity of the biomolecule. There remains a need in the art for labeled biomolecule conjugates exhibiting reduced aggregation and increased biomolecular activity along with superior detectability. There is also a need for improved methods for conjugating biomolecules, e.g., proteins, to labels wherein the stochiometry of the conjugated components can be reliably controlled and the activity of the biomolecule preserved.

SUMMARY

Disclosed herein are labeled biomolecule conjugates useful in a wide range of biological applications, methods of making and using such conjugates, as well as systems, apparatuses and kits comprising such conjugates.

For example, in one embodiment, the disclosure relates to a labeled polymerase conjugate comprising a polymerase linked to a plurality of labels. The conjugate can have polymerase activity.

In some embodiments, the disclosure relates to a method for creating a labeled polymerase conjugate, comprising linking a polymerase to a plurality of labels to form a labeled polymerase conjugate having polymerase activity.

In some embodiments, the disclosure relates to a labeled polymerase conjugate, comprising a polymerase linked to a plurality of labels to form a labeled polymerase conjugate, where the conjugate has polymerase activity, and where at least one label of the conjugate performs energy transfer with a labeled nucleotide bound to an active site of the polymerase.

In some embodiments, the disclosure relates to a method for generating a signal, comprising: contacting a labeled polymerase conjugate inculding a polymerase linked to a label with a labeled nucleotide under conditions where the polymerase catalyzes the incorporation of the labeled nucleotide into a nucleic acid, and the label emits, or induces the emission of, a signal indicative of such nucleotide incorporation.

In some embodiments, the disclosure relates to a labeled polymerase conjugate, comprising: a polymerase linked to one or more labels, where the conjugate has polymerase activity and emits upon continuous excitation a total photon count of at least $10^8$ photons before irreversibly photobleaching. In some embodiments, the conjugate emits a total photon count of at least $10^2$, $10^3$, $10^4$, $10^5$, $10^6$, $10^7$, $10^8$ or $10^9$ photons as measured using a test detection system.

In some embodiments, the disclosure relates to a labeled polymerase conjugate, comprising: a first member of a binding pair linked to a polymerase; and a second member of the binding pair linked to at least one label, where the first and the second member of the binding pair are linked to each other to form a labeled polymerase conjugate having polymerase activity.

DETAILED DESCRIPTION OF THE DRAWINGS

The following figures form part of the present specification and are included to further demonstrate certain aspects of the disclosure herein by way of illustrating non-limiting embodiments and examples. This disclosure may be better understood by reference to one or more of these figures in combination with the detailed description of specific embodiments presented herein.

FIG. 1 discloses SEQ ID NO: 62.

DETAILED DESCRIPTION OF THE SEQUENCE LISTINGS

Figure 1:
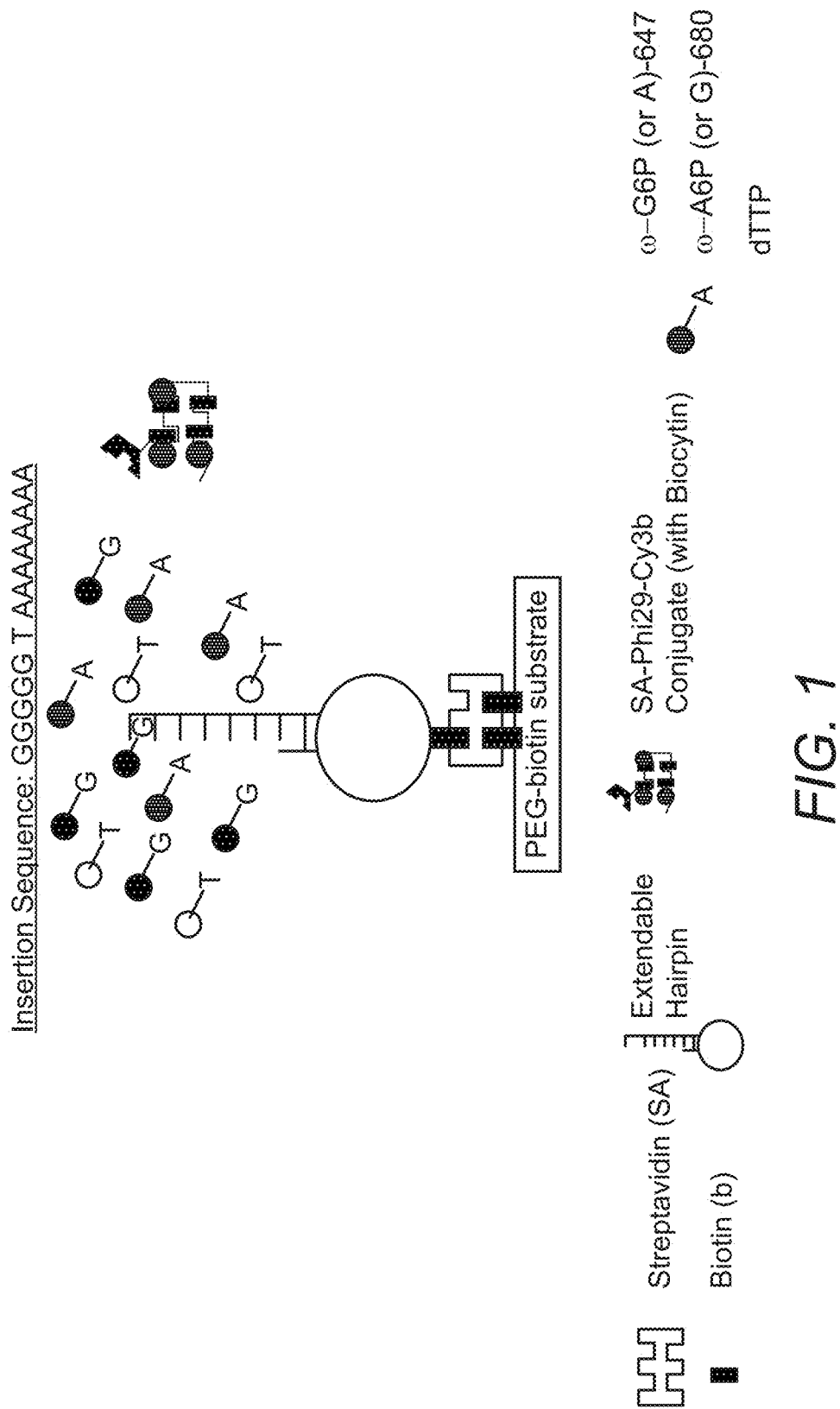
FIG. 1 depicts an exemplary reaction pathway for preparing a dye-labeled polymerase conjugate according to the present disclosure.

SEQ ID NO: 1 comprises the amino acid sequence of an *E. coli* K12 DNA polymerase.

SEQ ID NO: 2 comprises the amino acid sequence of the Klenow form of an *E. coli* K12 DNA polymerase.

SEQ ID NO: 3 comprises the amino acid sequence of a DNA polymerase of the bacteriophage Phi-29.

SEQ ID NO: 4 comprises the amino acid sequence of a peptide linker, herein referred to as "H-linker".

SEQ ID NO: 5 comprises the amino acid sequence of a peptide linker, herein referred to as "F-linker".

SEQ ID NO: 6 comprises the amino acid sequence of a Phi-29 polymerase peptide comprising a polycysteine tag and the F-linker sequence at its N-terminus.

SEQ ID NO: 7 comprises the amino acid sequence of a Phi-29 polymerase peptide comprising a polylysine tag and the F-linker sequence at its N-terminus.

SEQ ID NO: 8 comprises the amino acid sequence of a Phi-29 polymerase peptide comprising a His-tag, an F-linker peptide and a transglutaminase tag at its N-terminus.

SEQ ID NO: 9 comprises the amino acid sequence of a Phi-29 polymerase peptide comprising a protein kinase A (PKA) tag and the F-linker at its N-terminus.

SEQ ID NO: 10 comprises the amino acid sequence of a biotin acceptor peptide in an exemplary biotin ligase recognition sequence.

SEQ ID NO: 11 comprises the amino acid sequence of HBP1, a Phi-29 polymerase peptide comprising a His-tag and biotin acceptor peptide sequence at its N-terminus.

SEQ ID NO: 12 comprises the amino acid sequence of a Phi-29 polymerase peptide comprising a His-tag and the H-linker at its N-terminus.

SEQ ID NO: 13 comprises the amino acid sequence of a Phi-29 polymerase peptide comprising a His-tag and the F-linker at its N-terminus.

SEQ ID NO: 14 comprises the amino acid sequence of HP1, a Phi-29 polymerase peptide that lacks exonuclease activity and comprises an N-terminal His-tag, an intervening linker sequence, and the D12A and D66A mutations.

SEQ ID NO: 15 comprises the amino acid sequence of a Cyanophage S-CBP1 DNA polymerase.

SEQ ID NO: 16 comprises the amino acid sequence of a Cyanophage S-CBP2 DNA polymerase.

SEQ ID NO: 17 comprises the amino acid sequence of a Cyanophage S-CBP3 DNA polymerase.

SEQ ID NO: 18 comprises the amino acid sequence of a Cyanophage Syn-5 DNA polymerase.

SEQ ID NO: 19 comprises the amino acid sequence of a Cyanophage 5-CBP42 DNA polymerase.

SEQ ID NO: 20 comprises the amino acid sequence of be a Synechococcus phage P60 DNA polymerase.

SEQ ID NO: 21 comprises the amino acid sequence of a Roseobacter phage SIO1 DNA polymerase.

SEQ ID NO: 22 comprises the amino acid sequence of a *Oedogonium cardiacum* chloroplast DNA Polymerase.

SEQ ID NO: 23 comprises the amino acid sequence of a Salterprovirus Hist polymerase.

SEQ ID NO: 24 comprises the amino acid sequence of a Salterprovirus His2 polymerase.

SEQ ID NO: 25 comprises the amino acid sequence of an *Ostreococcus tauri* V5 DNA polymerase.

SEQ ID NO: 26 comprises the amino acid sequence of an *Ectocarpus siliculosus* virus 1 DNA polymerase.

SEQ ID NO: 27 comprises the amino acid sequence of HP1 Q380A, a mutant form of HP1 comprising the mutation Q380A.

SEQ ID NO: 28 comprises the amino acid sequence of HP1 S388G, a mutant form of HP1 comprising the mutation S388G.

SEQ ID NO: 29 comprises the amino acid sequence of an RB69 polymerase comprising a His-tag at its N-terminus.

SEQ ID NO: 30 comprises the amino acid sequence of a GA-1 polymerase comprising a His-tag at its N-terminus.

SEQ ID NO: 31 comprises the amino acid sequence of a B103 polymerase comprising a His-tag at its N-terminus.

SEQ ID NO: 32 comprises the amino acid sequence of B103 polymerase.

SEQ ID NO: 33 comprises the amino acid sequence of a mutant B103 polymerase.

SEQ ID NO: 34 comprises the amino acid sequence of a second mutant B103 polymerase.

SEQ ID NO: 35 comprises the amino acid sequence of an M2Y DNA polymerase.

SEQ ID NO: 36 comprises the amino acid sequence of an Nf DNA polymerase.

SEQ ID NO: 37 comprises the amino acid sequence of an exemplary recognition sequence for the Tobacco Etch Virus (TEV) protease.

SEQ ID NO: 38 comprises the amino acid sequence of a Phi-29 polymerase fused to a TEV protease cleavage site.

SEQ ID NO: 39 comprises the amino acid sequence of a B103 polymerase fused to a TEV protease cleavage site.

SEQ ID NO: 40 comprises the amino acid sequence of a mutant B103 polymerase fused to a His-tag and biotin acceptor peptide sequence at its N-terminus.

SEQ ID NO: 41 comprises the nucleotide sequence of an oligonucleotide template used in a nucleic acid binding assay.

SEQ ID NO: 42 comprises the nucleotide sequence of an oligonucleotide primer used in a nucleic acid binding assay.

SEQ ID NO: 43 comprises the nucleotide sequence of a fluorescein-labeled oligonucleotide primer used to measure primer extension activity of a polymerase sample according to the exemplary assays as described herein.

SEQ ID NO: 44 comprises the nucleotide sequence of an exemplary polynucleotide template used in a stopped-flow assay for nucleotide incorporation kinetics as described, for example, in Example 10.

SEQ ID NO: 45 comprises the nucleotide sequence of an exemplary oligonucleotide primer used in a stopped-flow assay for nucleotide incorporation kinetics as described, for example, in Example 10.

SEQ ID NO: 46 comprises the nucleotide sequence of an exemplary polynucleotide template used in a stopped-flow assay for nucleotide incorporation kinetics as described, for example, in Example 10.

SEQ ID NO: 47 comprises the nucleotide sequence of an exemplary oligonucleotide primer used in a stopped-flow assay for nucleotide incorporation kinetics as described, for example, in Example 10.

SEQ ID NO: 48 comprises the nucleotide sequence of an exemplary polynucleotide hairpin template used in an exemplary assay for nucleotide incorporation as described, for example, in Example 8.

SEQ ID NO: 49 comprises the nucleotide sequence of an exemplary polynucleotide template used in an exemplary assay for nucleotide incorporation.

SEQ ID NO: 50 comprises the nucleotide sequence of an exemplary oligonucleotide primer used in an exemplary assay for nucleotide incorporation.

SEQ ID NO: 51 comprises the nucleotide sequence of an exemplary oligonucleotide primer used in an exemplary assay for nucleotide incorporation.

DETAILED DESCRIPTION

The present disclosure relates to compositions, methods, systems, apparatuses and kits comprising labeled biomolecule conjugates including a biomolecule linked to a label, wherein the conjugate has a biological activity that is characteristic of the biomolecule. Typically, the label of the conjugate emits, or is capable of emitting, a signal. In some embodiments, the label induces emission, or is capable of inducing emission (e.g., via energy transfer) of the signal. Optionally, the signal can indicate various aspects of the biological activity of the conjugate. In some embodiments, the conjugate can be visualized and tracked in real time, optionally in single molecule format. Also disclosed herein are improved methods for preparing such conjugates, as well as methods, systems, apparatuses and kits for using such conjugates in biological applications, including for example single molecule reactions.

In some embodiments, the biomolecule is a polymerase and the labeled biomolecule conjugate is a labeled polymerase conjugate including a polymerase linked to a label, wherein the conjugate has polymerase activity.

Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is set forth herein that is contrary to or otherwise inconsistent with any definition set forth in the patents, patent applications, published applications, and other publications that are herein incorporated by reference, the definition and/or description set forth herein prevails over the definition that is incorporated by reference.

The practice of the present disclosure will employ, unless otherwise indicated, conventional techniques of molecular biology, microbiology and recombinant DNA techniques, which are within the skill of the art. Such techniques are explained fully in the literature. See, for example, Sambrook, J., and Russell, D. W., 2001, *Molecular Cloning: A Laboratory Manual*, Third Edition; Ausubel, F. M., et al., eds., 2002, *Short Protocols In Molecular Biology*, Fifth Edition.

As used herein, the terms "link", "linked", "linkage" and variants thereof comprise any type of fusion, bond, adherence or association that is of sufficient stability to withstand use in the particular biological application of interest. Such linkage can comprise, for example, covalent, ionic, hydrogen, dipole-dipole, hydrophilic, hydrophobic, or affinity bonding, bonds or associations involving van der Waals forces, mechanical bonding, and the like. Optionally, such linkage can occur between a combination of different molecules, including but not limited to: between a nanoparticle and a protein; between a protein and a label; between a linker and a functionalized nanoparticle; between a linker and a protein; and the like. Some examples of linkages can be found, for example, in Hermanson, G., *Bioconjugate Techniques*, Second Edition (2008); Aslam, M., Dent, A., *Bioconjugation: Protein Coupling Techniques for the Biomedical Sciences*, London: Macmillan (1998); Aslam, M., Dent, A., *Bioconjugation: Protein Coupling Techniques for the Biomedical Sciences*, London: Macmillan (1998).

As used herein, the term "linker" and its variants comprises any composition, including any molecular complex or molecular assembly, that serves to link two or more compounds.

As used herein, the term "polymerase" and its variants comprise any enzyme that can catalyze the polymerization of nucleotides (including analogs thereof) into a nucleic acid strand. Typically but not necessarily such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases (such as for example Phi-29 DNA polymerase, reverse transcriptases and *E. coli* DNA polymerase) and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide, such as, for example, a reporter enzyme or a processivity-enhancing domain. One exemplary embodiment of such a polymerase is Phusion® DNA polymerase (New England Biolabs), which comprises a *Pyrococcus*-like polymerase fused to a processivity-enhancing domain as described, for example, in in U.S. Pat. No. 6,627,424.

As used herein, the term "polymerase activity" and its variants, when used in reference to a given polymerase, comprises any in vivo or in vitro enzymatic activity characteristic of a given polymerase that relates to catalyzing the polymerization of nucleotides into a nucleic acid strand, e.g., primer extension activity, and the like. Typically, but not necessarily such nucleotide polymerization occurs in a template-dependent fashion. In addition to such polymerase activity, the polymerase can typically possess other enzymatic activities, for example, 3' to 5' exonuclease activity.

As used herein, the term "nucleotide" and its variants comprises any compound that can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally occurring nucleotides but also any analogs, regardless of their structure, that can bind selectively to, or can be polymerized by, a polymerase.

While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281. In some embodiments, the nucleotide comprises a label and referred to herein as a "labeled nucleotide"; the label of the labeled nucleotide is referred to herein as a "nucleotide label". In some embodiments, the label can be in the form of a fluorescent dye attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

As used herein, the term "nucleotide incorporation" and its variants comprises polymerization of one or more nucleotides into a nucleic acid strand.

As used herein, the term "biomolecule" and its variants comprises any compound isolated from a living organism, as well as analogs (including engineered and/or synthetic analogs), derivatives, mutants or variants and/or biologically active fragments of the same. For example, the biomolecule can be a protein (e.g., enzyme), nucleic acid, nucleotide, carbohydrate or lipid. In some embodiments, the biomolecule can be an engineered or synthetic analog of a compound isolated from a living cell that is structurally different from the compound but retains a biological activity characteristic of that compound. As used herein, the term "target" and its variants comprises any compound that is capable of binding specifically to a particular biomolecule. In one exemplary embodiment, the target of an enzyme can be, for example, a substrate of the enzyme.

As used herein, the term "biological activity" and its variants, when used in reference to a biomolecule (such as, for example, an enzyme) refers to any in vivo or in vitro activity that is characteristic of the biomolecule itself, including the interaction of the biomolecule with one or more targets. For example, biological activity can optionally include the selective binding of an antibody to an antigen, the enzymatic activity of an enzyme, and the like. Such activity can also include, without limitation, binding, fusion, bond formation, association, approach, catalysis or chemical reaction, optionally with another biomolecule or with a target molecule.

As used herein, the term "biologically active fragment" and its variants refers to any fragment, derivative or analog of a biomolecule that possesses an in vivo or in vitro activity that is characteristic of the biomolecule itself. For example, the biomolecule can be an antibody that is characterized by antigen-binding activity, or an enzyme characterized by the ability to catalyze a particular biochemical reaction, etc. Biologically active fragments can optionally exist in vivo, such as, for example, fragments which arise from post transcriptional processing or which arise from translation of alternatively spliced RNAs, or alternatively can be created through engineering, bulk synthesis, or other suitable manipulation. Biologically active fragments include fragments expressed in native or endogenous cells as well as those made in expression systems such as, for example, in bacterial, yeast, insect or mammalian cells. Because biomolecules often exhibit a range of physiological properties and because such properties can be attributable to different portions of the biomolecule, a useful biologically active fragment can be a fragment of a biomolecule that exhibits a biological activity in any biological assay. In some embodiments, the fragment or analog possesses 10%, 40%, 60%, 70%, 80% or 90% or greater of the activity of the biomolecule in any in vivo or in vitro assay of interest.

The term "modification" or "modified" and their variants, as used herein with reference to a protein, comprise any change in the structural, biological and/or chemical properties of the protein, particularly a change in the amino acid sequence of the protein. In some embodiments, the modification can comprise one or more amino acid mutations, including without limitation amino acid additions, deletions and substitutions (including both conservative and non-conservative substitutions).

As used herein, the terms "identical" or "percent identity," and their variants, when used in the context of two or more nucleic acid or polypeptide sequences, refer to two or more sequences or subsequences that are the same or have a specified percentage of amino acid residues or nucleotides that are the same, when compared and aligned for maximum correspondence, as measured using any one or more of the following sequence comparison algorithms: Needleman-Wunsch (see, e.g., Needleman, Saul B.; and Wunsch, Christian D. (1970). "*A general method applicable to the search for similarities in the amino acid sequence of two proteins*" *Journal of Molecular Biology* 48 (3):443-53); Smith-Waterman (see, e.g., Smith, Temple F.; and Waterman, Michael S., "*Identification of Common Molecular Subsequences*" (1981) *Journal of Molecular Biology* 147:195-197); or BLAST (Basic Local Alignment Search Tool; see, e.g., Altschul S F, Gish W, Miller W, Myers E W, Lipman D J, "*Basic local alignment search tool*" (1990) *J Mol Biol* 215 (3):403-410).

The terms "resonance energy transfer" and "RET" and their variants, as used herein, refer to a radiationless transmission of excitation energy from a first moiety, termed a donor moiety, to a second moiety termed an acceptor moiety. One type of RET includes Forster Resonance Energy Transfer (FRET), in which a fluorophore (the donor) in an excited state transfers its energy to a proximal molecule (the acceptor) by nonradiative dipole-dipole interaction. See, e.g., Forster, T. "Intermolecular Energy Migration and Fluorescence", *Ann. Phys.*, 2:55-75, 1948; Lakowicz, J. R., Principles of Fluorescence Spectroscopy, 2nd ed. Plenum, N.Y. 367-394, 1999. RET also comprises luminescence resonance energy transfer, bioluminescence resonance energy transfer, chemiluminescence resonance energy transfer, and similar types of energy transfer not strictly following the Forster's theory, such as nonoverlapping energy transfer occurring when nonoverlapping acceptors are utilized. See, for example, Anal. Chem. 2005, 77: 1483-1487.

The term "conservative" and its variants, as used herein with reference to any change in amino acid sequence, refers to an amino acid mutation wherein one or more amino acids is substituted by another amino acid having highly similar properties. For example, one or more amino acids comprising nonpolar or aliphatic side chains (for example, glycine, alanine, valine, leucine, isoleucine or proline) can be substituted for each other. Similarly, one or more amino acids comprising polar, uncharged side chains (for example, serine, threonine, cysteine, methionine, asparagine or glutamine) can be substituted for each other. Similarly, one or more amino acids comprising aromatic side chains (for example, phenylalanine, tyrosine or tryptophan) can be substituted for each other. Similarly, one or more amino acids comprising positively charged side chains (for example, lysine, arginine or histidine) can be substituted for each other. Similarly, one or more amino acids comprising negatively charged side chains (for example, aspartic acid or glutamic acid) can be substituted for each other. In some embodiments, the modified polymerase is a variant that comprises one or more of these conservative amino acid substitutions, or any combination thereof. In some embodiments, conservative substitutions for leucine include: alanine, isoleucine, valine, phenylalanine, tryptophan, methionine, and cysteine. In other embodiments, conservative substitutions for asparagine include: arginine, lysine, aspartate, glutamate, and glutamine.

The term "primer extension activity" and its variants, as used herein, when used in reference to a given polymerase, comprises any in vivo or in vitro enzymatic activity characteristic of a given polymerase that relates to catalyzing nucleotide incorporation onto the terminal 3'OH end of an extending nucleic acid molecule. Typically but not necessarily such nucleotide incorporation occurs in a template-dependent fashion. The primer extension activity is typically quantified as the total number of nucleotides incorporated (as measured by, e.g, radiometric or other suitable assay) by a unit amount of polymerase (in moles) per unit time (seconds) under a particular set of reaction conditions.

The terms "His tag" or "His-tag" and their variants as used herein refers to a stretch of amino acids comprising multiple histidine residues. Typically, the His tag can bind to metal ions, for example, $Zn^{2+}$, $Ni^{2+}$, $Co^{2+}$, or $Cu^{2+}$ ions. Optionally, the His tag comprises 2, 3, 4, 5, 6, 7, 8 or more histidine residues. In some embodiments, the His tag is fused to the N- or C-terminus of a protein; alternatively, it can be fused at any suitable location within the protein.

As used herein, the term "binding pair" and its variants refers to two molecules, or portions thereof, which have a specific binding affinity for one another and typically will bind to each other in preference to binding to other molecules. Typically but not necessarily some or all of the structure of one member of a specific binding pair is complementary to some or all of the structure possessed by the other member, with the two members being able to bind together specifically by way of a bond between the complementary structures, optionally by virtue of multiple noncovalent attractions. The two members of a binding pair are referred to herein as the "first member" and the "second member" respectively.

The following may be mentioned as non-limiting examples of molecules that can function as a member of a specific binding pair, without this being understood as any restriction: thyroxin-binding globulin, steroid-binding proteins, antibodies, antigens, haptens, enzymes, lectins, nucleic acids, repressors, oligonucleotides, polynucleotides, protein A, protein G, avidin, streptavidin, biotin, complement component C1q, nucleic acid-binding proteins, receptors, carbohydrates, complementary nucleic acid sequences, and the like. Examples of specific binding pairs include without limitation: an avidin moiety and a biotin moiety; an antigenic epitope and an antibody or immunogically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; and an oligonucleotide or polynucleotide and its corresponding complement.

As used herein, the term "biotin moiety" and its variants comprises biotin (cis-hexahydro-2-oxo-1H-thieno[3,4]imidazole-4-pentanoic acid) and any derivatives and analogs thereof, including biotin-like compounds. Such compounds include, for example, biotin-e-N-lysine, biocytin hydrazide, amino or sulfhydryl derivatives of 2-iminobiotin and biotinyl-ε-aminocaproic acid-N-hydroxysuccinimide ester, sulfosuccinimideiminobiotin, biotinbromoacetylhydrazide, p-diazobenzoyl biocytin, 3-(N-maleimidopropionyl)biocytin, and the like. "Biotin moiety" also comprises biotin variants that can specifically bind to an avidin moiety.

The term "biotinylated" and its variants, as used herein, refer to any covalent or non-covalent adduct of biotin with other moieties such as biomolecules, e.g., proteins, nucleic acids (including DNA, RNA, DNA/RNA chimeric molecules, nucleic acid analogs and peptide nucleic acids), proteins (including enzymes, peptides and antibodies), carbohydrates, lipids, etc.

The terms "avidin" and "avidin moiety" and their variants, as used herein, comprises the native egg-white glycoprotein avidin, as well as any derivatives, analogs and other non-native forms of avidin, that can specifically bind to biotin moieties. In some embodiments, the avidin moiety can comprise deglycosylated forms of avidin, bacterial streptavidins produced by selected strains of *Streptomyces*, e.g., *Streptomyces avidinii*, to truncated streptavidins, and to recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin®, Captavidin®, Neutravidin® and Neutralite Avidin®. All forms of avidin-type molecules, including both native and recombinant avidin and streptavidin as well as derivatized molecules, e.g. nonglycosylated avidins, N-acyl avidins and truncated streptavidins, are encompassed within the terms "avidin" and "avidin moiety". Typically, but not necessarily, avidin exists as a tetrameric protein, wherein each of the four tetramers is capable of binding at least one biotin moiety.

As used herein, the term "biotin-avidin bond" and its variants refers to a specific linkage formed between a biotin moiety and an avidin moiety. Typically, a biotin moiety can bind with high affinity to an avidin moiety, with a dissociation constant $K_d$ typically in the order of $10^{-14}$ to $10^{-15}$ mol/L. Typically, such binding occurs via non-covalent interactions.

As used herein, the term "modification enzyme recognition site" refers to an amino acid recognition sequence that is chemically modified in an enzyme-catalyzed reaction, wherein the enzyme catalyzing the reaction exhibits specificity for the amino acid recognition sequence. The amino acid recognition sequence may be inserted into a protein of interest, for example by conventional recombinant DNA techniques. Examples of modification enzyme recognition sites include, but are not limited to a biotin ligase modification site, for example a site comprising the amino acid sequence GLNDIFEAQKIEWHE (SEQ ID NO: 10), for introducing a biotin moiety; a protein kinase modification site, for example a site comprising the amino acid sequence LRRASLG (SEQ ID NO: 52), for introducing a phosphorothioate moiety; and a transglutaminase modification site, for example a site comprising the amino acid sequence PKPQQF (SEQ ID NO: 53), for introducing an amine moiety.

The terms "reporter" and "reporter moiety" and their variants, as used herein, refer to any moiety that generates, or causes to be generated, a detectable signal. Any suitable reporter moiety may be used, including luminescent, photoluminescent, electroluminescent, bioluminescent, chemiluminescent, fluorescent, phosphorescent, chromophore, radioisotope, electrochemical, mass spectrometry, Raman, hapten, affinity tag, atom, or an enzyme. The reporter moiety generates a detectable signal resulting from a chemical or physical change (e.g., heat, light, electrical, pH, salt concentration, enzymatic activity, or proximity events). A proximity event includes two reporter moieties approaching each other, or associating with each other, or binding each other. The appropriate procedures for detecting a signal, or change in the signal, generated by the reporter moiety are well known in the art. The reporter moieties can be linked to a solid surface, polymerase, nucleotide (or analog thereof), target nucleic acid molecule, or primer. In one embodiment, a nucleotide can be linked to a reporter moiety. The reporter moiety can generate a signal, or a change in a signal, upon excitation from an appropriated energy source (e.g., electromagnetic source). In another embodiment, the polymerase can be linked to a reporter moiety (e.g., energy transfer donor moiety), and the nucleotide (or analog thereof) can be linked to a reporter moiety (e.g., energy transfer acceptor moiety). The reporter moieties (energy transfer donor and acceptor moieties) can generate a signal, or a change in a signal, upon excitation from an appropriated energy source (e.g., electromagnetic source) and when the nucleotide is proximal to the polymerase. The nucleotide can be proximal to the polymerase when the nucleotide binds the polymerase or when the polymerase incorporates the nucleotide. Some energy transfer reporter moieties can be optically or spectrally detectable.

The term "label" and its variants, as used herein, comprises any optically detectable moiety and includes any moiety that can be detected using, for example, fluorescence, luminescence and/or phosphoresecence spectroscopy, Raman scattering, or diffraction. Exemplary labels according to the present disclosure include fluorescent and luminescent moieties as well as quenchers thereof. Some typical labels include without limitation nanoparticles and organic dyes.

The term "attachment site" and its variants, as used herein, refer to any location or region on the biomolecule or the label that is capable of supporting attachment to another moiety. For example, the biomolecule can comprise one or more attachment sites for a label; alternatively the label (e.g., nanoparticle or organic dye moiety) can comprise one or more attachment sites for the biomolecule. The attachment site can variously comprise one or more functional groups (e.g., carboxyl, amine, thiol groups, etc), a surface ligand, one or more amino acid side chains, an exposed region of the metal surface, a bound metal ion, or any other suitable moiety capable of supporting attachment to, e.g., a biomolecule or label.

"Nanoparticle" may refer to any particle with at least one major dimension in the nanosize range. In general, nanoparticles can be made from any suitable metal (e.g., noble metals, semiconductors, etc.) and/or non-metal atoms. Nanoparticles can have different shapes, each of which can have distinctive properties including spatial distribution of the surface charge; orientation dependence of polarization of the incident light wave; and spatial extent of the electric field. The shapes include, but are not limited to: spheres, rods, discs, triangles, nanorings, nanoshells, tetrapods, nanowires, etc.

In one embodiment, the nanoparticle can be a core/shell nanoparticle which typically comprises a core nanoparticle surrounded by at least one shell. For example, the core/shell nanoparticle can be surrounded by an inner and outer shell. In another embodiment, the nanoparticle is a core nanoparticle which has a core but no surrounding shell. The outmost surface of the core or shell can be coated with tightly associated ligands which are not removed by ordinary solvation.

Examples of a nanoparticle include a nanocrystal, such as a core/shell nanocrystal, plus any associated organic ligands (which are not removed by ordinary solvation) or other materials which may coat the surface of the nanocrystal. In one embodiment, a nanoparticle has at least one major dimension ranging from about 1 to about 1000 nm. In other embodiments, a nanoparticle has at least one major dimension ranging from about 1 to about 20 nm, about 1 to about 15 nm, about 1 to about 10 nm or about 1 to 5 nm.

In some embodiments, a nanoparticle can have a layer of ligands on its surface which can further be cross-linked to each other. In some embodiments, a nanoparticle can have other or additional surface coatings which can modify the properties of the particle, for example, increasing or decreasing solubility in water or other solvents. Such layers on the surface are included in the term 'nanoparticle.'

In one embodiment, nanoparticle can refer to a nanocrystal having a crystalline core, or to a core/shell nanocrystal, and may be about 1 nm to about 100 nm in its largest dimension, about 1 nm to about 20 nm, about 1 nm to about 15 nm, about 1 nm to about 10 nm or preferably about 5 nm to about 10 nm in its largest dimension. Small nanoparticles are typically less than about 20 nm in their largest dimension.

"Nanocrystal" as used herein can refer to a nanoparticle made out of an inorganic substance that typically has an ordered crystalline structure. It can refer to a nanocrystal having a crystalline core (core nanocrystal) or to a core/shell nanocrystal.

A core nanocrystal is a nanocrystal to which no shell has been applied. Typically, it is a semiconductor nanocrystal that includes a single semiconductor material. It can have a homogeneous composition or its composition can vary with depth inside the nanocrystal.

A core/shell nanocrystal is a nanocrystal that includes a core nanocrystal and a shell disposed over the core nanocrystal. Typically, the shell is a semiconductor shell that includes a single semiconductor material. In some embodiments, the core and the shell of a core/shell nanocrystal are composed of different semiconductor materials, meaning that at least one atom type of a binary semiconductor material of the core of a core/shell is different from the atom types in the shell of the core/shell nanocrystal.

The semiconductor nanocrystal core can be composed of a semiconductor material (including binary, ternary and quaternary mixtures thereof), from: Groups II-VI of the periodic table, including ZnS, ZnSe, ZnTe, CdS, CdSe, CdTe, HgS, HgSe, HgTe, MgTe; Groups III-V, including GaN, GaP, GaAs, GaSb, InN, InP, InAs, InSb, AlAs, AlP, AlSb, AlS; and/or Group IV, including Ge, Si, Pb.

The semiconductor nanocrystal shell can be composed of materials (including binary, ternary and quaternary mixtures thereof) comprising: ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, or AlSb.

Many types of nanocrystals are known, and any suitable method for making a nanocrystal core and applying a shell to the core may be employed. Nanocrystals can have a surface layer of ligands to protect the nanocrystal from degradation in use or during storage.

"Quantum dot" as used herein refers to a crystalline nanoparticle made from a material which in the bulk is a semiconductor or insulating material, which has a tunable photophysical property in the near ultraviolet (UV) to far infrared (IR) range.

As used herein, the term "interaction" and its variants comprise any selective or specific interaction between a biomolecule and one or more targets, including but not limited to approach of the biomolecule to the target, transmission of an electrical, optical, chemical or other impulse between a biomolecule and a target, and/or binding of the biomolecule with the target. Optionally, the interaction can involve the formation of one or more bonds between the biomolecule and a target including, without limitation covalent, ionic, hydrogen, hydrophilic, hydrophobic, or affinity bonding as well as bonding or associations involving van der Waals forces and mechanical bonding. Some exemplary biomolecule-target interactions can include, for example, approach of the biomolecule and target to each other, movement of the biomolecule and target away from each other, association or dissociation of the biomolecule and target with each other, formation of a linkage between the biomolecule and target, transmission of one or more signals between the biomolecule and the target, independent binding of the biomolecule and target to a common entity or surface, activation of either the biomolecule or target by the other; etc.

Disclosed herein is a labeled biomolecule conjugate comprising: a biomolecule linked to a label to form a labeled biomolecule conjugate, wherein the conjugate has biological activity. Typically, the biological activity is an activity that is characteristic of the biomolecule.

In some embodiments, the label of the labeled biomolecule conjugate emits, or is capable of emitting, a signal. In some embodiments, the label of the labeled biomolecule conjugate induces, or is capable of inducing, the emission of a signal by another label. In some embodiments, the label of the conjugate is positioned to emit a signal during interaction of the biomolecule with a target. Optionally, the signal indicates occurrence of the interaction. In some embodiments, the signal can indicate the identity of the target. Optionally, the signal can be detected to visualize and/or track the conjugate in real time.

In some embodiments, the biomolecule of the conjugate is capable of undergoing one or more transient interactions with a target, and the label of the conjugate is capable of emitting, or causing to be emitted, a signal during each of the one or more transient interactions. The one or more interactions can occur successively or simultaneously, and can involve one or multiple targets.

In some embodiments, the label of the conjugate is capable of emitting or inducing the emission of a series of signals, each signal corresponding to a transient interaction between the biomolecule and a target. The transient interactions can occur successively or simultaneously, and can involve one or multiple targets.

In some embodiments, the biomolecule can be selected from the group consisting of: a protein, a carbohydrate, a lipid, a nucleotide and a nucleic acid. In a typical embodiment, the biomolecule is an enzyme, even more typically a polymerase.

In some embodiments, the label of the conjugate can be selected from the group consisting of a nanoparticle and an organic dye. In some embodiments, the label is a fluorescent label. Optionally, the label is a fluorescent dye. The dye can be selected from the group consisting of: Cy3, ALEXA FLUOR, and fluorescein. In some embodiments, the nanoparticle can be a nanocrystal, typically a quantum dot.

In some embodiments, the biomolecule comprises an enzyme or a biologically active fragment thereof, the target is an enzyme substrate, the one or more transient interactions include one or more enzyme-mediated reactions. Such conjugates are referred to herein as labeled enzyme conjugates.

In some embodiments, the disclosure relates to a labeled enzyme conjugate comprising: an enzyme linked to at least one label to form a labeled enzyme conjugate. Optionally, the conjugate has enzymatic activity. Optionally, the enzyme is linked to two, three, four, five, six, seven or more detectable labels. In some embodiments, the enzymatic activity of the conjugate is at least about 1% relative to the enzymatic activity of the unconjugated enzyme. Optionally, the enzymatic activity of the conjugate can be at least about 10%, at least about 20%, at least about 30%, at least about 40%, at least about 50%, at least about 60%, at least about 70%, at least about 80%, at least about 90% or at least about 95% relative to the polymerase activity of the unconjugated enzyme.

In some embodiments, the enzyme can include one or more attachment sites for the plurality of labels. The enzyme can be engineered or otherwise modified to include the one or more attachment sites. Optionally, the labels can be same; alternatively, at least two of the labels can be different from each other. In some embodiments, the plurality of labels are linked to a single attachment site on the enzyme. Alternatively, two or more of the plurality of labels can be linked to different attachment sites on the enzyme.

In some embodiments, the enzyme further comprises a modification enzyme recognition sequence. Optionally, the modification enzyme recognition sequence comprises a biotin ligase modification site.

In some embodiments, the disclosure relates to a labeled enzyme conjugate, comprising: a enzyme linked to one or more labels, where the conjugate has enzymatic activity and emits upon continuous excitation a total photon count of at least $10^2$ photons before irreversibly photobleaching. In some embodiments, the conjugate emits a total photon count of at least $10^2$, $10^3$, $10^4$, $10^5$, $10^6$, $10^7$, $10^8$ or $10^9$ photons as measured using a test detection system. Optionally, the enzyme is linked to two, three, four, five, six, seven or more detectable labels. In some embodiments, the enzymatic activity of the conjugate is at least about 1% relative to the enzymatic activity of the unconjugated enzyme. Optionally, the enzymatic activity of the conjugate can be at least about 10%, at least about 20%, at least about 30%, at least about 40%, at least about 50%, at least about 60%, at least about 70%, at least about 80%, at least about 90% or at least about 95% relative to the polymerase activity of the unconjugated enzyme.

In some embodiments, the disclosure relates to a labeled enzyme conjugate, comprising: a first member of a binding pair linked to a enzyme; and a second member of the binding pair linked to at least one label, where the first and the second member of the binding pair are linked to each other to form a labeled enzyme conjugate having enzymatic activity. Optionally, the enzyme is linked to two, three, four, five, six, seven or more detectable labels. In some embodiments, the enzymatic activity of the conjugate is at least about 1% relative to the enzymatic activity of the unconjugated enzyme. Optionally, the enzymatic activity of the conjugate can be at least about 10%, at least about 20%, at least about 30%, at least about 40%, at least about 50%, at least about 60%, at least about 70%, at least about 80%, at least about 90% or at least about 95% relative to the polymerase activity of the unconjugated enzyme. Optionally, the first member comprises a biotin moiety and the second member comprises an avidin moiety. In some embodiments, the second member is linked to at least one label. In some embodiments, at least one label generates a signal. In some embodiments, the at least one label is positioned to undergo FRET with a labeled nucleotide bound to an active site of the enzyme. In some embodiments, the labeled nucleotide comprises a polyphosphate. Optionally, the nucleotide label can be linked to the terminal phosphate of the polyphosphate. In some embodiments, the energy transfer produces a signal that can be detected in a single molecule reaction using a test detection system.

In some embodiments, the disclosure relates to a method for creating a labeled enzyme conjugate, comprising linking a enzyme to a plurality of labels to form a labeled enzyme conjugate having enzymatic activity.

Optionally, the linking further comprises linking the plurality of labels to an attachment site on the enzyme. Optionally, the plurality of labels are linked to independent attachment sites on the enzyme.

In some embodiments, the linking further comprises linking the enzyme to at least three labels.

In some embodiments, the linking further comprises linking a enzyme including a modification enzyme recognition sequence to the plurality of labels. Optionally, the modification enzyme recognition sequence comprises a biotin ligase modification site. Optionally, the linking further comprises linking a biotin moiety to the enzyme to produce a biotinylated enzyme.

Optionally, the method further comprises contacting the biotinylated enzyme with an avidin moiety linked to the plurality of labels under conditions where the avidin moiety binds to the biotin moiety, thereby forming a labeled enzyme conjugate including the enzyme linked to the plurality of labels and having enzymatic activity.

In some embodiments, the label of the labeled enzyme conjugate is positioned to emit a detectable signal indicative of activity of the enzyme on a substrate. In some embodiments, the enzyme of the labeled enzyme conjugate is a nucleotide polymerase, the substrate is a labeled nucleotide, and the polymerase is linked to a label to form a labeled polymerase conjugate.

In some embodiments, the label of the labeled enzyme conjugate is positioned to emit a detectable signal indicative of incorporation of the labeled nucleotide by the polymerase of the conjugate.

In some embodiments, the label of the labeled enzyme conjugate is a RET moiety positioned to undergo RET with the label of a labeled substrate positioned in the active site of the enzyme. In some embodiments, the enzyme of the labeled enzyme conjugate is a nucleotide polymerase and the substrate is a labeled nucleotide.

In some embodiments, the label of the labeled enzyme conjugate is a RET moiety positioned to undergo RET with a labeled substrate bound to the active site of the enzyme.

In some embodiments, the enzyme of the labeled enzyme conjugate is capable of undergoing one or more transient interactions with a substrate. In some embodiments, the enzyme is capable of undergoing multiple transient interactions with one or more substrates, which can occur simultaneously or successively.

In some embodiments, the enzyme is capable of undergoing transient interactions with one or more substrates, which can occur simultaneously or successively.

In some embodiments, the enzyme of the labeled enzyme conjugate is capable of undergoing transient interactions with a plurality of substrates, and the label of the conjugate is capable of generating a signal upon each interaction.

Optionally, the signal can be detected and analyzed to determine the identity of the substrate. In some embodiments, the enzyme of the conjugate is capable of undergoing transient interaction with a series of substrates in succession and the label of the conjugate is capable of producing a series of signals that can be detected and analyzed to determine a time series of interactions.

In some embodiments, a label of the labeled enzyme conjugate is a fluorescent label. In some embodiments, the fluorescent label can comprise a dye selected from the group consisting of: Cy3, Cy3b, Alexa Fluors and fluorescein, and the polymerase is selected from the group consisting of: Phi-29 DNA polymerase, a variant of Phi-29 DNA polymerase, B103 DNA polymerase and a variant of B103 DNA polymerase.

In some embodiments, the polymerase of the labeled polymerase conjugate is an isolated variant of a naturally occuring polymerase, wherein the polymerase comprises an amino acid sequence that is at least 80%, 85%, 90%, 95%, 98% or 99% identical to an amino acid sequence selected from the group consisting of: SEQ ID NO: 3, SEQ ID NO: 33, SEQ ID NO: 34, SEQ ID NO: 35 and SEQ ID NO: 36.

In some embodiments, the enzyme of the labeled enzyme conjugate is linked to the label through a bond selected from group consisting of: a covalent bond, a hydrogen bond, a hydrophilic bond, a hydrophobic bond, an electrostatic bond, a Van der Waals bond, and an affinity bond. In some embodiments, the bond is a covalent bond formed between an amine group of a lysine residue of the enzyme and an amine-reactive moiety, wherein the amine reactive moiety is linked to the label. In some embodiments, the bond is a covalent bond formed between a carboxy group of an amino acid residue of the enzyme and a maleimide moiety, wherein the maleimide moiety is linked to the label.

In some embodiments, an attachment moiety serves to link the enzyme to the label. In one exemplary embodiment, the labeled enzyme conjugate comprises an enzyme linked to one or more labels through an attachment moiety. Typically, the polymerase is linked to the attachment moiety, and the attachment moiety is linked to the one or more labels to form a labeled polymerase conjugate. In some embodiments, the attachment moiety of is an avidin moiety, and the enzyme comprises a biotin moiety, and the enzyme and the attachment moiety are linked to each other through a further biotin-avidin bond. In some embodiments, the attachment moiety is covalently attached to the one or more labels. In some embodiments, the one or more labels each comprises a biotin moiety, and the attachment moiety is linked to the one or more labels through a second biotin-avidin bond. In some embodiments, the attachment moiety is linked to two, three, four, five, six, seven, eight, nine, ten or more labels. In some embodiments, at least two of the labels are different from each other. In some embodiments, at least two of the labels are the same. In some embodiments, at least two of the labels are positioned to undergo FRET with each other.

Also provided herein is a labeled enzyme conjugate, comprising: an enzyme linked to an attachment moiety, wherein the attachment moiety is linked to a label, thereby linking the enzyme to the label to form a labeled enzyme conjugate. Optionally, the attachment moiety can comprise a biotin moiety.

In some embodiments, the label of the labeled enzyme conjugate is positioned to emit a detectable signal indicative of activity of the enzyme on a substrate. In some embodiments, the enzyme is a nucleotide polymerase and the substrate is a labeled nucleotide.

In some embodiments, the label of the labeled enzyme conjugate is positioned to emit a detectable signal indicative of incorporation of the labeled nucleotide by the polymerase of the conjugate. In some embodiments, the label is a RET moiety positioned to undergo RET with the label of a labeled substrate positioned in the active site of the enzyme. In some embodiments, the enzyme is a nucleotide polymerase and the substrate is a labeled nucleotide.

In some embodiments, the label of the labeled enzyme conjugates or the labeled polymerase conjugates disclosed herein is a nanoparticle. In some embodiments, the label is a fluorescent label. In some embodiments, the fluorescent label comprises a dye selected from the group consisting of: Cy3, Cy3b, Alexa Fluors and fluorescein, and the polymerase is selected from the group consisting of: Phi-29 DNA polymerase, a variant of Phi-29 DNA polymerase, B103 DNA polymerase and a variant of B103 DNA polymerase.

In some embodiments, the polymerase is an isolated variant of a naturally occuring polymerase, wherein the polymerase comprises an amino acid sequence that is at least 80%, 85%, 90%, 95%, 98% or 99% identical to an amino acid sequence selected from the group consisting of: SEQ ID NO: 3, SEQ ID NO: 33, SEQ ID NO: 34, SEQ ID NO: 35 and SEQ ID NO: 36.

In some embodiments, the enzyme is linked to the label through a bond selected from group consisting of: a covalent bond, a hydrogen bond, a hydrophilic bond, a hydrophobic bond, an electrostatic bond, a Van der Waals bond, and an affinity bond. In some embodiments, the bond is a covalent bond formed between an amine group of a lysine residue of the enzyme and an amine-reactive moiety, wherein the amine reactive moiety is linked to the label. In some embodiments, the bond is a covalent bond formed between a carboxy group of an amino acid residue of the enzyme and a maleimide moiety, wherein the maleimide moiety is linked to the label.

In some embodiments, the attachment moiety of the labeled enzyme conjugate is an avidin moiety, the label and the enzyme are each linked to one or more biotin moieties, and the avidin moiety is linked to the enzyme and to the label through a biotin-avidin bond. In some embodiments, the attachment moiety is linked to two, three, four, five, six, seven, eight, nine, ten or more detectable labels. In some embodiments, at least two of the detectable labels are different from each other. In some embodiments, at least two of the detectable labels are the same. In some embodiments, at least two of the detectable labels are configured to undergo FRET with each other.

Also provided herein is a labeled enzyme conjugate, comprising: an enzyme linked to a first member of a binding pair; and a second member of the binding pair linked to a label; wherein the first member and the second member of the binding pair are linked to each other, thereby forming a labeled enzyme conjugate.

Also provided herein is a labeled enzyme conjugate, comprising: a first member of a binding pair linked to an enzyme; and a second member of the binding pair linked to a label; wherein the first member and the second member of the binding pair are linked to each other to form a labeled enzyme conjugate.

In some embodiments, the label of the labeled enzyme conjugate is positioned to emit a detectable signal indicative of activity of the enzyme on a substrate. In some embodiments, the enzyme of the labeled enzyme conjugate is a nucleotide polymerase and the substrate is a labeled nucleotide. In some embodiments, the label is positioned to emit a detectable signal indicative of incorporation of the labeled nucleotide by the polymerase of the conjugate.

In some embodiments, the label of the labeled enzyme conjugate is a RET moiety positioned to undergo RET with the label of a labeled substrate positioned in the active site of the enzyme. In some embodiments, the enzyme is a nucleotide polymerase and the substrate is a labeled nucleotide. In some embodiments, the second member of the binding pair is linked to two or more detectable labels. In some embodiments, at least two of the two or more detectable labels are different from each other.

In some embodiments, the binding pair is selected from the group consisting of: an avidin moiety and a biotin moiety; an antigenic epitope and an antibody or immunogically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunglobulin and protein A; and an oligonucleotide or polynucleotide and its corresponding complement.

In some embodiments, the label is a fluorescent label. In some embodiments, the fluorescent label comprises a dye selected from the group consisting of: Cy3, Cy3b, Alexa Fluors and fluorescein, and the polymerase is selected from the group consisting of: Phi-29 DNA polymerase, a variant of Phi-29 DNA polymerase, B103 DNA polymerase and a variant of B103 DNA polymerase.

In some embodiments, the label is a nanoparticle. In some embodiments, the polymerase is an isolated variant of a naturally occuring polymerase, wherein the polymerase comprises an amino acid sequence that is at least 80%, 85%, 90%, 95%, 98% or 99% identical to an amino acid sequence selected from the group consisting of: SEQ ID NO: 3, SEQ ID NO: 33, SEQ ID NO: 34, SEQ ID NO: 35 and SEQ ID NO: 36.

Also disclosed herein is a method of making a labeled enzyme conjugate, comprising: (a) linking a first member of a binding pair to an enzyme to form an enzyme binding conjugate; and (b) contacting the enzyme binding conjugate with a second member of the binding pair, wherein the second member is linked to one or more detectable labels, and wherein said contacting is performed under conditions where the first and second members of the binding pair become linked to each other, thereby forming a labeled enzyme conjugate comprising an enzyme linked to one or more labels.

In some embodiments of the method, the label is a RET moiety and is positioned to undergo RET with the label of a labeled substrate positioned in the active site of the enzyme.

In some embodiments of the method, the enzyme is a nucleotide polymerase and the substrate is a labeled nucleotide.

In some embodiments, the binding pair is selected from the group consisting of: an avidin moiety and a biotin moiety; an antigenic epitope and an antibody or immunogically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunglobulin and protein A; and an oligonucleotide or polynucleotide and its corresponding complement.

In some embodiments, the enzyme of the labeled enzyme conjugate is linked to the one or more labels of the conjugate through a bond selected from group consisting of: a covalent bond, a hydrogen bond, a hydrophilic bond, a hydrophobic bond, an electrostatic bond, a Van der Waals bond, and an affinity bond.

In some embodiments, the first member of the binding pair is a biotin moiety and the second member of the binding pair comprises a streptavidin moiety.

Also disclosed herein is a method of making a labeled enzyme conjugate, comprising: (a) linking a first member of a binding pair to an enzyme; (b) linking the second member of the binding pair to one or more labels, and (c) contacting the products of steps (a) and (b) with each other under conditions where the first member and second members of the binding pair become linked to each other to form a labeled enzyme conjugate comprising an enzyme linked to the one or more labels, where the conjugate has enzymatic activity.

In some embodiments, the first member of the binding pair is a biotin moiety and the second member of the binding pair comprises a streptavidin moiety.

Also disclosed herein is a labeled enzyme conjugate for use in single molecule reactions prepared by the above methods. In some embodiments, the labeled enzyme conjugate comprises a first member of a binding pair linked to a enzyme; and a second member of the binding pair linked to at least one label, where the first and the second member of the binding pair are linked to each other to form a labeled enzyme conjugate having enzymatic activity.

Optionally, the first member comprises a biotin moiety and the second member comprises an avidin moiety. Optionally, the second member of the binding pair is linked to two, three, four, five, six, seven or more detectable labels. In some embodiments, the enzymatic activity of the conjugate is at least about 1% relative to the enzymatic activity of the unconjugated enzyme. Optionally, the enzymatic activity of the conjugate can be at least about 10%, at least about 20%, at least about 30%, at least about 40%, at least about 50%, at least about 60%, at least about 70%, at least about 80%, at least about 90% or at least about 95% relative to the enzymatic activity of the unconjugated enzyme.

In some embodiments, at least one label generates a signal. In some embodiments, the at least one label is positioned to undergo FRET with a labeled substrate bound to an active site of the enzyme. In some embodiments, the labeled nucleotide comprises a polyphosphate. In some embodiments, the energy transfer produces a signal that can be detected in a single molecule reaction using a test detection system.

Also provided herein is a labeled enzyme conjugate, comprising: an enzyme linked to at least two detectable labels to form a labeled enzyme conjugate, wherein the enzyme of the conjugate has enzymatic activity.

In some embodiments, the label of the labeled enzyme conjugate is positioned to emit a detectable signal indicative of activity of the enzyme on a substrate.

In some embodiments, the enzyme is a nucleotide polymerase and the substrate is a labeled nucleotide.

In some embodiments, the label is positioned to emit a detectable signal indicative of incorporation of the labeled nucleotide by the polymerase of the conjugate.

In some embodiments, the label is a RET moiety positioned to undergo RET with the label of a labeled substrate positioned in the active site of the enzyme.

In some embodiments, the label comprises a fluorescent label. In some embodiments, the fluorescent label comprises a dye selected from the group consisting of: Cy3, Cy3b, Alexa Fluors and fluorescein, and the polymerase is selected from the group consisting of: Phi-29 DNA polymerase, a variant of Phi-29 DNA polymerase, B103 DNA polymerase and a variant of B103 DNA polymerase. In some embodiments, the label comprises a nanoparticle.

In some embodiments, the polymerase is an isolated variant of a naturally occuring polymerase, wherein the polymerase comprises an amino acid sequence that is at least 80%, 85%, 90%, 95%, 98% or 99% identical to an amino acid sequence selected from the group consisting of: SEQ ID NO: 3, SEQ ID NO: 33, SEQ ID NO: 34, SEQ ID NO: 35 and SEQ ID NO: 36. In some embodiments, the enzyme is linked to the label through a bond selected from group consisting of: a covalent bond, a hydrogen bond, a hydrophilic bond, a hydrophobic bond, an electrostatic bond, a Van der Waals bond, and an affinity bond. In some embodiments, the bond is a covalent bond formed between an amine group of a lysine residue of the enzyme and an amine-reactive moiety, wherein the amine reactive moiety is linked to the label. In some embodiments, the bond is a covalent bond formed between a carboxy group of an amino acid residue of the enzyme and a maleimide moiety, wherein the maleimide moiety is linked to the label.

In some embodiments, the enzyme of the labeled enzyme conjugate is linked to an attachment moiety, and wherein the attachment moiety is linked to the at least two detectable labels. In some embodiments, at least two of the detectable labels are different from each other. In some embodiments, at least two of the detectable labels are configured to undergo FRET with each other.

Also disclosed herein is a labeled enzyme conjugate for use in single molecule polymerization reactions.

Also disclosed herein is a system for monitoring successive enzyme-substrate interactions, comprising: one or more substrates; an enzyme that undergoes one or more transient interactions with the one or more substrates, and a label linked to the enzyme, wherein the label emits, or causes to be emitted, one or more detectable signals upon a transient interaction of the enzyme with the one or more substrates.

Also disclosed herein is a system for monitoring successive interactions of an enzyme (e.g., a polymerase), with one or more targets (e.g., nucleotides), comprising: a target; a labeled enzyme conjugate comprising an enzyme linked to at least one label, where the conjugate undergoes, or is capable of undergoing, a transient interaction with the target, and where the label of the conjugate is capable of emitting or inducing the emission of a signal upon each such transient interaction. In some embodiments, the label of the conjugate emits or induces the emission of a signal upon each such transient interaction. Optionally, the signal can be detected and analyzed to determine the identity of the target.

Optionally, the the conjugate can undergo multiple transient interactions with the target, which can occur simultaneously or successively. In some embodiments, the conjugate undergoes a series of transient interaction with a series of targets in succession, and the label is capable of emitting (or inducing the emission of) a series of signals that can be detected and analyzed to determine a time series of interactions.

In some embodiments, the target is a labeled nucleotide. In some embodiments, the nucleotide label is bonded to a portion of the nucleotide that is released during incorporation of the nucleotide. Optionally, the nucleotide comprises a polyphosphate chain that is released during incorporation, and the nucleotide label is bonded to the beta, gamma or other terminal phosphate of the labeled nucleotide.

In some embodiments, the biomolecule of the system comprises a polymerase, and the at least two transient and successive interactions comprise nucleotide incorporations.

In some embodiments, the enzyme of the labeled enzyme conjugate is a polymerase, the target is a nucleotide, and the one or more transient interactions each comprises a nucleotide incorporation catalyzed by the polymerase. When the biomolecule of the conjugate is a polymerase, the conjugate is typically referred as a "labeled polymerase conjugate".

One exemplary embodiment of the present disclosure is a labeled polymerase conjugate comprising a polymerase linked to a label. The conjugate can have polymerase activity. In some embodiments, the label can be a nanoparticle. In some embodiments, the label can be an organic dye.

In some embodiments, the disclosure relates to a labeled polymerase conjugate comprising a polymerase linked to a plurality of labels. The conjugate can have polymerase activity.

Optionally, the polymerase activity of the conjugate is at least about 10%, 20%, 30%, 40%, 50%, 60%, 70%, 80%, 90%, 95%, 97% or 99% relative to the polymerase activity of the unconjugated polymerase.

In some embodiments, the polymerase can be linked to at least three, four, five, six, seven or more labels.

In some embodiments, the label of the labeled polymerase conjugate is positioned to emit a signal during the interaction of the polymerase with a nucleotide. Optionally, the interaction comprises the incorporation of the nucleotide into a nucleic acid molecule by the polymerase. Optionally, the signal indicates the occurrence of the nucleotide incorporation. In some embodiments, the signal can indicate the identity of the nucleotide that is incorporated. Optionally, the signal can be detected to visualize and/or track the conjugate in real time. In some embodiments, a signal indicative of nucleotide incorporation is generated as each incoming nucleotide becomes incorporated by the polymerase of the conjugate.

In some embodiments, the disclosure relates to a labeled polymerase conjugate, comprising a polymerase linked to a plurality of labels to form a labeled polymerase conjugate, where the conjugate has polymerase activity, and where at least one label of the conjugate performs energy transfer with a labeled nucleotide bound to an active site of the polymerase.

In some embodiments, the labeled nucleotide comprises a polyphosphate. Optionally, the nucleotide label can be linked to the terminal phosphate of the polyphosphate.

In some embodiments, the energy transfer produces a signal that can be detected in a single molecule reaction using a test detection system.

In some embodiments, the polymerase can include one or more attachment sites for the plurality of labels. The polymerase can be engineered or otherwise modified to include the one or more attachment sites. Optionally, the labels can be same; alternatively, at least two of the labels can be different from each other. In some embodiments, the plurality of labels are linked to a single attachment site on the polymerase. Alternatively, two or more of the plurality of labels can be linked to different attachment sites on the polymerase. Optionally, the plurality of labels includes three, four, five, six, seven or more labels. Optionally, the polymerase comprises a modification enzyme recognition sequence.

In some embodiments, the label of the labeled polymerase conjugate is positioned to emit a detectable signal indicative of incorporation of a labeled nucleotide by the polymerase of the conjugate.

In some embodiments, the label of the conjugate is a RET moiety positioned to undergo RET with the label of a labeled nucleotide bound to an active site of the polymerase.

In some embodiments, the polymerase undergoes, or is capable of undergoing, one or more transient interactions with a nucleotide. Optionally, such transient interactions can occur simultaneously or successively, and can involve the same or different nucleotides.

In some embodiments, the polymerase undergoes, or is capable of undergoing, transient interactions with a plurality of nucleotides in succession, and the label of the conjugate generates, or is capable of generating, a signal upon each such interaction. Optionally, the signal can be detected and analyzed to determine the identity of the incorporated nucleotide. In some embodiments, the polymerase undergoes, or is capable of undergoing, transient interactions with a series of substrates in succession and the label emits or induces, or is capable of emitting or inducing, a series of detectable signals that can be detected and analyzed to determine a time series of interactions.

In some embodiments, the label of the labeled polymerase conjugate is a fluorescent label. In some embodiments, the fluorescent label can comprise a dye selected from the group consisting of: Cy3, Cy3b, Alexa Fluors and fluorescein. Optionally, the polymerase is selected from the group consisting of: Phi-29 DNA polymerase, a variant of Phi-29 DNA polymerase, B103 DNA polymerase and a variant of B103 DNA polymerase.

In some embodiments, the conjugate may optionally comprise a polymerase linked to a label through a linker or chemical linkage comprising a bond selected from the group consisting of: a covalent bond, an electrostatic bond and an affinity bond. In some embodiments, the linker or chemical linkage comprises a bond through a functional group, including, without limitation, a hydroxyl, a carboxyl, a carbonyl, a sulfhydryl, an amine, an amide, a nitrile, a nitrogen with a free lone pair of electrons, an amino acid, a thiol, a sulfonic acid, a sulfonyl halide, and an acyl halide.

In some embodiments, the labeled polymerase conjugate comprises a polymerase linked to the label through a covalent bond. The covalent bond can be formed using any suitable method, optionally including through use of cross-linking agents or linkers.

Optionally, the nucleotide comprises a label (referred to herein as "a nucleotide label"). The label can optionally be bonded to a portion of the nucleotide that is released during nucleotide incorporation. By releasing the label upon incorporation, successive extensions can each be detected without interference from nucleotides previously incorporated into the complementary strand.

In some embodiments, the labeled nucleotide comprises a polyphosphate. Optionally, the nucleotide label can be linked to the terminal phosphate of the polyphosphate. In some embodiments, the terminal phosphate is a beta or gamma phosphate.

In some embodiments, the polymerase of the labeled polymerase conjugate comprises one member of a binding pair and the label comprises a complementary member of the binding pair.

Optionally, the polymerase of the conjugate is a DNA polymerase. In some embodiments, the DNA polymerase is at least 95% identical to a DNA polymerase selected from the group consisting of: Phi-29 DNA polymerase, B103 DNA polymerase, the Klenow fragment of E. coli DNA polymerase and HIV reverse transcriptase.

Optionally, the label of the conjugate is positioned relative to the polymerase to perform an energy transfer reaction. In some embodiments, the label is positioned to perform FRET with a labeled nucleotide bound to the nucleotide binding site of the polymerase. Optionally, the label of the conjugate is positioned to perform FRET with a label linked to the terminal phosphate of a polyphosphate-comprising nucleotide bound to an active site of the polymerase. Optionally, the label of the conjugate undergoes FRET with the nucleotide label with a FRET efficiency of at least about 20%.

In other embodiments, the polymerase is a mutant or variant Phi-29 DNA polymerase comprising an N-terminal polyhistidine tag (His-tag) fused to an amino acid sequence at least 85% identical to a Phi-29 DNA polymerase comprising the amino acid sequence of SEQ ID NO: 3, or any biologically active fragment thereof.

In some embodiments, the disclosure relates to a method for creating a labeled polymerase conjugate, comprising linking a polymerase to a plurality of labels to form a labeled polymerase conjugate having polymerase activity.

Optionally, the linking further comprises linking the plurality of labels to an attachment site on the polymerase. Optionally, the plurality of labels are linked to independent attachment sites on the polymerase.

In some embodiments, the linking further comprises linking the polymerase to at least three labels.

In some embodiments, the linking further comprises linking a polymerase including a modification enzyme recognition sequence to the plurality of labels. Optionally, the modification enzyme recognition sequence comprises a biotin ligase modification site. Optionally, the linking further comprises linking a biotin moiety to the polymerase to produce a biotinylated polymerase.

Optionally, the method further comprises contacting the biotinylated polymerase with an avidin moiety linked to the plurality of labels under conditions where the avidin moiety binds to the biotin moiety, thereby forming a labeled polymerase conjugate including the polymerase linked to the plurality of labels and having polymerase activity.

In some embodiments, the disclosure relates to a labeled polymerase conjugate, comprising: a first member of a binding pair linked to a polymerase; and a second member of the binding pair linked to at least one label, where the first and the second member of the binding pair are linked to each other to form a labeled polymerase conjugate having polymerase activity.

Optionally, the first member comprises a biotin moiety and the second member comprises an avidin moiety. In some embodiments, the second member is linked to at least one label. Optionally, the second member of the binding pair is linked to two, three, four, five, six, seven or more detectable labels. In some embodiments, the enzymatic activity of the polymerase is at least about 1% relative to the polymerase activity of the unconjugated polymerase. Optionally, the polymerase activity of the conjugate can be at least about 10%, at least about 20%, at least about 30%, at least about 40%, at least about 50%, at least about 60%, at least about 70%, at least about 80%, at least about 90% or at least about 95% relative to the polymerase activity of the unconjugated polymerase.

In some embodiments, at least one label generates a signal. In some embodiments, the at least one label is positioned to undergo FRET with a labeled nucleotide bound to an active site of the polymerase. In some embodiments, the labeled nucleotide comprises a polyphosphate. Optionally, the nucleotide label can be linked to the terminal phosphate of the polyphosphate. In some embodiments, the energy transfer produces a signal that can be detected in a single molecule reaction using a test detection system.

In some embodiments, the disclosure relates to a labeled polymerase conjugate, comprising: a polymerase linked to one or more labels, where the conjugate has polymerase activity and emits upon continuous excitation a total photon count of at least $10^2$ photons before irreversibly photobleaching. In some embodiments, the conjugate emits a total photon count of at least $10^2$, $10^3$, $10^4$, $10^5$, $10^6$, $10^7$, $10^8$ or $10^9$ photons as measured using a test detection system. Optionally, the polymerase is linked to at least three labels.

In some embodiments, the disclosure relates to a labeled polymerase conjugate, comprising: a first member of a binding pair linked to a polymerase; and a second member of the binding pair linked to at least one label, where the first and the second member of the binding pair are linked to each other to form a labeled polymerase conjugate having polymerase activity.

Optionally, the first member comprises a biotin moiety and the second member comprises an avidin moiety. In some embodiments, the second member is linked to at least one label. In some embodiments, at least one label generates a signal. In some embodiments, the at least one label is positioned to undergo FRET with a labeled nucleotide bound to an active site of the polymerase. In some embodiments, the labeled nucleotide comprises a polyphosphate. Optionally, the nucleotide label can be linked to the terminal phosphate of the polyphosphate. In some embodiments, the energy transfer produces a signal that can be detected in a single molecule reaction using a test detection system.

Also disclosed herein is a method for performing nucleotide incorporation, comprising: contacting a labeled polymerase conjugate including a polymerase linked to a label with a nucleotide under conditions where the polymerase catalyzes incorporation of the nucleotide into a nucleic acid molecule. Optionally, the nucleotide comprises a label (referred to herein as "a nucleotide label"). The label can optionally be bonded to a portion of the nucleotide that is released during nucleotide incorporation. By releasing the label upon incorporation, successive extensions can each be detected without interference from nucleotides previously incorporated into the complementary strand.

In some embodiments, the labeled nucleotide comprises a polyphosphate. Optionally, the nucleotide label can be linked to the terminal phosphate of the polyphosphate. In some embodiments, the terminal phosphate is a beta or gamma phosphate.

Also disclosed herein is a method for nucleotide incorporation, comprising: contacting the labeled polymerase conjugate as provided herein with one or more labeled nucleotides under conditions where a labeled nucleotide is incorporated into an extending nucleic acid molecule by the labeled polymerase.

Also disclosed herein is kit for use in single molecule sequencing reactions, comprising a labeled polymerase conjugate according to the present disclosure. In some embodiments, the kit further comprises labeled nucleotides.

Also disclosed herein is kit for use in single molecule sequencing reactions, comprising a labeled polymerase conjugate including a polymerase linked to at least one label, wherein the conjugate has polymerase activity. Optionally, the polymerase can be linked to at least three labels. In some embodiments, the kit further comprises labeled nucleotides.

Also disclosed herein is system for single molecule sequencing, comprising: (a) a reaction chamber wherein the one or more template nucleic acid molecules are contacted with a labeled polymerase conjugate and one or more labeled nucleotides under conditions where the one or more nucleotides are polymerized by the polymerase onto the end of an extending nucleic acid molecule such that one or more detectable signals indicative of nucleotide incorporation are generated; (b) detection means for detecting the one or more detectable signals indicative of nucleotide incorporation; and (c) an analyzer for analyzing the one or more detected signals and converting them into nucleic acid sequence information. In some embodiments, the labeled polymerase conjugate comprises a polymerase linked to a label to form a labeled polymerase conjugate, wherein conjugate has polymerase activity. In some embodiments, the label of the labeled polymerase is positioned to emit a signal indicative of incorporation of the labeled nucleotide by the labeled polymerase. In some embodiments, the label of the labeled polymerase is positioned to emit a signal indicative of incorporation of the labeled nucleotide by the polymerase of the conjugate. In some embodiments, the detectable label of the labeled polymerase is a RET moiety positioned to undergo RET with the label of a labeled substrate positioned in the active site of the enzyme.

In some embodiments, the detectable label comprises a fluorescent label. In some embodiments, the fluorescent label comprises a dye selected from the group consisting of: Cy3, Cy3b, Alexa Fluors and fluorescein, and the polymerase is selected from the group consisting of: Phi-29 DNA polymerase, a variant of Phi-29 DNA polymerase, B103 DNA polymerase and a variant of B103 DNA polymerase. In some embodiments, the detectable label comprises a nanoparticle.

In some embodiments, the polymerase is an isolated variant of a naturally occurring polymerase, wherein the polymerase comprises an amino acid sequence that is at least 80%, 85%, 90%, 95%, 98% or 99% identical to an amino acid sequence selected from the group consisting of: SEQ ID NO: 3, SEQ ID NO: 33, SEQ ID NO: 34, SEQ ID NO: 35 and SEQ ID NO: 36. In some embodiments, the enzyme is linked to the detectable label through a bond selected from group consisting of: a covalent bond, a hydrogen bond, a hydrophilic bond, a hydrophobic bond, an electrostatic bond, a Van der Waals bond, and an affinity bond. In some embodiments, the bond is a covalent bond formed between an amine group of a lysine residue of the enzyme and an amine-reactive moiety, wherein the amine reactive moiety is linked to the detectable label. In some embodiments, the bond is a covalent bond formed between a carboxy group of an amino acid residue of the enzyme and a maleimide moiety, wherein the maleimide moiety is linked to the detectable label.

Also disclosed herein is system for single molecule sequencing, comprising: (a) a reaction chamber wherein a labeled polymerase conjugate including a polymerase linked to at least one label is contacted with at least one labeled nucleotide under conditions where the polymerase catalyzes the incorporation of the at least one labeled nucleotide such that a signal corresponding to each incorporation of a labeled nucleotide is generated; (b) a detector for detecting a time series of signals, each signal corresponding to each nucleotide incorporation; and (c) an analyzer to analyze the times series of signal to determine a sequence of nucleotide incorporations.

Provided herein are conjugate compositions comprising one or more biomolecules or biologically active fragments thereof operably linked to one or more nanoparticles, hereinafter referred to as "biomolecule/nanoparticle conjugates." Compositions comprising labeled biomolecule conjugates of the present disclosure can be useful in a wide variety of biological applications. For example, such conjugates can allow direct visualization of the biomolecule of the conjugate. Optionally, the biomolecule can be visualized and/or tracked in real time. In some embodiments, such visualization can be done in real time or near real time, optionally in high throughput and/or ingle molecule format. Such visualization can permit, for example, detection and evaluation of a wide range of biomolecular behavior over an extended period both in vivo and in vitro contexts, including but not limited to biomolecular movement and/or transport within a cell or living organism, association of dissociation of different biomolecules, protein expression patterns within living cells or organisms, approach and/or binding of a biomolecule to a particular target, detection of movement as a function of biomolecular activity such as, for example, polymerase movement along a template, etc. See, e.g., Jaiswal et al., "Use of quantum dots for live cell imaging", Nature Methods, 1(1):71-78. Observation of multiple different biomolecules or behaviors simultaneously can be achieved through use of different nanoparticles having different characteristic wavelengths, e.g., colors, and/or intensities.

Such conjugates can also be useful in applications requiring detection of biomolecular activity, including in single molecule and/or high-throughput format. For example, such conjugates can be useful in diagnostic assays involving detection of a signal generated as a result of biomolecular activity. In some embodiments, the biomolecule can be linked to the label such that the label is capable of functioning as a reporter of biomolecular activity in real time or near real time. Biomolecular activity can frequently involve interaction of the biomolecule with a specific target, such as, for example, the interaction of an enzyme with a substrate. Occasionally, the biomolecule is capable of undergoing interactions with multiple targets either successively or simultaneously. Elucidating the nature of such biomolecule-target interactions can be important in determining the biological function of the biomolecule. Studies of such interactions have traditionally involved use of a labeled target, which is frequently degraded as a result of the interaction. This problem can be avoided by conjugating a label, e.g., a nanoparticle or an organic dye moiety, directly to the biomolecule. Such conjugation can allow for direct visualization of individual biomolecules, as well as the monitoring of multiple interactions of a biomolecule with multiple targets over time.

In some embodiments, the conjugates can permit not only visualization but also manipulation and sorting of biomolecules within a large population. For example, in some embodiments the conjugates can be sorted using suitable optical manipulation techniques such as "optical tweezers". See, e.g., Jauffred et al., "Three-dimensional optical control of individual quantum dots", Nano Lett. 8(10):3376-3380 (2008).

The labeled polymerase conjugates disclosed herein can be advantageously employed in the sequencing methods described in U.S. Pat. No. 7,329,492 to Hardin et al.; U.S. Pat. No. 6,982,146 to Schneider et al. The superior photostability and/or signal strength of the polymerase conjugates provided herein can be used to produce superior read length or accuracy in such single molecule sequence methods employing FRET between a labeled polymerase and labeled nucleotide.

Some additional disclosures relating to methods of making labeled polymerase conjugates and to modified polymerases that can be used to make the conjugates provided herein, are disclosed, for example, in U.S. provisional application nos. 61/184,770, filed Jun. 5, 2009; 61/245,457, filed on Sep. 24, 2009; 61/299,919, filed on Jan. 29, 2010; 61/242,771, filed on Sep. 15, 2009; and 61/293,618, filed on Jan. 8, 2010, as well as in U.S. application Ser. No. 12/748,355 titled "Conjugates of Biomolecules to Nanoparticles", filed concurrently herewith; and U.S. application Ser. No. 12/748,359 titled "Polymerase Compositions & Methods", filed concurrently herewith.

In some embodiments, the label of the labeled biomolecule conjugate comprises a nanoparticle, and the labeled biomolecule conjugate comprises a biomolecule or biologically active fragment thereof linked to a nanoparticle (a type of conjugate referred to herein as a "biomolecule/nanoparticle conjugate"). The superior detectability of nanoparticles as compared to conventional organic dye molecules can allow for increased signal in high-throughput in single molecule applications. Additionally, the conjugates of the present disclosure can be useful in highly multiplexed applications. For example, the size-tunable emission properties of labeled biomolecule conjugates comprising nanoparticle-based labels can also exploited to design assays involving wavelength and/or intensity multiplexing. Such conjugates can be useful in, e.g., performing multiple optical coding for biological assays. For example, the use of 10 different intensity levels and 6 colors could theoretically be used to code one million different biomolecules, opening new opportunities in gene expression, high throughput, diagnostic and other biological applications. See, e.g., Han et al., "Quantum-dot-tagged microbeads for multiplexed optical coding of biomolecules", Nat. Biotech. 19:631-635 (2001).

In some embodiments, the surfaces, labels (including, e.g., nanoparticles and organic dyes), polymerases, nucleotides aand nucleic acid molecules (including, e.g., targets, primers and/or oligonucleotides) of the present disclosure can be linked to each other, in any combination and in any order, using well known linking chemistries. Such linkage can optionally include a covalent bond and/or a non-covalent bond selected from the group consisting of an ionic bond, a hydrogen bond, an affinity bond, a dipole-dipole bond, a van der Waals bond, and a hydrophobic bond.

In some embodiments, the linking procedure used to link the biomolecules, labels and/or surfaces of the present disclosure comprises a chemical reaction that includes formation of one or more covalent bonds between a first and second moiety, resulting in the linkage of the first moiety to the second moiety. In some embodiments, the chemical reaction occurs between a first group of the moiety and a second group of the second moiety. Such chemical reaction can include, for example, reaction of activated esters, acyl azides, acyl halides, acyl nitriles, or carboxylic acids with amines or anilines to form carboxamide bonds. Reaction of acrylamides, alkyl halides, alkyl sulfonates, aziridines, haloacetamides, or maleimides with thiols to form thioether bonds. Reaction of acyl halides, acyl nitriles, anhydrides, or carboxylic acids with alcohols or phenols to form an ester bond. Reaction of an aldehyde with an amine or aniline to form an imine bond. Reaction of an aldehyde or ketone with a hydrazine to form a hydrazone bond. Reaction of an aldehyde or ketone with a hydroxylamine to form an oxime bond. Reaction of an alkyl halide with an amine or aniline to form an alkyl amine bond. Reaction of alkyl halides, alkyl sulfonates, diazoalkanes, or epoxides with carboxylic acids to form an ester bond. Reaction of an alkyl halides or alkyl sulfonates with an alcohol or phenol to form an ether bond. Reaction of an anhydride with an amine or aniline to form a carboxamide or imide bond. Reaction of an aryl halide with a thiol to form a thiophenol bond. Reaction of an aryl halide with an amine to form an aryl amine bond. Reaction of a boronate with a glycol to form a boronate ester bond. Reaction of a carboxylic acid with a hydrazine to form a hydrazide bond. Reaction of a carbodiimide with a carboxylic acid to form an N-acylurea or anhydride bond. Reaction of an epoxide with a thiol to form a thioether bond. Reaction of a haloplatinate with an amino or heterocyclic group to form a platinum complex. Reaction of a halotriazine with an amine or aniline to form an aminotriazine bond. Reaction of a halotriazines with an alcohol or phenol to form a triazinyl ether bond. Reaction of an imido ester with an amine or aniline to form an amidine bond. Reaction of an isocyanate with an amine or aniline to form a urea. Reaction of an isocyanate with an alcohol or phenol to form a urethane bond. Reaction of an isothiocyanate with an amine or aniline to form a thiourea bond. Reaction of a phosphoramidate with an alcohol to form a phosphite ester bond. Reaction of a silyl halide with an alcohol to form a silyl ether bond. Reaction of a sulfonate ester with an amine or aniline to form an alkyl amine bond. Reaction of a sulfonyl halide with an amine or aniline to form a sulfonamide bond. Reaction of a thioester with thiol group of a cysteine followed by rearrangement to form an amide bond. Reaction of an azide with an alkyne to form a 1,2,3-triazole. Reaction of an aldehyde with an N-terminal cysteine to form a 5-membered thiazolidine ring.

In some embodiments, water-insoluble substances can be chemically modified in an aprotic solvent such as dimethylformamide, dimethylsulfoxide, acetone, ethyl acetate, toluene, or chloroform. Similar modification of water-soluble substances can be accomplished using reactive compounds to make them more readily soluble in organic solvents.

In some embodiments the biomolecules and/or labels of the present disclosure are linked to a surface. Optionally, such linkage can result in reversible or non-reversible immobilization of the nanoparticles, polymerases, nucleotides, nucleic acid molecules, primers, and/or oligonucleotides onto the surface. Non-limiting examples of such linkage can include: nucleic acid hybridization, protein aptamer-target binding, non-specific adsorption, and solvent evaporation. In some embodiments, the biomolecule that is linked to a surface is a polymerase (such as, for example, a polymerase fusion protein). The polymerase can be attached to a surface via a linker comprising an anchor or tethering moiety. The anchor or tethering moiety can be flexible or rigid. The anchor or tether can orient the polymerase, or polymerase fusion protein, in a manner that does not interfere with the nucleotide binding and/or polymerase activity.

Linkage of biomolecules to labels, surfaces and/or to each other can be accomplished by any suitable method (for example, Brinkley et al., 1992 Bioconjugate Chem. 3: 2). In some embodiments, a biomolecule can comprise a single type of reactive site (as is typical for polysaccharides), or it can comprise multiple types of reactive sites, e g, amines, thiols, alcohols, phenols, may be available (as is typical for proteins). Conjugation selectivity can be obtained by selecting an appropriate reactive moiety. For example, modification of thiols with a thiol-selective reagent such as a haloacetamide or maleimide, or modification of amines with an amine-reactive reagent such as 1-ethyl-3-(3-dimethyl-aminopropyl) carbodiimide (variously known as EDC or EDAC), an activated ester, acyl azide, isothiocyanate or 3,5-dichloro-2,4,6-triazine. Partial selectivity can also be obtained by careful control of the reaction conditions.

In some embodiments, the biomolecule of the labeled biomolecule conjugate is linked to the label through a bond selected from group consisting of: a covalent bond, a hydrogen bond, a hydrophilic bond, a hydrophobic bond, an electrostatic bond, a Van der Waals bond, and an affinity bond.

In some embodiments, the biomolecule comprises a peptide and the bond is a covalent bond formed between an amine group of a lysine residue of the biomolecule and an amine-reactive moiety, wherein the amine reactive moiety is linked to the label. In some embodiments, the biomolecule comprises a peptide and the bond is a covalent bond formed between a carboxy group of an amino acid residue of the biomolecule and a maleimide moiety, wherein the maleimide moiety is linked to the label.

In some embodiments, the label of the labeled biomolecule conjugate comprises a nanoparticle. Optionally, the nanoparticle further comprises a carboxyl group on its surface, and the one or more biomolecules or fragments a primary amine group, and the cross-linking agent EDC is employed to form a covalent amide bond between the nanoparticle and the one or more biomolecules or fragments.

In some embodiments, the biomolecule can be attached to label (including, e.g., a FRET donor or acceptor moiety) using any suitable chemical linking procedure, including chemical linking procedures that are known in the art. In some embodiments, the biomolecule or biologically active fragment can be linked to the nanoparticle via chemical linking procedures. Many linking procedures are well known in the art, including: maleimide, iodoacetyl, or pyridyl disulfide chemistry which targets thiol groups on polypeptides; or succinimidyl esters (NHS), sulfonyl chlorides, iso(thio)cyanates, or carbonyl azide chemistry which targets primary amines in a polypeptide, and dichlorotriazine-based linking procedures. Additional exemplary linking procedures are described in more detail herein.

In some embodiments, the appropriate reactive compounds can be dissolved in a nonhydroxylic solvent (usually DMSO or DMF) in an amount sufficient to give a suitable degree of conjugation when added to a solution of the protein to be conjugated. These methods have been used to prepare protein conjugates from antibodies, antibody fragments, avidins, lectins, enzymes, proteins A and G, cellular proteins, albumins, histones, growth factors, hormones, and other proteins. The resulting protein (e.g., polymerase) attached to the energy transfer or reporter moiety can be used directly or enriched, e.g., chromatographically enriched to separate the desired linked compound from the undesired unlinked compound. Several linking procedures are described in U.S. Pat. No. 5,188,934. Other suitable linking procedures are also known in the art.

When conjugating biomolecules to nanoparticles, the residual, unreacted compound or a compound hydrolysis product can be removed by dialysis, chromatography or precipitation. The presence of residual, unconjugated moieties can be detected by methods such as thin layer chromatography which elutes the unconjugated forms away from its conjugate. In some embodiments, the reagents are kept concentrated to obtain adequate rates of conjugation.

In some embodiments, the surfaces, labels (including, e.g., dyes and/or nanoparticles) and/or biomolecules (including, e.g., polymerases, nucleotides and nucleic acid molecules) disclosed herein can be modified to facilitate their linkage to each other. Such modification can optionally include chemical or enzymatic modification. The modification can be practiced in any combination and in any order. In some embodiments, the modification can mediate covalent or non-covalent linkage of the surfaces, labels and/or biomolecules with each other.

In some embodiments, the biomolecule can be attached, fused or otherwise associated with a moiety that facilitates purification and/or isolation of the biomolecule. For example, the moiety can be a modification enzyme recognition site, an epitope or an affinity tag that facilitates purification of the biomolecule.

In some embodiments, the polymerase can include an amino acid analog which provides a reactive group for linking to the nanoparticle, target, substrate and/or surface. For example, the amino acid analog can be produced using a cell (e.g., bacterial cell) which is genetically engineered to have a 21 amino acid genetic code which is capable of inserting the amino acid analog into the encoded polymerase (or fusion protein). The inserted amino acid analog can be used in a linking chemistry procedure to attach the polymerase (or fusion protein) to the energy transfer donor moiety, biomolecule or the surface.

In some embodiments, the biomolecule is a protein and is modified with a Hig tag. In some embodiments, the His tag may be fused directly with the protein; alternatively, a linker comprising various lengths of amino acid residues can be placed between the protein and the His tag. The linker can be flexible or rigid.

Optionally, the presence of the His tag can facilitate purification of the protein. For example, His tagged protein can be purified from a raw bacterial lysate by contacting the lysate with any suitable affinity medium comprising bound metal ions to which the histidine residues of the His-tag can bind, typically via chelation. The bound metal ions can comprise, e.g., zinc, nickel or cobalt, to which the His tag can bind with micromolar affinity. Suitable affinity media include Ni Sepharose, NTA-agarose, HisPur® resin (Thermo Scientific, Pierce Protein Products, Rockford, Ill.), or Talon® resin (Clontech, Mountain View, Calif.). The affinity matrix can then be washed with suitable buffers, e.g., phosphate buffers, to remove proteins that do not specifically interact with the cobalt or nickel ion. Washing efficiency can be improved by the addition of 20 mM imidazole. The biomolecule can optionally be eluted from the proteins are usually eluted with 150-300 mM imidazole). The purity and amount of purified biomolecule can then be assessed using suitable methods, e.g., SDS-PAGE and Western blotting.

Optionally, the His tag can be fused to a suitable amino acid sequence that facilitates removal of the His-tag using a suitable endopeptidase. Alternatively, the His tag may be removed using a suitable exopeptidase, for example the Qiagen TAGZyme exopeptidase.

In some embodiments, the His tag can facilitate linkage of the biomolecule to a metal surface, for example, a surface comprising $Zn^{2+}$, $Ni^{2+}$, $Co^{2+}$, or $Cu^{2+}$ ions. Optionally, the His-tag can facilitate linkage of the biomolecule to the surface of a nanoparticle comprising one or more metal ions, typically via chelation interactions, as described in more detail herein.

Any suitable linkers can be used to link the biomolecules (including, e.g., the polymerases, nucleotides and nucleic acid molecules), the labels (including, e.g., nanoparticles, organic dyes, energy transfer moieties and/or other reporter moieties) and/or the surfaces of the present disclosure to each other, in any combination. The linkers can be attached (to the surfaces, nanoparticles, polymerases, nucleotides, target nucleic acid molecules, primers, oligonucleotides, reporter moieties, and/or energy transfer moieties) via covalent bonding, non-covalent bonding, ionic bonding, hydrophobic interactions or any combination thereof. The type and length of the linker can be selected to optimize tethering, proximity, flexibility, rigidity, or orientation. The attachment can be reversible or non-reversible.

Suitable linkers include without limitation homobifunctional linkers and heterobifunctional linkers. For example, heterobifunctional linkers contain one end having a first reactive functionality to specifically link to a first molecule, and an opposite end having a second reactive functionality to specifically link to a second molecule. Depending on such factors as the molecules to be linked and the conditions in which the method of strand synthesis is performed, the linker can vary in length and composition for optimizing properties such as stability, length, FRET efficiency, resistance to certain chemicals and/or temperature parameters, and be of sufficient stereo-selectivity or size to link a label to the biomolecule such that the resultant conjugate is useful reporting biomolecular behavior such as approach, bonding, fusion or catalysis of a particular chemical reaction. Linkers can be employed using standard chemical techniques and include but not limited to, amine linkers for attaching labels to nucleotides (see, for example, U.S. Pat. No. 5,151,507); a linker containing a primary or secondary amine for linking a label to a nucleotide; and a rigid hydrocarbon arm added to a nucleotide base (see, for example, *Science* 282:1020-21, 1998).

In some embodiments, the linker comprises a polyethylene glycol (PEG) or PEG derivative. See, e.g., U.S. Provisional Applications 61/086,750; 61/102,709; 61/102,683; and 61/102,666. Such PEG moieties can be functionalized at one or both ends. In some embodiments, functionalization at both ends with the same reactive moiety can be employed to create a homobifunctional PEG derivative. Some examples of homobifunctional PEG derivatives include without limitation COOH-PEG-COOH; NH2-PEG-NH2; and MAL-PEG-MAL (where MAL denotes a maleimide group).

The linker moiety can optionally include: a covalent or non-covalent bond; amino acid tag; chemical compound (e.g., polyethylene glycol); protein-protein binding pair (e.g., biotin-avidin); affinity coupling; capture probes; or any combination of these.

Optionally, the linker can be selected such that it does not significantly interfere with the function or activity of the biomolecules, labels and/or surfaces that it links to each other. For example, when the biomolecule is a polymerase, the linker can be selected such that it does not significantly interfere with nucleotide binding to the polymerase, or with cleavage of the phosphodiester bonds, or with nucleotide incorporation, or with release of the polyphosphate product, or with translocation of the polymerase or with energy transfer, or with emission of a signal.

In some embodiments, the linker can comprise a single covalent bond or a series of covalent bonds. Optionally, the linker can be linear, branched, bifunctional, trifunctional, homofunctional, or heterofunctional. The linker can be cleavable. The linkers can be rigid or flexible. The linker can be capable of energy transfer. The linker can be a chemical chain or a chemical compound. The linker can be resistant to heat, salts, acids, bases, light and chemicals. The linker can include a short or long spacer, a hydrophilic spacer, or an extended spacer.

In another embodiment, a rigid linker can be used to link the biomolecule to the label. Examples of rigid linkers include benzyl linkers, proline or poly-proline linkers (S. Flemer, et al., 2008 Journal Org. Chem. 73:7593-7602), bis-azide linkers (M. P. L. Werts, et al., 2003 Macromolecules 36:7004-7013), and rigid linkers synthesized by modifying the so-called "click" chemistry scheme which is described by Megiatto and Schuster 2008 Journal of the Am. Chem. Soc. 130:12872-12873. In yet another embodiment, the linker can be an energy transfer linker synthesized using methods described in U.S. published patent application No. 2006/0057565, which is incorporated in its entirety. In yet another embodiment, the spacer linking moiety can be a cationic arginine spacer or an imidazolium spacer molecule.

In some embodiments, the linker moiety comprises about 1-40 μlural valent atoms or more selected from the group consisting of C, N, O, S and P. The number of plural valent atoms in a linker may be, for example, 0, 1, 2, 3, 4, 5, 6, 7, 8, 9, 10, 20, 25, 30, or 40, or more. A linker may be linear or non-linear; some linkers have pendant side chains or pendant functional groups (or both). Examples of such pendant moieties are hydrophilicity modifiers, for example solubilizing groups like, e.g., sulfo (—$SO_3H$— or —$SO^3$—). In some embodiments, a linker is composed of any combination of single, double, triple or aromatic carbon-carbon bonds, carbon-nitrogen bonds, nitrogen-nitrogen bonds, carbon-oxygen bonds and carbon-sulfur bonds. Exemplary linking members include a moiety which includes —C(O)NH—, —C(O)O, NH, S, O, and the like. Linkers may by way of example consist of a combination of moieties selected from alkyl, alkylene, aryl, —C(O)NH—, —C(O)O—, —NH—, —S—, —O—, —C(O)—, $S(O)_n$— where n is 0, 1, 2, 3, 4, 5, or 6-membered monocyclic rings and optional pendant functional groups, for example sulfo, hydroxy and carboxy.

In some embodiments, the linker can result from "click" chemistries schemes (see, e.g., Gheorghe, et al., 2008 Organic Letters 10:4171-4174) which can be used to attach any combination of biomolecules, labels and surfaces as disclosed herein to each other In one aspect, the linker can attach two or more energy transfer or reporter moieties to each other (the same type or different types of moieties).

In another aspect, a trifunctional linker (e.g., Graham, U.S. published patent application No. 2006/0003383) can be linked to two fluorescent dye moieties (the same type or different types) to amplify the fluorescent signal upon nucleotide binding or nucleotide incorporation. For example, a trifunctional linker can be linked to two energy transfer acceptor moieties, or to an energy transfer acceptor and a reporter moiety. In another example, multiple trifunctional linkers can be linked to each other, which can be linked to multiple fluorescent dyes for dendritic amplification of the fluorescent signal (e.g., Graham, U.S. published patent application No. 2007/0009980).

In some embodiments, the linker can be a cleavable linker such as, for example, a photocleavable linker, a chemically cleavable linker or a self-cleaving linker.

In some embodiments, the linker is a self-cleaving linker. Optionally, such linker can be a trimethyl lock or a quinone methide linker, which can each optionally link to two energy transfer acceptor and/or reporter moieties and the nucleotide.

In some embodiments, the linkers can be cleavable where cleavage is mediated by a chemical reaction, enzymatic activity, heat, acid, base, or light. For example, photocleavable linkers include nitrobenzyl derivatives, phenacyl groups, and benzoin esters. Many cleavable groups are known in the art and are commercially available. See, for example, J. W. Walker, et al., 1997 Bioorg. Med. Chem. Lett. 7:1243-1248; R. S. Givens, et al., 1997 Journal of the American Chemical Society 119:8369-8370; R. S. Givens, et al., 1997 Journal of the American Chemical Society 119:2453-2463; Jung et al., 1983 Biochem. Biophys. Acta, 761: 152-162; Joshi et al., 1990 J. Biol. Chem., 265: 14518-14525; Zarling et al., 1980 J. Immunol., 124: 913-920; Bouizar et al., 1986 Eur. J. Biochem., 155: 141-147; Park et al., 1986 J. Biol. Chem., 261: 205-210; and Browning et al., 1989 J. Immunol., 143: 1859-1867; see also U.S. Pat. No. 7,033,764. A broad range of cleavable, bifunctional (both homo- and hetero-bifunctional) spacer arms with varying lengths are commercially available.

In yet another embodiment, the linker can be an energy transfer linker synthesized using methods described in U.S. Published Patent Application No. 2006/0057565.

In yet another embodiment, the linker can comprise a spacer, for example a cationic arginine spacer or an imidazolium spacer molecule.

In some embodiments, the linker can be a fragmentable linker, including non-lamellar "detergent-like" micelles or lamellar vesicle-like micelles such as small unilamellar vesicles or liposomes ("SUVs"), small multilamellar vesicles or liposomes (SMVs"), large unilamellar vesicles or liposomes ("LUVs") and/or large multilamellar vesicles or liposomes ("LMVs") (see U.S. application Ser. No. 11/147, 827) and see U.S. Application Nos. 60/577,995, and 12/188, 165.

In some embodiments, the linker can include multiple amino acid residues (e.g., arginine) which serve as an intervening linker between an attachment site on the biomolecule and the label. For example, the linker can be can four arginine residues which connect a dye moiety to a nucleotide comprising one or more phosphate groups, wherein the linker links the dye moiety to the terminal phosphate group of the nucleotide.

In some embodiments, linkers can be used to attach energy transfer or reporter moieties to biomolecules using any suitable linking procedure, including: amine linkers (see, for example, Hobbs, U.S. Pat. No. 5,151,507); a linker comprising a primary or secondary amine; and a rigid hydrocarbon arm (see, for example, R. F. Service, 1998 Science 282(5391):1020-21). Some exemplary linking procedures for attaching energy transfer or reporters moieties exemplary biomolecules are provided in European Patent Application 87310256.0; International Application PCT/US90/05565; Marshall, 1975 Histochemical Journal 7:299-303; and Barone et al., 2001 Nucleosides, Nucleotides, and Nucleic Acids, 20(4-7): 1141-1145. Other examples include linkers for attaching energy transfer or reporter moieties to exemplary biomolecules, using the specific example of oligonucleotides synthesized using phosphoramidate to incorporate amino-modified dT (see Mathies, U.S. Pat. No. 5,707,804).

In one aspect, a linker comprising a polymer of ethylene oxide can be used to attach the surfaces, labels (including, e.g., dyes and nanoparticles), polymerases, nucleotides and/or nucleic acid molecules of the present disclosure to each other in any combination. Non-limiting examples of such polymers of ethylene oxide include polyethylene glycol (PEG), including short to very long PEG, branched PEG, amino-PEG-acids, PEG-amines, PEG-hydrazines, PEG-guanidines, PEG-azides, biotin-PEG, PEG-thiols, and PEG-maleinimides. For example, PEG includes: PEG-1000, PEG-2000, PEG-12-OMe, PEG-8-OH, PEG-12-COOH, and PEG-12-NH2. In some embodiments, the PEG molecule may be linear or branched. In some embodiments, it can have a molecular weight greater than or approximately equal to 1000, 2000, 3000, 4000, 5000 or greater.

In some embodiments, functionalization with different reactive moieties can be used create a heterobifunctional PEG derivative comprising different reactive groups at each end. Such heterobifunctional PEGs can be useful in linking two entities, where a hydrophilic, flexible and biocompatible spacer is needed. Some examples of heterobifunctional PEG derivatives include without limitation Hydroxyl PEG Carboxyl (HO-PEG-COOH): Thiol PEG Carboxyl (HS-PEG-COOH); Hydroxyl PEG Amine (HO-PEG-NH2); t-Boc Amine PEG Amine (TBOC-PEG-NH2); Amine PEG Carboxyl (NH2-PEG-COOH); t-Boc Amine PEG NHS Ester (TBOC-PEG-NHS); FMOC Amine PEG NHS Ester (FMOC-PEG-NHS): Acrylate PEG NHS Ester (ACLT-PEG-NHS); Maleimide PEG Carboxyl (MAL-PEG-COOH); Maleimide PEG Amine (MAL-PEG-NH2), including the TFA Salt thereof; Maleimide PEG NHS Ester (MAL-PEG-NHS); Biotin PEG NHS Ester (BIOTIN-PEG-NHS); Biotin Polyethylene Glycol Maleimide (BIOTIN-PEG-MAL); OPSS PEG NHS Ester (OPSS-PEG-NHS).

Optionally, the PEG derivative can be a multi-arm PEG derivative. In some embodiments, the multi-arm PEG derivative can be a PEG derivative having a core structure comprising pentaerythritol (including, for example, 4arm PEG Amine (4ARM-PEG-NH2); 4arm PEG Carboxyl (4ARM-PEG-COOH); 4arm PEG Maleimide (4ARM-PEG-MAL); 4arm PEG Succinimidyl Succinate (4ARM-PEG-SS); 4arm PEG Succinimidyl Glutarate (4ARM-PEG-SG)); a PEG derivative having a core structure comprising hexaglycerin (including, for example, 8arm PEG Amine (8ARM-PEG-NH2); 8arm PEG Carboxyl (8ARM-PEG-COOH); 8arm PEG Succinimidyl Succinate (8ARM-PEG-SS); 8arm PEG Amine (8ARM-PEG-SG); PEG derivative having a core structure comprising tripentaerythritol (including, for example, 8arm PEG Amine (8ARM(TP)-PEG-NH2); 8arm PEG Carboxyl (8ARM(TP)-PEG-COOH); 8arm PEG Succinimidyl Succinate (8ARM(TP)-PEG-SS);

8arm PEG Amine (8ARM(TP)-PEG-SG)). Optionally, end groups for heterobifunctional PEGs can include maleimide, vinyl sulfones, pyridyl disulfide, amine, carboxylic acids and NHS esters. The activated PEG derivatives can then be used to attach the PEG to the desired biomolecule and/or label. Optionally, one or both ends of the PEG derivative can be attached to the N-terminal amino group or the C-terminal carboxylic acid of a protein-comprising biomolecule.

For methods, systems, compositions and kits comprising labeled biomolecule conjugates, the biomolecule can be linked to the label in any manner, and using any suitable linking procedures, that suffiicently preserves a particular biological activity of interest. Typically, when the biomolecule is a polymerase, the conjugate is a labeled polymerase conjugate and the biological activity of interest is polymerase activity. The polymerase of the labeled polymerase conjugate conjugate can be linked to the label using any suitable method that retains polymerase activity.

In some embodiments, the biomolecule and the label can be linked through a linker.

In some embodiments, the biomolecule-nanoparticle conjugate comprises a biomolecule covalently linked to a nanoparticle, wherein the biomolecule are linked to the nanoparticle through one or more covalent bonds.

In some embodiments, the label can be covalently linked to the biomolecule using any suitable method that permits linkage without loss of biological activity. Typically, the reagents employed are selected to allow the covalent linkage of the biomolecule to the label under defined reaction conditions. In some embodiments, the linkage can be performed in a site-specific manner.

In one exemplary embodiment, the label and the biomolecule can be reacted with each other in a suitable solvent in which both are soluble. The labels can optionally be treated or functionalized with suitable moieties to enhance their solubility in a suitable solvent.

In a typical embodiment, the biomolecule comprises a protein, more typically an enzyme, which can optionally be a polymerase. The various linking methods described herein have particular applicability for linking enzymes, e.g., polymerases, to labels such as nanoparticles or organic dyes.

In some embodiments, the label (e.g., nanoparticle or dye) can optionally be treated to create suitable sites for covalent attachment of the biomolecule. For example, the label and/or the biomolecule can be modified via introduction of a cysteine amino acid residue to create an attachment site comprising a free sulfhydryl group of the cysteine. In another embodiment, the label can be modified via introduction of a moiety comprising a reactive chemical group selected from any one of: a thiol group, an amino group (e.g., a primary or secondary amine) and a carboxyl group. The reactive chemical group of one member of the labeled biomolecule conjugate can then be reacted with a second reactive chemical group of a second member of the conjugate.

In one example, the label can be treated to introduce one or more reactive chemical groups that form suitable attachment sites for the biomolecule. Optionally, the label can be linked to with a cysteine-rich compound such as bovine serum albumin (BSA) or ovalbumin, resulting in the association of the cysteine-rich compound with the label. The label can then be treated with reducing agents such as DTT, resulting in the formation of a large number of free sulfhydryl groups on the protein molecule to serve as potential sites for covalent attachment of the biomolecule. For example, reduction of a single BSA molecule on the nanoparticle surface results in the generation of approximately 34 free sulfhydryl groups, since a single BSA molecule typically comprises 17 disulfide bonds and one free thiol group. Such a poly-dentate thiol-modified protein could serve as a platform for initial modification of the label, onto which other biomolecules of interest can be added after the initial modification. In one embodiment, the BSA-treated label is a nanoparticle.

In some embodiments, the label can treated or otherwise modified by the introduction of one or more reactive groups that can react with a second group on the biomolecule to link the label to the biomolecule.

In some embodiments, the label is a nanoparticle, and the reactive group is introduced via a "capping" process.

In one exemplary embodiment, the label can be modified by the introduction of one or more mercaptoacetic acid groups, and the resulting modified label can be are covalently linked to the biomolecule through the acid group.

Optionally, the biomolecule can be engineered to include thiol-terminated residues that react with suitable groups on the label.

In another embodiment, the biomolecule and the label can be covalently linked through a condensation reaction between an amines of the biomolecule and a carboxyl group of the label using a suitable cross-linking agent. In some embodiments, the linker EDC is used to activate free —COOH ligands on the label. For example, the cross-linking agent 1-ethyl-3-(3-dimethyl-aminopropyl) carbodiimide (EDC) can be used to cross-link the amine-containing biomolecule with the carboxyl-containing label. The carboxyl group can be part of, or derived from, a mercaptoacetic acid or a dihydrolipoic acid (DHLA).

In some embodiments, the conjugation method can exploit the presence of cysteine residues within the biomolecule to be conjugated because such residues can serve as points of attachment to the label. For example, the thiol group of cysteine residues can be covalently linked to a label by using linking agents such as SMCC. In some embodiments, the biomolecule is a polymerase that is genetically modified to introduce one or more cysteine residues placed in strategic positions, e.g., proximal to the active site/NTP binding pocket of the polypeptide. The polymerase can then be linked to a nanoparticle using SMCC. The covalent bond(s) between the polymerase and the label will not only stabilize the conjugate but also orient the polypeptide with respect to the nanoparticle in the preferred orientation for binding, resulting both in an increase of conjugate stability (manifested as reduced propensity of the conjugate to disassociate) and preservation of high affinity binding.

In some embodiments, the labeled biomolecule conjugate is produced by covalently linking the biomolecule to the label having one or more carboxyl groups using the heterobifunctional cross-linking agent succinimidyl-4-(N-maleimidomethyl)cyclohexane-1-carboxylate ("SMCC"). This agent comprises a maleimide reactive group capable of reacting with cysteine residues to form a thioether bond as well as an amine reactive NHS ester capable of reacting with primary amines to form an amide bond. Such a linker has utility in cross-linking, inter alia, biomolecules comprising one or more sulfhydryl groups (e.g., proteins comprising cysteine residues) to labels comprising one or more amine groups. Under suitable conditions, the double bond of the maleimide can undergo an alkylation reaction with a sulfhydryl group of the biomolecule to form a stable thioether bond. The NHS ester contains an amine-reactive group that can react with, inter alia, amine groups on the label. Optionally, the label includes a PEG amine, and the amine group that reacts with the NHS ester of SMCC can be the amine group of the PEG-amine.

In some embodiments, the labeled biomolecule conjugate comprises a biomolecule covalently linked to a label. In one exemplary embodiment, the biomolecule comprises one or more primary amine groups and the label is covalently linked to the one or more amine groups using the linking agents such as tris(hydroxymethyl)phosphine (TMP) and/or β-[tris(hydroxymethyl)phosphino] propionic acid (THPP). TMP and THPP are phosphine derivatives that can react with amines to form covalent linkages. See, e.g., Cochran, F., et al., "Application of tris(hydroxymethyl)phosphine as a coupling agent for alcohol dehydrogenase immobilization, Enzyme & Microbial Technology 18:373-378 (1996); Hermanson, G., *Bioconjugate Techniques*, Second Edition (2008).

Figure 3:
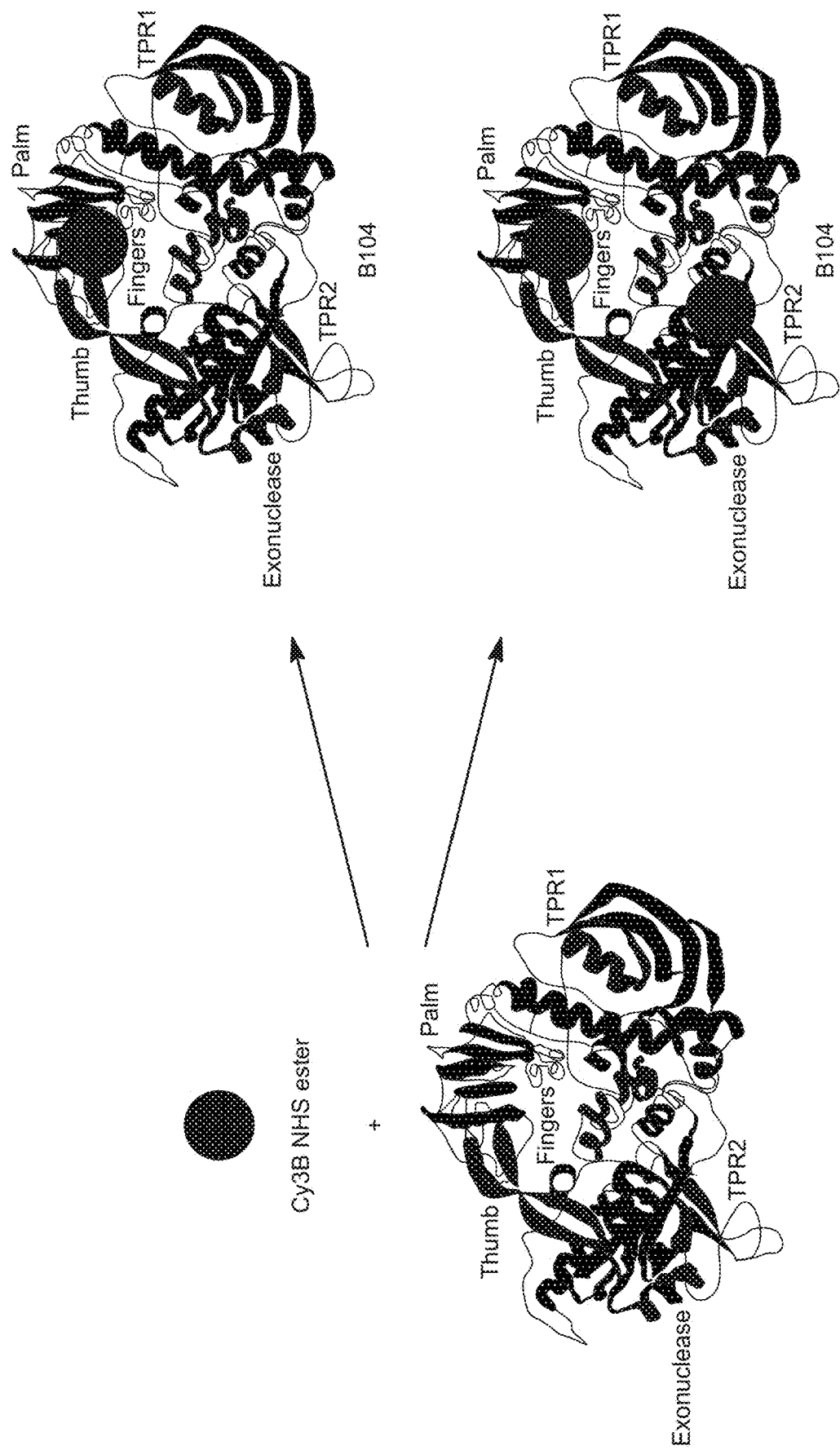
FIG. 3 depicts one exemplary method for preparing a dye-labeled polymerase conjugate according to the present disclosure.

In another exemplary embodiment, a lysine side chain of the biomolecule can be reacted with one or more labels comprising reactive NHS ester groups under conditions where the one or more labels bind to the one or more lysine side chains. The conditions can be selected such that one, few, some or all the lysine side chains are reacted with the NHS ester groups of the label. An exemplary embodiment wherein Cy3B comprising reactive NHS ester groups is reacted with Phi-29 polymerase to form a Cy3B-Phi-29 labeled polymerase conjugate comprising an average of one or two Cy3B dye molecules per polymerase is depicted in FIG. 3. Exemplary methods of preparing such conjugates are described in Examples 4 and 5, respectively.

In some embodiments, the conjugation method can exploit the presence of cysteine residues within the biomolecule to be conjugated because such residues can serve as points of attachment to the nanoparticle surface. For example, the thiol group of cysteine residues can be covalently linked to the surface of metal-containing nanoparticles by using linking agents such as SMCC. Such conjugation methods result in stable, oriented binding of the peptide and the nanoparticle. In some embodiments, the biomolecule is a protein or polypeptide, for example an enzyme, that comprises naturally occurring amino acid side chains that can be modified or otherwise treated so as to generate attachment sites for the nanoparticle. For example, the protein or polypeptide can be genetically modified to introduce one or more cysteine residues placed in strategic positions, e.g., proximal to the active site/NTP binding pocket of the polypeptide. The engineered polypeptide can then be linked to a nanoparticle using linkers such as SMCC. The covalent bond(s) between the polypeptide and the nanoparticle will not only stabilize the conjugate but also orient the polypeptide with respect to the nanoparticle in the preferred orientation for binding, resulting both in an increase of conjugate stability (manifested as reduced propensity of the conjugate to disassociate) and preservation of high affinity binding.

The nanoparticle can optionally be derivatized with PEG-amine. In some embodiments, the nanoparticle can be capped with ovalbumin or other proteinaceous coating using any suitable cross-linkers (e.g., EDC, BS3 SMCC).

In some embodiments, nanoparticles containing free —COOH ligands on their surface are derivatized via formation of amide bonds with the terminal amino group of PEG-amine. The PEG-ylated nanoparticles are activated by treatment with agents such as SMCC, and the activated nanoparticles are then conjugated to polymerase via formation of thioether bonds involving the maleimide group of SMCC and a cysteine thiol group on the polymerase. In some embodiments, the linker EDC is used to activate free —COOH ligands on the surface of nanoparticles.

In some embodiments, the biomolecule is linked to the label via a covalent bond formed between a reactive α-thioester and an N-terminal cysteine residue. Such reactions are described, for example, in Dawson et al., Science 266:776-779 (1994); Dawson et al., Ann. Rev. Biochem. 69:923-960 (2000); Johnson et al., JACS 128:6640-6646 (2006). In some embodiments, a biomolecule that comprises, or is modified to comprise, an N-terminal cysteine group is linked to a label comprising a thioester ligand. In one example, a thioester-comprising crosslinker is first attached to the label using any suitable chemistry, resulting in a modified label comprising a reactive thioester. This modified label is then reacted with a biomolecule comprising, or modified to comprise, an N-terminal cysteine residue. Optionally, such reaction can be done in the presence of a suitable aromatic or aliphatic thiol catalyst. The thiol group of the cysteine reacts with the thioester on the label, forming a second thioester that undergoes intramolecular rearrangement. Such rearrangement results in the formation of a natural peptide bond linking the biomolecule to the label. See, e.g., Dawson et al., Science 266:776-779 (1994); Dawson et al., Ann. Rev. Biochem. 69:923-960 (2000); Johnson et al., JACS 128: 6640-6646 (2006).

In another exemplary embodiment, a label including a reactive aldehyde can be reacted with a biomolecule including an N-terminal cysteine residue. The reaction product is a five-membered thiazolidine ring that is stable over a pH range of 3-9. See, e.g., Shao & Tam, "*Unprotected Peptides as Building Blocks for the Synthesis of Peptide Dendrimers with Oxime, Hydrazone and Thiazolidine Linkages,*" JACS 117(14):3893-3899 (1995)). In some embodiments, the label includes an amine, which can be converted to an aldehyde through treatment with the heterobifunctional crosslinking reagent SFB (Pierce). The aldehyde of the label can then be reacted with an N-terminal cysteine group of a biomolecule to form a covalent linkage between the biomolecule and the label.

In yet another embodiment, a biomolecule comprising a ketone can be reacted with a label in the presence of a hydroxylamine to covalently link the biomolecule to the label.

In another exemplary embodiment, either the biomolecule or the label is modified to include an alkyne, and the other is modified to include an azide. The alkyne and azide can undergo a "click" reaction to form a covalent conjugate. Optionally, the click reaction can be a "copperless" click reaction.

In some embodiments, the biomolecule of the labeled biomolecule conjugate can be non-covalently linked to the label. See, for example, Goldman et al., 2005, *Anal. Chim. Acta* 534:63-67. For example, in some embodiments the biomolecule can be linked to the label via a non-covalent interaction between a first and second member of a binding pair, as described further herein.

In some embodiments, the conjugation of the biomolecule to the label can be achieved through a process of self-assembly, wherein suitably modified biomolecules and labels are contacted under conditions where they will bind spontaneously to each other. For example, one or more thiolated proteins can be conjugated to a sulfur-comprising label using dative thiol-bonding between the cysteine residues on the protein and a sulfur atom of the label. The label can be a nanoparticle. See, e.g., Akerman, M. E., et al., "Nanocrystal targeting in vivo", Proc. Natl. Acad. Sci. USA 99:12617-12621 (2002). Optionally, the conjugate can be formed through adsorption or non-covalent self-assembly of proteins with the label.

In some embodiments, the conjugate can be formed through self-assembly via electrostatic interactions, wherein biomolecules having either a natural positive surface charge or that are engineered to include positively charged domains, interact with labels having a negative surface charge, (e.g., nanoparticles capped with substances comprising COOH moieties). See, for example, Mattoussi et al., "Self-assembly of CdSe—ZnS nanoparticle bioconjugates using an engineered recombinant protein", J. Am. Chem. Soc. 122(49): 12142-50 (2000); Mattoussi et al., "Bioconjugation of highly luminescent colloidal CdSe—ZnS nanoparticles with an engineered two-domain recombinant protein", Phys. Status Solido B-Basic Res. 224:277-83 (2001). In some embodiments, the label can be modified via the introduction of one or more —COOH ligands or other negatively charged moieties (for example, lipoic acid moieties), and then contacted with engineered recombinant protein-comprising biomolecules comprising positively charged attachment domains (for example, leucine zippers, polylysine or polyarginine linkers or the like).

Another assembly-based approach involves the use of affinity ligands. In some embodiments, conjugation is accomplished through use of binding pairs.

Provided herein are labeled biomolecule conjugates comprising a biomolecule linked to a label by means of a binding pair. In one example, a first members of a binding pair is linked to a biomolecule and a second member of the binding pair is linked to the label. The first and second members of the binding pair are linked to each other, thereby linking the biomolecule to the label.

Also provided herein are methods for making a labeled biomolecule conjugate, comprising: linking a first member of a binding pair to a biomolecule; linking a second member of the binding pair to at least one label; and contacting the first and second members under conditions where they bind to each other, thereby linking the biomolecule to the at least one label.

Optionally, the biomolecule can be an enzyme, for example a polymerase. In some embodiments, the first member of the binding pair is a biotin moiety and the second member is an avidin moiety. In some embodiments, the second member of the binding pair is linked to three, four, five, six, seven or more labels.

In some embodiments, the biomolecule is a polymerase and the conjugate is a labeled polymerase conjugate. In some embodiments, the polymerase of the conjugate can retain at least about 10%, 20%, 30%, 40%, 50%, 60%, 70%, 80%, 90%, or 95% polymerase activity relative to the unconjugated form of the polymerase. Typically, the polymerase activity can be measured using any one of the primer extension activity assays described herein.

Suitable binding pairs include: a biotin moiety (including, for example, biotin, desthiobiotin or photoactivatable biotin, bound with an avidin moiety, such as streptavidin or neutravidin); His-tag bound with nickel or cobalt; maltose bound with a maltose binding protein (MBP); lectin bound with a carbohydrate; calcium bound with a calcium binding protein (CBP); antigen or epitope tags bound with an antibody or antibody fragment; particular antigens such as digoxigenin, fluorescein, nitrophenol or bromodeoxyuridine and their respective antibodies; IgG bound with protein A; receptor bound with a receptor agonist or antagonist; enzyme bound with an enzyme cofactors; and thyroxine bound with cortisol.

In some embodiments, the members of a binding pair can be naturally occurring substances or else substances which are prepared, for example, by means of chemical synthesis, microbiological techniques and/or recombinant DNA methods.

In some embodiments, the binding pair members can be selected and/or identified using phage display libraries, synthetic peptide databases or recombinatorial antibody libraries. See, e.g., Larrick & Fry (1991) Human Antibodies and Hybridomas, 2: 172-189.

In one exemplary embodiment, the biomolecule and the label are linked by means of a binding pair comprising a biotin moiety and an avidin moiety. The strong interaction between streptavidin (or avidin) and biotin (cis-hexahydro-2-oxo-1H-thieno[3,4]imidazole-4-pentanoic acid) is well known. The affinity binding between streptavidin and biotin, having a dissociation constant, $K_d$, of approximately $10^{-15}M$, is regarded as one of the strongest known, non-covalent, biochemical interactions. The biotin-avidin bond forms very rapidly and is considered to be stable under a wide range of pH, temperature and other denaturing conditions. See, e.g., Savage et al., Avidin-Biotin Chemistry: A Handbook, 1992:1-23, Rockford, Pierce Chemical Company; Goldman et al., "Avidin: A natural bridge for quantum dot-antibody conjugates", J. Am. Chem. Soc. 124:6378-6382 (2002). Without being bound by any particular theory, it is believed that biotin and avidin moieties bond with each other through a combination of ionic (electrostatic) and hydrophobic interactions.

The avidin moiety can in some embodiments comprisie any suitable naturally occurring avidin, as well as non-naturally occuring deriviatives and analogs thereof. Some of these materials are commercially available, e.g. native avidin and streptavidin, nonglycosylated avidins, N-acyl avidins and truncated streptavidin, or can be prepared by well-known methods (see Green, 1990, for preparation of avidin and streptavidin; Hiller et al., 1990, for preparation of non-glycosylated avidin; Bayer et al., 1990, for the preparation of streptavidin and truncated streptavidin).

In an exemplary embodiment, a biomolecule and a label can be linked to form a labeled biomolecule conjugate, where the linkage between the biomolecule and the label comprises one or more affinity interactions between a biotin moiety and an avidin moiety. In some embodiments, a biomolecule can be linked to a biotin moiety and a label can be linked to an avidin moiety, where the biomolecule is linked to the label via an affinity interaction between the biotin and avidin moieties. The label can comprise, for example, an organic dye moiety or a nanoparticle.

In some embodiments, a biotin moiety is linked to either the biomolecule or the label through treatment with an enzyme that is capable of covalently attaching a biotin moiety to a substrate, such as a biotin ligase. For example, the biotin ligase can be the *E. coli* biotin ligase (EC 6.3.4.15) encoded by the birA gene of *E. coli*. The *E. coli* biotin ligase is also commonly referred to as biotin-protein ligase; other names for this enzyme include: biotin ligase; biotin operon repressor protein; birA; biotin holoenzyme synthetase; biotin-[acetyl-CoA carboxylase] synthetase. This enzyme can activate a biotin moiety to form a biotinyl-5' adenylate and can transfer the activated biotin moiety to a biotin-accepting protein, such as an acceptor peptide for biotin ligase (hereinafter, "a biotin acceptor peptide"). In some embodiments, the biotin acceptor site can comprise the amino acid sequence of SEQ ID NO: 10: See, e.g., Howarth et al., "Targeting quantum dots to surface proteins in living cells with biotin ligase", Proc. Natl. Acad. Sci. USA 102(21):

7583-7588 (2005). In some embodiments, the biotin acceptor peptide can comprise the amino acid sequence of SEQ ID NO: 10 (GLNDIFEAQKIEWHE). Optionally, the biotin acceptor peptide is the AviTag™ peptide (Avidity, LLC). See, e.g., U.S. Pat. Nos. 5,723,584, 5,874,239 and 5,932,433.

In some embodiments, the biotin can be linked to a thiol group of the biomolecule. For example, the biomolecule can comprise a free cysteine residue (including but not limited to a naturally occurring or an engineered replacement cysteine residue), and the biotin moiety can be linked to the free cysteine residue. Optionally, the biotin moiety can be linked to the cysteine residue by use of a thiol-reactive reagent, such as a biotin-maleimide reagent, to form a biotin-labeled biomolecule. See, e.g., U.S. Pat. No. 7,521,541.

In one exemplary embodiment, the label of the conjugate is linked to an avidin moiety and contacted with a biomolecule linked to a biotin moiety.

In some embodiments, the label is linked to the biomolecule through use of an attachment site that is engineered or otherwise introduced into the biomolecule and serves as the site of attachment for one or more labels. In some embodiments, the introduced attachment site comprises an enzyme modification recognition sequence. In some embodiments, the modification enzyme recognition sequence can comprise a biotin ligase acceptor site, to which one or more biotin moieties can be attached by a biotin ligase, thus forming an attachment site for a label linked to an avidin moiety.

In some embodiments, the biomolecule of the conjugate is a protein that comprises a biotin ligase acceptor site, such that the biomolecule can be biotinylated via treatment with a suitable biotin ligase in the presence of a biotin. Typically, the biomolecule or the nanoparticle to be biotinylated comprises a biotin acceptor site.

In another embodiment, the modification enzyme recognition site is an N-terminal recognition site for the TEV (Tobacco Etch Virus) protease enzyme. Typically, such recognition site comprises the following amino acid sequence:

ENLYFQ SEQ ID NO: 37

Figure 17A:
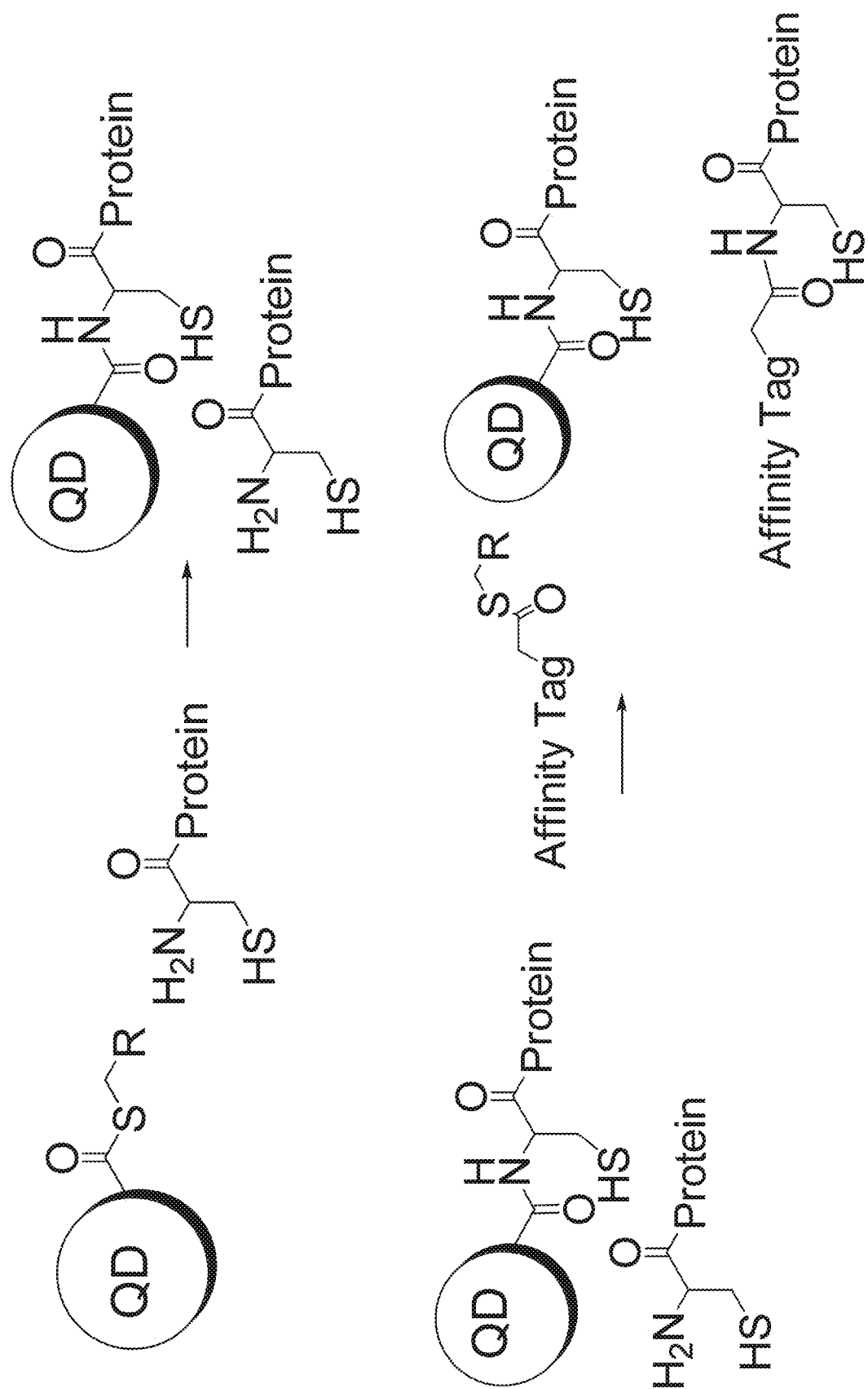
FIG. 17A depicts an exemplary reaction pathway for forming a labeled polymerase conjugate according to the present disclosure, for example an N-terminal cysteine reacting with a thioester.
Figure 17B:
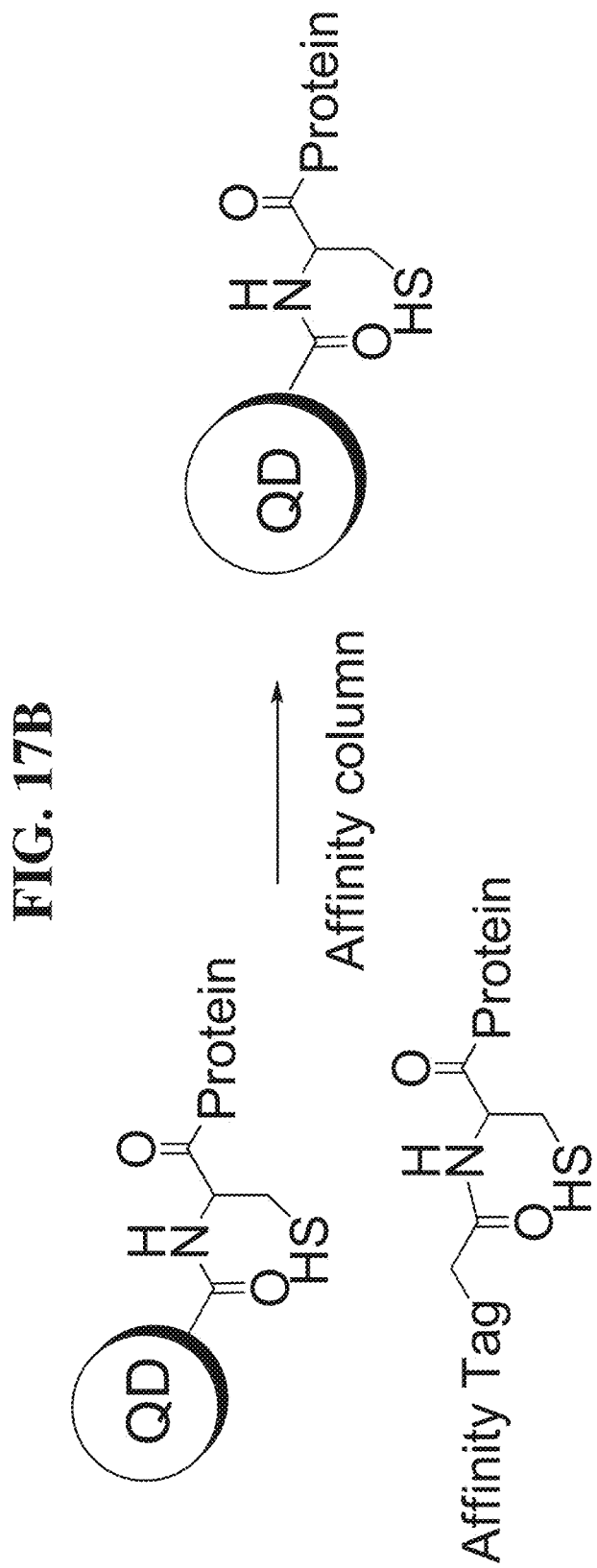
FIG. 17B depicts an exemplary reaction pathway for forming a labeled polymerase conjugate according to the present disclosure, for example is a schematic showing formation of a peptide bond.

The TEV protease can specifically cleave this modification enzyme recognition sequence after the glutamine (Q) residue. See, e.g., de Graaf et al., "Nonnatural Amino Acids for Site-Specific Protein Conjugation," 20(7):1281-1295 (2009); Tolbert & Wong, "Conjugation of Glycopeptide Thioesters To Expressed Protein Fragments", Methods in Mol. Bio., Vol. 283 ("Bioconjugation Protocols"), pp. 255-266 (2004). Optionally the protein to be conjugated is fused at its N-terminus with a peptide tag comprising the TEV protease recognition sequence, and the recombinant protein is then cleaved with TEV protease to remove the tag and uncover an N-terminal cysteine. The amino acid sequences of exemplary polymerases comprising a TEV protease recognition sequence at their N-terminus are disclosed herein. Biomolecules comprising a N-terminal cysteine are especially desirable because the N-terminal cysteine group can serve as an attachment site for the site-specific attachment of a label using a variety of different chemistries. In one example, the N-terminal cysteine can be reacted with a thioester to form a peptide bond (see FIG. 17A).

Figure 18:
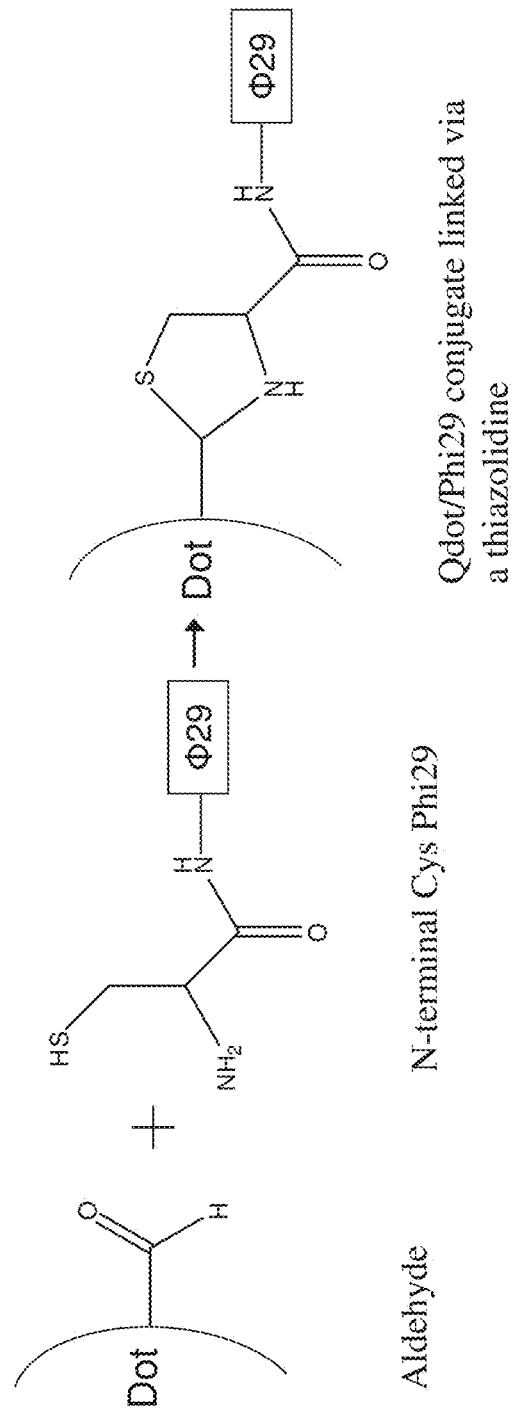
FIG. 18 depicts a second exemplary reaction pathway for forming a labeled polymerase conjugate according to the present disclosure.

In another embodiment, the N-terminal cysteine can be reacted with an aldehyde to form a 5-membered thiazolidine ring (see FIG. 18). Specific examples using such conjugation strategies are described further herein.

In some embodiments, the enzyme can be labeled in a site-specific manner through incorporation of unnatural or modified amino acids during translation of the mRNA encoding the enzyme using modified aminoacyl tRNAs and/or modified tRNA synthetases. Briefly, such unnatural amino acids are genetically encoded in mammalian and other cells by using a mutant E. coli aminoacyl-tRNA synthetase that has been evolved to selectively aminoacylate its tRNA with the unnatural amino acid of interest. This mutant synthetase, together with an amber suppressor tRNA, can be used to selective incorporate the unnatural amino acid into a protein at selected sites in response to amber nonsense codes. See, e.g., Brustad et al., "A general and efficient method for the site-specific dual-labeling of proteins for single molecule fluorescence resonance energy transfer" J. Am. Chem. Soc. 130(52):17664-5 (2008); Liu et al., "Genetic incorporation of unnatural amino acids into proteins in mammalian cells" Nat. Methods, 4(3):239-244 (2007).

In another covalent conjugation approaches can also involve the insertion of other non-natural amino acids besides an N-terminal cysteine at defined sites within the biomolecule via site-specific engineering. Such introduced non-natural amino acids can then serve is attachment sites for a label. In one exemplary embodiment, an azido non-natural amino acid is engineered into the polymerase, which is then undergoes a click chemistry reaction with a DIBO moiety (DIBO being a reactive "click" complement to the azide). The DIBO moiety can optionally be linked to the termini of PEG surface ligands of a nanoparticle. In another embodiment, a heterobifunctional crosslinker can be used; one end of the linker can include a His-tag for metal affinity binding to the nanoparticle surface, and the other end can include a DIBO moiety for covalent coupling to the azido non-natural amino acid. The linker can optionally comprise peptide or PEG chains. Use of such a heterobifunctional crosslinker eliminates the need to develop nanoparticles with specific covalent chemistry.

Figure 19:
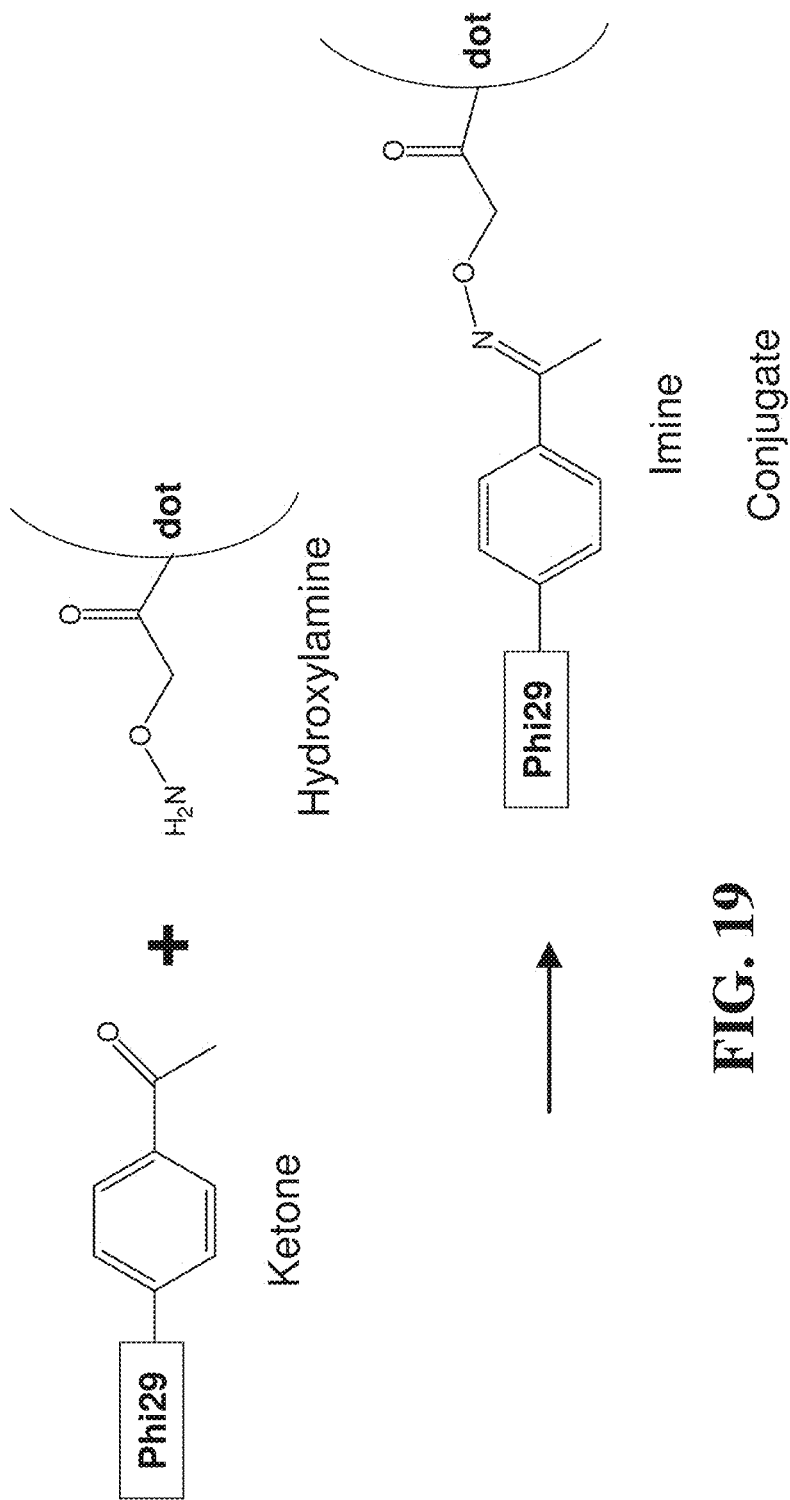
FIG. 19 depicts a third exemplary reaction pathway for forming a labeled polymerase conjugate according to the present disclosure.

In another embodiment, a ketone-comprising non-natural amino acid is introduced into a biomolecule, which can serve as an attachment site for a nanoparticle. For example, the introduced ketone group can allow site-specific modification of the biomolecule using chemistry unique to the ketone functional group. FIG. 19 depicts one exemplary pathway by which the insertion of the nonnatural amino acid, acetylphenyl alanine, into an exemplary biomolecule (Phi29 DNA polymerase) can be used to covalently couple a nanoparticle to the biomolecule.

Figure 20:
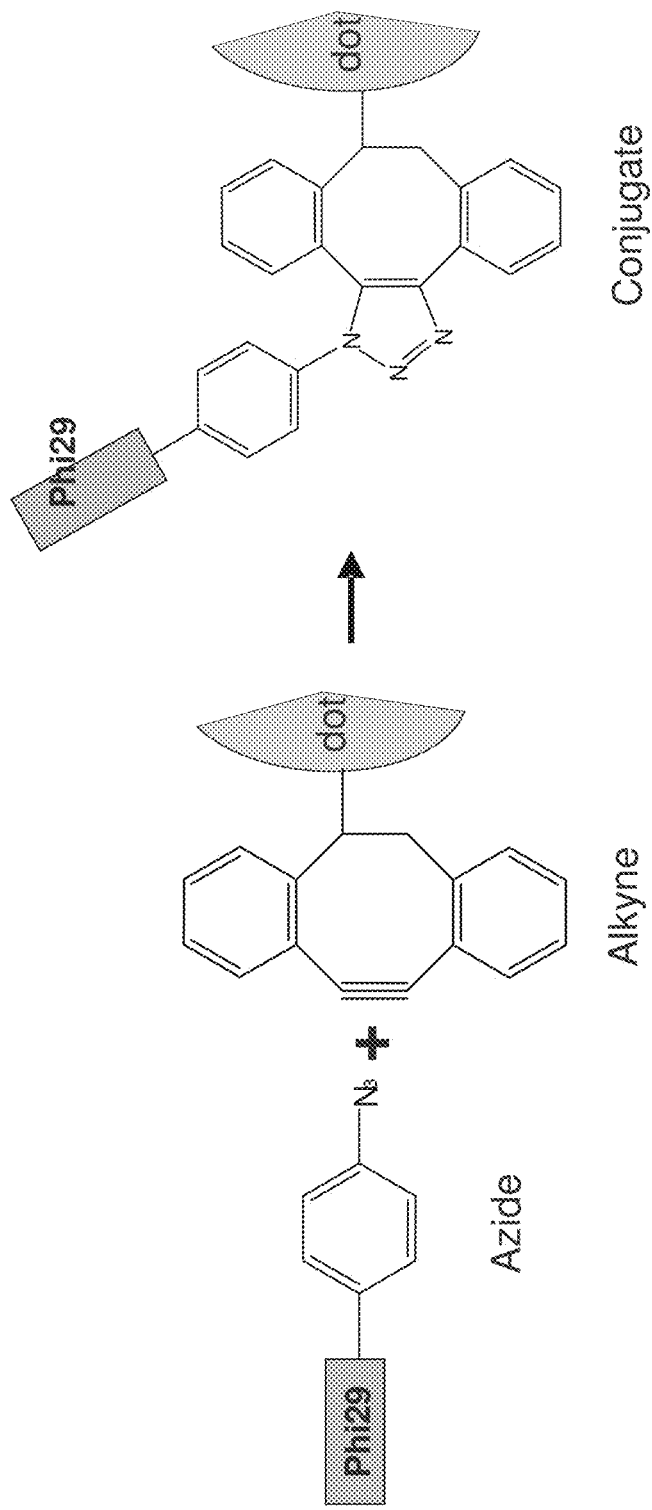
FIG. 20 depicts a fourth exemplary reaction pathway for forming a labeled polymerase conjugate according to the present disclosure.

In another embodiment, an azide-comprising non-natural amino acid such as, for example, azidophenyl alanine, can be introduced into a biomolecule; the introduced azide can then be used in a "click" reaction to covalently couple the biomolecule to an alkyne-comprising biomolecule. Normally, alkyne-azide click reactions utilize copper as a catalyst. In some embodiments, a "copperless click" reaction is utilized where a strained, eight-membered ring containing an alkyne can undergo reaction with an azide without the use of a copper catalyst. FIG. 20 depicts one exemplary pathway by which the insertion of the nonnatural amino acid, azidophenyl alanine, into an exemplary biomolecule (Phi29 DNA polymerase) can be used to covalently couple a nanoparticle to the biomolecule.

In some embodiments, the conjugate can be formed through self-assembly of the biomolecule with the label, where the self-assembly involves the formation of one or more metal affinity-based interactions, a phenomenon also referred to herein as "chelation". In some embodiments, one or more polypeptides can be conjugated to a label through metal-affinity coordination between a histidine residue of the polypeptide and a metal atom of the label. This strong interaction ($Zn^{2+}$-His) has a dissociation constant, $K_D$, stronger than most antigen-antibody bindings ($10^6$-$10^9$). See, e.g., Hainfeld at al., "Ni-NTA-gold clusters target his-tagged proteins", J. Struct. Biol. 127:185-198 (1999). Nanoparticles are one example of a label that comprises metal atoms that are accesible for binding by histidine residues of a biomolecule.

In some embodiments, the biomolecule can be engineered to contain, or otherwise fused to, a genetically encoded domain that exhibits chelation-based interactions with a metal-containing label. See, for example, Clapp et al., Nature Protocols 1(3):1258 (2006). In some embodiments, such domain can comprise one or more His tags. For example, the His tagged biomolecules, e.g., proteins, can bind via metal affinity-based interactions to labels comprising lipoic acid or other negatively charged moieties. It is theorized that the strength of such binding is determined by the degree to which the imidazole side chains of the oligohistidine segment of the His tag interact with the metal ions of the label. Without being bound to any particular theory or mechanism for such linkage, such methods are within the scope and spirit of the present disclosure. Overall, such methods can simplify the bioconjugation procedure and reduce the overall hydrodynamic size of the resulting conjugate by eliminating the need for a bridging protein. Such preparation methods can be particular suitable for FRET applications that require reduced spacing between the donor and acceptor moieties. The bioconjugate size can be further reduced by using only the shorter polymerase fragments that eliminate regions not required for core polymerase function.

In some embodiments, the biomolecule, e.g., protein, comprises one or more consecutive histidine residues, linked to the label. In one exemplary embodiment, the biomolecule comprises between four and twelve consecutive histidine residues.

In some embodiments, the label can be linked to a chelating compound, e.g., nickel-nitriloacetic acid, Ni-NTA) that quantitatively binds to His-tagged biomolecules with controlled molar ratio and biomolecular orientation. The $K_D$ for the hexahistidine tag ($His_6$) (SEQ ID NO: 54) and Ni-NTA is $10^{-13}$.

In some embodiments, the conjugate comprises a polymerase fused to a His-tag and linked to a label. The His-tag can comprise 3, 4, 5, 6, 7, 8, 9, 10, 11, 12 or more consecutive Histidine residues (SEQ ID NO: 55). The His-tag can be conjugated to the N-terminus of the polymerase, the C-terminus of the polymerase, or to any other suitable site within the polymerase. In some embodiments, a His-tag comprising six consecutive histidine residues (SEQ ID NO: 54) is fused to the N-terminus of the polymerase. Optionally, the His-tag and the polymerase open reading frame can be separated by a peptide linker sequence, which can comprise the F-linker or H-linker sequence.

In some embodiments, the F-linker is situated between an N-terminal His-tag comprising six consecutive histidine residues and the protein.

Also disclosed herein are compositions relating to multiply labeled biomolecule conjugates comprising a biomolecule linked to a plurality of labels, wherein the conjugate has a biological activity that is characteristic of the biomolecule. The plurality of labels can comprise two, three, four, five, six, seven or more labels. Also disclosed herein are methods of making labeled biomolecule conjugates comprising a biomolecule linked to a plurality of labels, as well as methods, systems and kits for making and using such conjugates.

Such labeled biomolecule conjugates comprising a polymerase linked to two, three, four, five, six, seven or more labels and having polymerase activity can provide a range of benefits. For example, such compositions can be provide several advantages in FRET based assays. In some embodiments, such conjugates can be used in conjunction with shorter excitation wavelengths, resulting in reduced direct excitation of the acceptor dye (false positive signal), and/or reduced donor emission bleed-through into the acceptor emission channel. A higher signal-to-noise ratio can thereby be achieved.

In some embodiments, the multiply labeled biomolecule conjugate can include a biomolecule (e.g., polymerase) linked to a first member of the binding pair, and a second member of a binding pair linked to a plurality of labels, wherein the first member and second member of the binding pair are linked to each other, thereby linking the biomolecule to the plurality of labels. In some embodiments, the binding pair comprises an avidin moiety and a biotin moiety, but in more general terms such dual labeled constructs can be generated using a variety of attachment moieties, wherein the attachment moiety serves to link the polymerase to two or more labels.

Attachment Moiety

Also disclosed herein are labeled enzyme conjugates, comprising: an enzyme linked to an attachment moiety, wherein the attachment moiety is linked to one or more labels, thereby linking the enzyme to the label to form a labeled enzyme conjugate. In some embodiments, the attachment moiety can be linked to at least three, four, five, six, seven or more labels.

The attachment moiety can be any suitable moiety, molecule or structure that serves to link one or more labels to the enzyme. In some embodiments, the attachment moiety can have reactive sites or groups, which can facilitate the formation of a linkage between the attachment moiety and the enzyme on the one hand, and/or between the attachment moiety and the one or more labels on the other. In some embodiments, the attachment moiety comprises one, two, three, four or more reactive sites that can facilitate linkage of the attachment moiety with an enzyme and/or labels. In some embodiments, one, some or all of the reactive sites of the attachment moiety can spontaneously bind to the enzyme and/or the one or more labels, thereby creating a linkage between the attachment moiety and the enzyme and/or the one or more labels. In other embodiments, the reactive site may need to undergo activation or other suitable treatment before it can bind to the enzyme and/or the one or more labels.

In some embodiments, the attachment moiety comprises an avidin moiety. In some embodiments, the avidin moiety comprises one, two three, four or more reactive sites capable of spontaneously binding to the biotin moiety of a biotinylated label. In some embodiments, the enzyme is a polymerase, the attachment moiety is linked to a polymerase, and the attachment moiety further comprises an avidin moiety linked to four biotinylated labels, thereby forming a polymerase linked to four labels through the attachement moiety.

Figure 2:
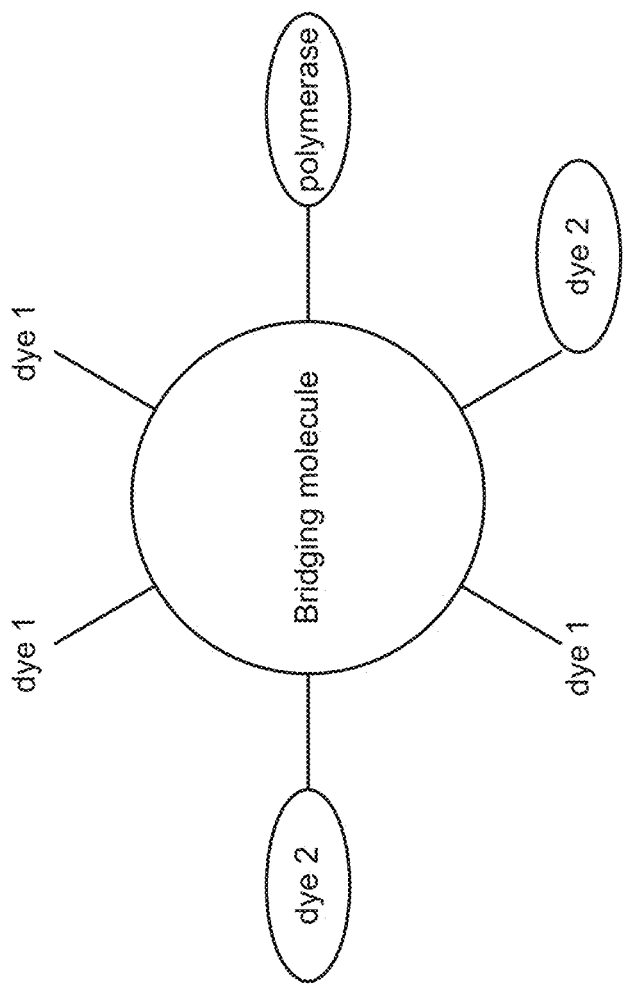
FIG. 2 depicts an exemplary labeled polymerase conjugate comprising a polymerase linked to multiple Cy3 dyes according to the present disclosure

In some embodiments, the attachment moiety can be linked to two or more different types of labels. Optionally, the attachment moiety can be further linked to a biomolecule, which in some embodiments can be a polymerase. An illustrative non-limiting example of a labeled polymerase conjugate, comprising a polymerase linked to an attachment moiety, wherein the attachment moiety is linked to two different types of labels, is depicted in FIG. 2. (In FIG. 2, the attachment moiety is referred to as a "bridging molecule", but this phrase is in no way intended to limit the attachment moiety in terms of function or structure). Preparation of an exemplary labeled polymerase conjugate comprising a polymerase linked to two different kinds of labels using an attachment moiety is described in Example 3, below.

Any suitable method capable of generating conjugates suitable for use in the desired applications, as well as by combination of such techniques, both covalent and non-covalent, may be employed to form conjugates according to the present disclosure. For example, a conjugate may be formed through a combination of both electrostatic and affinity-based interactions. In some embodiments, the polymerase can be engineered to include attachment domains that can mediate a range of interactions with the nanoparticle surface. For example, the polymerase can be fused both to a polyhistidine tag as well as a leucine zipper. Alternatively, the polymerase can be fused to a single attachment domain comprising histidines interspersed with, or flanked by, several lysine and/or arginine residues. Advantages of using such "multifunctional" attachment domains include increased strength of binding, the ability to orient binding between the polymerase and nanoparticle, and the ability to perform conjugations at ultra-high dilutions.

In addition to assembling the conjugate via direct interactions between the tagged peptide and metal atoms (or metal ions) present in the label, another option is to attach or cross-link ligands derivatized distally with species capable of interacting with and immobilizing a suitably modified peptide. A chelator molecule such as nitrilotriacetic acid (NTA) can be attached covalently to the label. This can be achieved by carbodiimide mediated coupling of one of the acetic acid side chains of NTA to a functional group of the label such as an amine. The resulting product can then be contacted with a solution of metal ions, such as $Ni^{2+}$, allowing some of the latter to bind to the chelating functional groups of NTA. After removal of the excess non-chelated metal ions, the metal-derivatized labels can be contacted with a solution of a His tag modified biomolecule, whereby the histidine residues of the poly-His tag will form additional coordinative chemical bonds with the NTA-chelated $Ni^{2+}$ ions. As result, the His-tagged biomolecule will be immobilized to the label. This technique results in strong, oriented binding between the peptide and the nanoparticle, with only minor sacrifices in FRET $R_0$ distance compared to direct binding of the His tag to the nanoparticle surface, and creates a conjugate with a more fully protected surface that better withstands environmental stresses.

One general advantage of all assembly-based methods is that the need for linkers and/or cross-linking treatments is obviated, resulting in much greater simplicity and ease of synthesis. Unlike covalent cross-linking techniques, self-assembly of fusion peptides tagged with an attachment domain, such as a His tag, with labels eliminates the requirement for developing specific chemical synthetic routes for each label on a case-by-case basis. Another advantage of self-assembly based methods is the ability to selectively engineer the properties of the attachment domain, e.g., size, charge, and pH or temperature stability so as to control its binding properties. This also allows control of the assembly of individual peptides, e.g., into monomers, dimers, trimers, tetramers, etc., ultimately allowing control of the protein packing around the nanoparticles to form complex bioconjugates.

In some embodiments, the conjugate can be formed through a combination of methods, including self-assembly and covalent attachment. For example, the metal affinity- or chelation-based binding of fusion proteins to the label can be reinforced by subsequent treatment to induce the formation of covalent bonds between the polymerase and the label. In one exemplary embodiment a photoreactive crosslinker, such as substituted arylazide, diazirine or benzophenone derivatives, can be attached to the label, which is subsequently contacted with a His-tagged polymerase. Following affinity-based assembly of the polymerase and label, the assembled complex can be photoirradiated to generate a covalently linked conjugate via crosslinking.

Further provided herein is a composition comprising a population of labeled biomolecule conjugates, wherein an average of at least about 30%, 40%, 50%, 60%, 70%, 80%, 90%, 95%, 96%, 97% or 99% of the population include three or more labels linked to the biomolecule.

Further provided herein is a composition comprising a population of labeled biomolecule conjugates, wherein an average of at least about 30%, 40%, 50%, 60%, 70%, 80%, 90%, 95%, 96%, 97% or 99% of the population include four or more labels linked to the biomolecule.

Further provided herein is a composition comprising a population of labeled biomolecule conjugates, wherein an average of at least about 30%, 40%, 50%, 60%, 70%, 80%, 90%, 95%, 96%, 97% or 99% of the population include five or more labels linked to the biomolecule.

Further provided herein is a composition comprising a population of labeled biomolecule conjugates, wherein an average of at least about 30%, 40%, 50%, 60%, 70%, 80%, 90%, 95%, 96%, 97% or 99% of the population include six or more labels linked to the biomolecule.

In some embodiments, provided herein is a population of labeled biomolecule conjugates wherein an average of at least about 30%, 40%, 50%, 60%, 70%, 80%, 90%, 95%, 96%, 98%, or 99% of the biomolecule-nanoparticle conjugates in the population comprise an average of about one biomolecule and about one label.

In some embodiments, provided herein is a population of labeled biomolecule conjugates where an average of at least 30%, at least 40%, at least 50%, at least 60% at least 70%, at least 80%, at least 90%, at least 95%, at least 96%, at least 98%, at least 99% or more of conjugates in the population comprise an average of about one biomolecule per conjugate.

Also disclosed herein is a population of conjugates, each conjugate comprising a biomolecule linked to a label, and the population comprising an average of between 0.5-1.5 biomolecules per label.

Also disclosed herein is a method for preparing a 1:2 biomolecule:label conjugate using linker moieties. For example, a label dimer linked by a short organic molecule, for example, 4,4'-biphenyldithiol, can be attached to the biomolecule via a linker attached to any suitable moiety, e.g., a phenyl group, within the dimer linker. For example, the biomolecule could first be attached to the linker molecule using another linking moiety, and then each end of the linker could be attached to a label. Dimers could be purified via filtration or other suitable techniques.

In some embodiments, the label can be conjugated both to a biomolecule as well as other proteins, especially proteins known to enhance biomolecular activity or have other beneficial side effects. For example, the label can optionally be conjugated both to a polymerase and to Single-Stranded DNA Binding Protein (SSBP), various processivity factors such as LEF-3, or the herpes simplex virus UL42 protein. The presence of such proteins can help to reduce the number of biomolecules linked to the label and at the same time stabilize the conjugate complex, resulting in enhancement of DNA synthesis and increased read lengths. Alternatively, proteins that reduce the potential photodamage caused by reactive oxygen species, such as catalase or superoxide dismutase (SOD), can also be conjugated to the label in combination with the biomolecule.

The labeled biomolecule conjugates of the present disclosure can optionally comprise any polymerase suitable for use in the particular biological application of interest.

In some embodiments, the compositions, methods, systems and kits of the present disclosure relate to labeled biomolecule conjugates comprising a polymerase. In some embodiments, the polymerase incorporates one or more nucleotides into a nucleic acid molecule and the resulting one or more nucleotide incorporations is detected and/or analyzed in real time.

In some embodiments, the polymerase can bind a target nucleic acid molecule, which may or may not be base-paired with a polymerization initiation site (e.g., primer).

Typically, the polymerase can selectively bind to a nucleotide. Such nucleotide binding can occur in a template-dependent or non-template-dependent manner Typically, the polymerase can mediate cleavage of the bound nucleotide. Typically, such cleavage of the nucleotide results in the formation of at least two nucleotide cleavage products. For polyphosphate-comprising nucleotides, such cleavage will typically occur between the a and 13 phosphate groups. Typically, the polymerase can mediate incorporation of one of the nucleotide cleavage products into a nucleic acid molecule, and release of another nucleotide cleavage product. When used in conjunction with polyphosphate-comprising nucleotides, the released nucleotide cleavage product can comprise one or more phosphates (for example, a polyphosphate chain); for nucleotides that are non-phosphate-comprising analogs, the nucleotide cleavage product may not comprise any phosphorus.

In some embodiments, the polymerase can mediate incorporation of a nucleotide on to a polymerization initiation site (e.g., terminal 3'OH of a primer).

In some embodiments, the polymerase can be unlabeled. Alternatively, the polymerase can be linked to one or more label. In some embodiments, the label comprises at least one energy transfer moiety.

The polymerase may be linked with at least one energy transfer donor moiety. One or more energy transfer donor moieties can be linked to the polymerase at the amino end or carboxyl end or may be inserted at any site therebetween. Optionally, the energy transfer donor moiety can be attached to the polymerase in a manner which does not significantly interfere with the nucleotide binding activity, or with the nucleotide incorporation activity of the polymerase. In such embodiments, the energy transfer moiety is attached to the polymerase in a manner that does not significantly interfere with polymerase activity.

In one aspect, a single energy transfer donor moiety can be linked to more than one polymerase and the attachment can be at the amino end or carboxyl end or may be inserted within the polymerase.

In another aspect, a single energy transfer donor moiety can be linked to one polymerase.

In one aspect, the energy transfer donor moiety can be a nanoparticle (e.g., a fluorescent nanoparticle) or a fluorescent dye. The polymerase, which can be linked to the nanoparticle or fluorescent dye, typically retains one or more activities that are characteristic of the polymerase, e.g., polymerase activity, exonuclease activity, nucleotide binding, and the like.

In one aspect, the polymerases can be replicases, DNA-dependent polymerases, primases, RNA-dependent polymerases (including RNA-dependent DNA polymerases such as, for example, reverse transcriptases), strand-displacement polymerases, or thermo-stable polymerases. In another aspect, the polymerase can be any Family A or B type polymerase. Many types of Family A (e.g., E. coli Pol I), B (e.g., E. coli Pol II), C (e.g., E. coli Pol III), D (e.g., Euryarchaeotic Pol II), X (e.g., human Pol beta), and Y (e.g., E. coli UmuC/DinB and eukaryotic RAD30/xeroderma pigmentosum variants) polymerases are described in Rothwell and Watsman 2005 Advances in Protein Chemistry 71:401-440.

In yet another aspect, the polymerases can be isolated from a cell, or generated using recombinant DNA technology or chemical synthesis methods. In another aspect, the polymerases can be expressed in prokaryote, eukaryote, viral, or phage organisms. In another aspect, the polymerases can be post-translationally modified proteins or fragments thereof.

In one aspect, the polymerase can be a recombinant protein which is produced by a suitable expression vector/host cell system. The polymerases can be encoded by suitable recombinant expression vectors carrying inserted nucleotide sequences of the polymerases. The polymerase sequence can be linked to a suitable expression vector. The polymerase sequence can be inserted in-frame into the suitable expression vector. The suitable expression vector can replicate in a phage host, or a prokaryotic or eukaryotic host cell. The suitable expression vector can replicate autonomously in the host cell, or can be inserted into the host cell's genome and be replicated as part of the host genome. The suitable expression vector can carry a selectable marker which confers resistance to drugs (e.g., kanamycin, ampicillin, tetracycline, chloramphenicol, or the like), or confers a nutrient requirement. The suitable expression vector can have one or more restriction sites for inserting the nucleic acid molecule of interest. The suitable expression vector can include expression control sequences for regulating transcription and/or translation of the encoded sequence. The expression control sequences can include: promoters (e.g., inducible or constitutive), enhancers, transcription terminators, and secretion signals. The expression vector can be a plasmid, cosmid, or phage vector. The expression vector can enter a host cell which can replicate the vector, produce an RNA transcript of the inserted sequence, and/or produce protein encoded by the inserted sequence. The recombinant polymerase can include an affinity tag for enrichment or purification, including a poly-amino acid tag (e.g., poly His tag), GST, and/or HA sequence tag. Methods for preparing suitable recombinant expression vectors and expressing the RNA and/or protein encoded by the inserted sequences are well known (Sambrook et al, *Molecular Cloning* (1989)).

The polymerases may be DNA polymerases and include without limitation bacterial DNA polymerases, prokaryotic DNA polymerase, eukaryotic DNA polymerases, archaeal DNA polymerases, viral DNA polymerases and phage DNA polymerases. The polymerase can be a commercially available polymerase.

In some embodiments, the polymerase can be a DNA polymerase and include without limitation bacterial DNA polymerases, eukaryotic DNA polymerases, archaeal DNA polymerases, viral DNA polymerases and phage DNA polymerases.

Suitable bacterial DNA polymerase include without limitation E. coli DNA polymerases I, II and III, IV and V, the Klenow fragment of E. coli DNA polymerase, *Clostridium*

*stercorarium* (Cst) DNA polymerase, *Clostridium thermocellum* (Cth) DNA polymerase and *Sulfolobus solfataricus* (Sso) DNA polymerase.

Suitable eukaryotic DNA polymerases include without limitation the DNA polymerases α, δ, ε, η, ζ, γ, β, σ, λ, μ, ι, and κ, as well as the Rev1 polymerase (terminal deoxycytidyl transferase) and terminal deoxynucleotidyl transferase (TdT).

Suitable viral and/or phage DNA polymerases include without limitation T4 DNA polymerase, T5 DNA polymerase, T7 DNA polymerase, Phi-15 DNA polymerase, Phi-29 DNA polymerase (see, e.g., U.S. Pat. No. 5,198,543; also referred to variously as Φ29 polymerase, phi29 polymerase, phi 29 polymerase, Phi 29 polymerase, and Phi29 polymerase); Φ15 polymerase (also referred to herein as Phi-15 polymerase); Φ21 polymerase (Phi-21 polymerase); PZA polymerase; PZE polymerase, PRD1 polymerase; Nf polymerase; M2Y polymerase; SF5 polymerase; f1 DNA polymerase, Cp-1 polymerase; Cp-5 polymerase; Cp-7 polymerase; PR4 polymerase; PR5 polymerase; PR722 polymerase; L17 polymerase; M13 DNA polymerase, RB69 DNA polymerase, G1 polymerase; GA-1 polymerase, BS32 polymerase; B103 polymerase; BA103 polymerase, a polymerase obtained from any phi-29 like phage or derivatives thereof, etc. See, e.g., U.S. Pat. No. 5,576,204, filed Feb. 11, 1993; U.S. Pat. Appl. No. 2007/0196846, published Aug. 23, 2007.

Suitable archaeal DNA polymerases include without limitation the thermostable and/or thermophilic DNA polymerases such as, for example, DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavus* (Tfl) DNA polymerase, *Pyrococcus woesei* (Pwo) DNA polymerase, *Pyrococcus furiosus* (Pfu) DNA polymerase as well as Turbo Pfu DNA polymerase, *Thermococcus litoralis* (Tli) DNA polymerase or Vent DNA polymerase, *Pyrococcus* sp. GB-D polymerase, "Deep Vent" DNA polymerase, New England Biolabs), *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. 9° N-7 DNA polymerase; *Thermococcus* sp. NA1; *Pyrodictium occultum* DNA polymerase; *Methanococcus voltae* DNA polymerase; *Methanococcus thermoautotrophicum* DNA polymerase; *Methanococcus jannaschii* DNA polymerase; Desulfurococcus strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; the heterodimeric DNA polymerase DP1/DP2, etc.

Suitable RNA polymerases include, without limitation, T3, T5, T7, and SP6 RNA polymerases.

Suitable reverse transcriptases include without limitation reverse transcriptases from HIV, HTLV-I, HTLV-II, FeLV, FIV, SIV, AMV, MMTV and MoMuLV, as well as the commercially available "Superscript" reverse transcriptases, (Life Technologies Corp., Carlsbad, Calif.) and telomerases.

In some embodiments, the polymerase is selected from the group consisting of: Phi-29 DNA polymerase, a mutant or variant of Phi-29 DNA polymerase, B103 DNA polymerase and a mutant or variant of B103 DNA polymerase.

In another aspect, the polymerases can include one or more mutations that improve the performance of the polymerase in the particular biological assay of interest. The mutations can include amino acid substitutions, insertions, or deletions.

Selecting a Polymerase

The selection of the polymerase for use in the disclosed methods can be based on the desired polymerase behavior in the particular biological assay of interest. For example, the polymerase can be selected to exhibit enhanced or reduced activity in a particular assay, or enhanced or reduced interaction with one or more particular substrates.

For example, in some embodiments the polymerase is selected based on the polymerization kinetics of the polymerase either in unconjugated form or when linked to a label (labeled polymerase conjugate). Optionally, the label can be a nanoparticle or fluorescent dye; in some embodiments, the label can be energy transfer donor moiety. For example, the polymerase can be selected on the basis of kinetic behavior relating to nucleotide binding (e.g., association), nucleotide dissociation (intact nucleotide), nucleotide fidelity, nucleotide incorporation (e.g., catalysis), and/or release of the cleavage product. The selected polymerase can be wild-type or mutant.

In one embodiment, polymerases may be selected that retain the ability to selectively bind complementary nucleotides. In another embodiment, the polymerases may be selected which exhibit a modulated rate (faster or slower) of nucleotide association or dissociation. In another embodiment, the polymerases may be selected which exhibit a reduced rate of nucleotide incorporation activity (e.g., catalysis) and/or a reduced rate of dissociation of the cleavage product and/or a reduced rate of polymerase translocation (after nucleotide incorporation). Some modified polymerases which exhibit nucleotide binding and a reduced rate of nucleotide incorporation have been described (Rank, U.S. published patent application No. 2008/0108082; Hanzel, U.S. published patent application No. 2007/0196846).

In polymerases from different classes (including DNA-dependent polymerases), an active-site lysine can interact with the phosphate groups of a nucleoside triphosphate molecule bound to the active site. The lysine residue has been shown to protonate the pyrophosphate leaving-group upon nucleotidyl transfer. Mutant polymerases having this lysine substituted with leucine, arginine, histidine or other amino acids, exhibit greatly reduced nucleotide incorporation rates (Castro, et al., 2009 Nature Structural and Molecular Biology 16:212-218). One skilled in the art can use amino acid alignment and/or comparison of crystal structures of polymerases as a guide to determine which lysine residue to replace with alternative amino acids. The sequences of Phi29 polymerase (SEQ ID NO: 3), RB69 polymerase (SEQ ID NO: 29), an exemplary B103-like polymerase (SEQ ID NO: 33), and Klenow fragment (SEQ ID NO: 3) can be used as the basis for selecting the amino acid residues to be modified (for B103-like polymerase of SEQ ID NO: 33, see, e.g., Hendricks, et al., U.S. Ser. No. 61/242,771, filed on Sep. 15, 2009; U.S. Ser. No. 61/293, 618, filed on Jan. 8, 2010; or Ser. No. 12/748,359 titled "Polymerase Compositions & Methods", filed concurrently herewith). In one embodiment, a modified phi29 polymerase can include lysine at position 379 and/or 383 substituted with leucine, arginine or histidine, wherein the numbering is relative to the amino acid sequence of SEQ ID NO: 3.

In other embodiments, the polymerase can be selected based on the combination of the polymerase and nucleotides, and the reaction conditions, to be used for the nucleotide binding and/or nucleotide incorporation reactions. For example, certain polymerases in combination with nucleotides which comprise 3, 4, 5, 6, 7, 8, 9, 10 or more phosphate groups can be selected for performing the disclosed methods. In another example, certain polymerases in combination with nucleotides which are linked to an energy transfer moiety can be selected for performing the nucleotide incorporation methods.

The polymerases, nucleotides, and reaction conditions, can be screened for their suitability for use in the nucleotide binding and/or nucleotide incorporation methods, using well known screening techniques. For example, the suitable polymerase may be capable of binding nucleotides and/or incorporating nucleotides. For example, the reaction kinetics for nucleotide binding, association, incorporation, and/or dissociation rates, can be determined using rapid kinetics techniques (e.g., stopped-flow or quench flow techniques). Using stopped-flow or quench flow techniques, the binding kinetics of a nucleotide can be estimated by calculating the $1/k_d$ value. Stopped-flow techniques which analyze absorption and/or fluorescence spectroscopy properties of the nucleotide binding, incorporation, or dissociation rates to a polymerase are well known in the art (Kumar and Patel 1997 Biochemistry 36:13954-13962; Tsai and Johnson 2006 Biochemistry 45:9675-9687; Hanzel, U.S. published patent application No. 2007/0196846). Other methods include quench flow (Johnson 1986 Methods Enzymology 134:677-705), time-gated fluorescence decay time measurements (Korlach, U.S. Pat. No. 7,485,424), plate-based assays (Clark, U.S. published patent application No. 2009/0176233), and X-ray crystal structure analysis (Berman 2007 EMBO Journal 26:3494). Nucleotide incorporation by a polymerase can also be analyzed by gel separation of the primer extension products. In one embodiment, stopped-flow techniques can be used to screen and select combinations of nucleotides with polymerases having a $t_{pol}$ value (e.g., $1/k_{pol}$) which is less than a $t_{-1}$ (e.g., $1/k_{-1}$) value. Stopped-flow techniques for measuring $t_{pol}$ (MP Roettger 2008 Biochemistry 47:9718-9727; M Bakhtina 2009 Biochemistry 48:3197-320) and $t_{-1}$ (M Bakhtina 2009 Biochemistry 48:3197-3208) are known in the art.

For example, some phi29 or B103 polymerases (wild-type or mutant) exhibit $t_{pol}$ values which are less than $t_{-1}$ values, when reacted with nucleotide tetraphosphate or hexaphosphate molecules. In another embodiment, polymerases can be modified by binding it to a chemical compound or an antibody, in order to inhibit nucleotide incorporation.

In some embodiments, the selection of the polymerase may be determined by the level of processivity desired for conducting nucleotide incorporation or polymerization reactions. The polymerase processivity can be gauged by the number of nucleotides incorporated for a single binding event between the polymerase and the target molecule base-paired with the polymerization initiation site. For example, the processivity level of the polymerase may be about 1, 5, 10, 20, 25, 50, 100, 250, 500, 750, 1000, 2000, 5000, or 10,000 or more nucleotides incorporated with a single binding event. Processivity levels typically correlate with read lengths of a polymerase. Optionally, the polymerase can be selected to retain the desired level of processivity when conjugated to a label.

The selection of the polymerase may be determined by the level of fidelity desired, such as the error rate per nucleotide incorporation. The fidelity of a polymerase may be partly determined by the 3'→5' exonuclease activity associated with a DNA polymerase. The fidelity of a DNA polymerase may be measured using assays well known in the art (Lundburg et al., 1991 Gene, 108:1-6). The error rate of the polymerase can be one error per about 100, or about 250, or about 500, or about 1000, or about 1500 incorporated nucleotides. In some embodiments, the polymerase is selected to exhibit high fidelity. Such high-fidelity polymerases include those exhibiting error rates typically of about $5 \times 10^{-6}$ per base pair or lower.

In some embodiments, the selection of the polymerase may be determined by the rate of nucleotide incorporation such as about one nucleotide per 2-5 seconds, or about one nucleotide per second, or about 5 nucleotides per second, or about 10 nucleotides per second, or about 20 nucleotides per second, or about 30 nucleotides per second, or more than 40 nucleotides per second, or more than 50-100 per second, or more than 100 per second. In one embodiment, polymerases exhibiting reduced nucleotide incorporation rates include mutant phi29 polymerase having lysine substituted with leucine, arginine, histidine or other amino acids (Castro 2009 Nature Structural and Molecular Biology 16:212-218).

In some embodiments, the polymerase can be selected to exhibit either reduced or enhanced rates of incorporation for polyphosphate-comprising nucleotides comprising a label bonded to the terminal phosphate.

In some embodiments, the polymerase can be selected to exhibit either reduced or enhanced residence times for a particular nucleotide of interest. In some embodiments, the residence time of the selected polymerase for the particular labeled nucleotide of interest can be between about 20 msec and about 300 msec, typically between about 55 msec and about 100 msec. In some embodiments, the residence time of the selected polymerase for the particular labeled nucleotide of interest can be between about 1.5 and about 4 times the residence time of the corresponding wild-type polymerase for the labeled nucleotide.

In some embodiments, the polymerase can be selected, mutated, modified, evolved or otherwise engineered to exhibit either reduced or enhanced entry of nucleotides, particularly labeled nucleotides, into the polymerase active site. Some exemplary polymerases exhibiting altered residence times for labeled nucleotides are disclosed in U.S. Pub. No. 20080108082, published May 8, 2008.

In some embodiments, the polymerase can be selected to exhibit a reduced $K_{sub}$ for a substrate, particularly a labeled nucleotide analog. In some embodiments, the polymerase can comprise one or more mutations resulting in altered $K_{cat}/K_{sub}$ and/or $V_{max}/K_{sub}$ for a particular labeled nucleotide. In some embodiments, the $K_{cat}/K_{sub}$, the $V_{max}/K_{sub}$, or both, are increased as compared to the wild type polymerase.

Fusion Proteins

In one aspect, the polymerase can be a fusion protein comprising the amino acid sequence of a nucleic acid-dependent polymerase (the polymerase portion) linked to the amino acid sequence of a second enzyme or a biologically active fragment thereof (the second enzyme portion). The second enzyme portion of the fusion protein may be linked to the amino or carboxyl end of the polymerase portion, or may be inserted within the polymerase portion. The polymerase portion of the fusion protein may be linked to the amino or carboxyl end of the second enzyme portion, or may be inserted within the second enzyme portion. In some embodiments, the polymerase and second enzyme portions can be linked to each other in a manner which does not significantly interfere with polymerase activity of the fusion or with the ability of the fusion to bind nucleotides, or does not significantly interfere with the activity of the second enzyme portion. In the fusion protein, the polymerase portion or the second enzyme portions can be linked with at least one energy transfer donor moiety. The fusion protein can be a recombinant protein having a polymerase portion and a second enzyme portion. In some embodiments, the fusion protein can include a polymerase portion chemically linked to the second enzyme portion.

Evolved Polymerases

The polymerase can be a modified polymerase having certain desired characteristics, such as an evolved polymerase selected from a directed or non-directed molecular evolution procedure. The evolved polymerase can exhibit modulated characteristics or functions, such as changes in: affinity, specificity, or binding rates for substrates (e.g., target molecules, polymerization initiation sites, or nucleotides); binding stability to the substrates (e.g., target molecules, polymerization initiation sites, or nucleotides); nucleotide incorporation rate; nucleotide analog permissiveness; exonuclease activity (e.g., 3'→5' or 5'→3'); rate of extension; processivity; fidelity; stability; or sensitivity and/or requirement for temperature, chemicals (e.g., DTT), salts, metals, pH, or electromagnetic energy (e.g., excitation or emitted energy). Many examples of evolved polymerases having altered functions or activities can be found in U.S. provisional patent application No. 61/020,995, filed Jan. 14, 2008.

Methods for creating and selecting proteins and enzymes having the desired characteristics are known in the art, and include: oligonucleotide-directed mutagenesis in which a short sequence is replaced with a mutagenized oligonucleotide; error-prone polymerase chain reaction in which low-fidelity polymerization conditions are used to introduce point mutations randomly across a sequence up to about 1 kb in length (R. C. Caldwell, et al., 1992 PCR Methods and Applications 2:28-33; H. Gramm, et al., 1992 Proc. Natl. Acad. Sci. USA 89:3576-3580); and cassette mutagenesis in which a portion of a sequence is replaced with a partially randomized sequence (A. R. Oliphant, et al., 1986 Gene 44:177-183; J. D. Hermes, et al., 1990 Proc. Natl. Acad. Sci. USA 87:696-700; A. Arkin and D. C. Youvan 1992 Proc. Natl. Acad. Sci. USA 89:7811-7815; E. R. Goldman and D. C. Youvan 1992 Bio/Technology 10:1557-1561; Delagrave et al., 1993 Protein Engineering 6: 327-331; Delagrave et al., 1993 Bio/Technology 11: 1548-155); and domain shuffling.

Methods for creating evolved antibody and antibody-like polypeptides can be adapted for creating evolved polymerases, and include applied molecular evolution formats in which an evolutionary design algorithm is applied to achieve specific mutant characteristics. Many library formats can be used for evolving polymerases including: phage libraries (J. K. Scott and G. P. Smith 1990 Science 249:386-390; S. E. Cwirla, et al. 1990 Proc. Natl. Acad. Sci. USA 87:6378-6382; J. McCafferty, et al. 1990 Nature 348:552-554) and lad (M. G. Cull, et al., 1992 Proc. Natl. Acad. Sci. USA 89:1865-1869).

Another adaptable method for evolving polymerases employs recombination (crossing-over) to create the mutagenized polypeptides, such as recombination between two different plasmid libraries (Caren et al. 1994 Bio/Technology 12: 517-520), or homologous recombination to create a hybrid gene sequence (Calogero, et al., 1992 FEMS Microbiology Lett. 97: 41-44; Galizzi et al., WO91/01087).

Another recombination method utilizes host cells with defective mismatch repair enzymes (Radman et al., WO90/07576). Other methods for evolving polymerases include random fragmentation, shuffling, and re-assembly to create mutagenized polypeptides (published application No. U.S. 2008/0261833, Stemmer). Adapting these mutagenesis procedures to generate evolved polymerases is well within the skill of the art.

In some embodiments, the polymerase can be fused with, or otherwise engineered to include, DNA-binding or other domains from other proteins that are capable of modulating DNA polymerase activity. For example, fusion of suitable portions of the Single-Stranded DNA Binding Protein (SSBP), thioredoxin and/or T7 DNA polymerase to bacterial or viral DNA polymerases has been shown to enhance both the processivity and fidelity of the DNA polymerase. Similarly, other groups have described efforts to engineer polymerases so as to broaden their substrate range. See, e.g., Ghadessy et al, Nat. Biotech., 22 (6):755-759 (2004). Similarly, the conjugates of the present disclosure can optionally comprise any polymerase engineered to provide suitable performance characteristics, including for example a polymerase fused to intact SSBP or fragments thereof, or to domains from other DNA-binding proteins (such as the herpes simplex virus UL42 protein.)

In some embodiments, a blend of different conjugates, each of which comprises a polymerase of unique sequence and characteristics, can be used according to the methods described herein. Use of such conjugate blends can additionally increase the fidelity and processivity of DNA synthesis. For example, use of a blend of processive and non-processive polymerases has been shown to result in increased overall read length during DNA synthesis, as described in U.S. Published App. No. 2004/0197800. Alternatively, conjugates comprising polymerases of different affinities for specific acceptor-labeled nucleotides can be used so as to achieve efficient incorporation of all four nucleotides.

In one embodiment, the polymerase can be a mutant which retains nucleotide polymerization activity but lacks the 3'→5' or 5'→3' exonuclease activity. In another embodiment, the polymerase can be an exonuclease minus mutant which is based on wild type phi29 polymerase of SEQ ID NO: 1 (Blanco, U.S. Pat. Nos. 5,001,050, 5,198,543, and 5,576,204; and Hardin PCT/US2009/31027 with an International filing date of Jan. 14, 2009) and comprising one or more substitution mutations, including: D12A, D66A, D169A, H61R, N62D, Q380A, and/or S388G, and any combination thereof.

In some embodiments, the polymerase can comprise the amino acid sequence of any polymerase disclosed in U.S. Provisional Application No. 61/242,771, filed on Sep. 15, 2009; 61/263,974, filed on Nov. 24, 2009 and 61/299,919, filed on Jan. 29, 2010, or any variant thereof.

In some embodiments, the polymerase is an *E. coli* K12 DNA polymerase I having the following amino acid sequence:

(SEQ ID NO: 1)
```
  1 MVQIPQNPLI LVDGSSYLYR AYHAFPPLTN SAGEPTGAMY GVLNMLRSLI MQYKPTHAAV

61 VFDAKGKTFR DELFEHYKSH RPPMPDDLRA QIEPLHAMVK AMGLPLLAVS GVEADDVIGT
```

```
121 LAREAEKAGR PVLISTGDKD MAQLVTPNIT LINTMTNTIL GPEEVVNKYG VPPELIIDFL

181 ALMGDSSDNI PGVPGVGEKT AQALLQGLGG LDTLYAEPEK IAGLSFRGAK TMAAKLEQNK

241 EVAYLSYQLA TIKTDVELEL TCEQLEVQQP AAEELLGLFK KYEFKRWTAD VEAGKWLQAK

301 GAKPAAKPQE TSVADEAPEV TATVISYDNY VTILDEETLK AWIAKLEKAP VFAFDTETDS

361 LDNISANLVG LSFAIEPGVA AYIPVAHDYL DAPDQISRER ALELLKPLLE DEKALKVGQN

421 LKYDRGILAN YGIELRGIAF DTMLESYILN SVAGRHDMDS LAERWLKHKT ITFEEIAGKG

481 KNQLTFNQIA LEEAGRYAAE DADVTLQLHL KMWPDLQKHK GPLNVFENIE MPLVPVLSRI

541 ERNGVKIDPK VLHNHSEELT LRLAELEKKA HEIAGEEFNL SSTKQLQTIL FEKQGIKPLK

601 KTPGGAPSTS EEVLEELALD YPLPKVILEY RGLAKLKSTY TDKLPLMINP KTGRVHTSYH

661 QAVTATGRLS STDPNLQNIP VRNEEGRRIR QAFIAPEDYV IVSADYSQIE LRIMAHLSRD

721 KGLLTAFAEG KDIHRATAAE VFGLPLETVT SEQRRSAKAI NFGLIYGMSA FGLARQLNIP

781 RKEAQKYMDL YFERYPGVLE YMERTRAQAK EQGYVETLDG RRLYLPDIKS SNGARRAAAE

841 RAAINAPMQG TAADIIKRAM IAVDAWLQAE QPRVRMIMQV HDELVFEVHK DDVDAVAKQI

901 HQLMENCTRL DVPLLVEVGS GENWDQAH
```

In some embodiments, the polymerase can comprise an amino acid sequence that is at least 70%, 80%, 85%, 90%, 95%, 99% or 100% identical to the above amino acid sequence, or a biologically active fragment thereof.

In some embodiments, the polymerase comprises an amino acid sequence at least 70% identical to the amino acid sequence of DNA polymerase I (SEQ ID NO: 1) or Klenow DNA polymerase (SEQ ID NO: 2), wherein the cysteine residue corresponding to the cysteine residue at position 907 is mutated to a serine or some other residue, the numbering being relative to E. coli K12 DNA polymerase I (SEQ ID NO: 1). In some embodiments, the mutant, variant, mutated or otherwise mutated polymerase lacks 3' to 5' exonuclease activity.

In some embodiments, the polymerase comprises an amino acid sequence at least 70%, 80%, 85%, 90%, 95%, 99% or 100% identical to the amino acid of DNA polymerase I (SEQ ID NO: 1) or Klenow DNA polymerase (SEQ ID NO: 2) and further comprises one or more substitutions wherein any amino acid residue is substituted with an engineered cysteine residue, which can serve as an attachment site for a label. Optionally, the label can be attached to the engineered cysteine residue using the linking agent SMCC.

In some embodiments, the engineered cysteine residue is substituted for the threonine residue at position 748, the numbering being relative to wild-type E. coli K12 DNA polymerase (SEQ ID NO: 1)

In some embodiments, the engineered cysteine residue is substituted for the threonine residue at position 750, the numbering being relative to wild-type E. coli K12 DNA polymerase (SEQ ID NO: 1).

In some embodiments, the engineered cysteine residue is substituted for the serine residue at position 751, the numbering being relative to wild-type E. coli K12 DNA polymerase (SEQ ID NO: 1).

In some embodiments, the engineered cysteine residue is substituted for the asparagine residue at position 778, the numbering being relative to wild-type E. coli K12 DNA polymerase (SEQ ID NO: 1).

In some embodiments, the engineered cysteine residue is substituted for the glycine residue at position 730, the numbering being relative to wild-type E. coli K12 DNA polymerase (SEQ ID NO: 1).

In some embodiments, the engineered cysteine residue is substituted for the asparagine residue at position 922, the numbering being relative to wild-type E. coli K12 DNA polymerase (SEQ ID NO: 1).

In some embodiments, the engineered cysteine residue is substituted for the Q (glutamine) residue at position 926, the numbering being relative to wild-type E. coli K12 DNA polymerase (SEQ ID NO: 1).

In some embodiments, the engineered cysteine residue is substituted for the alanine residue at position 927, the numbering being relative to wild-type E. coli K12 DNA polymerase (SEQ ID NO: 1).

In some embodiments, the engineered cysteine residue is substituted for the histidine residue at position 928, the numbering being relative to wild-type E. coli K12 DNA polymerase (SEQ ID NO: 1).

In some embodiments, the polymerase can comprise the Klenow form of DNA polymerase. In some embodiments, the polymerase comprises the Klenow truncated form of E. coli K12 DNA polymerase I ("Klenow DNA polymerase") having the following sequence:

```
                                                    (SEQ ID NO: 2)
    MVISYDNY VTILDEETLK AWIAKLEKAP VFAFDTETDS

361 LDNISANLVG LSFAIEPGVA AYIPVAHDYL DAPDQISRER ALELLKPLLE DEKALKVGQN

421 LKYDRGILAN YGIELRGIAF DTMLESYILN SVAGRHDMDS LAERWLKHKT ITFEEIAGKG

481 KNQLTFNQIA LEEAGRYAAE DADVTLQLHL KMWPDLQKHK GPLNVFENIE MPLVPVLSRI
```

-continued

```
541 ERNGVKIDPK VLHNHSEELT LRLAELEKKA HEIAGEEFNL SSTKQLQTIL FEKQGIKPLK

601 KTPGGAPSTS EEVLEELALD YPLPKVILEY RGLAKLKSTY TDKLPLMINP KTGRVHTSYH

661 QAVTATGRLS STDPNLQNIP VRNEEGRRIR QAFIAPEDYV IVSADYSQIE LRIMAHLSRD

721 KGLLTAFAEG KDIHRATAAE VFGLPLETVT SEQRRSAKAI NFGLIYGMSA FGLARQLNIP

781 RKEAQKYMDL YFERYPGVLE YMERTRAQAK EQGYVETLDG RRLYLPDIKS SNGARRAAAE

841 RAAINAPMQG TAADIIKRAM IAVDAWLQAE QPRVRMIMQV HDELVFEVHK DDVDAVAKQI

901 HQLMENCTRL DVPLLVEVGS GENWDQAH
```

In some embodiments, the polymerase can comprise an amino acid sequence that is at least 70%, 80%, 85%, 90%, 95%, 99% or 100% identical to the above amino acid sequence, or a biologically active fragment thereof.

In some embodiments, the polymerase of the conjugate is a mutant or variant Klenow form of DNA polymerase comprising amino acid sequence at least about 85% identical to the amino acid sequence of SEQ ID NO: 2, or a biologically active fragment thereof. Optionally, the polymerase lacks 3' to 5' exonuclease activity.

In some embodiments, the modified polymerase is derived from a polymerase of any member of the Phi-29-like family of phages. The Phi-29-like phages are a genus of phages that are related to Phi-29 that includes the phages PZA, D15, BS32, B103, M2Y (M2), Nfl and GA-1. Phages of this group have been sub-classified into three groups based on serological properties, DNA and/or polymerase maps and partial or complete DNA sequences, and share several characteristics in common. For example, such phages can typically undergo protein-primed DNA replication. See, for example, Meijer et al., "Phi-29 family of phages" Microbiol. & Mol. Biol. Revs. 65(2):261-287 (2001).

In some embodiments, the polymerase is homologous to a polymerase of one or more of the following organisms: B103, Phi-29, GA-1, PZA, Phi-15, BS32, M2Y, Nf, G1, Cp-1, PRD1, WE, SF5, Cp-5, Cp-7, PR4, PR5, PR722, or L17. See, e.g., Meijer et al., "Phi-29 family of phages," Microbiol. & Mol. Biol. Revs. 65(2):261-287 (2001).

In some embodiments, the polymerase can comprise the Phi-29 DNA polymerase or a biologically active fragment thereof. (See, e.g., U.S. Pat. Nos. 5,001,050; 5,198,543 and 5,576,204). Typically, the Phi-29 polymerase comprises the following sequence:

```
                                                          (SEQ ID NO: 3)
         MKHMPRKMYS CDFETTTKVE DCRVWAYGYM NIEDHSEYKI GNSLDEFMAW VLKVQADLYF 70         80         90        100        110        120
         HNLKFDGAFI INWLERNGFK WSADGLPNTY NTIISRMGQW YMIDICLGYK GKRKIHTVIY 130        140        150        160        170        180
         DSLKKLPFPV KKIAKDFKLT VLKGDIDYHK ERPVGYKITP EEYAYIKNDI QIIAEALLIQ 190        200        210        220        230        240
         FKQGLDRMTA GSDSLKGFKD IITTKKFKKV FPTLSLGLDK EVRYAYRGGF TWLNDRFKEK 250        260        270        280        290        300
         EIGEGMVFDV NSLYPAQMYS RLLPYGEPIV FEGKYVWDED YPLHIQHIRC EFELKEGYIP 310        320        330        340        350        360
         TIQIKRSRFY KGNEYLKSSG GEIADLWLSN VDLELMKEHY DLYNVEYISG LKFKATTGLF 370        380        390        400        410        420
         KDFIDKWTYI KTTSEGAIKQ LAKLMLNSLY GKFASNPDVT GKVPYLKENG ALGFRLGEEE 430        440        450        460        470        480
         TKDPVYTPMG VFITAWARYT TITAAQACYD RIIYCDTDSI HLTGTEIPDV IKDIVDPKKL 490        500        510        520        530        540
         GYWAHESTFK RAKYLRQKTY IQDIYMKEVD GKLVEGSPDD YTDIKFSVKC AGMTDKIKKE 550        560        570
         VTFENFKVGF SRKMKPKPVQ VPGGVVLVDD TFTIK
```

In some embodiments, the polymerase can comprise an amino acid sequence that is at least 70%, 80%, 85%, 90%, 95%, 99% or 100% identical to the amino acid sequence of SEQ ID NO: 3.

In some embodiments, the polymerase is derived from a Phi-29-like polymerase and comprises an amino acid sequence that is at least 70%, 80%, 85%, 90%, 95%, 97%, 98%, 99% or 100% identical to the amino acid sequence of SEQ ID NO: 3 and further including one or more amino acid mutations at positions selected from the group consisting of: 132, 135, 250, 266, 332, 342, 368, 370, 371, 372, 373, 375, 379, 380, 383, 387, 390, 458, 478, 480, 484, 486 and 512, wherein the numbering is relative to the amino acid sequence of SEQ ID NO: 3. In some embodiments, the Phi-29-like polymerase can comprise an amino acid deletion, wherein the deletion includes some of all of the amino acids spanning positions 306 to 311.

Without being bound to any particular theory, it is thought that the domain comprising amino acid residues 304-314 of the amino acid sequence of SEQ ID NO: 3 (Phi-29 polymerase), or homologs thereof, can reduce or otherwise interfere with DNA initiation and/or elongation by inhibiting access to the Phi-29 polymerase active site, and that this region must be displaced in order to allow access to the active site. See, e.g., Kamtekar et al., "The D29 DNA polymerase:protein primer structure suggests a model for the initiation to elongation transition", EMBO J., 25:1335-1343 (2005).

In some embodiments, the polymerase is derived from a Phi-29-like polymerase and comprises an amino acid sequence that is at least 70%, 80%, 85%, 90%, 95%, 97%, 98%, 99% or 100% identical to the amino acid sequence of SEQ ID NO: 3 and further includes one or more amino acid mutations selected from the group consisting of: K132A, K135A, K135D, K135E, V250A, V250C, Y266F, D332Y, L342G, T368D, T368E, T368F, K370A, K371E, T372D, T372E, T372R, T372K, T373A, T373F, T373H, T373K, T373Q, T373R, T373S, T373W, T373Y, T373A, T373E, E375A, E375F, E375H, E375K, E375Q, E375R, E375S, E375W, E375Y, K379A, Q380A, K383E, K383H, K383L, K383R, N387Y, Y390F, D458N, K478D, K478E, K478R, L480K, L480R, A484E, E486A, E486D, K512A K512D, K512E, K512R, K512Y, K371E/K383E/N387Y/D458N, Y266F/Y390F, Y266F/Y390F/K379A/Q380A, K379A/Q380A, E375Y/Q380A/K383R, E375Y/Q380A/K383H, E375Y/Q380A/K383L, E375Y/Q380A/V250A, E375Y/Q380A/V250C, E375Y/K512Y/T368F, E375Y/K512Y/T368F/A484E, K379A/E375Y, K379A/K383R, K379A/K383H, K379A/K383L, K379A/Q380A, V250A/K379A, V250A/K379A/Q380A, V250C/K379A/Q380A, K132A/K379A and deletion of some or all of the amino acid residues spanning R306 to K311, wherein the numbering is relative to the amino acid sequence of SEQ ID NO: 3. In some embodiments, the mutant Phi-29-like polymerase can exhibit increased branching ratio and/or increased $t_{-1}$ value in the presence of dye-labeled nucleotides relative to a reference polymerase having the amino acid sequence of SEQ ID NO: 3. In some embodiments, the branching ratio and/or $t_{-1}$ value of the polymerase is increased by at least about 105%, 110%, 125%, 150%, 175%, 200%, 250%, 500%, 750%, or 1000% relative to the reference polymerase. In some embodiments, the branching ratio and/or $t_{-1}$ value is increased in the presence of the dye-labeled nucleotide AF647-C6-dG6P. Optionally, the polymerase can further include one or more mutations reducing 3' to 5' exonuclease activity selected from the group consisting of: D12A, E14I, E14A, T15I, N62D, D66A, Y165F, Y165C, and D169A, wherein the numbering is relative to the amino acid sequence of SEQ ID NO: 3.

In some embodiments, the polymerase is derived from a Phi-29-like polymerase and comprises an amino acid sequence that is at least 70%, 80%, 85%, 90%, 95%, 97%, 98%, 99% or 100% identical to the amino acid sequence of SEQ ID NO: 3 and further includes the amino acid mutation H370R, wherein the numbering is relative to the amino acid sequence of SEQ ID NO: 3.

In other embodiments, the polymerase of the conjugate is a mutant or variant Phi-29 DNA polymerase comprising an N-terminal polyhistidine tag (His-tag) fused to an amino acid sequence at least about 85% identical to a Phi-29 DNA polymerase comprising the amino acid sequence of SEQ ID NO: 3, or biologically active fragment thereof. Optionally, the polymerase lacks 3' to 5' exonuclease activity. In some embodiments, the enzyme is a Klenow DNA polymerase having the amino acid sequence of SEQ ID NO: 2 and further comprising an engineered cysteine introduced at amino acid positions 730, 748, 750, 751, 778, 922, 926, 927 and 928, or any combination thereof. In some embodiments, the enzyme is Phi-29 DNA polymerase having the amino acid sequence of SEQ ID NO: 3, and the cysteine at amino acid position 473 serves as an attachment site for the label.

In some embodiments, the polymerase can be a deletion mutant which retains nucleotide polymerization activity but lacks the 3'→5' or 5'→3' exonuclease activity. For example, mutant phi29 polymerases having exonuclease-minus activity, or reduced exonuclease activity, can optionally comprise the amino acid sequence of SEQ ID NO: 3 and further comprise one or more amino acid substitutions at positions selected from the group consisting of: 12, 14, 15, 62, 66, 165 and 169 (wherein the numbering is relative to the amino acid sequence of SEQ ID NO: 3).

In some embodiments, the polymerase is derived from a Phi-29-like polymerase and comprises an amino acid sequence that is at least 70%, 80%, 90%, 95%, 97%, 98%, or 99% identical to the amino acid sequence of SEQ ID NO: 3 and comprises one or more of the following amino acid substitutions: D12A, E14I, E14A, T151, N62D, D66A, Y165F, Y165C, and D169A, wherein the numbering is relative to SEQ ID NO: 3.

In some embodiments, the conjugate can comprise at least one biomolecule linked to a label through a peptide linker comprising a series of amino acid residues.

In some embodiments, the peptide linker can comprise the amino acid sequence:

```
                                        (SEQ ID NO: 4)
            LLGAAAKGAAAKGSAA
```

This linker is hereinafter referred to as the "H-linker".

In some embodiments, the peptide linker can comprise the amino acid sequence:

```
                                        (SEQ ID NO: 5)
            LLGGGGSGGGGSAAAGSAA
```

This linker is hereinafter referred to as the "F-linker".

Optionally, the peptide linker can be fused to the N-terminus of the biomolecule, the C-terminus of the biomolecule, or any suitable position along the length of the biomolecule.

In some embodiments, the conjugate comprises a protein or biologically active fragment thereof linked to a label, wherein the protein comprises one or more cysteine replacements, i.e., one or more cysteine residues of the protein have been selectively replaced through mutation, deletion or other suitable modification so as to reduce the number of thiol residues capable of acting as points of covalent attachment for the label. For example, the polymerase can comprise the Klenow form of DNA polymerase, having the sequence of SEQ ID NO: 2, or biologically active fragment or variant thereof. Klenow DNA polymerase typically comprises a single cysteine residue at amino acid position 907 of the protein. In some embodiments, this residue is selectively mutated to another residue, for example, serine. Alternatively, the polymerase can comprise Phi-29 DNA polymerase or variant thereof, having the sequence of SEQ ID NO: 3, which typically comprises at least seven different cysteine residues. In some embodiments, some or all of these cysteine residues are selectively mutated so as to replace them with another residue. For example, the polymerase can be a protein comprising an amino acid sequence that is 60%, 70%, 80%, 85%, 90%, 95% or 100% identical to the amino acid sequence of SEQ ID NO: 3, wherein cysteine residues at amino acid positions 47, 315, and 555 have been selectively replaced with non-cysteine residues.

In some embodiments, the protein can optionally be fused with a polycysteine tag comprising multiple cysteine residues, and the cysteine residues of the poly-cysteine tag can serve as sites of attachment of the label mediated by SMCC. For example, the biomolecule can be a fusion protein that comprises a polycysteine tag fused to the open reading frame of a protein or biologically active fragment thereof. The polycysteine tag can comprise a stretch of 6, 7, 8, 9, 10, 11, 12 or more consecutive cysteine residues (SEQ ID NO: 56). The polycysteine tag can be fused to the N-terminus, the C-terminus or any other suitable position of the protein.

Optionally, a polycysteine tag can be separated from the amino acid residues of the protein by a linker. In some embodiments, the linker comprises the amino acid sequence of SEQ ID NO: 4 and/or SEQ ID NO: 5.

In some embodiments, the fusion protein comprises a polycysteine tag fused to the N-terminus of the Klenow form of *E. coli* DNA polymerase. In some embodiments, the polycysteine tag and the Klenow polymerase peptide can be separated by a peptide linker. In some embodiments, the fusion protein comprises an amino acid sequence that is at least 70%, 80%, 85%, 90%, 95%, 99% or 100% identical to the following amino acid sequence:

tide that are available as targets for NHS-ester crosslinking reagents. Alternatively, the protein can be conjugated to a poly-lysine tag comprising multiple lysine residues, and the lysine residues of the poly-lysine tag can serve as sites of attachment of the label mediated by BS3. In some embodiments, the biomolecule is a fusion protein and comprises a polylysine tag fused to the open reading frame of a protein or biologically active fragment thereof. The polylysine tag can comprise a stretch of 6, 7, 8, 9, 10, 11, 12 or more consecutive lysine residues (SEQ ID NO: 57). The polylysine tag can be fused to the N-terminus, the C-terminus or any other suitable position of the protein. Optionally, a polylysine tag can be separated from the amino acid residues of the protein by a linker. In some embodiments, the linker comprises the amino acid sequence of SEQ ID NO: 5 or SEQ ID NO: 5.

In some embodiments, the polymerase of the conjugate is fused with a polylysine tag at its N-terminus, and then linked to labels coated with amine groups (e.g., PEG-amine) using

```
                                                       (SEQ ID NO: 6)
         10         20         30         40         50         60
MCCCCCCCCC CCCLLGGGGS GGGGSAAAGS AARKMYSCDF ETTTKVEDCR VWAYGYMNIE 70         80         90        100        110        120
DHSEYKIGNS LDEFMAWVLK VQADLYFHNL KFDGAFIINW LERNGFKWSA DGLPNTYNTI 130        140        150        160        170        180
ISRMGQWYMI DICLGYKGKR KIHTVIYDSL KKLPFPVKKI AKDFKLTVLK GDIDYHKERP 190        200        210        220        230        240
VGYKITPEEY AYIKNDIQII AEALLIQFKQ GLDRMTAGSD SLKGFKDIIT TKKFKKVFPT 250        260        270        280        290        300
LSLGLDKEVR YAYRGGFTWL NDRFKEKEIG EGMVFDVNSL YPAQMYSRLL PYGEPIVFEG 310        320        330        340        350        360
KYVWDEDYPL HIQHIRCEFE LKEGYIPTIQ IKRSRFYKGN EYLKSSGGEI ADLWLSNVDL 370        380        390        400        410        420
ELMKEHYDLY NVEYISGLKF KATTGLFKDF IDKWTYIKTT SEGAIKQLAK LMLNSLYGKF 430        440        450        460        470        480
ASNPDVTGKV PYLKENGALG FRLGEEETKD PVYTPMGVFI TAWARYTTIT AAQACYDRII 490        500        510        520        530        540
YCDTDSIHLT GTEIPDVIKD IVDPKKLGYW AHESTFKRAK YLRQKTYIQD IYMKEVDGKL 550        560        570        580        590        600
VEGSPDDYTD IKFSVKCAGM TDKIKKEVTF ENFKVGFSRK MKPKPVQVPG GVVLVDDTFT

IK
```

In some embodiments, covalent conjugation of a protein to a label comprising one or more carboxyl groups on its surface can be achieved through use of the homobifunctional cross-linking agent Bis(sulfosuccinimidyl)suberate (BS3), which can be useful in linking amines to amines BS3 contains an amine-reactive N-hydroxysulfosuccinimide (NHS) ester at each end of an 8-carbon spacer arm. NHS esters can react with primary amines at pH 7-9 to form stable amide bonds, along with release of the N-hydroxysulfosuccinimide leaving group. Various proteins, including antibodies, generally have several primary amines in the side chain of lysine (K) residues and the N-terminus of each polypeptide the linking agent Bis(sulfosuccinimidyl)suberate (BS3), which is useful in linking amines to amines.

In some embodiments, the fusion protein comprises a polylysine tag fused to the N-terminus of the Klenow form of *E. coli* DNA polymerase. In some embodiments, the polylysine tag and the Klenow polymerase peptide are separated by a peptide linker. In some embodiments, the fusion protein comprises an amino acid sequence that is at least 70%, 80%, 85%, 90%, 95%, 99% or 100% identical to the following amino acid sequence:

```
                                                       (SEQ ID NO: 7)
         10         20         30         40         50         60
MKKKKKKKKK KKKLLGGGGS GGGGSAAAGS AARKMYSCDF ETTTKVEDCR VWAYGYMNIE
```

-continued

```
              70         80         90        100        110        120
        DHSEYKIGNS LDEFMAWVLK VQADLYFHNL KFDGAFIINW LERNGFKWSA DGLPNTYNTI 130        140        150        160        170        180
        ISRMGQWYMI DICLGYKGKR KIHTVIYDSL KKLPFPVKKI AKDFKLTVLK GDIDYHKERP 190        200        210        220        230        240
        VGYKITPEEY AYIKNDIQII AEALLIQFKQ GLDRMTAGSD SLKGFKDIIT TKKFKKVFPT 250        260        270        280        290        300
        LSLGLDKEVR YAYRGGFTWL NDRFKEKEIG EGMVFDVNSL YPAQMYSRLL PYGEPIVFEG 310        320        330        340        350        360
        KYVWDEDYPL HIQHIRCEFE LKEGYIPTIQ IKRSRFYKGN EYLKSSGGEI ADLWLSNVDL 370        380        390        400        410        420
        ELMKEHYDLY NVEYISGLKF KATTGLFKDF IDKWTYIKTT SEGAIKQLAK LMLNSLYGKF 430        440        450        460        470        480
        ASNPDVTGKV PYLKENGALG FRLGEEETKD PVYTPMGVFI TAWARYTTIT AAQACYDRII 490        500        510        520        530        540
        YCDTDSIHLT GTEIPDVIKD IVDPKKLGYW AHESTFKRAK YLRQKTYIQD IYMKEVDGKL 550        560        570        580        590        600
        VEGSPDDYTD IKFSVKCAGM TDKIKKEVTF ENFKVGFSRK MKPKPVQVPG GVVLVDDTFT

IK
```

In some embodiments, the biomolecule is a protein that is fused or otherwise coupled to a Transglutaminase tag comprising the amino acid sequence PKPQQF (SEQ ID NO: 53), which can be used as a site of attachment for amine reactive groups mediated by the enzyme transglutaminase. The transglutaminase tag can be fused to the N-terminus, the C-terminus or any other suitable position of the protein. Optionally, a transglutaminase tag can be separated from the amino acid residues of the protein by a peptide linker.

In some embodiments, the fusion protein comprises an amino acid sequence that is at least 70%, 80%, 85%, 90%, 95%, 99% or 100% identical to the following amino acid sequence:

In some embodiments, covalent conjugation of a biomolecule to a label can be accomplished via use of a Protein Kinase A (PKA) site fused, inserted or otherwise engineered into the biomolecular structure, which can permit more selectivity in choosing a point of attachment for the label to the biomolecule. For example, although a given protein may have several primary amines and cysteine thiols available for covalent conjugation, attempted modification of these reactive groups is not specific for one particular primary amine or thiol and frequently modification of the primary amine or thiol can result in decreased activity of the protein. Another method of conjugation that avoids such problems involves the engineering of a Protein Kinase A recognition

```
                                                                 (SEQ ID NO: 8)
        MHHHHHHLLG GGGSGGGGSA AAPKPQQFGS AARKMYSCDF ETTTKVEDCR VWAYGYMNIE 70         80         90        100        110        120
        DHSEYKIGNS LDEFMAWVLK VQADLYFHNL KFDGAFIINW LERNGFKWSA DGLPNTYNTI 130        140        150        160        170        180
        ISRMGQWYMI DICLGYKGKR KIHTVIYDSL KKLPFPVKKI AKDFKLTVLK GDIDYHKERP 190        200        210        220        230        240
        VGYKITPEEY AYIKNDIQII AEALLIQFKQ GLDRMTAGSD SLKGFKDIIT TKKFKKVFPT 250        260        270        280        290        300
        LSLGLDKEVR YAYRGGFTWL NDRFKEKEIG EGMVFDVNSL YPAQMYSRLL PYGEPIVFEG 310        320        330        340        350        360
        KYVWDEDYPL HIQHIRCEFE LKEGYIPTIQ IKRSRFYKGN EYLKSSGGEI ADLWLSNVDL 370        380        390        400        410        420
        ELMKEHYDLY NVEYISGLKF KATTGLFKDF IDKWTYIKTT SEGAIKQLAK LMLNSLYGKF 430        440        450        460        470        480
        ASNPDVTGKV PYLKENGALG FRLGEEETKD PVYTPMGVFI TAWARYTTIT AAQACYDRII 490        500        510        520        530        540
        YCDTDSIHLT GTEIPDVIKD IVDPKKLGYW AHESTFKRAK YLRQKTYIQD IYMKEVDGKL 550        560        570        580        590        600
        VEGSPDDYTD IKFSVKCAGM TDKIKKEVTF ENFKVGFSRK MKPKPVQVPG GVVLVDDTFT

IK
``` sequence, typically comprising the amino acid sequence LRRASLG (SEQ ID NO: 52), into the protein at a desired location. After incubation of the engineered protein with Protein Kinase A and ATP-yS, the protein will contain a single reactive phosphorothioate at the desired location. This single phosphorothioate can be selectively modified to create a covalent conjugate linked at the sulfur atom of the phosphorothioate.

In some embodiments, the protein containing the single phosphorothioate can be covalently conjugated to labels containing residual carboxylate groups on their surface using the following synthetic route: The labels are first modified with an excess of adipic dihydrazide via EDC coupling. After purification, the hydrazide functionalized labels are then reacted in the dark with an excess of iodoacetic acid also using EDC as the coupling agent. The resulting purified product comprises an iodoacetal functional group that is reactive with thiols and phosphorothioates. Consequently, in the final reaction an excess of the phosphorothioate-containing protein is incubated with iodoacetal modified labels at pH 5.5. The reaction product can be purified by size exclusion chromatography and characterized for activity and binding.

In some embodiments, the biomolecule is a protein that is fused or otherwise coupled to a protein kinase A (PKA) tag comprising the amino acid sequence LRRASL (SEQ ID NO: 58), which can be used as a site of attachment mediated by the enzyme protein kinase A enzyme.

The PKA tag can be fused to the N-terminus, the C-terminus or any other suitable position of the protein. Optionally, the PKA tag can be separated from the amino acid residues of the protein by a linker, typically a peptide linker. In some embodiments, the fusion protein comprises an amino acid sequence that is at least 70%, 80%, 85%, 90%, 95%, 99% or 100% identical to the following amino acid sequence:

In some embodiments, the biomolecule comprises a Phi-29 polymerase further comprise a biotin ligase recognition sequence and optionally including a His-tag. The biotin ligase site and/or optionally the His-tag can be located at the N-terminus, the C-terminus or any other suitable position of the Phi-29 polymerase. Optionally, the biotin ligase sequence and/or the His-tag can be separated from the amino acid residues of the Phi-29 protein by a linker, typically a peptide linker. In some embodiments, the biotin ligase recognition site comprises a biotin acceptor peptide. In some embodiments, the biotin acceptor site can comprise the amino acid sequence of SEQ ID NO: 10:

GLNDIFEAQKIEWHE (SEQ ID NO: 10)

See, e.g., Howarth et al., "Targeting quantum dots to surface proteins in living cells with biotin ligase", Proc. Natl. Acad. Sci. USA 102(21):7583-7588 (2005).

In some embodiments, the fusion protein comprises an amino acid sequence that is at least 70%, 80%, 85%, 90%, 95%, 99% or 100% identical to the following amino acid sequence:

```
                                            (SEQ ID NO: 11)
MSHHHHHHSMSGLNDIFEAQKIEWHEGAPGARGSKHMPRKMYSCAFETTT

KVEDCRVWAYGYMNIEDHSEYKIGNSLDEFMAWVLKVQADLYFHNLKFAG

AFIINWLERNGFKWSADGLPNTYNTIISRMGQWYMIDICLGYKGKRKIHT

VIYDSLKKLPFPVKKIAKDFKLTVLKGDIDYHKERPVGYKITPEEYAYIK

NDIQIIAEALLIQFKQGLDRMTAGSDSLKGFKDIITTKKFKKVFPTLSLG

LDKEVRYAYRGGFTWLNDRFKEKEIGEGMVFDVNSLYPAQMYSRLLPYGE

PIVFEGKYVWDEDYPLHIQHIRCEFELKEGYIPTIQIKRSRFYKGNEYLK

SSGGEIADLWLSNVDLELMKEHYDLYNVEYISGLKFKATTGLFKDFIDKW

TYIKTTSEGAIKQLAKLMLNSLYGKFASNPDVTGKVPYLKENGALGFRLG

EEETKDPVYTPMGVFITAWARYTTITAAQACYDRIIYCDTDSIHLTGTEI
```

```
                                                 (SEQ ID NO: 9)
         10         20         30         40         50         60
MGLRRASLHH LLGGGGSGGG GSAAAGSAAR KMYSCDFETT TKVEDCRVWA YGYMNIEDHS 70         80         90        100        110        120
EYKIGNSLDE FMAWVLKVQA DLYFHNLKFD GAFIINWLER NGFKWSADGL PNTYNTIISR 130        140        150        160        170        180
MGQWYMIDIC LGYKGKRKIH TVIYDSLKKL PFPVKKIAKD FKLTVLKGDI DYHKERPVGY 190        200        210        220        230        240
KITPEEYAYI KNDIQIIAEA LLIQFKQGLD RMTAGSDSLK GFKDIITTKK FKKVFPTLSL 250        260        270        280        290        300
GLDKEVRYAY RGGFTWLNDR FKEKEIGEGM VFDVNSLYPA QMYSRLLPYG EPIVFEGKYV 310        320        330        340        350        360
WDEDYPLHIQ HIRCEFELKE GYIPTIQIKR SRFYKGNEYL KSSGGEIADL WLSNVDLELM 370        380        390        400        410        420
KEHYDLYNVE YISGLKFKAT TGLFKDFIDK WTYIKTTSEG AIKQLAKLML NSLYGKFASN 430        440        450        460        470        480
PDVTGKVPYL KENGALGFRL GEEETKDPVY TPMGVFITAW ARYTTITAAQ ACYDRIIYCD 490        500        510        520        530        540
TDSIHLTGTE IPDVIKDIVD PKKLGYWAHE STFKRAKYLR QKTYIQDIYM KEVDGKLVEG 550        560        570        580        590
SPDDYTDIKF SVKCAGMTDK IKKEVTFENF KVGFSRKMKP KPVQVPGGVV LVDDTFTIK
```

```
PDVIKDIVDPKKLGYWAHESTFKRAKYLRQKTYIQDIYMKEVDGKLVEGS

PDDYTDIKFSVKCAGMTDKIKKEVTFENFKVGFSRKMKPKPVQVPGGVVL

VDDTFTIK
```

Hereinafter, the protein of SEQ ID NO: 11 is referred to variously as "HBP1" or "HBP-1." It comprises a His-tagged Phi-29 polymerase peptide comprising a biotin ligase site that is fused to the N-terminus of the Phi-29 polymerase, which is exonuclease-minus and includes the D12A and D66A mutations. In some embodiments, the polymerase of the labeled polymerase conjugate comprises an amino acid sequence that is at least 70%, 80%, 85%, 90%, 95%, 99% or 100% identical to the amino acid sequence of SEQ ID NO: 11.

In some embodiments, the polymerase comprises a fusion protein having an amino acid sequence that is at least 70%, 80%, 85%, 90%, 95%, 99% or 100% identical to the following amino acid sequence, which comprises a Phi-29 polymerase peptide comprising an N-terminal His-tag and an intervening H-linker sequence, as follows:

```
                                                         (SEQ ID NO: 12)
            MHHHHHHLLG AAAKGAAAKG SAARKMYSCD FETTTKVEDC RVWAYGYMNI EDHSEYKIGN 70         80         90        100        110        120
            SLDEFMAWVL KVQADLYFHN LKFDGAFIIN WLERNGFKWS ADGLPNTYNT IISRMGQWYM 130        140        150        160        170        180
            IDICLGYKGK RKIHTVIYDS LKKLPFPVKK IAKDFKLTVL KGDIDYHKER PVGYKITPEE 190        200        210        220        230        240
            YAYIKNAIQI IAEALLIQFK QGLDRMTAGS DSLKGFKDII TTKKFKKVFP TLSLGLDKEV 250        260        270        280        290        300
            RYAYRGGFTW LNDRFKEKEI GEGMVFDVNS LYPAQMYSRL LPYGEPIVFE GKYVWDEDYP 310        320        330        340        350        360
            LHIQHIRCEF ELKEGYIPTI QIKRSRFYKG NEYLKSSGGE IADLWLSNVD LELMKEHYDL 370        380        390        400        410        420
            YNVEYISGLK FKATTGLFKD FIDKWTYIKT TSEGAIKQLA KLMLNSLYGK FASNPDVTGK 430        440        450        460        470        480
            VPYLKENGAL GFRLGEEETK DPVYTPMGVF ITAWARYTTI TAAQACYDRI IYCDTDSIHL 490        500        510        520        530        540
            TGTEIPDVIK DIVDPKKLGY WAHESTFKRA KYLRQKTYIQ DIYMKEVDGK LVEGSPDDYT 550        560        570        580        590
            DIKFSVKCAG MTDKIKKEVT FENFKVGFSR KMKPKPVQVP GGVVLVDDTF TIK
```

In some embodiments, the fusion protein comprises an amino acid sequence that is at least 70%, 80%, 85%, 90%, 95%, 99% or 100% identical to the following amino acid sequence, which comprises a Phi-29 polymerase peptide comprising an N-terminal His-tag and an intervening F-linker sequence, as follows:

```
                                                         (SEQ ID NO: 13)
            MHHHHHHLLG GGGSGGGGSA AAGSAARKMY SCDFETTTKV EDCRVWAYGY MNIEDHSEYK 70         80         90        100        110        120
            IGNSLDEFMA WVLKVQADLY FHNLKFDGAF IINWLERNGF KWSADGLPNT YNTIISRMGQ 130        140        150        160        170        180
            WYMIDICLGY KGKRKIHTVI YDSLKKLPFP VKKIAKDFKL TVLKGDIDYH KERPVGYKIT 190        200        210        220        230        240
            PEEYAYIKNA IQIIAEALLI QFKQGLDRMT AGSDSLKGFK DIITTKKFKK VFPTLSLGLD 250        260        270        280        290        300
            KEVRYAYRGG FTWLNDRFKE KEIGEGMVFD VNSLYPAQMY SRLLPYGEPI VFEGKYVWDE 310        320        330        340        350        360
            DYPLHIQHIR CEFELKEGYI PTIQIKRSRF YKGNEYLKSS GGEIADLWLS NVDLELMKEH 370        380        390        400        410        420
            YDLYNVEYIS GLKFKATTGL FKDFIDKWTY IKTTSEGAIK QLAKLMLNSL YGKFASNPDV 430        440        450        460        470        480
            TGKVPYLKEN GALGFRLGEE ETKDPVYTPM GVFITAWARY TTITAAQACY DRIIYCDTDS
```

```
                -continued
      490        500        510        520        530        540
IHLTGTEIPD VIKDIVDPKK LGYWAHESTF KRAKYLRQKT YIQDIYMKEV DGKLVEGSPD 550        560        570        580        590
DYTDIKFSVK CAGMTDKIKK EVTFENFKVG FSRKMKPKPV QVPGGVVLVD DTFTIK
```

In some embodiments, the biomolecule comprises a fusion protein having an amino acid sequence that is at least 70%, 80%, 85%, 90%, 95%, 99% or 100% identical to the following amino acid sequence, which comprises a Phi-29 polymerase peptide that lacks exonuclease activity and comprises an N-terminal His-tag, an intervening linker sequence, and the D12A and D66A mutations, as follows:

```
                                                        (SEQ ID NO: 14)
MNHLVHHHHH HIEGRHMELG TLEGSMKHMP RKMYSCAFET TTKVEDCRVW AYGYMNIEDH 70         80         90        100        110        120
SEYKIGNSLD EFMAWVLKVQ ADLYFHNLKF AGAFIINWLE RNGFKWSADG LPNTYNTIIS 130        140        150        160        170        180
RMGQWYMIDI CLGYKGKRKI HTVIYDSLKK LPFPVKKIAK DFKLTVLKGD IDYHKERPVG 190        200        210        220        230        240
YKITPEEYAY IKNDIQIIAE ALLIQFKQGL DRMTAGSDSL KGFKDIITTK KFKKVFPTLS 250        260        270        280        290        300
LGLDKEVRYA YRGGFTWLND RFKEKEIGEG MVFDVNSLYP AQMYSRLLPY GEPIVFEGKY 310        320        330        340        350        360
VWDEDYPLHI QHIRCEFELK EGYIPTIQIK RSRFYKGNEY LKSSGGEIAD LWLSNVDLEL 370        380        390        400        410        420
MKEHYDLYNV EYISGLKFKA TTGLFKDFID KWTYIKTTSE GAIKQLAKLM LNSLYGKFAS 430        440        450        460        470        480
NPDVTGKVPY LKENGALGFR LGEEETKDPV YTPMGVFITA WARYTTITAA QACYDRIIYC 490        500        510        520        530        540
DTDSIHLTGT EIPDVIKDIV DPKKLGYWAH ESTFKRAKYL RQKTYIQDIY MKEVDGKLVE 550        560        570        580        590        600
GSPDDYTDIK FSVKCAGMTD KIKKEVTFEN FKVGFSRKMK PKPVQVPGGV VLVDDTFTIK
```

This fusion polymerase of amino acid sequence of SEQ ID NO: 14 is herein variously referred to as "HP1" or "HP-1". See, e.g., U.S. Provisional Application No. 61/184,770, filed Jun. 5, 2009. This fusion polymerase comprises a Phi-29 polymerase peptide that lacks exonuclease activity and comprises an N-terminal His-tag, an intervening linker sequence, and the D12A and D66A mutations.

In some embodiments, the biomolecule comprises a fusion protein having an amino acid sequence that is at least 70%, 80%, 85%, 90%, 95%, 99% or 100% identical to the amino acid sequence of SEQ ID NO: 14 (HP-1).

In some embodiments, a naturally occurring or engineered cysteine of SEQ ID NO: 14 (HP1) is used as an attachment site for a label. In some embodiments, the attachment site is a site for covalent attachment of the label using the linking agent SMCC. In some embodiments, the cysteine occurring at amino acid position 473 of SEQ ID NO: 14 (HP1) is used as the attachment site.

In some embodiments, the polymerase can comprise a His-tagged version of a Phi-29 polymerase and an N-terminal linker as well as various mutations that reduce the exonuclease activity of the Phi-29 polymerase.

In some embodiments, the polymerase, or any biologically active fragment thereof, can be linked to a label through a peptide linker comprising a series of amino acid residues. In some embodiments, the peptide linker comprises the amino acid sequence of SEQ ID NO: 12 or SEQ ID NO: 13.

In some embodiments, polymerase of the labeled polymerase conjugate comprises an amino acid sequence that is at least 70%, 80%, 85%, 90%, 95%, 99% or 100% identical to the amino acid sequence of SEQ ID NO: 14.

In some embodiments, the polymerase comprises mutated Phi-29 DNA polymerase that lacks 3' to 5' exonuclease activity. In some embodiments, the mutant Phi-29 DNA polymerase comprises the mutations D12A, D66A, the mutation D169A, the mutation H61R, the mutation N62D, the mutation Q380A, the mutation S388G, or any combination thereof, wherein the numbering is relative to wild-type Phi-29 polymerase (SEQ ID NO: 3). In some embodiments, the polymerase comprises any two, three, four, five or all of these mutations.

In some embodiments, the polymerase falls with the family of Family type-B delta polymerases, the Type B DNA polymerases, or the Family A T7 like polymerases.

In some embodiments, the polymerase is capable of withstanding exposure to laser irradiation and/or exposure to labels for a duration of at least 5, 10, 15, 20, 30, 45, 60, 90, 120, 180 or 240 minutes. Without being bound to any particular theory, it is believed that the polymerases of phototrophic and/or halotrophic organisms can exhibit enhanced tolerance to laser irradiation, fluorescent dyes, nanoparticles, photo-breakdown products and/or excited state molecules such as superoxides, triplet oxygen, peroxides, etc. In some embodiments, the polymerase can be, for example, a polymerase isolated from a phototrophic and/or halotrophic organism. The polymerase can be a polymerase isolated from Cyanophage S-CBP1, Cyanophage S-CBP2, Cyanophage S-CBP3, Cyanophage Syn5, Cyanophage S-CBP42, Synechococcus phage P60, Roseobacter phage SIO1 DNA Polymerase, *Oedogonium cardiacum* chloroplast DNA Polymerase, Salterprovirus His1 Polymerase, Salterprovirus His2 Polymerase, *Ostreococcus tauri* V5, *Ectocarpus siliculosus* virus 1, or any combination of such polymerases.

In some embodiments, the biomolecule of the conjugate can be a Cyanophage S-CBP1 DNA polymerase having the following sequence:

```
                                                              (SEQ ID NO: 15)
  1 mtlifdietd glyndascih cigihdlnag etyvfndvgt qqpitkgiql ledadlivgh 61 niigydipvi sklfpwfsrt ngvldtivls rlyhtdlldi dqkrkwkhmp lqlygrhsle 121 aygyrlgeyk gsfgktadwk ewsqdmedym iqdvnvtrkl wkhfpqipew vqlehrvaqi 181 lteqeiygwy fdenaarela qtlytelddl kgvlrkrypy vagreftpkr vnrslgyveg 241 atctklvefs ptsrdhiawv mknlhgwkpd kktkagktai deivlkeigt eealqffrcl 301 eitkqlgmls egknawlkls rkdrvhhhcs vatvthrcah rnpnlaqvps dlnfrrlfca 361 spghimvgad lsgielrmla hylaryddgr ygdillhgdi hqenadkigi srrlvktvty 421 aflygagdqk iglsydqgls pdkakqkgke irqaymdaip gleklveatk kaadrgfirs 481 idgrhinvds shkalnmllq ssagciakrw mviandnfpt idneylahth glafihdelq 541 feclplyaed lkthlelcae lageyynlri piaaegkigs twadvh
```

In some embodiments, the biomolecule can comprise a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Cyanophage S-CBP1 DNA polymerase that lacks 3' to 5' exonuclease activity. For example, the so-called "DIET" motif (SEQ ID NO: 59) comprising the amino acid residues DIET (SEQ ID NO: 59) from positions 6-9 of the above amino acid sequence can be mutated via substitution of both the Asp and Glu residues of the DIET motif (SEQ ID NO: 59) with Alanine, resulting in a polymerase that lacks 3' to 5' exonuclease activity.

In some embodiments, the biomolecule of the conjugate can be a Cyanophage S-CBP2 DNA polymerase. In some embodiments, this DNA polymerase can have the following sequence:

```
                                                              (SEQ ID NO: 16)
  1 mklvfdietd gflrklttvh cvvakdietg evfkfddsgr hqsvssgltl lmeaeelwgh 61 niigfdvpai qeiypffqpw estyydtlil srlfftdmld rdlrskpanm pgnlygrhsl 121 eawgyrlgvl kseygkqlhg dwatytpeml eyceqdvean lpivklfqpk leqyadaikt 181 ehdcalvmtr qeqagfpfdi dkaraleskl rseletlsde mratftfvag keftparnna 241 trgyitgcpf tkltefspts rdhiawafqq hrgwepiemt dtgkpkidee vlnaigteea 301 kkfgrilelq khvgmlsegk nswlqmvekd grihhscvln tatgrnahmr pnlaqvpsgh 361 efrelftpge gyvqvgadas glelrclahy larfdggkfg kvllegdiht dlaniygtdr 421 ktgktvtycl iygggdtklg lsagepkksa asrgkkirqa imkdldgfaq litavqeraq 481 sgvitgidgr pirmrkahaa lnyllqscga vickkwvvrs nellteagid ytplafvhde 541 qqlavrpdqv emastlisla mkdvehaikf rvpldcdvqs ganwgdth
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Cyanophage S-CBP2 DNA polymerase that lacks 3' to 5' exonuclease activity. For example, the so-called "DIET" motif (SEQ ID NO: 59) comprising the amino acid residues DIET (SEQ ID NO: 59) from positions 6-9 of the above amino acid sequence can be mutated via substitution of both the Asp and Glu residues of the DIET motif (SEQ ID NO: 59) with Alanine, resulting in a polymerase that lacks 3' to 5' exonuclease activity.

In some embodiments, the biomolecule of the conjugate can be a Cyanophage S-CBP3 DNA polymerase. In some embodiments, the DNA polymerase can have the following sequence:

```
                                                                   (SEQ ID NO: 17)
  1 mtlifdietd glyndvtcih cigihdlntk etyvfndvgt qqpitkgiql ledadiivgh 61 niigydlpvi rklypwfsnv grvldtlvls rlyhadllkt dqkrnwkhmp vqlwgrhsle 121 aygyrlgeyk gcfgkttdwk dwsqemedym vqdvnitrkl wkdfpeipew vqlehrvaqi 181 lteqeihgwy fdepaawele stlrrelesl kavlrnrhpf ilgeeftpkr pnstqgyftg 241 atftrlkemn ptsrdhiayi lqkfydwept ertekgkpvv deivlkdigs eialqffrcl 301 eltkqigmlt egvnawlklv rndrihhhcs vatnthrcah rkpnlaqvpa eaefrklfra 361 tpgmvmvgad lagielrmla hylaqwdggr ygdvllngdi hqenadkigi srrlvktvty 421 aflygagnqk iglsydqsls pdkakkkgqe irqaymdaip glrklveatk kaanrgyira 481 idgrhisvds phkslnyllq ssagviakrw laltheaiir adikahqlaf ihdelqfett 541 pehvedlkfa llwgaasage yynlripiaa daksgndwse vh
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Cyanophage S-CBP3 DNA polymerase that lacks 3' to 5' exonuclease activity. For example, the so-called "DIET" motif (SEQ ID NO: 59) comprising the amino acid residues DIET (SEQ ID NO: 59) from positions 6-9 of the above amino acid sequence can be mutated via substitution of both the Asp and Glu residues of the DIET motif (SEQ ID NO: 59) with Alanine, resulting in a polymerase that lacks 3' to 5' exonuclease activity.

In some embodiments, the biomolecule of the conjugate can be a Cyanophage Syn5 DNA polymerase. In some embodiments, the DNA polymerase can have the following sequence:

```
                                                                   (SEQ ID NO: 18)
  1 mrlvfdietd gllrglsvih civardldtn eehrfephqt kaglqllkea delwghnivg 61 ydieaikely pkwttkakly dtlilsrlff tdlldrdfrs kpanmpgnly grhsleawgh 121 rlgvhksefg kqldgdwsty spemleycaq dvtvsvqvaq mfepkleqya dcidtehrla 181 timawqereg fpfdvtaaqq lesrlrteld alsdqmrstf lfvdggtftp rrnnkpqgyi 241 adapmcklke fnptsrhhia wafqqfrnwe pkeftdsgkp kideptltai gtdeakafar 301 ilelqkhlgq laegknawlk leskgrvhhs cvlntntgrq ahmrpnlaqv psaseyralf 361 gpgdsrvqvg adasglelrc lahylapfdn gsfaetvvng dihtelasiy gtdrksgkgv 421 tycliygggd hklgstagas kaqaskkgke irgrimrdld gfaalsdavs rrartgvlrg 481 ldgrpirlqg kshaalnyll qsagavickq wllrsyelld eanidywpla fvhdelqisv 541 apsqaematl litaamkdvq hnlkfrceld seaqtgnswa dch
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Cyanophage Syn5 DNA polymerase that lacks 3' to 5' exonuclease activity. For example, the so-called "DIET" motif (SEQ ID NO: 59) comprising the amino acid residues DIET (SEQ ID NO: 59) from positions 6-9 of the above amino acid sequence can be mutated via substitution of both the Asp and Glu residues of the DIET motif (SEQ ID NO: 59) with Alanine, resulting in a polymerase that lacks 3' to 5' exonuclease activity.

In some embodiments, the biomolecule of the conjugate can be a Cyanophage S-CBP42 DNA polymerase. In some embodiments, the DNA polymerase can have the following sequence:

(SEQ ID NO: 19)
```
  1 mrlafdietd gllrnltkih civaqdldtn evykfdgtgd hpsireglal lkdadelwgh
 61 niigydfeai kevfprwnys stvydtlils rlfftdlldr dfrsrpanmp aqlygrhsle
121 awghrlsvhk sefgkslsgd wstyspemld ycardvvvsv slarlftakv aeyrdciste
181 hrlatimawq esegfpfdva kaerlegqlr sellklseqm retfpyvdgg sftprtnngp
241 rgyvkgaamc rlkefnptsr qhiawafatf rdwepkeltd tgkpkidett lleygtdeak
301 tfarilelqk hlgqlsegan awlkkvesdg rihhscvlnt ntgrqahmkp nlaqvpsghe
361 yrelfhpgan rsqvgadasg lelrclghyl arfdggkfak evvqgdihta laeiygtdrk
421 sgkgvtycli ygggdsklgl tagaskaqav kkgkeirsri manldgfaal naavqeraks
481 gvlkgldgrp irlqgknhaa lnyllqsaga vicklwllrs yelldeagid yfpmafvhde
541 vhisvapsqa eqagqliqia mkdvehqikf rcaldseyqi gnswadch
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Cyanophage S-CBP42 DNA polymerase that lacks 3' to 5' exonuclease activity. For example, the so-called "DIET" motif (SEQ ID NO: 59) comprising the amino acid residues DIET (SEQ ID NO: 59) from positions 6-9 of the above amino acid sequence can be mutated via substitution of both the Asp and Glu residues of the DIET motif (SEQ ID NO: 59) with Alanine, resulting in a polymerase that lacks 3' to 5' exonuclease activity.

In some embodiments, the biomolecule of the conjugate can be a Synechococcus phage P60 DNA polymerase. In some embodiments, the DNA polymerase can have the following sequence:

(SEQ ID NO: 20)
```
  1 mklafdietd glipdltiih civardidtd eefrfdgtgd ypsikeglel lskadelwgh
 61 nivnydypai qklhpdwtpp sctrdtlils rlfftdlldr dfrsrpalmp gnlygrhsle
121 awghrlghhk sefgkslegd wstyspemle ycardvevsv alaktfvpki peyqwsvdte
181 heiarimswq eqmgfpfdvr aaqalegklr leldtlsddm retfhfvdgg vmtpkrsnkv
241 rhyfenapfc klrefnptsr hhiawafehh rgwepkerta ggqpkiddei lreintkesl
301 afarilelqk hlgqlsegkn awlklerkgr lhhscvlntn tgrqahmrpn laqvpsahey
361 rslfkpsdnh lqvgsdasgl elrclghyls rydggkfaee vvngdihtal aeiygtdrks
421 gkgvtycliy gggnhklglt agaskssasr kgqeirgkim qglsgfadln aaiqeraksg
481 vlkgldgrpi rlqgknhaal nyllqsagai icklwvirth ellqeagidy yplafvhdeq
541 qlsvradqae maaqlttlam kdvehqvkfr caldseyqig nswadch
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Synechococcus phage P60 DNA polymerase that lacks 3' to 5' exonuclease activity. For example, the so-called "DIET" motif (SEQ ID NO: 59) comprising the amino acid residues DIET (SEQ ID NO: 59) from positions 6-9 of the above amino acid sequence can be mutated via substitution of both the Asp and Glu residues of the DIET motif (SEQ ID NO: 59) with Alanine, resulting in a polymerase that lacks 3' to 5' exonuclease activity.

In some embodiments, the biomolecule of the conjugate can be a Roseobacter phage SIO1 DNA polymerase. In some embodiments, the Roseobacter phage SIO1 DNA polymerase can have the following sequence:

(SEQ ID NO: 21)
```
  1 mevvfdietd aldatvihvl vakrvgqkgf yvvrdaetfk rlakqvtlwi ghnvigfdip
 61 qikklwgygi plkdvadtlv msrlldptrk gghsldalsg nekidfhdfs tytpemlayc
```

```
121 kqdvainekv ylqlkeelsn fgkasiqleh qmqaivceqe kngfmldtdi aeeiyttclr 181 etnrieaeik efmvpiavpv keviikrkkd gsiysnqlle gcnvqgdytk iaweefnlgs 241 paqvnkrldr lgwkptvktk sgnsykicpe nlatipdtap eavkglkawk vletrwklaq 301 ewlqksqetg rvhgrviltg avthraahqg pnmanipsvp hgkdgilwkm egmygaecrq 361 afkvpegkll vgtdaagiql rvlahymndp iyteqvidgd ihtfnkealg ryckdrptak 421 tfiyafllga gtgmiasilg cnnrqaneam anfyeaipsl kklksqasqa asmgwmkgld 481 grvlrigsdh lalsvylqgg etvimrlanv fwqrqakkeg infkqcawvh dewqtevded 541 qaqrlgeiqv qaikdagtff klncpmdgea kigknwleth
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Roseobacter phage SIO1 DNA Polymerase DNA polymerase that lacks 3' to 5' exonuclease activity. For example, the so-called "DIET" motif (SEQ ID NO: 59) comprising the amino acid residues DIET (SEQ ID NO: 59) from positions 6-9 of the above amino acid sequence can be mutated via substitution of both the Asp and Glu residues of the DIET motif (SEQ ID NO: 59) with Alanine, resulting in a polymerase that lacks 3' to 5' exonuclease activity.

In some embodiments, the biomolecule of the conjugate can be a DNA polymerase from *Oedogonium cardiacum*. In some embodiments, the *Oedogonium cardiacum* polymerase can be a *Oedogonium cardiacum* chloroplast DNA Polymerase. In some embodiments, this polymerase can have the following sequence:

(SEQ ID NO: 22)
```
  1 miefyasfdk dkeieinked semnkediem nkedieidld evneeerfdv nremlqtnyf 61 vkrfknilfp iaasfytseg nknvsktfsl tsnifdkkip stinilkesq immqefliel 121 islaedllkk rnptnslfyg ddkviiymhn lssfdgffil qtllksriln ytfnlnkklk 181 vtsyegliyr ikignlcfqd syrvipmsln klsflllnkq kkdfdvenin sqklqhifkn 241 keilekmley clydsillye smiliqktfw delkfditse stisntainf ffskyyefpt 301 qyywhtttkk dglsaklkyd nkrvtvsthh naifytkpfl dqqlrsayfg grtelykpqt 361 sngyvfdins lyafalmydm pygspiyene yknwttnefe sffgflkiif itppnydilp 421 vlprrypppi shnvyclgig egwyfseeik larqkgyklk ilesikftph kgfekfvrdf 481 fsirqqypkg hplnllakli lnstygrfgi altthkqmkt fnqiklkekk nkkinini
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of *Oedogonium cardiacum* chloroplast DNA Polymerase DNA polymerase that lacks 3' to 5' exonuclease activity.

In some embodiments, the biomolecule of the conjugate can be a Salterprovirus His1 polymerase. In some embodiments, the polymerase can have the following sequence:

(SEQ ID NO: 23)
```
  1 makcdkslea idldraytap rkakwaenkr ingldtetsd gdifcisvcw egekpmvqhn 61 drekltskqv wqvltdhkar sslnmwynld fdanvvlnhv cseeqlaelv vsgttlansd 121 rtyrqymdtd kelrkgeyli tyiqskflei kdhnshiyth ydasqffyts lenavtewlg 181 eskandglea glfgsqtpnq lretvaesdc vtwtnlslty nvskgdkwti hnaksyiskn 241 wsdilkyaqi daelvrdlwq eavnvgeeld ipmgrpfstg ylaesyldnr lrekpglgpm 301 pmakmawesy aggrfevlkr gnvgrvagpd insaypavla elpdpktlrw krakhasise 361 ietadygfmt vkvstdptre iqpfavkdek qdklvypspq nteitvvkdi fihaynqgyv
```

-continued
```
421 tdyevidcwl gyktegttfp fdfipelydn rktaeangle krglllkivl nsmygktcqt 481 tpkrrelaes telelhesyv pdmslpkmir ekysegfies ltagawfnpf lasyitgltr 541 lelhkqickh dleentvmla tdcvmieekp feesnfvenl vqdglgywdm eykgdafvlg 601 agvyqidfdt cqkgckdncn kfshkhkvkt rgfseadlek glvnaaekan ghieiestrp 661 qtiseiiwsn eelsqvgnfl eqerkikpem dtkrkwsent dfkkllstce tslplki
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Salterprovirus His1 DNA polymerase that lacks 3' to 5' exonuclease activity.

In some embodiments, the biomolecule of the conjugate can be a DNA polymerase from Salterprovirus His2. In some embodiments, this polymerase can have the following amino acid sequence:

(SEQ ID NO: 24)
```
  1 maksdrnlde vnlypayqdq ysatfvdgkl inafdtetss gtvfmltsay gdktqayynr 61 dvseldaeti mdaltdyktr sniniwynld fdanailsgi lsqkemselv vtnettttva 121 gieyeifyik gkmlrivden gnisphydia qffytsldna aeewlgenkk egidtskfdd 181 keyikdnfde ilkyakkdas ltqdlaielt neaenldipm grpistgyls aeylrantee 241 kpslgneamq nlfwesyygg rfevfqrgnv gevvapdins aypaimkdlp dpttlnwnhy 301 lnevsdkepf shsinkfgye eienghygvv karvttdssr miqpfackid gkvkfpamtn 361 kvvtvikpif efavnnglvt dfelieawig nitdrtskpf efigdmyaer kvfeqlknkp 421 kkgqllkivl nssygktcqt tekrhkhdld kdgkkimqah etqyprfyls kkqrealgdd 481 eiiiteleag krfnpffasy itgltrlelh kqvvehdied stvmfatdcl mvekeayens 541 sfdeqihvpd dslpesefrk eatrslgawd fdyegsafiv gsgvyevdti qgktktktrg 601 fiesnlgdtl kglakkhkea ipldnerplt maevlinter gsvsefvens kklkpdfddk 661 rnwnrenpnf hdllndkeys kpidlqeqke emiqeqmdin ekmigdatpn gnetvvvkdd
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Salterprovirus His2 DNA polymerase that lacks 3' to 5' exonuclease activity.

In some embodiments, the biomolecule of the conjugate can be a DNA polymerase from *Ostreococcus tauri* V5. In some embodiments, this DNA polymerase can have the following amino acid sequence:

(SEQ ID NO: 25)
```
  1 mvvfqaltwe srdtddehli sifgkteegk svclttaftp yffiklpeki dagkirriyn 61 ildekckdsl vaysvmkskd vwgfqnneef vfmkvnfkhl qarrlvdsfl rkpldrtpel 121 fnifgvrnvk vyesnldpvl rlmhrtgiqs tgwldtgdkc irshlarvdl dlfcndwttl 181 kpvarddiap fvvasvdiec nsstgkfpda dvtgdacfqi aislckfgsd epydktclcy 241 kktdpnlegs tirsyetere mleafqkylh tkdvdiitgw nifgfdmeyi ykraqvnrch 301 yeffnlgklr dteselvikk lsssalgdnl lkllpmpgrf ifdmfhevkk gykldsykld 361 nvsklylgdq kidmapkemf aryreedpvk lrevaeycik dtllphrlmk klctllnmve 421 makatwvpan flvergqqik vfsqltkkar elgfmvptir ygaipeepye gatvleaqkg 481 ayytpitald fealypsimm ahnlcyssyv mdekrygsvp gityetfnig drtykfaqdv
```

```
541 psllpailae lkqfrkqakr dmaaatgfmk evyngkqlay kvsmnsvygf tgagkgilpc 601 vpiastttsk grsmieetkn yveknfpgak vrygdtdsvm vefdvgdrkg eeaiayswev 661 geraaeecsa lfkkpnnlel ekvywpyfly skkryaaklw tkgkdgkmhm dyidikglqv 721 vrrdntphvr evckelldvi ltssdpgppk elakeraiel lsgdvpndkl ilsqglsdty 781 kvggknvsvt sadsvninqs hvqvvtkmrq rkpgsepqsg drvpylltkt qdpkakayek 841 aedpkyveeh gvpvdyhyyf lnkflnpvcd lldplyenvk edifgeiina hkpvkppklp 901 slsgmkkddl iaecqrlgle etgtlailra rlkdarhgsv edlfknyelt qskdess
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of *Ostreococcus tauri* V5 DNA polymerase that lacks 3' to 5' exonuclease activity.

In some embodiments, the biomolecule of the conjugate can be a DNA polymerase from *Ectocarpus siliculosus* virus 1. In some embodiments, this polymerase can have the following amino acid sequence:

```
                                                              (SEQ ID NO: 26)
   1 melylhdird nsgsfqnptm qlfameedgt nvfvsvknfk tylyvgfdld isedsvrsny 61 lekfkqekwe rnvykmsvvk rkrligfsng dlfpyilmef tgtisfyivr khlhelcger 121 dpgpntfvdl nkypgmcvye sksvdsilkf fhasgvrpss yfrmenyvrv adkarkthca 181 kefivdfvnv rpvgeevvdr kpppmticsy dletsglntn edyifqasmi fsrlgdpcpd 241 segsatghav dsytdgvvic vgdtesvdgt pllivenelq lldkfreilv ergcnilcgy 301 ntfkfdsafl ykraerygfd gfkklsfikd lacdlevktl qsaalgknel kqiiipgrve 361 idlfmvmrrs qklssyklna vcdkffggkk ddvtyadilq actskdpkkl gviakycyqd 421 sglvlklldk ikevydatem aklctvplty ivgrgqqikc mslilnrihg eyvcnyaaak 481 kkmaadgkqv lnegykgasv idakkgfyek dpivtmdfas lypsimrlkq lcyttivrdv 541 kyrgiegvny edhqisdgvs vtfahrpgsr silceleeml geerkatkkl mksekdpfay 601 slldskqkaq kvtmnsiygf tgtvnngmlp lveiaaavts tgrdmikrtk eyaekehgcn 661 viygdtdsvm vifpehrnie nlgdkmrycf dmgtkvskei semfghpill efeniyfkyl 721 lvskkryagl swetvegppt mtmkglvtvr rdnapfvgrc aseaihmlmd vdvtdgrgav 781 kkhltetllr lergqisied ltirkelkqw vyktpsphat lalkilertk eqavfrefik 841 payetiggyd dsllssvwtk mtnlksylsv rakreiamsd mvesirgdtt spfkaeayav 901 valrqlyddv hsvlvgesfa rvvglvmagi gdvhklgery mafvrynivd wdpptlgeri 961 pyvittgkgd issraedprm vnvgrcrpdf lyyidhqlrn pmvdllqhvi espsslfves 1021 qrrmsnlnhg rkeittffkk rkvteg
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of *Ectocarpus siliculosus* virus 1 DNA polymerase that lacks 3' to 5' exonuclease activity.

In some embodiments, the biomolecule comprises the amino acid sequence of SEQ ID NO: 14 (HP1), further comprising a mutation of one, some or all of the cysteines occurring at amino acid positions 47, 315, 473 and/or 555 to any other amino acid. In some embodiments, the cysteine is replaced with a serine or alanine residue. In some embodiments, the cysteines at amino acid positions 47, 315 and 555 are mutated to another residue, e.g., alanine or serine, and the cysteine at position 473 is not mutated and can serve as a site for covalent attachment of a label.

In some embodiments, the biomolecule comprises the amino acid sequence of SEQ ID NO: 14 (HP1) and further comprises the mutation Q380A:

```
                                           (SEQ ID NO: 27)
         10         20         30         40         50         60
MNHLVHHHHH HIEGRHMELG TLEGSMKHMP RKMYSCAFET TTKVEDCRVW AYGYMNIEDH 70         80         90        100        110        120
SEYKIGNSLD EFMAWVLKVQ ADLYFHNLKF AGAFIINWLE RNGFKWSADG LPNTYNTIIS 130        140        150        160        170        180
RMGQWYMIDI CLGYKGKRKI HTVIYDSLKK LPFPVKKIAK DFKLTVLKGD IDYHKERPVG 190        200        210        220        230        240
YKITPEEYAY IKNDIQIIAE ALLIQFKQGL DRMTAGSDSL KGFKDIITTK KFKKVFPTLS 250        260        270        280        290        300
LGLDKEVRYA YRGGFTWLND RFKEKEIGEG MVFDVNSLYP AQMYSRLLPY GEPIVFEGKY 310        320        330        340        350        360
VWDEDYPLHI QHIRCEFELK EGYIPTIQIK RSRFYKGNEY LKSSGGEIAD LWLSNVDLEL 370        380        390        400        410        420
MKEHYDLYNV EYISGLKFKA TTGLFKDFID KWTYIKTTSE GAIKALAKLM LNSLYGKFAS 430        440        450        460        470        480
NPDVTGKVPY LKENGALGFR LGEEETKDPV YTPMGVFITA WARYTTITAA QACYDRIIYC 490        500        510        520        530        540
DTDSIHLTGT EIPDVIKDIV DPKKLGYWAH ESTFKRAKYL RQKTYIQDIY MKEVDGKLVE 550        560        570        580        590        600
GSPDDYTDIK FSVKCAGMTD KIKKEVTFEN FKVGFSRKMK PKPVQVPGGV VLVDDTFTIK
```

This fusion polymerase having the amino acid sequence of SEQ ID NO: 27 is hereinafter referred to as HP1 Q380A. In some embodiments, the biomolecule comprises a fusion protein having an amino acid sequence that is at least 70%, 80%, 85%, 90%, 95%, 99% or 100% identical to the amino acid sequence of SEQ ID NO: 27.

In some embodiments, the biomolecule comprises the amino acid sequence of SEQ ID NO: 28, below, which is the HP1 sequence further comprising the mutation S388G:

```
                                           (SEQ ID NO: 28)
         10         20         30         40         50         60
MNHLVHHHHH HIEGRHMELG TLEGSMKHMP RKMYSCAFET TTKVEDCRVW AYGYMNIEDH 70         80         90        100        110        120
SEYKIGNSLD EFMAWVLKVQ ADLYFHNLKF AGAFIINWLE RNGFKWSADG LPNTYNTIIS 130        140        150        160        170        180
RMGQWYMIDI CLGYKGKRKI HTVIYDSLKK LPFPVKKIAK DFKLTVLKGD IDYHKERPVG 190        200        210        220        230        240
YKITPEEYAY IKNDIQIIAE ALLIQFKQGL DRMTAGSDSL KGFKDIITTK KFKKVFPTLS 250        260        270        280        290        300
LGLDKEVRYA YRGGFTWLND RFKEKEIGEG MVFDVNSLYP AQMYSRLLPY GEPIVFEGKY 310        320        330        340        350        360
VWDEDYPLHI QHIRCEFELK EGYIPTIQIK RSRFYKGNEY LKSSGGEIAD LWLSNVDLEL 370        380        390        400        410        420
MKEHYDLYNV EYISGLKFKA TTGLFKDFID KWTYIKTTSE GAIKQLAKLM LNGLYGKFAS 430        440        450        460        470        480
NPDVTGKVPY LKENGALGFR LGEEETKDPV YTPMGVFITA WARYTTITAA QACYDRIIYC 490        500        510        520        530        540
DTDSIHLTGT EIPDVIKDIV DPKKLGYWAH ESTFKRAKYL RQKTYIQDIY MKEVDGKLVE 550        560        570        580        590        600
GSPDDYTDIK FSVKCAGMTD KIKKEVTFEN FKVGFSRKMK PKPVQVPGGV VLVDDTFTIK
```

This fusion polymerase of amino acid sequence of SEQ ID NO: 28 is herein referred to as HP1 S388G. In some embodiments, the biomolecule comprises a fusion protein having an amino acid sequence that is at least 70%, 80%, 85%, 90%, 95%, 99% or 100% identical to the amino acid sequence of SEQ ID NO: 28 (HP1 S388G).

In some embodiments, the biomolecule is a His-tagged version of a polymerase isolated from the phage RB69. The His-tag can be fused to the N-terminus, the C-terminus or any other suitable position of the RB69 polymerase. Optionally, the His-tag can be separated from the amino acid residues of the protein by a linker, typically a peptide linker. In some embodiments, the fusion protein comprises an amino acid sequence that is at least 70%, 80%, 85%, 90%, 95%, 99% or 100% identical to the following amino acid sequence:

```
                                                    (SEQ ID NO: 29)
         10         20         30         40         50         60
MHHHHHHKHM KEFYLTVEQI GDSIFERYID SNGRERTREV EYKPSLFAHC PESQATKYFD 70         80         90        100        110        120
IYGKPCTRKL FANMRDASQW IKRMEDIGLE ALGMDDFKLA YLSDTYNYEI KYDHTKIRVA 130        140        150        160        170        180
NFDIEVTSPD GFPEPSQAKH PIDAITHYDS IDDRFYVFDL LNSPYGNVEE WSIEIAAKLQ 190        200        210        220        230        240
EQGGDEVPSE IIDKIIYMPF DNEKELLMEY LNFWQQKTPV ILTGWNVESF DIPYVYNRIK 250        260        270        280        290        300
NIFGESTAKR LSPHRKTRVK VIENMYGSRE IITLFGISVL DYIDLYKKFS FTNQPSYSLD 310        320        330        340        350        360
YISEFELNVG KLKYDGPISK LRESNHQRYI SYNIIDVYRV LQIDAKRQFI NLSLDMGYYA 370        380        390        400        410        420
KIQIQSVFSP IKTWDAIIFN SLKEQNKVIP QGRSHPVQPY PGAFVKEPIP NRYKYVMSFD 430        440        450        460        470        480
LTSLYPSIIR QVNISPETIA GTFKVAPLHD YINAVAERPS DVYSCSPNGM MYYKDRDGVV 490        500        510        520        530        540
PTEITKVFNQ RKEHKGYMLA AQRNGEIIKE ALHNPNLSVD EPLDVDYRFD FSDEIKEKIK 550        560        570        580        590        600
KLSAKSLNEM LFRAQRTEVA GMTAQINRKL LINSLYGALG NVWFRYYDLR NATAITTFGQ 610        620        630        640        650        660
MALQWIERKV NEYLNEVCGT EGEAFVLYGD TDSIYVSADK IIDKVGESKF RDTNHWVDFL 670        680        690        700        710        720
DKFARERMEP AIDRGFREMC EYMNNKQHLM FMDREAIAGP PLGSKGIGGF WTGKKRYALN 730        740        750        760        770        780
VWDMEGTRYA EPKLKIMGLE TQKSSTPKAV QKALKECIRR MLQEGEESLQ EYFKEFEKEF 790        800        810        820        830        840
RQLNYISIAS VSSANNIAKY DVGGFPGPKC PFHIRGILTY NRAIKGNIDA PQVVEGEKVY 850        860        870        880        890        900
VLPLREGNPF GDKCIAWPSG TEITDLIKDD VLHWMDYTVL LEKTFIKPLE GFTSAAKLDY

910
EKKASLFDMF DF
```

In some embodiments, the biomolecule is a His-tagged version of a polymerase isolated from the GA-1 phage. The His-tag can be fused to the N-terminus, the C-terminus or any other suitable position of the GA-1 polymerase. Optionally, the His-tag can be separated from the amino acid residues of the protein by a linker. In some embodiments, the linker comprises the F-linker sequence LLGGGGSGGGGSAAAGSAA (SEQ ID NO: 5). In some embodiments, the fusion protein comprises an amino acid sequence that is at least 70%, 80%, 85%, 90%, 95%, 99% or 100% identical to the following amino acid sequence:

```
                                                    (SEQ ID NO: 30)
         10         20         30         40         50         60
MHHHHHHKHM ARSVYVCDFE TTTDPEDCRL WAWGWMDIYN TDKWSYGEDI DSFMEWALNS 70         80         90        100        110        120
NSDIYFHNLK FDGSFILPWW LRNGYVHTEE DRTNTPKEFT TTISGMGQWY AVDVCINTRG
```

```
               130        140        150        160        170        180
         KNKNHVVFYD SLKKLPFKVE QIAKGFGLPV LKGDIDYKKY RPVGYVMDDN EIEYLKHDLL 190        200        210        220        230        240
         IVALALRSMF DNDFTSMTVG SDALNTYKEM LGVKQWEKYF PVLSLKVNSE IRKAYKGGFT 250        260        270        280        290        300
         WVNPKYQGET VYGGMVFDVN SMYPAMMKNK LLPYGEPVMF KGEYKKNVEY PLYIQQVRCF 310        320        330        340        350        360
         FELKKDKIPC IQIKGNARFG QNEYLSTSGD EYVDLYVTNV DWELIKKHYD IFEEEFIGGF 370        380        390        400        410        420
         MFKGFIGFFD EYIDRFMEIK NSPDSSAEQS LQAKLMLNSL YGKFATNPDI TGKVPYLDEN 430        440        450        460        470        480
         GVLKFRKGEL KERDPVYTPM GCFITAYARE NILSNAQKLY PRFIYADTDS IHVEGLGEVD 490        500        510        520        530        540
         AIKDVIDPKK LGYWDHEATF QRARYVRQKT YFIETTWKEN DKGKLVVCEP QDATKVKPKI 550        560        570        580
         ACAGMSDAIK ERIRFNEFKI GYSTHGSLKP KNVLGGVVLM DYPFAIK
```

In some embodiments, the biomolecule is a His-tagged version of a polymerase isolated from the B103 phage. The His-tag can be fused to the N-terminus, the C-terminus or any other suitable position of the B103 polymerase. Optionally, the His-tag can be separated from the amino acid residues of the protein by a linker. In some embodiments, the linker comprises the amino acid sequence LLGGGGSGGGGSAAAGSAA (SEQ ID NO: 5). In some embodiments, the fusion protein comprises an amino acid sequence that is at least 70%, 80%, 85%, 90%, 95%, 99% or 100% identical to the following amino acid sequence:

```
                                                              (SEQ ID NO: 31)
                10         20         30         40         50         60
         MHHHHHHKHM PRKMFSCDFE TTTKLDDCRV WAYGYMEIGN LDNYKIGNSL DEFMQWVMEI 70         80         90        100        110        120
         QADLYFHNLK FDGAFIVNWL EHHGFKWSNE GLPNTYNTII SKMGQWYMID ICFGYKGKRK 130        140        150        160        170        180
         LHTVIYDSLK KLPFPVKKIA KDFQLPLLKG DIDYHAERPV GHEITPEEYE YIKNDIEIIA 190        200        210        220        230        240
         RALDIQFKQG LDRMTAGSDS LKGFKDILST KKFNKVFPKL SLPMDKEIRR AYRGGFTWLN 250        260        270        280        290        300
         DKYKEKEIGE GMVFDVNSLY PSQMYSRPLP YGAPIVFQGK YEKDEQYPLY IQRIRFEFEL 310        320        330        340        350        360
         KEGYIPTIQI KKNPFFKGNE YLKNSGAEPV ELYLTNVDLE LIQEHYEMYN VEYIDGFKFR 370        380        390        400        410        420
         EKTGLFKEFI DKWTYVKTHE KGAKKQLAKL MFDSLYGKFA SNPDVTGKVP YLKEDGSLGF 430        440        450        460        470        480
         RVGDEEYKDP VYTPMGVFIT AWARFTTITA AQACYDRIIY CDTDSIHLTG TEVPEIIKDI 490        500        510        520        530        540
         VDPKKLGYWA HESTFKRAKY LRQKTYIQDI YAKEVDGKLI ECSPDEATTT KFSVKCAGMT 550        560                   570                    580
         DTIKKKVTFD NFRVGFSSTG KPKPVQVNGG VVLVDSVFTI K
```

In some embodiments, the polymerase of the labeled polymerase conjugate is derived from a DNA polymerase of the Phi-29-like phage B103. The genome of B103, including a gene encoding a B103 DNA polymerase, has been sequenced. See, e.g., Pecenkova et al., "Bacteriophage B103: complete DNA sequence of its genome and relationship to other *Bacillus* phages" Gene 199:157-163 (1999). The DNA polymerase of B103 is homologous to the DNA polymerase of Phi-29 and of other Phi-29-like phages. Collectively, these polymerases share several highly conserved regions. See, e.g., Meijer et al., "Phi-29 family of phages" Microbiol. & Mol. Biol. Revs. 65(2):261-287 (2001). These conserved regions are typically characterized by several conserved amino acid motifs. See, e.g., Blanco et al., Gene 100:27-38 (1991); Blasco et al., "Φ29 DNA polymerase Active Site" J. Biol. Chem. 268:16763-16770

(1993) (describing regions of sequence homology and mutational analysis of consensus regions of Phi-29 and Phi-29-like DNA polymerases); Berman et al., "Structures of phi29 DNA polymerase complexed with substrate: the mechanism of translocation in B-family polymerases", EMBO J., 26:3494-3505 (2007). Site-directed mutagenesis indicates that these three regions can form an evolutionarily conserved polymerase active site.

In some embodiments, the polymerase of the labeled polymerase conjugate is derived from a B103 polymerase comprising the amino acid sequence of SEQ ID NO: 32 as follows:

```
                                                              (SEQ ID NO: 32)
  1 mprkmfscdf etttklddcr vwaygymeig nldnykigns ldefmqwvme iqadlyfhnl 61 kfdgafivnw lehhgfkwsn eglpntynti iskmgqwymi dicfgykgkr klhtviydsl 121 kklpfpvkki akdfqlpllk gdidyhaerp vgheitpeey eyikndieii araldiqfkq 181 gldrmtagsd slkgfkdils tkkfnkvfpk lslpmdkeir rayrggftwl ndkykekeig 241 egmvfdvnsl ypsqmysrpl pygapivfqg kyekdeqypl yiqrirfefe lkegyiptiq 301 ikknpffkgn eylknsgaep velyltnvdl eliqehyemy nveyidgfkf rektglfkef 361 idkwtyvkth ekgakkqlak lmfdslygkf asnpdvtgkv pylkedgslg frvgdeeykd 421 pvytpmgvfi tawarfttit aaqacydrii ycdtdsihlt gtevpeiikd ivdpkklgyw 481 ahestfkrak ylrqktyiqd iyakevdgkl iecspdeatt tkfsvkcagm tdtikkkvtf 541 dnfrvgfsst gkpkpvqvng gvvlvdsvft ik
```

In some embodiments, the polymerase of the labeled polymerase conjugate is a variant of a B103 polymerase, wherein the modified polymerase comprises an amino acid sequence that is at least 80%, 85%, 90%, 95%, 97%, 98% or 99% identical to the amino acid sequence of SEQ ID NO: 32, or any biologically active fragment thereof.

In some embodiments, the polymerase of the labeled polymerase conjugate is homologous to a polymerase of one or more of the following organisms: B103, Phi-29, GA-1, PZA, Phi-15, BS32, M2Y, Nf, G1, Cp-1, PRD1, PZE, SF5, Cp-5, Cp-7, PR4, PR5, PR722, or L17. See, e.g., Meijer et al., "Phi-29 family of phages," Microbiol. & Mol. Biol. Revs. 65(2):261-287 (2001).

In some embodiments, the polymerase of the labeled polymerase conjugate comprises a B103 polymerase having the amino acid sequence of SEQ ID NO: 32 and further comprises one or more mutations in the amino acid sequence of SEQ ID NO: 32. In some embodiments, the one or more mutations can include, for example, substitution, chemical modification, addition, deletion and/or inversion of one or more amino acid residues, or any combination of the foregoing.

The mutant B103 polymerase can optionally further comprise comprise the amino acid sequence of any of the polymerases disclosed in U.S. Ser. No. 61/242,771, filed on Sep. 15, 2009; U.S. Ser. No. 61/293,618, filed on Jan. 8, 2010 or U.S. Ser. No. 12/748,359 titled "Polymerase Compositions & Methods", filed concurrently herewith.

In some embodiments, the polymerase of the labeled polymerase conjugate comprises an amino acid modification at position 383, at position 384, or at both positions 383 and 384, wherein the numbering is relative to a B103 polymerase having the amino acid sequence of SEQ ID NO: 32. The modification can include, for example, one or more amino acid substitutions, additions, deletions or chemical modifications.

In some embodiments, the polymerase of the labeled polymerase conjugate is a variant of a B103 polymerase comprising the amino acid sequence of SEQ ID NO: 32, wherein the modified polymerase comprises an amino acid sequence that is at least 80%, 85%, 90%, 95%, 97%, 98% or 99% identical to the amino acid sequence of SEQ ID NO: 32, or any biologically active fragment thereof, wherein the amino acid at position 383 is not phenylalanine (F), where the numbering is relative to the amino acid sequence of SEQ ID NO: 32.

In some embodiments, the polymerase of the labeled polymerase conjugate comprises the amino acid sequence of SEQ ID NO: 32, and further comprises an amino acid substitution at position 383, wherein the numbering is relative to a B103 polymerase having the amino acid sequence of SEQ ID NO: 32. In some embodiments, the modified polymerase is a variant of B103 polymerase that comprises an amino acid sequence that is at least 80%, 85%, 90%, 95%, 97%, 98% or 99% identical to the amino acid sequence of SEQ ID NO: 32, or any biologically active fragment thereof, wherein the modified polymerase further comprises the amino acid mutation F383L.

In some embodiments, the polymerase of the labeled polymerase conjugate is a variant of a B103 polymerase that comprises an amino acid sequence that is at least 80%, 85%, 90%, 95%, 97%, 98% or 99% identical to the amino acid sequence of SEQ ID NO: 32, or any biologically active fragment thereof, wherein the amino acid at position 384 is not aspartic acid (D), where the numbering is relative to the amino acid sequence of SEQ ID NO: 32.

In some embodiments, the polymerase of the labeled polymerase conjugate comprises the amino acid sequence of SEQ ID NO: 32 and further comprises an amino acid substitution at position 384, wherein the numbering is relative to a B103 polymerase having the amino acid sequence of SEQ ID NO: 32. In some embodiments, the polymerase is a variant of B103 polymerase that comprises an amino acid sequence that is at least 80%, 85%, 90%, 95%, 97%, 98% or 99% identical to the amino acid sequence of SEQ ID NO: 32, or any biologically active fragment thereof, wherein the modified polymerase further comprises the amino acid mutation D384N.

In some embodiments, the polymerase of the labeled polymerase conjugate is a variant of B103 polymerase, or any biologically active fragment thereof, having the amino acid sequence of SEQ ID NO: 32, wherein the variant further comprises amino acid substitutions at positions 383 and 384, wherein the numbering is relative to the amino acid sequence of SEQ ID NO: 32. In some embodiments, the polymerase comprises the amino acid sequence of SEQ ID NO: 32 and further comprises the amino acid substitutions F383L and D384N, wherein the numbering is relative to the amino acid sequence of SEQ ID NO: 32. The amino acid sequence of this polymerase can be represented as follows:

```
                                                             (SEQ ID NO: 33)
    1 mprkmfscdf etttklddcr vwaygymeig nldnykigns ldefmqwvme iqadlyfhnl 61 kfdgafivnw lehhgfkwsn eglpntynti iskmgqwymi dicfgykgkr klhtviydsl 121 kklpfpvkki akdfqlpllk gdidyhaerp vgheitpeey eyikndieii araldiqfkq 181 gldrmtagsd slkgfkdils tkkfnkvfpk lslpmdkeir rayrggftwl ndkykekeig 241 egmvfdvnsl ypsqmysrpl pygapivfqg kyekdeqypl yiqrirfefe lkegyiptiq 301 ikknpffkgn eylknsgaep velyltnvdl eliqehyemy nveyidgfkf rektglfkef 361 idkwtyvkth ekgakkqlak lmlnslygkf asnpdvtgkv pylkedgslg frvgdeeykd 421 pvytpmgvfi tawarfttit aaqacydrii ycdtdsihlt gtevpeiikd ivdpkklgyw 481 ahestfkrak ylrqktyiqd iyakevdgkl iecspdeatt tkfsvkcagm tdtikkkvtf 541 dnfrvgfsst gkpkpvqvng gvvlvdsvft ik
```

In some embodiments, the polymerase of the labeled polymerase conjugate comprises an amino acid sequence that is at least 80%, 85%, 90%, 95%, 97%, 98% or 99% identical to the amino acid sequence of SEQ ID NO: 33, or any biologically active fragment thereof.

In some embodiments, the polymerase comprises an amino acid sequence that is at least 80%, 85%, 90%, 95%, 97%, 98%, 99% or 100% identical to the amino acid sequence of SEQ ID NO: 33 and further includes one or more mutations reducing the 3' to 5' exonuclease activity of the polymerase. In some embodiments, the one or more mutations reducing the 3' to 5' exonuclease activity are selected from the group consisting of: D9A, E11A, E11I, T12I, H58R, N59D, D63A, Y162F, Y162C, D166A, Q377A and S385G.

In some embodiments, the polymerase of the labeled polymerase conjugate comprises the amino acid of SEQ ID NO: 34, below:

```
                                                             (SEQ ID NO: 34)
    1 mprkmfscdf etttklddcr vwaygymeig nldnykigns ldefmqwvme iqadlyfhnl 61 kfdgafivnw lehhgfkwsn eglpntynti iskmgqwymi dicfgykgkr klhtviydsl 121 kklpfpvkki akdfqlpllk gdidyhaerp vgheitpeey eyiknaieii araldiqfkq 181 gldrmtagsd slkgfkdils tkkfnkvfpk lslpmdkeir rayrggftwl ndkykekeig 241 egmvfdvnsl ypsqmysrpl pygapivfqg kyekdeqypl yiqrirfefe lkegyiptiq 301 ikknpffkgn eylknsgaep velyltnvdl eliqehyemy nveyidgfkf rektglfkef 361 idkwtyvkth ekgakkqlak lmlnslygkf asnpdvtgkv pylkedgslg frvgdeeykd 421 pvytpmgvfi tawarfttit aaqacydrii ycdtdsihlt gtevpeiikd ivdpkklgyw 481 ahestfkrak ylrqktyiqd iyakevdgkl iecspdeatt tkfsvkcagm tdtikkkvtf 541 dnfrvgfsst gkpkpvqvng gvvlvdsvft ik
```

In some embodiments, the polymerase of the labeled polymerase conjugate comprises an amino acid sequence that is at least 70%, 75%, 80%, 85%, 90%, 95%, 97%, 98% or 99% identical to the amino acid sequence of SEQ ID NO: 34, or any biologically active fragment thereof. Typically, the polymerase of SEQ ID NO: 34 will exhibit reduced exonuclease activity relative to a reference polymerase comprising the amino acid sequence of SEQ ID NO: 3, SEQ ID NO: 32 or SEQ ID NO: 33.

In some embodiments, the polymerase of the labeled polymerase conjugate is a variant of a B103 polymerase comprising the amino acid sequence of SEQ ID NO: 32, SEQ ID NO: 33 or SEQ ID NO: 34, wherein the variant further comprises one, two, three or more modifications at amino acid positions 2, 9, 58, 59, 63, 129, 166, 246, 247, 339, 370, 371, 372, 373, 374, 375, 376, 377, 380, 383, 384, 385, 455, 507 and 509, or any combinations thereof, wherein the numbering is relative to the amino acid sequence of SEQ ID NO: 33.

In some embodiments, the amino acid sequence of the polymerase of the labeled polymerase conjugate is fused to a peptide sequence that encodes a stretch of amino acid acids capable of functioning as a peptide linker to facilitate the formation of a linkage between the polymerase and another reactive moiety. The reactive moiety can in some embodiments be a label, or another attachment moiety that is itself linked to one or more labels. This peptide linker sequence can be fused to the N-terminus, the C-terminus or any suitable position between the N-terminus and the C-terminus of the polymerase.

In some embodiments, the polymerase is derived from a Phi-29-like polymerase and comprises an amino acid sequence that is at least 70%, 80%, 85%, 90%, 95%, 97%, 98%, 99% or 100% identical to the amino acid sequence of SEQ ID NO: 33 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 33. In some embodiments, the modifications can include deletions, additions and substitutions. The substitutions can be conservative or non-conservative substitutions. In some embodiments, the polymerase comprises an amino acid sequence that is at least 80%, 85%, 90%, 95%, 97%, 98%, 99% or 100% identical to the amino acid sequence of SEQ ID NO: 33 and further includes one or more mutations reducing the 3' to 5' exonuclease activity of the polymerase. In some embodiments, the one or more mutations reducing the 3' to 5' exonuclease activity are selected from the group consisting of: D9A, E11A, E11I, T12I, H58R, N59D, D63A, Y162F, Y162C, D166A, Q377A and S385G.

In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, F383L, D384N, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 33. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 33. Optionally, this polymerase comprises the amino acid substitution H370R and/or K380R.

In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes an amino acid mutation selected from the group: H370G, H370T, H370S, H370K, H370R, H370A, H370Q, H370W, H370Y and H370F, wherein the numbering is relative to the amino acid sequence of SEQ ID NO: 33. Typically, this polymerase can exhibit an increased $t_{-1}$ value in the presence of the dye-labeled nucleotides relative to a reference polymerase having the amino acid sequence of SEQ ID NO: 33. In some embodiments, the $t_{-1}$ value of the polymerase is increased by at least about 105%, 110%, 125%, 150%, 175%, 200%, 250%, 500%, 750%, or 1000% relative to the reference polymerase. In some embodiments, the $t_{-1}$ value is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 33. In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes the amino acid mutation H370R, wherein the numbering is relative to the amino acid sequence of SEQ ID NO: 33.

In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes an amino acid mutation selected from the group: K380G, K380E, K380T, K380S, K380R, K380A, K380Q, K380W, K380Y and K380F, wherein the numbering is relative to the amino acid sequence of SEQ ID NO: 33. Typically, this polymerase can exhibit an increased $t_{pol}$ value in the presence of the dye-labeled nucleotides relative to a reference polymerase having the amino acid sequence of SEQ ID NO: 33. In some embodiments, the $t_{pol}$ value of the polymerase is increased by at least about 105%, 110%, 125%, 150%, 175%, 200%, 250%, 500%, 750%, or 1000% relative to the reference polymerase. In some embodiments, the $t_{pol}$ value is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 33. In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes the amino acid mutation K380R, wherein the numbering is relative to the amino acid sequence of SEQ ID NO: 33.

In some embodiments, the polymerase comprises an amino acid sequence that is at least 70%, 80%, 85%, 90%, 95%, 97%, 98%, 99% or 100% identical to the amino acid sequence of SEQ ID NO: 3 and further includes an amino acid mutation selected from the group: T373G, T373E, T373T, T373S, T373R, T373A, K T373Q, T373W, T373Y and T373F, wherein the numbering is relative to the amino acid sequence of SEQ ID NO: 3. Typically, this polymerase can exhibit an increased $t_{-1}$ value in the presence of the dye-labeled nucleotides relative to a reference polymerase having the amino acid sequence of SEQ ID NO: 3. In some embodiments, the $t_{-1}$ value of the polymerase is increased by at least about 105%, 110%, 125%, 150%, 175%, 200%, 250%, 500%, 750%, or 1000% relative to the reference polymerase. In some embodiments, the $t_{-1}$ value is increased in the presence of the dye-labeled nucleotide AF647-C6-dG6P. Optionally, the polymerase can further include one or more mutations reducing 3' to 5' exonuclease activity selected from the group consisting of: D12A, E14I, E14A, T15I, N62D, D66A, Y165F, Y165C, and D169A, wherein the numbering is relative to the amino acid sequence of SEQ ID NO: 3. In some embodiments, the polymerase comprises an amino acid sequence that is at least 70%, 80%, 85%, 90%, 95%, 97%, 98%, 99% or 100% identical to the amino acid sequence of SEQ ID NO: 3 and further includes the amino acid mutation T373R, wherein the numbering is relative to the amino acid sequence of SEQ ID NO: 3. In some embodiments, the polymerase further includes the mutations D12A and D66A.

In some embodiments, the biomolecule is derived from a M2 polymerase (also known as M2Y DNA polymerase) having the amino acid sequence of the SEQ ID NO: 35 as follows:

relative to reference polymerase having the amino acid sequence of SEQ ID NO: 35.

In some embodiments, the polymerase comprises an amino acid sequence that is at least 85%, 90%, 95%, 97%, 98% or 99% identical to the amino acid sequence of SEQ ID NO: 35 and further comprises one, two, three or more amino acid mutations selected from the group consisting of: D9A, E11A, E11I, T121, H58R, N59D, D63A, Y162F, Y162C, D166A, Q377A and S385G, wherein the numbering is relative to the amino acid sequence of SEQ ID NO: 32. In some embodiments, the polymerase comprises any one, two, three, four, five or all of these mutations. In some embodiments, the polymerase comprises the amino acid substitution D166A. In some embodiments, the polymerase comprises the amino acid substitutions D9A and D63A. In some embodiments, the polymerase comprises the amino acid substitutions N59D and T121. Typically, such polymerases will exhibit reduced 3' to 5' exonuclease activity relative to reference polymerase having the amino acid sequence of SEQ ID NO: 35.

In some embodiments, the polymerase comprises an amino acid sequence that is at least 80%, 85%, 90%, 95%, 97%, 98%, 99% or 100% identical to the amino acid sequence of SEQ ID NO: 35 and further comprises an amino acid substitution at one or more positions selected from the group consisting of: 2, 73, 147, 221, 318, 339, 359, 372, 405, 503, 511, 544 and 550, wherein the numbering is relative to the amino acid sequence of SEQ ID NO: 32.

In some embodiments, the polymerase comprises an amino acid sequence that is at least 80%, 85%, 90%, 95%, 97%, 98%, 99% or 100% identical to the amino acid sequence of SEQ ID NO: 35 and further includes any one, two, three or more amino acid mutations selected from the group consisting of: S2P, Q73H, T147A, K221R, V318A, L339M, D359E, E372K, D405E, V503A, K511I, A544R and M550T, wherein the numbering is relative to the amino acid sequence of SEQ ID NO: 32.

In some embodiments, the polymerase comprises an amino acid sequence that is at least 80%, 85%, 90%, 95%,

```
                                                                  (SEQ ID NO: 35)
  1 msrkmfscdf etttklddcr vwaygymeig nldnykigns ldefmqwvme iqadlyfhnl 61 kfdgafivnw leqhgfkwsn eglpntynti iskmgqwymi dicfgykgkr klhtviydsl 121 kklpfpvvki akdfqlpllk gdidyhterp vgheitpeey eyikndieii araldiqfkq 181 gldrmtagsd slkgfkdils tkkfnkvfpk lslpmdkeir kayrggftwl ndkykekeig 241 egmvfdvnsl ypsqmysrpl pygapivfqg kyekdeqypl yiqrirfefe lkegyiptiq 301 ikknpffkgn eylknsgvep velyltnvdl eliqehyely nveyidgfkf rektglfkdf 361 idkwtyvkth eegakkqlak lmlnslygkf asnpdvtgkv pylkddgslg frvgdeeykd 421 pvytpmgvfi tawarfttit aaqacydrii ycdtdsihlt gtevpeiikd ivdpkklgyw 481 ahestfkrak ylrqktyiqd iyvkevdgkl kecspdeatt tkfsvkcagm tdtikkkvtf 541 dnfavgfssm gkpkpvqvng gvvlvdsvft ik
```

In some embodiments, the polymerase comprises an amino acid sequence that is at least 85%, 90%, 95%, 97%, 98% or 99% identical to the amino acid sequence of SEQ ID NO: 35 and further comprises an amino acid mutation at one, two, three or more amino acid positions selected from the group consisting of: 9, 11, 12, 58, 59, 63, 162, 166, 377 and 385, wherein the numbering is relative to the amino acid sequence of SEQ ID NO: 32. Typically, such a polymerase will exhibit reduced 3' to 5' exonuclease activity 97%, 98%, 99% or 100% identical to the amino acid sequence of SEQ ID NO: 35 and further includes a mutation at position 370. In some embodiments, the mutation is selected from the group consisting of: H370G, H370T, H370S, H370K, H370R, H370A, H370Q, H370W, H370Y and H370F, wherein the numbering is relative to the amino acid sequence of SEQ ID NO: 32. Optionally, this polymerase comprises the amino acid mutation H370R. Typically, this polymerase can exhibit an increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 35 and further includes a mutation at position 365, wherein the numbering is relative to the amino acid sequence of SEQ ID NO: 32. In some embodiments, the mutation is selected from the group consisting of: T365H, T365F, T365G, T365S, T365K, T365R, T365A, T365Q, T365W and T365Y, wherein the numbering is relative to the amino acid sequence of SEQ ID NO: 32. Optionally, this polymerase comprises the amino acid mutation T365F. Typically, this polymerase can exhibit an increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 35 and further includes a mutation at position 372, wherein the numbering is relative to the amino acid sequence of SEQ ID NO: 32. In some embodiments, the mutation is selected from the group consisting of: K372G, K372E, K372T, K372S, K372R, K372A, K372Q, K372W, K372Y and K372F, wherein the numbering is relative to the amino acid sequence of SEQ ID NO: 32. Optionally, this polymerase comprises the amino acid mutation K372Y. Typically, this polymerase can exhibit an increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 35 and further includes a mutation at position 481, wherein the numbering is relative to the amino acid sequence of SEQ ID NO: 32. In some embodiments, the mutation is selected from the group consisting of: A481E, A481F, A481G, A481S, A481R, A481K, A481A, A481T, A481Q, A481W and A481Y, wherein the numbering is relative to the amino acid sequence of SEQ ID NO: 32. Optionally, this polymerase comprises the amino acid mutation A481E. Typically, this polymerase can exhibit an increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 35 and further includes a mutation at position 509, wherein the numbering is relative to the amino acid sequence of SEQ ID NO: 32. In some embodiments, the mutation is selected from the group consisting of: K509E, K509F, K509G, K509S, K509R, K509K, K509A, K509T, K509Q, K509W and K509Y, wherein the numbering is relative to the amino acid sequence of SEQ ID NO: 32. Optionally, this polymerase comprises the amino acid mutation K509Y. Typically, this polymerase can exhibit an increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 70%, 80%, 85%, 90%, 95%, 97%, 98%, 99% or 100% identical to the amino acid sequence of SEQ ID NO: 35 and further includes an amino acid mutation at any one, two, three or more positions selected from the group consisting of: 9, 12, 14, 15, 58, 59, 61, 63, 98, 129, 176, 185, 186, 187, 195, 208, 246, 247, 248, 251, 252, 256, 300, 302, 310, 357, 360, 362, 365, 367, 368, 369, 370, 371, 372, 373, 374, 375, 376, 377, 378, 380, 383, 384, 385, 386, 387, 389, 390, 392, 399, 411, 419, 430, 455, 475, 477, 481, 483, 493, 494, 497, 507, 509, 511, 526, 528, 529, 531, 535, 544, 555, 567, 569 and 572, wherein the numbering is relative to the amino acid sequence of SEQ ID NO: 32. In some embodiments, the modifications can include deletions, additions and substitutions. The substitutions can be conservative or non-conservative substitutions. Optionally, this polymerase comprises the amino acid substitution H370R. In some embodiments, the polymerase further comprises one or more mutations reducing the exonuclease activity as described herein such as, for example, the amino acid substitution D166A. Typically, this polymerase can exhibit increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 70%, 80%, 85%, 90%, 95%, 97%, 98%, 99% or 100% identical to the amino acid sequence of SEQ ID NO: 35 and further comprise amino acid mutations at any one, two, three or more positions selected from the group consisting of: 2, 9, 12, 14, 15, 58, 59, 61, 63, 73, 98, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 32. In some embodiments, the modifications can include deletions, additions and substitutions. The substitutions can be conservative or non-conservative substitutions. Optionally, this polymerase comprises the amino acid substitution H370R. In some embodiments, the polymerase further comprises one or more mutations reducing the exonuclease activity as described herein such as, for example, the amino acid substitution D166A. Typically, this polymerase can exhibit increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 35 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 32. Typically, this polymerase can exhibit an increased branching ratio and/or increased $t_{-1}$ value relative to a reference polymerase having the amino acid sequence of SEQ ID NO: 35. In some embodiments, the branching ratio and/or $t_{-1}$ value of the polymerase is increased by at least about 105%, 110%, 125%, 150%, 175%, 200%, 250%, 500%, 750%, or 1000% relative to the reference polymerase. In some embodiments, the branching ratio and/or $t_{-1}$ value is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T121, H58R, N59D, D63A, Y162F, Y162C, D166A, Q377A and S385G, wherein the numbering is relative to the amino acid sequence of SEQ ID NO: 32. In some embodiments, the branching ratio and/or $t_{-1}$ value is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 35 and further includes amino acid mutations at positions 372 and 509, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 35 and further includes the amino acid substitutions E372Y and K509Y, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 35 and further includes amino acid mutations at positions 365, 372 and 509, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 35 and further includes the amino acid substitutions T365F, E372Y and K509Y, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 35 and further includes amino acid mutations at positions 365, 372, 481 and 509, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 35 and further includes the amino acid substitutions T365F, E372Y, A481E and K509Y, wherein the numbering is relative to the amino acid sequence of SEQ ID NO: 32. Typically, such polymerases can exhibit an increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T121, H58R, N59D, D63A, Y162F, Y162C, D166A, Q377A and S385G, wherein the numbering is relative to the amino acid sequence of SEQ ID NO: 32.

In some embodiments, the polymerase comprises an amino acid sequence that is at least 70%, 80%, 85%, 90%, 95%, 97%, 98%, 99% or 100% identical to the amino acid sequence of SEQ ID NO: 35 and further comprises the amino acid mutation H370R. Optionally, the polymerase can further comprise any one, two, three or more amino acid mutations selected from the group consisting of: S2P, Q73H, R107K, T147A, K221R, V318A, L339M, D359E, E372K, D405E, V503A, K511I, A544R, M550T, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 32. Typically, this polymerase can exhibit increased branching ratio and/or increased $t_{-1}$ value and/or $t_{-1}$ increased $t_{pol}$ value relative to a reference polymerase having the amino acid sequence of SEQ ID NO: 35. In some embodiments, the branching ratio and/or $t_{-1}$ value and/or $t_{pol}$ value is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T121, H58R, N59D, D63A, Y162F, Y162C, D166A, Q377A and S385G, wherein the numbering is relative to the amino acid sequence of SEQ ID NO: 32.

In some embodiments, the polymerase comprises an amino acid sequence that is at least 70%, 80%, 85%, 90%, 95%, 97%, 98%, 99% or 100% identical to the amino acid sequence of SEQ ID NO: 35 and further includes the amino acid mutation H370R, wherein the numbering is relative to the amino acid sequence of SEQ ID NO: 32. In some embodiments, the polymerase comprises an amino acid sequence that is at least 70%, 80%, 85%, 90%, 95%, 97%, 98%, 99% or 100% identical to the amino acid sequence of SEQ ID NO: 35 and further comprises any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 32. Optionally, the polymerase can further comprise one, two or three amino acid mutations selected from the group: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 32. Typically, this polymerase can exhibit increase branching ratio in the presence of the dye-labeled nucleotide AF647-C6-dG6P relative to a reference polymerase having the amino acid sequence of SEQ ID NO: 35. Optionally, the polymerase can further include one or more mutations reducing 3' to 5' exonuclease activity selected from the group consisting of: D9A, E11A, E11I, T121, H58R, N59D, D63A, Y162F, Y162C, D166A, Q377A and S385G, wherein the numbering is relative to the amino acid sequence of SEQ ID NO: 32.

In some embodiments, the polymerase comprises an amino acid sequence that is at least 70%, 80%, 85%, 90%, 95%, 97%, 98%, 99% or 100% identical to the amino acid sequence of SEQ ID NO: 35 and further includes an amino acid mutation selected from the group: H370G, H370T, H370S, H370K, H370R, H370A, H370Q, H370W, H370Y and H370F, wherein the numbering is relative to the amino acid sequence of SEQ ID NO: 33. Typically, this polymerase can exhibit an increase $t_{-1}$ value in the presence of the dye-labeled nucleotides relative to a reference polymerase having the amino acid sequence of SEQ ID NO: 35. In some embodiments, the $t_{-1}$ value of the polymerase is increased by at least about 105%, 110%, 125%, 150%, 175%, 200%, 250%, 500%, 750%, or 1000% relative to the reference polymerase. Optionally, the polymerase can further include one or more mutations reducing 3' to 5' exonuclease activity selected from the group consisting of: D9A, E11A, E11I, T121, H58R, N59D, D63A, Y162F, Y162C, D166A, Q377A and S385G, wherein the numbering is relative to the amino acid sequence of SEQ ID NO: 33. Optionally, the polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 32. In some embodiments, the $t_{-1}$ value is increased in the presence of the dye-labeled nucleotide AF647-C6-dG6P. In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes the amino acid mutation H370R, wherein the numbering is relative to the amino acid sequence of SEQ ID NO: 33.

In some embodiments, the polymerase comprises an amino acid sequence that is at least 70%, 80%, 85%, 90%, 95%, 97%, 98%, 99% or 100% identical to the amino acid sequence of SEQ ID NO: 35 and further includes an amino acid mutation selected from the group: K380G, K380E, K380T, K380S, K380R, K380A, K380Q, K380W, K380Y and K380F, wherein the numbering is relative to the amino acid sequence of SEQ ID NO: 33. Typically, this polymerase can exhibit an increased $t_{pol}$ value in the presence of the dye-labeled nucleotides relative to a reference polymerase having the amino acid sequence of SEQ ID NO: 35. In some embodiments, the $t_{pol}$ value of the polymerase is increased by at least about 105%, 110%, 125%, 150%, 175%, 200%, 250%, 500%, 750%, or 1000% relative to the reference polymerase. In some embodiments, the $t_{pol}$ value is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T121, H58R, N59D, D63A, Y162F, Y162C, D166A, Q377A and S385G, wherein the numbering is relative to the amino acid sequence of SEQ ID NO: 33. Optionally, the polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 33. In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes the amino acid mutation K380R, wherein the numbering is relative to the amino acid sequence of SEQ ID NO: 33.

In some embodiments, the polymerase is derived from a bacteriophage Nf polymerase having the amino acid sequence of the SEQ ID NO: 36 as follows:

```
                                                          (SEQ ID NO: 36)
  1 msrkmfscdf etttklddcr vwaygymeig nldnykigns ldefmqwvme iqadlyfhnl 61 kfdgafivnw leqhgfkwsn eglpntynti iskmgqwymi dicfgyrgkr klhtviydsl 121 kklpfpvkki akdfqlpllk gdidyhterp vgheitpeey eyikndieii araldiqfkq 181 gldrmtagsd slkgfkdils tkkfnkvfpk lslpmdkeir kayrggftwl ndkykekeig 241 egmvfdvnsl ypsqmysrpl pygapivfqg kyekdeqypl yiqrirfefe lkegyiptiq 301 ikknpffkgn eylknsgvep velyltnvdl eliqehyely nveyidgfkf rektglfkdf 361 idkwtyvkth eegakkqlak lmlnslygkf asnpdvtgkv pylkddgslg frvgdeeykd 421 pvytpmgvfi tawarfttit aaqacydrii ycdtdsihlt gtevpeiikd ivdpkklgyw 481 ahestfkrak ylrqktyiqd iyvkevdgkl kecspdeatt tkfsvkcagm tdtikkkvtf 541 dnfavgfssm gkpkpvqvng gvvlvdsvft ik
```

In some embodiments, the polymerase can comprise an amino acid sequence that is at least 85%, 90%, 95%, 97%, 98% or 99% or 100% identical to the amino acid of SEQ ID NO: 36.

In some embodiments, the polymerase comprises an amino acid sequence that is at least 85%, 90%, 95%, 97%, 98% or 99% identical to the amino acid sequence of SEQ ID NO: 36 and further comprises an amino acid mutation at one, two, three or more amino acid positions selected from the group consisting of: 9, 11, 12, 58, 59, 63, 162, 162, 166, 377 and 385, wherein the numbering is relative to the amino acid sequence of SEQ ID NO: 32. Typically, such a polymerase will exhibit reduced 3' to 5' exonuclease activity relative to reference polymerase having the amino acid sequence of SEQ ID NO: 36.

In some embodiments, the polymerase comprises an amino acid sequence that is at least 85%, 90%, 95%, 97%, 98% or 99% identical to the amino acid sequence of SEQ ID NO: 36 and further comprises one, two, three or more amino acid mutations selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 32. In some embodiments, the polymerase comprises any one, two, three, four, five or all of these mutations. In some embodiments, the polymerase comprises the amino acid substitution D166A. In some embodiments, the polymerase comprises the amino acid substitutions D9A and D63A. In some embodiments, the polymerase comprises the amino acid substitutions N59D and T12I. Typically, such polymerases will exhibit reduced 3' to 5' exonuclease activity relative to reference polymerase having the amino acid sequence of SEQ ID NO: 36.

In some embodiments, the polymerase comprises an amino acid sequence that is at least 80%, 85%, 90%, 95%, 97%, 98%, 99% or 100% identical to the amino acid sequence of SEQ ID NO: 36 and further comprises an amino acid substitution at one or more positions selected from the group consisting of: 2, 73, 107, 147, 221, 318, 339, 359, 372, 405, 503, 511, 544 and 550, wherein the numbering is relative to the amino acid sequence of SEQ ID NO: 32.

In some embodiments, the polymerase comprises an amino acid sequence that is at least 80%, 85%, 90%, 95%, 97%, 98%, 99% or 100% identical to the amino acid sequence of SEQ ID NO: 36 and further includes a mutation at position 370. In some embodiments, the mutation is selected from the group consisting of: H370G, H370T, H370S, H370K, H370R, H370A, H370Q, H370W, H370Y and H370F, wherein the numbering is relative to the amino acid sequence of SEQ ID NO: 32. Optionally, this polymerase comprises the amino acid mutation H370R. Typically, this polymerase can exhibit an increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes a mutation at position 365, wherein the numbering is relative to the amino acid sequence of SEQ ID NO: 32. In some embodiments, the mutation is selected from the group consisting of: T365H, T365F, T365G, T365S, T365K, T365R, T365A, T365Q, T365W and T365Y, wherein the numbering is relative to the amino acid sequence of SEQ ID NO: 32. Optionally, this polymerase comprises the amino acid mutation T365F. Typically, this polymerase can exhibit an increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes a mutation at position 372, wherein the numbering is relative to the amino acid sequence of SEQ ID NO: 32. In some embodiments, the mutation is selected from the group consisting of: K372G, K372E, K372T, K372S, K372R, K372A, K372Q, K372W, K372Y and K372F, wherein the numbering is relative to the amino acid sequence of SEQ ID NO: 32. Optionally, this polymerase comprises the amino acid mutation K372Y. Typically, this polymerase can exhibit an increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes a mutation at position 481, wherein the numbering is relative to the amino acid sequence of SEQ ID NO: 32. In some embodiments, the mutation is selected from the group consisting of: A481E, A481F, A481G, A481S, A481R, A481K, A481A, A481T, A481Q, A481W and A481Y, wherein the numbering is relative to the amino acid sequence of SEQ ID NO: 32. Optionally, this polymerase comprises the amino acid mutation A481E. Typically, this polymerase can exhibit an increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes a mutation at position 509, wherein the numbering is relative to the amino acid sequence of SEQ ID NO: 32. In some embodiments, the mutation is selected from the group consisting of: K509E, K509F, K509G, K509S, K509R, K509K, K509A, K509T, K509Q, K509W and K509Y, wherein the numbering is relative to the amino acid sequence of SEQ ID NO: 32. Optionally, this polymerase comprises the amino acid mutation K509Y. Typically, this polymerase can exhibit an increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes any one, two, three or more amino acid mutations selected from the group consisting of: S2P, Q73H, R107K, T147A, K221R, V318A, L339M, D359E, E372K, D405E, V503A, K511I, A544R and M550T, wherein the numbering is relative to the amino acid sequence of SEQ ID NO: 32.

In some embodiments, the polymerase comprises an amino acid sequence that is at least 70%, 80%, 85%, 90%, 95%, 97%, 98%, 99% or 100% identical to the amino acid sequence of SEQ ID NO: 36 and further includes an amino acid mutation at any one, two, three or more positions selected from the group consisting of: 9, 12, 14, 15, 58, 59, 61, 63, 98, 129, 176, 185, 186, 187, 195, 208, 246, 247, 248, 251, 252, 256, 300, 302, 310, 357, 360, 362, 365, 367, 368, 369, 370, 371, 372, 373, 374, 375, 376, 377, 378, 380, 383, 384, 385, 386, 387, 389, 390, 392, 399, 411, 419, 430, 455, 475, 477, 481, 483, 493, 494, 497, 507, 509, 511, 526, 528, 529, 531, 535, 544, 555, 567, 569 and 572, wherein the numbering is relative to the amino acid sequence of SEQ ID NO: 32. In some embodiments, the modifications can include deletions, additions and substitutions. The substitutions can be conservative or non-conservative substitutions. Optionally, this polymerase comprises the amino acid substitution H370R. In some embodiments, the polymerase further comprises one or more mutations reducing the exonuclease activity as described herein such as, for example, the amino acid substitution D166A. Typically, this polymerase can exhibit increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 70%, 80%, 85%, 90%, 95%, 97%, 98%, 99% or 100% identical to the amino acid sequence of SEQ ID NO: 36 and further comprise amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 32. In some embodiments, the modifications can include deletions, additions and substitutions. The substitutions can be conservative or non-conservative substitutions. Optionally, this polymerase comprises the amino acid substitution H370R. In some embodiments, the polymerase further comprises one or more mutations reducing the exonuclease activity as described herein such as, for example, the amino acid substitution D166A. Typically, this polymerase can exhibit increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D5075, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 32. In some embodiments, the polymerase comprises the amino acid mutations Typically, this polymerase can exhibit an increased branching ratio and/or increased nucleotide binding affinity relative to a reference polymerase having the amino acid sequence of SEQ ID NO: 36. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 32. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes amino acid mutations at positions 372 and 509, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 36 and further includes the amino acid substitutions E372Y and K509Y, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 36 and further includes amino acid mutations at positions 365, 372 and 509, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 36 and further includes the amino acid substitutions T365F, E372Y and K509Y, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 36 and further includes amino acid mutations at positions 365, 372, 481 and 509, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 36 and further includes the amino acid substitutions T365F, E372Y, A481E and K509Y, wherein the numbering is relative to the amino acid sequence of SEQ ID NO: 32. Typically, such polymerases can exhibit an increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 32.

In some embodiments, the polymerase comprises an amino acid sequence that is at least 70%, 80%, 85%, 90%, 95%, 97%, 98%, 99% or 100% identical to the amino acid sequence of SEQ ID NO: 36 and further comprises the amino acid mutation H370R. Optionally, the polymerase can further comprise any one, two, three or more amino acid mutations selected from the group consisting of: S2P, Q73H, R107K, T147A, K221R, V318A, L339M, D359E, E372K, D405E, V503A, K511I, A544R, M550T, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 32. Typically, this polymerase can exhibit increased branching ratio, increased $t_{-1}$ and/or increased $t_{pol}$ values relative to a reference polymerase having the amino acid sequence of SEQ ID NO: 36. In some embodiments, the branching ratio, $t_{-1}$ value and/or $t_{pol}$ value is increased in the presence of the dye-labeled nucleotide AF647-C6-dG6P.

In some embodiments, the polymerase comprises an amino acid sequence that is at least 70%, 80%, 85%, 90%, 95%, 97%, 98%, 99% or 100% identical to the amino acid sequence of SEQ ID NO: 36 and further includes the amino acid mutation H370R, wherein the numbering is relative to the amino acid sequence of SEQ ID NO: 32. In some embodiments, the polymerase comprises an amino acid sequence that is at least 70%, 80%, 85%, 90%, 95%, 97%, 98%, 99% or 100% identical to the amino acid sequence of SEQ ID NO: 36 and further comprises any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 32. Optionally, the polymerase can further comprise one, two or three amino acid mutations selected from the group: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 32. Typically, this polymerase can exhibit increase branching ratio and/or increased $t_{-1}$ value and/or increased $t_{pol}$ value relative to a reference polymerase having the amino acid sequence of SEQ ID NO: 36. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 32. In some embodiments, the branching ratio, $t_{-1}$ value and/or $t_{pol}$ value is increased in the presence of the dye-labeled nucleotide AF647-C6-dG6P.

In some embodiments, the polymerase comprises an amino acid sequence that is at least 70%, 80%, 85%, 90%, 95%, 97%, 98%, 99% or 100% identical to the amino acid sequence of SEQ ID NO: 36 and further includes an amino acid mutation selected from the group: H370G, H370T, H370S, H370K, H370R, H370A, H370Q, H370W, H370Y and H370F, wherein the numbering is relative to the amino acid sequence of SEQ ID NO: 33. Typically, this polymerase can exhibit an increase $t_{-1}$ value in the presence of the dye-labeled nucleotides relative to a reference polymerase having the amino acid sequence of SEQ ID NO: 36. In some embodiments, the $t_{-1}$ value of the polymerase is increased by at least about 105%, 110%, 125%, 150%, 175%, 200%, 250%, 500%, 750%, or 1000% relative to the reference polymerase. Optionally, the polymerase can further include one or more mutations reducing 3' to 5' exonuclease activity selected from the group consisting of: D9A, E11A, E11I, T121, H58R, N59D, D63A, Y162F, Y162C, D166A, Q377A and S385G, wherein the numbering is relative to the amino acid sequence of SEQ ID NO: 33. Optionally, the polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 33. In some embodiments, the $t_{-1}$ value is increased in the presence of the dye-labeled nucleotide AF647-C6-dG6P. In some embodiments, the polymerase comprises an amino acid sequence that is at least 70%, 80%, 85%, 90%, 95%, 97%, 98%, 99% or 100% identical to the amino acid sequence of SEQ ID NO: 36 and further includes the amino acid mutation H370R, wherein the numbering is relative to the amino acid sequence of SEQ ID NO: 33.

In some embodiments, the polymerase comprises an amino acid sequence that is at least 70%, 80%, 85%, 90%, 95%, 97%, 98%, 99% or 100% identical to the amino acid sequence of SEQ ID NO: 36 and further includes an amino acid mutation selected from the group: K380G, K380E, K380T, K380S, K380R, K380A, K380Q, K380W, K380Y and K380F, wherein the numbering is relative to the amino acid sequence of SEQ ID NO: 33. Typically, this polymerase can exhibit an increased $t_{pol}$ value in the presence of the dye-labeled nucleotides relative to a reference polymerase having the amino acid sequence of SEQ ID NO: 36. In some embodiments, the $t_{pol}$ value of the polymerase is increased by at least about 105%, 110%, 125%, 150%, 175%, 200%, 250%, 500%, 750%, or 1000% relative to the reference polymerase. Optionally, the polymerase can further include one or more mutations reducing 3' to 5' exonuclease activity selected from the group consisting of: D9A, E11A, E11I, T121, H58R, N59D, D63A, Y162F, Y162C, D166A, Q377A and S385G, wherein the numbering is relative to the amino acid sequence of SEQ ID NO: 33. Optionally, the polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 32. In some embodiments, the $t_{pol}$ value is increased in the presence of the dye-labeled nucleotide AF647-C6-dG6P. In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes the amino acid mutation K380R, wherein the numbering is relative to the amino acid sequence of SEQ ID NO: 33.

In some embodiments, the biomolecule is a Phi-29 polymerase comprising the TEV protease recognition sequence at its N-terminal end. Optionally, the biomolecule can also comprise a His tag. The His-tag can be fused to the N-terminus, the C-terminus or any other suitable position of the Phi-29 polymerase. Optionally, the His-tag can be separated from the amino acid residues of the protein by a linker comprising the TEV protease recognition sequence. In some embodiments, the fusion protein comprises an amino acid sequence that is at least 70%, 80%, 85%, 90%, 95%, 99% or 100% identical to the following amino acid sequence:

```
                                                      (SEQ ID NO: 38)
         10         20         30         40         50         60
MNHKVHHHHH HIEGRENLYF QCMELGTLEG SMKHMPRKMY SCAFETTTKV EDCRVWAYGY 70         80         90        100        110        120
MNIEDHSEYK IGNSLDEFMA WVLKVQADLY FHNLKFAGAF IINWLERNGF KWSADGLPNT 130        140        150        160        170        180
YNTIISRMGQ WYMIDICLGY KGKRKIHTVI YDSLKKLPFP VKKIAKDFKL TVLKGDIDYH 190        200        210        220        230        240
KERPVGYKIT PEEYAYIKND IQIIAEALLI QFKQGLDRMT AGSDSLKGFK DIITTKKFKK 250        260        270        280        290        300
VFPTLSLGLD KEVRYAYRGG FTWLNDRFKE KEIGEGMVFD VNSLYPAQMY SRLLPYGEPI 310        320        330        340        350        360
VFEGKYVWDE DYPLHIQHIR CEFELKEGYI PTIQIKRSRF YKGNEYLKSS GGEIADLWLS 370        380        390        400        410        420
NVDLELMKEH YDLYNVEYIS GLKFKATTGL FKDFIDKWTY IKTTSEGAIK QLAKLMLNSL 430        440        450        460        470        480
YGKFASNPDV TGKVPYLKEN GALGFRLGEE ETKDPVYTPM GVFITAWARY TTITAAQACY 490        500        510        520        530        540
DRIIYCDTDS IHLTGTEIPD VIKDIVDPKK LGYWAHESTF KRAKYLRQKT YIQDIYMKEV 550        560        570        580        590        600
DGKLVEGSPD DYTDIKFSVK CAGMTDKIKK EVTFENFKVG FSRKMKPKPV QVPGGVVLVD

DTFTIK
```

In some embodiments, the biomolecule is a mutant Phi-29-like polymerase comprising the TEV protease recognition sequence at its N-terminal end. Optionally, the biomolecule can also comprise a His tag. The His-tag can be fused to the N-terminus, the C-terminus or any other suitable position of the mutant B103 polymerase. Optionally, the His-tag can be separated from the amino acid residues of the protein by a linker comprising the TEV protease recognition sequence. In some embodiments, the fusion protein comprises an amino acid sequence that is at least 70%, 80%, 85%, 90%, 95%, 99% or 100% identical to the following amino acid sequence:

```
                                                      (SEQ ID NO: 39)
         10         20         30         40         50         60
MHHHHHHLLG GGGENLYFQC GGGGSAAAGS AARKMFSCDF ETTTKLDDCR VWAYGYMEIG 70         80         90        100        110        120
NLDNYKIGNS LDEFMQWVME IQADLYFHNL KFDGAFIVNW LEHHGFKWSN EGLPNTYNTI 130        140        150        160        170        180
ISKMGQWYMI DICFGYKGKR KLHTVIYDSL KKLPFPVKKI AKDFQLPLLK GDIDYHAERP 190        200        210        220        230        240
VGHEITPEEY EYIKNAIEII ARALDIQFKQ GLDRMTAGSD SLKGFKDILS TKKFNKVFPK 250        260        270        280        290        300
LSLPMDKEIR RAYRGGFTWL NDKYEKEIG EGMVFDVNSL YPSQMYSRPL PYGAPIVFQG 310        320        330        340        350        360
KYEKDEQYPL YIQRIRFEFE LKEGYIPTIQ IKKNPFFKGN EYLKNSGAEP VELYLTNVDL
```

```
       370        380        390        400        410        420
ELIQEHYEMY NVEYIDGFKF REKTGLFKEF IDKWTYVKTH EKGAKKQLAK LMLNSLYGKF 430        440        450        460        470        480
ASNPDVTGKV PYLKEDGSLG FRVGDEEYKD PVYTPMGVFI TAWARFTTIT AAQACYDRII 490        500        510        520        530        540
YCDTDSIHLT GTEVPEIIKD IVDPKKLGYW AHESTFKRAK YLRQKTYIQD IYAKEVDGKL 550        560        570        580        590        600
IECSPDEATT TKFSVKCAGM TDTIKKKVTF DNFRVGFSST GKPKPVQVNG GVVLVDSVFT
```

In some embodiments, the biomolecule is a fusion protein comprising a mutant Phi-29-like polymerase comprising a His tag linked to its N-terminal end, and including one or more amino acid substitutions selected from the group consisting of D166A, H370R, F383L and D384N, wherein the numbering is relative to the amino acid sequence of wild type B103 having the amino acid sequence of SEQ ID NO: 32. In some embodiments, the fusion protein comprises all four amino acid substitutions. In some embodiments, the fusion protein comprises an amino acid sequence that is at least 70%, 80%, 85%, 90%, 95%, 99% or 100% identical to the following amino acid sequence:

```
                                                   (SEQ ID NO: 40)
        10         20         30         40         50         60
MSHHHHHHSM SGLNDIFEAQ KIEWHEGAPG ARGSKHMPRK MFSCDFETTT KLDDCRVWAY 70         80         90        100        110        120
GYMEIGNLDN YKIGNSLDEF MQWVMEIQAD LYFHNLKFDG AFIVNWLEHH GFKWSNEGLP 130        140        150        160        170        180
NTYNTIISKM GQWYMIDICF GYKGKRKLHT VIYDSLKKLP FPVKKIAKDF QLPLLKGDID 190        200        210        220        230        240
YHAERPVGHE ITPEEYEYIK NAIEIIARAL DIQFKQGLDR MTAGSDSLKG FKDILSTKKF 250        260        270        280        290        300
NKVFPKLSLP MDKEIRRAYR GGFTWLNDKY KEKEIGEGMV FDVNSLYPSQ MYSRPLPYGA 310        320        330        340        350        360
PIVFQGKYEK DEQYPLYIQR IRFEFELKEG YIPTIQIKKN PFFKGNEYLK NSGAEPVELY 370        380        390        400        410        420
LTNVDLELIQ EHYEMYNVEY IDGFKFREKT GLFKEFIDKW TYVKTREKGA KKQLAKLMLN 430        440        450        460        470        480
SLYGKFASNP DVTGKVPYLK EDGSLGFRVG DEEYKDPVYT PMGVFITAWA RFTTITAAQA 490        500        510        520        530        540
CYDRIIYCDT DSIHLTGTEV PEIIKDIVDP KKLGYWAHES TFKRAKYLRQ KTYIQDIYAK 550        560        570        580        590        600
EVDGKLIECS PDEATTTKFS VKCAGMTDTI KKKVTFDNFR VGFSSTGKPK PVQVNGGVVL

VDSVFTIK
```

As the skilled artisan will readily appreciate, the scope of the present disclosure encompasses not only the specific amino acid and/or nucleotide sequences disclosed herein, but also, for example, to many related sequences encoding genes and/or peptides with the functional properties described herein. For example, the nucleotide and amino acid sequence of the polymerase of the labeled polymerase conjugate can include any nucleotide and amino acid sequence encoding conservative variants of the polymerases disclosed herein are also within the scope of the present disclosure.

In some embodiments, the methods, compositions, systems and/or kits disclosed herein can involve the use of moieties capable of undergoing energy transfer. Such energy transfer moieties can include energy transfer donors and acceptors. The energy transfer moieties can be linked to the solid surfaces, nanoparticles, polymerases, nucleotides, target nucleic acid molecules, primers, and/or oligonucleotides.

In one exemplary embodiment, the labeled biomolecule conjugates of the present disclosure comprise a polymerase linked to a label that includes an energy transfer moiety, wherein the conjugate has polymerase activity. In some embodiments, the energy transfer moiety of the conjugate performs energy transfer, which can be RET or FRET. In some embodiments, the energy transfer moiety of the conjugate performs energy transfer with the label of a nucleotide.

In one aspect, the energy transfer moiety can be an energy transfer donor. For example, the energy transfer donor can be a nanoparticle or an energy transfer donor moiety (e.g., fluorescent dye). In another aspect, the energy transfer moiety can be an energy transfer acceptor. For example, the energy transfer acceptor can be an energy acceptor dye. In another aspect, the energy transfer moiety can be a quencher moiety.

In one aspect, the energy transfer pair can be linked to the same molecule. For example, the energy transfer donor and acceptor pair can be linked to a single polymerase, which can provide detection of conformational changes in the polymerase. In another aspect, the donor and acceptor can be linked to different molecules in any combination. For example, the donor can be linked to the polymerase, target molecule, or primer molecule, and/or the acceptor can be linked to the nucleotide, the target molecule, or the primer molecule.

The energy transfer donor is capable of absorbing electromagnetic energy (e.g., light) at a first wavelength and emitting excitation energy in response. The energy acceptor is capable of absorbing excitation energy emitted by the donor and fluorescing at a second wavelength in response.

The donor and acceptor moieties can interact with each other physically or optically in a manner which produces a detectable signal when the two moieties are in proximity with each other. A proximity event includes two different moieties (e.g., energy transfer donor and acceptor) approaching each other, or associating with each other, or binding each other.

The donor and acceptor moieties can transfer energy in various modes, including: fluorescence resonance energy transfer (FRET) (L. Stryer 1978 Ann. Rev. Biochem. 47: 819-846; Schneider, U.S. Pat. No. 6,982,146; Hardin, U.S. Pat. No. 7,329,492; Hanzel U.S. published patent application No. 2007/0196846), scintillation proximity assays (SPA) (Hart and Greenwald 1979 Molecular Immunology 16:265-267; U.S. Pat. No. 4,658,649), luminescence resonance energy transfer (LRET) (G. Mathis 1995 Clin. Chem. 41:1391-1397), direct quenching (Tyagi et al, 1998 Nature Biotechnology 16:49-53), chemiluminescence energy transfer (CRET) (Campbell and Patel 1983 Biochem. Journal 216:185-194), bioluminescence resonance energy transfer (BRET) (Y. Xu. et al., 1999 Proc. Natl. Acad, Sci. 96:151-156), and excimer formation (J. R. Lakowicz 1999 "Principles of Fluorescence Spectroscopy", Kluwer Academic/Plenum Press, New York).

In one exemplary embodiment, the energy transfer moieties can be a FRET donor/acceptor pair. FRET is a distance-dependent radiationless transmission of excitation energy from a first moiety, referred to as a donor moiety, to a second moiety, referred to as an acceptor moiety. Typically, the efficiency of FRET energy transmission is dependent on the inverse sixth-power of the separation distance between the donor and acceptor, r. For a typical donor-acceptor pair, r can vary between approximately 10-100 Angstroms. FRET is useful for investigating changes in proximity between and/or within biological molecules. In some embodiments, FRET efficiency may depend on donor-acceptor distance r as $1/r^6$ or $1/r^4$. The efficiency of FRET energy transfer can sometimes be dependent on energy transfer from a point to a plane which varies by the fourth power of distance separation (E. Jares-Erijman, et al., 2003 Nat. Biotechnol. 21:1387). The distance where FRET efficiency is at 50% is termed $R_0$, also know as the Forster distance. $R_0$ can be unique for each donor-acceptor combination and can range from between about 5 nm to about 10 nm. A change in fluorescence from a donor or acceptor during a FRET event (e.g., increase or decrease in the signal) can be an indication of proximity between the donor and acceptor.

FRET efficiency (E) can be defined as the quantum yield of the energy transfer transition, i.e. the fraction of energy transfer event occurring per donor excitation event. It is a direct measure of the fraction of photon energy absorbed by the donor which is transferred to an acceptor, as expressed in Equation 1: $E = k_{ET}/k_f + k_{ET} + \Sigma k_i$ where $k_{ET}$ is the rate of energy transfer, $k_f$ the radiative decay rate and the $k_i$ are the rate constants of any other de-excitation pathway.

FRET efficiency E generally depends on the inverse of the sixth power of the distance r (nm) between the two fluorophores (i.e., donor and acceptor pair), as expressed in Equation 2: $E = 1/1 + (r/R_0)^6$.

Therefore, the FRET efficiency of a donor describes the maximum theoretical fraction of photon energy which is absorbed by the donor (i.e., nanoparticle) and which can then be transferred to a typical organic dye (e.g., fluoresceins, rhodamines, cyanines, etc.).

In biological applications, FRET can provide an on-off type signal indicating when the donor and acceptor moieties are proximal (e.g., within $R_0$) of each other. Additional factors affecting FRET efficiency include the quantum yield of the donor, the extinction coefficient of the acceptor, and the degree of spectral overlap between the donor and acceptor. Procedures are well known for maximizing the FRET signal and detection by selecting high yielding donors and high absorbing acceptors with the greatest possible spectral overlap between the two (D. W. Piston and G. J. Kremers 2007 Trends Biochem. Sci. 32:407). Resonance energy transfer may be either an intermolecular or intramolecular event. Thus, the spectral properties of the energy transfer pair as a whole, change in some measurable way if the distance and/or orientation between the moieties are altered.

The production of signals from FRET donors and acceptors can be sensitive to the distance between donor and acceptor moieties, the orientation of the donor and acceptor moieties, and/or a change in the environment of one of the moieties (Deuschle et al. 2005 Protein Science 14: 2304-2314; Smith et al. 2005 Protein Science 14:64-73). For example, a nucleotide linked with a FRET moiety (e.g., acceptor) may produce a detectable signal when it approaches, associates with, or binds a polymerase linked to a FRET moiety (e.g., donor). In another example, a FRET donor and acceptor linked to one protein can emit a FRET signal upon conformational change of the protein. Some FRET donor/acceptor pairs exhibit changes in absorbance or emission in response to changes in their environment, such as changes in pH, ionic strength, ionic type ($NO_2$, $Ca^{+2}$, $Mg^{+2}$, $Zn^{+2}$, $Na^+$, $Cl^-$, $K^+$), oxygen saturation, and solvation polarity.

The FRET donor and/or acceptor may be a fluorophore, luminophore, chemiluminophore, bioluminophore, or quencher (P. Selvin 1995 Methods Enzymol 246:300-334; C. G. dos Remedios 1995 J. Struct. Biol. 115:175-185; P. Wu and L. Brand 1994 Anal Biochem 218:1-13).

In some embodiments, the energy transfer moieties may not undergo FRET, but may undergo other types of energy transfer with each other, including luminescence resonance energy transfer, bioluminescence resonance energy transfer, chemiluminescence resonance energy transfer, and similar types of energy transfer not strictly following the Forster's theory, such as the non-overlapping energy transfer when non-overlapping acceptors are utilized (Laitala and Hemmila 2005 Anal. Chem. 77: 1483-1487).

In one embodiment, the polymerase can be linked to an energy transfer donor moiety. In another embodiment, the nucleotide can be linked to an energy transfer acceptor moiety. For example, in one embodiment the nucleotide comprises a polyphosphate chain and an energy transfer moiety linked to the the terminal phosphate group of the polyphosphate chain. A change in a fluorescent signal can occur when the labeled nucleotide is proximal to the labeled polymerase.

In one embodiment, when an acceptor-labeled nucleotide is proximal to a donor-labeled polymerase, the signal emitted by the donor moiety decreases. In another embodiment, when the acceptor-labeled nucleotide is proximal to the donor-labeled polymerase, the signal emitted by the acceptor moiety increases. In another embodiment, a decrease in donor signal and increase in acceptor signal correlates with nucleotide binding to the polymerase and/or correlates with polymerase-dependent nucleotide incorporation.

Quenchers

The energy transfer moiety can be a FRET quencher. Typically, quenchers have an absorption spectrum with large extinction coefficients, however the quantum yield for quenchers is reduced, such that the quencher emits little to no light upon excitation. Quenching can be used to reduce the background fluorescence, thereby enhancing the signal-to-noise ratio. In one aspect, energy transferred from the donor may be absorbed by the quencher which emits moderated (e.g., reduced) fluorescence. In another aspect, the acceptor can be a non-fluorescent chromophore which absorbs the energy transferred from the donor and emits heat (e.g., the energy acceptor is a dark quencher).

For an example, a quencher can be used as an energy acceptor with a nanoparticle donor in a FRET system, see I. L. Medintz, et al., 2003 Nature Materials 2:630. One exemplary method involves the use of quenchers in conjunction with reporters comprising fluorescent reporter moieties. In this strategy, certain nucleotides in the reaction mixture are labeled with a reporter comprising a fluorescent label, while the remaining nucleotides are labeled with a quencher. Alternatively, each of the nucleotides in the reaction mixture is labeled with a quencher. Discrimination of the nucleotide bases is based on the wavelength and/or intensity of light emitted from the FRET acceptor, as well as the intensity of light emitted from the FRET donor. If no signal is detected from the FRET acceptor, a corresponding reduction in light emission from the FRET donor indicates incorporation of a nucleotide labeled with a quencher. The degree of intensity reduction may be used to distinguish between different quenchers.

Examples of fluorescent donors and non-fluorescent acceptor (e.g., quencher) combinations have been developed for detection of proteolysis (Matayoshi 1990 Science 247: 954-958) and nucleic acid hybridization (L. Morrison, in: Nonisotopic DNA Probe Techniques, ed., L. Kricka, Academic Press, San Diego, (1992) pp. 31 1-352; S. Tyagi 1998 Nat. Biotechnol. 16:49-53; S. Tyagi 1996 Nat. Biotechnol. 14:947-8). FRET donors, acceptors and quenchers can be moieties which absorb electromagnetic energy (e.g., light) at about 300-900 nm, or about 350-800 nm, or about 390-800 nm.

Materials for Energy Transfer Moieties

Energy transfer donor and acceptor moieties can be made from materials which typically fall into four general categories (see the review in: K. E. Sapford, et al., 2006 Angew. Chem. Int. Ed. 45:4562-4588), including: (1) organic fluorescent dyes, dark quenchers and polymers (e.g., dendrimers); (2) inorganic material such as metals, metal chelates and semiconductors nanoparticles; (3) biomolecules such as proteins and amino acids (e.g., green fluorescent protein and derivatives thereof); and (4) enzymatically catalyzed bioluminescent molecules. The material for making the energy transfer donor and acceptor moieties can be selected from the same or different categories.

The FRET donor and acceptor moieties which are organic fluorescent dyes, quenchers or polymers can include traditional dyes which emit in the UV, visible, or near-infrared region. The UV emitting dyes include coumarin-, pyrene-, and naphthalene-related compounds. The visible and near-infrared dyes include xanthene-, fluorescein-, rhodol-, rhodamine-, and cyanine-related compounds. The fluorescent dyes also includes DDAO ((7-hydroxy-9H-(1,3-dichloro-9, 9-dimethylacridin-2-one)), resorufin, ALEXA FLUOR and BODIPY dyes (both Molecular Probes), HILYTE Fluors (AnaSpec), ATTO dyes (Atto-Tec), DY dyes (Dyomics GmbH), TAMRA (Perkin Elmer), tetramethylrhodamine (TMR), TEXAS RED, DYLIGHT (Thermo Fisher Scientific), FAM (AnaSpec), JOE and ROX (both Applied Biosystems), and Tokyo Green.

Additional fluorescent dyes which can be used as quenchers includes: DNP, DABSYL, QSY (Molecular Probes), ATM (Atto-Tec), BHQ (Biosearch Technologies), QXL (AnaSpec), BBQ (Berry and Associates) and CY5Q/7Q (Amersham Biosciences).

The FRET donor and acceptor moieties which comprise inorganic materials include gold quencher), silver, copper, silicon, semiconductor nanoparticles, and fluorescence-emitting metal such as a lanthanide complex, including those of Europium and Terbium.

Suitable FRET donor/acceptor pairs include: PAM as the donor and JOE, TAMRA, and ROX as the acceptor dyes. Other suitable pairs include: CYA as the donor and R6G, TAMRA, and ROX as the donor dyes. Other suitable donor/acceptor pairs include: a nanoparticle as the donor, and ALEXA FLUORS dyes (e.g., 610, 647, 660, 680, 700). DYOMICS dyes, such as 634 and 734 can be used as energy transfer acceptor dyes.

The compositions, methods, systems and kits of the present disclosure have particular use in single molecule sequencing reactions. Typically, such applications comprise the performance of a polymerase reaction using the a conjugate comprising a polymerase linked to a label and having polymerase activity according to the present disclosure.

In one exemplary embodiment, the temporal order of nucleotide incorporations during the polymerase reaction is detected and monitored in real time based on detection of FRET signals resulting from FRET between the labeled polymerase conjugates and the nucleotide label of an incorporating acceptor-labeled nucleotide.

In some embodiments, the polymerase is linked to a FRET donor and contacted with a nucleotide comprising a FRET acceptor. In some embodiments, the donor performs FRET with the acceptor when the polymerase and nucleotide are bought into sufficient proximity (for example, during a productive incorporation, a non-productive incorporation or during association of a nucleotide with the polymerase active site), resulting in the emission of a FRET signal. The FRET signal can optionally be detected and analyzed to determine the occurrence of a polymerase-nucleotide interaction.

In some embodiments, the FRET can occur prior to, during or after productive incorporation of the nucleotide into a nucleic acid molecule. Alternatively, the FRET can occur prior to binding of the nucleotide to the polymerase active site, or while the nucleotide resides within the polymerase active site, during a non-productive incorporation.

In some embodiments, the FRET acceptor moiety can in some embodiments be attached to, or comprise part of, the nucleotide sugar, the nucleobase, or analogs thereof. In some embodiments, the FRET acceptor is attached to a phosphate group of the nucleotide that is cleaved and released upon incorporation of the underlying nucleotide into the primer strand, for example the γ-phosphate, the β-phosphate or some other terminal phosphate of the incoming nucleotide. When this acceptor-labeled nucleotide polyphosphate is incorporated by the labeled polymerase conjugate into a nucleic acid molecule, the polymerase cleaves the bond between the alpha and beta phosphate, thereby releasing a pyrophosphate moiety comprising the acceptor that diffuses away. Thus, in these embodiments, a signal indicative of nucleotide incorporation is generated through FRET between the nanoparticle and the acceptor bonded to the gamma, beta or other terminal phosphate as each incoming nucleotide is incorporated into the newly synthesized strand. By releasing the label upon incorporation, successive incorporation of labeled nucleotides can each be detected without interference from nucleotides previously incorporated into the complementary strand. Alternatively, the nucleotide may be labeled with a FRET acceptor moiety on an internal phosphate, for example, the alpha phosphate, the beta phosphate, or another internal phosphate. Although such alpha-phosphate adducts are not cleaved and released during the polymerization process, they can be removed and/or rendered inoperable through appropriate treatments, e.g., chemical cleavage or photobleaching, later in the sequencing process.

The polymerase reaction conditions can comprise any suitable reaction conditions that permit nucleotide polymerization by labeled polymerase conjugates of the present disclosure. In one non-limiting example of nucleotide polymerization, the steps of polymerization can comprise: (1) complementary base-pairing of a target DNA molecule (e.g., a template molecule) with a primer molecule having a terminal 3' OH (the terminal 3' OH provides the polymerization initiation site for the polymerase); (2) binding of the polymerase of the conjugate to the base-paired target DNA/primer duplex to form a complex (e.g., open complex); (3) binding of the candidate nucleotide by the polymerase of the conjugate, which polymerase interrogates the candidate nucleotide for complementarity with the template nucleotide on the target DNA molecule; (4) catalysis of nucleotide polymerization by the polymerase of the conjugate.

In one embodiment, the polymerase of the conjugate comprises cleavage of the incorporating nucleotide by the polymerase, accompanied by liberation of a nucleotide cleavage product. When the nucleotide is a phosphate-comprising nucleotide, the cleavage product can include one or more phosphate groups. In other embodiments, where the polymerase incorporates a nucleotide analog having substituted phosphate groups, the cleavage product may include one or more substituted phosphate groups.

The candidate nucleotide may or may not be complementary to the template nucleotide on the target molecule. The candidate nucleotide may dissociate from the polymerase. If the candidate nucleotide dissociates from the polymerase, it can be liberated; in some embodiments, the liberated nucleotide carries intact polyphosphate groups. When the candidate nucleotide dissociates from the DNA polymerase, the event is known as a "non-productive binding" event. The dissociating nucleotide may or may not be complementary to the template nucleotide on the target molecule.

The incorporated nucleotide may or may not be complementary to the template nucleotide on the target. When the candidate nucleotide binds the DNA polymerase and is incorporated, the event is a "productive binding" event. The incorporated nucleotide may or may not be complementary to the template nucleotide on the target molecule.

The length of time, frequency, or duration of the binding of the complementary candidate nucleotide to the polymerase can differ from that of the non-complementary candidate nucleotide. This time difference can be used to distinguish between the complementary and non-complementary nucleotides, and/or can be used to identify the incorporated nucleotide, and/or can be used to deduce the sequence of the target molecule.

The signal (or change in signal) generated by the energy transfer donor and/or acceptor can be detected before, during, and/or after any nucleotide incorporation event.

In some embodiments, the polymerase reaction includes RNA polymerization which does not require a 3' polymerization initiation site. Polymerase reactions involving RNA polymerization are well known in the art.

Productive and Non-Productive Binding

Also provided herein are energy transfer compositions and methods for distinguishing between the productive and non-productive binding events. The compositions and methods can also provide base identity information during nucleotide incorporation. The compositions include nucleotides and polymerases each attached to a energy transfer moiety.

The compositions and methods provided herein can be used to distinguish events such as productive and non-productive nucleotide binding to the polymerase. In a productive binding event, the nucleotide can bind/associate with the polymerase for a time period which is distinguishable (e.g., longer or shorter time period), compared to a non-productive binding event. In a non-productive binding event, the nucleotide can bind/associate with the polymerase and then dissociate. The donor and acceptor energy transfer moieties produce detectable signals when they are in proximity to each other and can be associated with productive and non-productive binding events. Thus, the time-length difference between signals from the productive and non-productive binding events can provide distinction between the two types of events.

The detectable signals can be classified into true positive and false positive signals. For example, the true positive signals can arise from productive binding in which the nucleotide binds the polymerase and is incorporated. The incorporated nucleotide can be complementary to the template nucleotide. In another example, the false positive signals can arise from different binding events, including: non-specific binding, non-productive binding, and any event which brings the energy transfer donor and acceptor into sufficient proximity to induce a detectable signal.

Optionally, polymerase reactions performed using the methods, systems, compositions and kits of the present disclosure can be performed under any conditions which are suitable for: forming the complex (target/polymerase or target/initiation site/polymerase); binding the nucleotide to the polymerase; permitting the energy transfer and reporter moieties to generate detectable signals when the nucleotide binds the polymerase; incorporating the nucleotide; permitting the energy transfer and reporter moieties to generate a signal upon close proximity and/or nucleotide incorporation; and/or detecting the signal, or change in the signal, from the energy transfer or reporter moieties. The suitable conditions include well known parameters for time, temperature, pH, reagents, buffers, reagents, salts, co-factors, nucleotides, target DNA, primer DNA, enzymes such as nucleic acid-dependent polymerase, amounts and/or ratios of the components in the reactions, and the like. The reagents or buffers can include a source of monovalent ions, such as KCl, K-acetate, $NH_4$-acetate, K-glutamate, $NH_4Cl$, or ammonium sulfate. The reagents or buffers can include a source of divalent ions, such as $Mg^{2+}$ and/or $Mn^{2+}$, $MgCl_2$, or Mg-acetate. The buffer can include Tris, Tricine, HEPES, MOPS, ACES, or MES, which can provide a pH range of about 5.0 to about 9.5. The buffer can include chelating agents such as EDTA and EGTA, and the like.

Reducing Photo-Damage

The suitable polymerase reaction conditions can also include compounds which reduce photo-damage. For example, the compounds may reduce oxygen-damage or photo-damage. Illuminating the nucleotide binding and/or nucleotide incorporation reactions with electromagnetic radiation at an excitation wavelength can induce formation of reactive oxygen species from the fluorophore or other components in the reaction. The reactive oxygen species can cause photo-damage to the fluorophores, polymerases, or any other component of the binding or incorporation reactions. The nucleotide binding or nucleotide incorporation reactions can include compounds which are capable of reducing photo-damage, including: protocatechuate-3,4-dioxygenase, protocatechuic acid; 6-Hydroxy-2,5,7,8-tetramethylchroman-2-carboxylic Acid (TROLOX); or cycloocta-tetraene (COT).

Other compounds for reducing photo-damage include: ascorbic acid, astazanthin, bilirubin, biliverdin, bixin, captopril, canthazanthin, carotene (alpha, beta, and gamma), cysteine, beta-dimethyl cysteine, N-acetyl cysteine, diazobicyclooctane (DABCO), dithiothreitol (DTT), ergothioneine, glucose oxidase/catalase (GO/Cat), glutathione, glutathione peroxidase, hydrazine ($N_2H_4$), hydroxylamine, lycopene, lutein, polyene dialdehydes, melatonin, methionine, mercaptopropionylglycine, 2-mercaptoethane sulfonate (MESNA), pyridoxinel and its derivatives, mercaptoethylamine (MEA), β-mercaptoethanol (BME), n-propyl gallate, p-phenylenediamene (PPD), hydroquinone, sodium azide ($NaN_3$), sodium sulfite ($Na_2SO_3$), superoxide dismutase, tocopherols, α-tocopheryl succinate and its analogs, and zeaxanthin.

Also provided herein are methods of using the labeled biomolecule conjugates of the present disclosure.

For example, disclosed herein are methods for incorporation of one or more nucleotides onto the end of a nucleic acid molecule, comprising: contacting a conjugate including a polymerase linked to a label with a nucleotide under conditions where the nucleotide is incorporated into a nucleic acid molecule by the conjugate. The nucleic acid molecule can be any suitable target nucleic acid molecule of interest. In some embodiments, the labeled polymerase can be a polymerase having or comprising the amino acid sequence of SEQ ID NO: 3, SEQ ID NO: 33, SEQ ID NO: 34, SEQ ID NO: 35 or SEQ ID NO: 36, or any sequence at least 80% identical thereto. In some embodiments, the nucleotide can be become incorporated onto the 3' end of an extending nucleic acid molecule by the polymerase. In some embodiments, the nucleotide can be a labeled nucleotide analog. The labeled nucleotide analog can further comprise a label linked to the base, sugar, phosphate or any other portion of the nucleotide analog. In some embodiments, the nucleotide can also comprise a blocking group that inhibits, slows down or blocks further incorporation of nucleotides onto the end of the nucleic acid molecule until the blocking group is removed from the nucleotide. In some embodiments, the nucleotide comprising a blocking group is a reversible terminator for nucleic acid synthesis, as described further below. In some embodiments, the blocking group can be removed from the nucleotide by chemical, enzymatic, or photocleaving reactions.

In some embodiments, the method further includes the step of adding one or more divalent cations to the polymerase reaction mixture in an amount sufficient for inhibiting further incorporation of nucleotides onto the end of the nucleic acid molecule by the labeled polymerase. In some embodiments, the divalent cation that inhibits nucleotide incorporation is calcium. In another embodiment, omitting, reducing, or chelating cations that permit nucleotide incorporation (e.g, manganese and/or magnesium) can be employed. Such methods are described, for example, in U.S. Provisional Application 61/242,762, filed Sep. 15, 2009; and in U.S. Provisional Application No. 61/184,774, filed on Jun. 5, 2009. In some embodiments, the polymerase can be linked to a label, as, for example, disclosed herein and in U.S. Provisional Application No. 61/184,770, filed Jun. 5, 2009.

Also provided herein is a method for detecting one or more nucleotide incorporations, comprising: contacting a conjugate including a polymerase linked to a label with a labeled nucleotide under conditions where the labeled nucleotide is incorporated by the conjugate into a nucleic acid molecule, and where the label of the labeled nucleotide emits a signal indicative of such nucleotide incorporation; and detecting the signal indicative of such nucleotide incorporation. In some embodiments, the detecting can be performed in real or near real time. In some embodiments, the method can further include analyzing the detected signal indicative of nucleotide incorporation to determine the identity of the incorporated nucleotide. In some embodiments, the labeled polymerase conjugate catalyzes a time series of nucleotide incorporations, which can collectively be detected and analyzed to determine some or all of the sequence of the target nucleic acid molecule.

Also disclosed herein is a method for determining a nucleotide sequence of a single nucleic acid molecule, comprising: (a) conducting a polymerase reaction comprising a labeled biomolecule conjugate and a labeled nucleotide under conditions where the conjugate incorporates the labeled nucleotide into a nucleic acid molecule and a signal indicative of such nucleotide incorporation is generated; (b) detecting the signal indicative of such nucleotide incorporation; and (c) analyzing the signal to determine the identity of the incorporated nucleotide. Optionally, a time series of nucleotide incorporation signals can be detected and analyzed, thereby determining some or all of the nucleotide sequence of a single nucleic acid molecule.

Also provided herein are methods of sequencing a nucleic acid molecule, comprising: (a) performing a polymerase reaction comprising a labeled polymerase conjugate and labeled nucleotides under conditions resulting in a series of labeled nucleotide incorporations by the polymerase and the generation of a signal indicative of each nucleotide incorporation the series; (b) detecting a time sequence of nucleotide incorporations; and (c) determining the identity of one or more incorporated nucleotides, thereby determining some or all of the nucleotide sequence of a single nucleic acid molecule.

In some embodiments, the polymerase is attached to or associated with a substrate or surface. In some embodiments, the polymerase can be attached to or associated with a nucleic acid molecule (termed a template), and polymerize one or more nucleotides in a template-dependent fashion. In some embodiments, the template can be attached to or associated with a substrate or surface. In some embodiments, the polymerase, template, nucleotide, substrate or surface, or some combination thereof, can also be labeled.

In some embodiments, the methods of the present disclosure can be performed in multiplex and/or "high-throughput" format wherein multiple units of the labeled polymerase conjugates of the present disclosure can each be visualized and monitored in parallel with each other. For example, in some embodiments, multiple labeled polymerase conjugates may be positioned, associated with, or attached to different locations on a substrate, and a polymerase activity of one or more of these polymerases may be detected in isolation. In some embodiments, the polymerase or the template nucleic acid molecule are associated with or attached to a substrate or surface in array format. The array can be spatially addressable.

In some embodiments, the sequencing reaction can be performed using buffer conditions comprising 50 mM Tris buffer pH 7.5, 50 mM NaCl, 0-10 mM $MgCl_2$, 2 mM $MnCl_2$, 330 nM polymerase, 100 nM primed template and 4 µM labeled nucleotide hexaphosphate. Optionally, 0.3% BSA and/or 0.05% Tween20 can be included in the reaction mix. In some embodiments, the reaction mix is further supplemented with 2 mM DTT and/or single stranded binding protein (SSBP) at a concentration of 100 µg/ml.

Alternatively, in some embodiments the sequencing reaction can be performed using buffer conditions comprising 50 mM Tris pH 8.0, 50 mM NaCl and 10 mM $MgCl_2$.

In one exemplary embodiment, a nucleic acid sequencing system can comprise a template nucleic acid molecule attached to a substrate, a labeled polymerase conjugate comprising a FRET donor label linked to a polymerase, and labeled nucleotides each comprising a nucleotide linked to one or more FRET acceptor labels.

The template nucleic acid molecule of this sequencing system can be attached to any suitable substrate or surface using any suitable method. In some embodiments, the template nucleic acid molecule can comprise one or more biotin moieties, the surface can comprise an avidin moiety, and the template nucleic acid is linked to the surface via one or more biotin-avidin bonds. In some embodiments, the template and surface can each comprise one or more biotin moieties, and be linked to each other through a linkage comprising an avidin moiety.

An exemplary sequencing system according to the present disclosure is depicted in FIG. 1. This exemplary system comprises a biotinylated nucleic acid template (here, a hairpin oligonucleotide) linked to a surface though one or more biotin-avidin bonds, a labeled polymerase conjugate comprising biotinylated Phi-29 linked to dye-labeled streptavidin, and acceptor-labeled nucleotides. This exemplary system was used to generate the sequence data depicted in FIG. 14 and FIG. 15, according to the methods described in Example 6.

Polymerization Initiation Sites

In some embodiments, the polymerase of the labeled polymerase conjugate initiations polymerization at a polymerization initiation site. In some embodiments, the polymerization initiation site can be a terminal 3' OH group of a nucleic acid molecule. The 3' OH group can serve as a substrate for the polymerase for nucleotide polymerization. The 3' OH group can serve as a substrate for the polymerase to form a phosphodiester bond between the terminal 3' OH group and an incorporated nucleotide. The 3' OH group can be provided by: the terminal end of a primer molecule; a nick or gap within a nucleic acid molecule (e.g., oligonucleotide) which is base-paired with the target molecule; the terminal end of a secondary structure (e.g., the end of a hairpin-like structure); or an origin of replication.

In some embodiments, the polymerization initiation site can be provided by an accessory protein (e.g., RNA polymerase or helicase/primase). The polymerization initiation site can be provided by a terminal protein which can be bound (covalently or non-covalently) to the end of the target nucleic, including terminal protein (e.g., TP) found in phage (e.g., TP from phi29 phage). Thus, the polymerization initiation site may be at a terminal end or within a base-paired nucleic acid molecule.

In other embodiments, the polymerization initiation site used by some polymerases (e.g., RNA polymerase) may not include a 3' OH group.

The portion of the target molecule which is base paired with the primer or with the oligonucleotide, or the self-primed portion of the target molecule, can form hydrogen bonding by Watson-Crick or Hoogstein binding to form a duplex nucleic acid structure. The primer, oligonucleotide, and self-priming sequence may be complementary, or partially complementary, to the nucleotide sequence of the target molecule. The complementary base pairing can be the standard A-T or C-G base pairing, or can be other forms of base-pairing interactions.

Primer Molecules

In some embodiments, the primer molecule can hybridize with the target nucleic acid molecule. The sequence of the primer molecule can be complementary or non-complementary with the sequence of the sequence of the target molecule. The 3' terminal end of the primer molecule can provide the polymerization initiation site.

Optionally, the primers can be modified with a chemical moiety to protect the primer from serving as a polymerization initiation site or as a restriction enzyme recognition site. The chemical moiety can be a natural or synthetic amino acid linked through an amide bond to the primer.

The primer, oligonucleotide, or self-priming portion, may be naturally-occurring, or may be produced using enzymatic or chemical synthesis methods. The primer, oligonucleotide, or self-priming portion may be any suitable length including 5, 10, 15, 20, 25, 30, 40, 50, 75, or 100 nucleotides or longer in length. The primer, oligonucleotide, or self-priming portion may be linked to an energy transfer moiety (e.g., donor or acceptor) or to a reporter moiety (e.g., a dye) using methods well known in the art.

The primer molecule, oligonucleotide, and self-priming portion of the target molecule, may comprise ribonucleotides, deoxyribonucleotides, ribonucleotides, deoxyribonucleotides, peptide nucleotides, modified phosphate-sugar backbone nucleotides including phosphorothioate and phosphoramidate, metallonucleosides, phosphonate nucleosides, and any analogs or variants thereof, or combinations thereof.

In one embodiment, the primer molecule can be a recombinant DNA molecule. The primer can be linked at the 5' or 3' end, or internally, with a binding partner, such as biotin. The biotin can be used to immobilize the primer molecule to the surface (via an avidin-like molecule), or for attachment to a reporter moiety. The primer can be linked to a energy transfer moiety, such as a fluorescent dye or a nanoparticle, or to a reporter moiety. The primer molecule can hybridize to the target nucleic acid molecule. The primer molecule can be used as a capture probe to immobilize the target molecule.

The compositions, methods, systems, apparatuses and kits disclosed herein can be practiced using nucleotides. In some embodiments, the nucleotides can be linked with at least one energy transfer moiety. The energy transfer moiety can be an energy transfer acceptor moiety. The different types of nucleotides (e.g., adenosine, thymidine, cytidine, guanosine, and uridine) can be labeled with different energy transfer acceptor moieties so that the detectable signals from each of the different types nucleotides can be distinguishable to permit base identity. The nucleotides can be labeled in a way that does not interfere with the events of polymerization. For example the attached energy transfer acceptor moiety does not interfere with nucleotide binding and/or does not interfere with nucleotide incorporation and/or does not interfere with cleavage of the phosphodiester bonds and/or does not interfere with release of the polyphosphate product. See for example, U.S. Ser. No. 61/164,091, Ronald Graham, concurrently filed Mar. 27, 2009. See for example U.S. Pat. Nos. 7,041,812, 7,052,839, 7,125,671, and 7,223,541; U.S. Pub. Nos. 2007/072196 and 2008/0091005; Sood et al., 2005, J. Am. Chem. Soc. 127:2394-2395; Arzumanov et al., 1996, J. Biol. Chem. 271:24389-24394; and Kumar et al., 2005, Nucleosides, Nucleotides & Nucleic Acids, 24(5):401-408.

In one aspect, the energy transfer acceptor moiety may be linked to any position of the nucleotide. For example, the energy transfer acceptor moiety can be linked to any phosphate group (or derivatized phosphate group), the sugar or the base. In another example, the energy transfer moiety can be linked to any phosphate group (or derivatized phosphate group) which is released as part of a phosphate cleavage product upon incorporation. In yet another example, the energy transfer acceptor moiety can be linked to the terminal phosphate group (or derivatized phosphate group). In another aspect, the nucleotide may be linked with an additional energy transfer acceptor moiety, so that the nucleotide is attached with two or more energy transfer acceptor moieties. The additional energy transfer acceptor moiety can be the same or different as the first energy transfer acceptor moiety. In one embodiment, the energy transfer acceptor moiety can be a FRET acceptor moiety.

In one aspect, the nucleotide may be linked with a reporter moiety which is not an energy transfer moiety. For example, the reporter moiety can be a fluorophore.

In one aspect, the energy transfer acceptor moieties and/or the reporter moiety can be attached to the nucleotide via a linear or branched linker moiety. An intervening linker moiety can connect the energy transfer acceptor moieties with each other and/or to the reporter moiety, any combination of linking arrangements.

In another aspect, the nucleotides comprise a sugar moiety, base moiety, and at least three, four, five, six, seven, eight, nine, ten, or more phosphate groups linked to the sugar moiety by an ester or phosphoramide linkage. The phosphates can be linked to the 3' or 5' C of the sugar moiety. The nucleotides can be incorporated and/or polymerized into a growing nucleic acid strand by a naturally occurring, modified, or engineered nucleic acid dependent polymerase.

In one aspect, different linkers can be used to operably link the different nucleotides (e.g., A, G, C, or T/U) to the energy transfer moieties or reporter moieties. For example, adenosine nucleotide can be attached to one type of energy transfer moiety using one type of linker, and guanosine nucleotide can be linked to a different type of energy transfer moiety using a different type of linker. In another example, adenosine nucleotide can be attached to one type of energy transfer moiety using one type of linker, and the other types of nucleotides can be attached to different types of energy transfer moieties using the same type of linker. One skilled in the art will appreciate that many different combinations of nucleotides, energy transfer moieties, and linkers are possible.

In one aspect, the distance between the nucleotide and the energy transfer moiety can be altered. For example, the linker length and/or number of phosphate groups can lengthen or shorten the distance from the sugar moiety to the energy transfer moiety. In another example, the distance between the nucleotide and the energy transfer moiety can differ for each type of nucleotide (e.g., A, G, C, or T/U).

In another aspect, the number of energy transfer moieties which are linked to the different types of nucleotides (e.g., A, G, C, or T/U) can be the same or different. For example: A can have one dye, and G, C, and T have two; A can have one dye, C has two, G has three, and T has four; A can have one dye, C and G have two, and T has four. One skilled in the art will recognize that many different combinations are possible.

In another aspect, the concentration of the labeled nucleotides used to conduct the nucleotide binding or nucleotide incorporation reactions can be about 0.0001 nM-1 µM, or about 0.0001 nM-0.001 nM, or about 0.001 nM-0.01 nM, or about 0.01 nM-0.1 nM, or about 0.1 nM-1.0 nM, or about 1 nM-25 nM, or about 25 nM-50 nM, or about 50 nM-75 nM, or about 75 nM-100 nM, or about 100 nM-200 nM, or about 200 nM-500 nM, or about 500 nM-750 nM, or about 750 nM-1000 nM, or about 0.1 µM-20 µM, or about 20 µM-50 µM, or about 50 µM-75 µM, or about 75 µM-100 µM, or about 100 µM-200 µM, or about 200 µM-500 µM, or about 500 µM-750 µM, or about 750 µM-1000 µM.

In another aspect, the concentration of the different types of labeled nucleotides, which are used to conduct the nucleotide binding or incorporation reaction, can be the same or different from each other.

Sugar Moieties

The nucleotides typically comprise suitable sugar moieties, such as carbocyclic moieties (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other suitable sugar moieties (Joeng, et al., 1993 J. Med. Chem. 36: 2627-2638; Kim, et al., 1993 J. Med. Chem. 36: 30-7; Eschenmosser 1999 Science 284: 2118-2124.; and U.S. Pat. No. 5,558,991). The sugar moiety may be selected from the following: ribosyl, 2'-deoxyribosyl, 3'-deoxyribosyl, 2',3'-dideoxyribosyl, 2',3'-didehydrodideoxyribosyl, 2'-alkoxyribosyl, 2'-azidoribosyl, 2'-aminoribosyl, 2'-fluororibosyl, 2'-mercaptoriboxyl, 2'-alkylthioribosyl, 3'-alkoxyribosyl, 3'-azidoribosyl, 3'-aminoribosyl, 3'-fluororibosyl, 3'-mercaptoriboxyl, 3'-alkylthioribosyl carbocyclic, acyclic and other modified sugars. In one aspect, the 3'-position has a hydroxyl group, for strand/chain elongation.

Base Moieties

The nucleotides can include a hetero cyclic base which includes substituted or unsubstituted nitrogen-containing parent heteroaromatic ring which is commonly found in nucleic acids, including naturally-occurring, substituted, modified, or engineered variants. The base is capable of forming Watson-Crick and/or Hoogstein hydrogen bonds with an appropriate complementary base. Exemplary bases include, but are not limited to, purines and pyrimidines such as: 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2ms 6iA), $N^6$-methyladenine, guanine (G), isoguanine, $N^2$-dimethylguanine (dmG), 7-methylguanine (7mG), 2-thiopyrimidine, 6-thioguanine (6sG), hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; inosines; hydroxymethylcytosines; 5-methycytosines; base (Y); as well as methylated, glycosylated, and acylated base moieties; and the like. Additional exemplary bases can be found in Fasman, 1989, in: Practical Handbook of Biochemistry and Molecular Biology, pp. 385-394, CRC Press, Boca Raton, Fla., and the references cited therein.

Examples of nucleotides include ribonucleotides, deoxyribonucleotides, modified ribonucleotides, modified deoxyribonucleotides, ribonucleotides, deoxyribonucleotides, modified ribonucleotides, modified deoxyribonucleotides, peptide nucleotides, modified peptide nucleotides, metallonucleosides, phosphonate nucleosides, and modified phosphate-sugar backbone nucleotides, and any variants of the foregoing.

Phosphate Groups

The nucleotides can optionally include phosphate groups which can be linked to the 2',3' and/or 5' position of the sugar moiety. The phosphate groups include analogs, such as phosphoramidate, phosphorothioate, phosphorodithioate, and O-methylphosphoroamidite groups. In one embodiment, at least one of the phosphate groups can be substituted with a fluoro and/or chloro group. The phosphate groups can be linked to the sugar moiety by an ester or phosphoramide linkage. Typically, the nucleotide comprises three, four, five, six, seven, eight, nine, ten, or more phosphate groups linked to the 5' position of the sugar moiety.

The disclosed compositions and methods can be practiced using any nucleotide which can be incorporated by a polymerase, including naturally-occurring or recombinant polymerases. In one embodiment, the nucleotides can include a nucleoside linked to a chain of 1-10 phosphorus atoms. The nucleoside can include a base (or base analog) linked to a sugar (or sugar analog). The phosphorus chain can be linked to the sugar, for example linked to the 5' position of the sugar. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, C(O), $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotides are described in Xu, U.S. Pat. No. 7,405,281.

Figure 21:
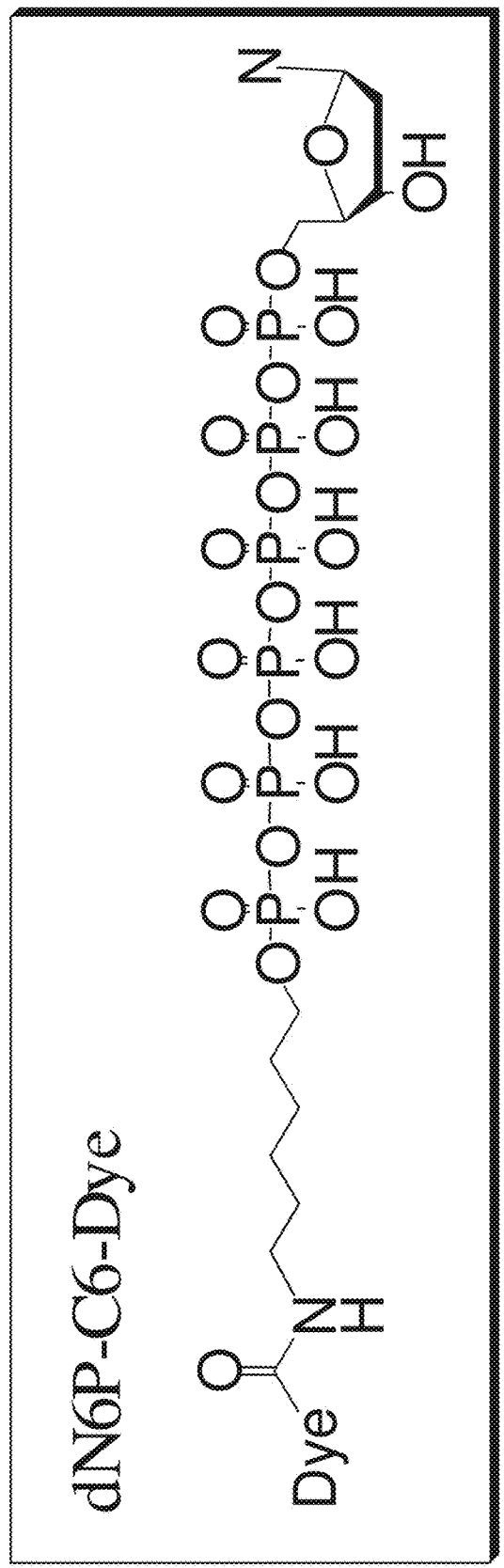
FIG. 21 depicts the structure of an exemplary nucleotide that can be used in conjunction with the labeled polymerase conjugates of the present disclosure according to the methods provided herein.

In some embodiments, the nucleotide is a dye-labeled nucleotide that comprises a polyphosphate chain and a dye moiety linked to the terminal phosphate group. In some embodiments, the dye-labeled nucleotide comprises a dye moiety linked to the terminal phosphate through an alkyl linker. Optionally, the linker comprises a 6-carbon chain and has a reactive amine group, and the dye moiety is linked to the terminal phosphate bond though a covalent bond formed with the amine group of the linker. In some embodiments, the polyphosphate chain comprises 4, 5, 6, 7, 8, 9, 10 or more phosphates. One exemplary dye-labeled nucleotide that can be used in the disclosed methods and systems has the general structure shown in FIG. 21. This structure includes a sugar bonded to a hexaphosphate chain at the 5' carbon position, and to a nucleotide base (denoted as "N"). The terminal phosphate group of the hexaphosphate is linked to a 6-carbon linker, and the other end of the 6-carbon linker is attached to a dye moiety (denoted as "dye"), typically through an amide bond. In some embodiments, the dye moiety can optionally comprise any one or more of the following dyes: rhodols; resorufins; coumarins; xanthenes; acridines; fluoresceins; rhodamines; erythrins; cyanins; phthalaldehydes; naphthylamines; fluorescamines; benzoxadiazoles; stilbenes; pyrenes; indoles; borapolyazaindacenes; quinazolinones; eosin; erythrosin; Malachite green; CY dyes (GE Biosciences), including Cy3 (and its derivatives) and Cy5 (and its derivatives); DYOMICS and DYLIGHT dyes (Dyomics) including DY-547, DY-630, DY-631, DY-632, DY-633, DY-634, DY-635, DY-647, DY-649, DY-652, DY-678, DY-680, DY-682, DY-701, DY-734, DY-752, DY-777 and DY-782; Lucifer Yellow; CASCADE BLUE; TEXAS RED; BODIPY (boron-dipyrromethene) (Molecular Probes) dyes including BODIPY 630/650 and BODIPY 650/670; ATTO dyes (Atto-Tec) including ATTO 390, ATTO 425, ATTO 465, ATTO 610 611X, ATTO 610 (N-succinimidyl ester), ATTO 635 (NHS ester); ALEXA FLUORS including ALEXA FLUOR 633, ALEXA FLUOR 647, ALEXA FLUOR 660, ALEXA FLUOR 700, ALEXA FLUOR 750, and ALEXA FLUOR 680 (Molecular Probes); DDAO (7-hydroxy-9H-(1,3-dichloro-9,9-dimethylacridin-2-one or any derivatives thereof) (Molecular Probes); QUASAR dyes (Biosearch); IRDYES dyes (LiCor) including IRDYE 700DX (NHS ester), IRDYE 800RS (NHS ester) and IRDYE 800CW (NHS ester); EVOBLUE dyes (Evotech Biosystems); JODA 4 dyes (Applied Biosystems); HILYTE dyes (AnaSpec); MR121 and MR200 dyes (Roche); Hoechst dyes 33258 and 33242 (Invitrogen); FAIR OAKS RED (Molecular Devices); SUNNYVALE RED (Molecular Devices); LIGHT CYCLER RED (Roche); EPOCH (Glen Research) dyes including EPOCH REDMOND RED (phosphoramidate), EPOCH YAKIMA YELLOW (phosphoramidate), EPOCH GIG HARBOR GREEN (phosphoramidate); Tokyo green (M Kamiya, et al., 2005 Angew. Chem. Int. Ed. 44:5439-5441); and CF dyes including CF 647 and CF555 (Biotium).

In some embodiments, such dye-labeled nucleotides can be used to assay for the nucleotide incorporation kinetics of a particular polymerase according to the procedures described herein (see, e.g., Example 10).

Non-Hydrolyzable Nucleotides

The nucleotide binding and nucleotide incorporation methods can be practiced using incorporatable nucleotides and non-hydrolyzable nucleotides. In the presence of the incorporatable nucleotides (e.g., labeled), the non-hydrolyzable nucleotides (e.g., non-labeled) can compete for the polymerase binding site to permit distinction between the complementary and non-complementary nucleotides, or for distinguishing between productive and non-productive binding events. In the nucleotide incorporation reaction, the presence of the non-hydrolyzable nucleotides can alter the length of time, frequency, and/or duration of the binding of the labeled incorporatable nucleotides.

The non-hydrolyzable nucleotides can be non-labeled or can be linked to a reporter moiety (e.g., energy transfer moiety). The labeled non-hydrolyzable nucleotides can be linked to a reporter moiety at any position, such as the sugar, base, or any phosphate (or substituted phosphate group). For example, the non-hydrolyzable nucleotides can have the general structure:

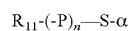

Where B can be a base moiety, such as a hetero cyclic base which includes substituted or unsubstituted nitrogen-containing heteroaromatic ring. Where S can be a sugar moiety, such as a riboxyl, riboxyl, or glucosyl group. Where n can be 1-10, or more. Where P can be one or more substituted or unsubstituted phosphate or phosphonate groups. Where $R_{11}$, if included, can be a reporter moiety (e.g., a fluorescent dye). In one embodiment, the non-hydrolyzable nucleotide having multiple phosphate or phosphonate groups, the linkage between the phosphate or phosphonate groups can be non-hydrolyzable by the polymerase. The non-hydrolyzable linkages include, but are not limited to, amino, alkyl, methyl, and thio groups. Non-hydrolyzable nucleotide tetraphosphates having alpha-thio or alpha boreno substitutions having been described (Rank, U.S. published patent application No. 2008/0108082; and Gelfand, U.S. published patent application No. 2008/0293071).

The phosphate or phosphonate portion of the non-hydrolyzable nucleotide can have the general structure:

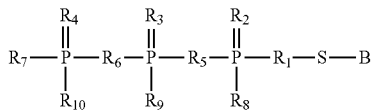

Where B can be a base moiety and S can be a sugar moiety. Where any one of the $R_1$-$R_7$ groups can render the nucleotide non-hydrolyzable by a polymerase. Where the sugar CS position can be $CH_2$, $CH_2O$, CH=, CHR, or $CH_2CH_2$. Where the $R_1$ group can be O, S, CH=, CH(CN), or NH. Where the $R_2$, $R_3$, and $R_4$, groups can independently be O, $BH_3$, or SH. Where the $R_5$ and $R_6$ groups can independently be an amino, alkyl, methyl, thio group, or CHF, $CF_2$, CHBr, $CCl_2$, O—O, or —C≡C—. Where the $R_7$ group can be oxygen, or one or more additional phosphate or phosphonate groups, or can be a reporter moiety. Where $R_8$ can be SH, $BH_3$, $CH_3$, $NH_2$, or a phenyl group or phenyl ring. Where $R_9$ can be SH. Where $R_{10}$ can be $CH_3$, $N_3CH_2CH_2$, $NH_2$, ANS, $N_3$, MeO, SH, Ph, F, PhNH, PhO, or RS (where Ph can be a phenyl group or phenyl ring, and F can be a fluorine atom or group). The substituted groups can be in the S or R configuration.

The non-hydrolyzable nucleotides can be alpha-phosphate modified nucleotides, alpha-beta nucleotides, beta-phosphate modified nucleotides, beta-gamma nucleotides, gamma-phosphate modified nucleotides, caged nucleotides, or di-nucleotides.

Many examples of non-hydrolyzable nucleotides are known (Rienitz 1985 Nucleic Acids Research 13:5685-5695), including commercially-available ones from Jena Bioscience (Jena, Germany).

In some embodiments, the labeled polymerase conjugates retain polymerase activity. For example, disclosed herein are labeled polymerase conjugates, wherein the polymerase activity of the conjugate can be at least about 10%, at least about 20%, at least about 30%, at least about 40%, at least about 50%, at least about 60%, at least about 70%, at least about 80%, at least about 90% or at least about 95% relative to the polymerase activity of the unconjugated enzyme. In a typical assay, the polymerase activity is primer extension activity.

Various methods of measuring primer extension activity are known in the art. Primer extension activity can be measured using any suitable assay that provides a quantitative indication of the amount of extension product obtained using defined reaction conditions comprising a known concentration of polymerase. Regardless of which assay is used, differences in primer extension activity between two samples, when obtained using identical reaction conditions, can be evaluated by simply comparing levels of observed primer activity obtained from each sample. Optionally, the observed primer extension activity can normalized for amount of polymerase by dividing the amount of incorporated radioactivity by the polymerase concerntration in the reaction mixture, to allow comparison between reactions containing different polymerase concentrations.

In one exemplary embodiment, the primer extension activity of a polymerase can be measured using a radiometric assay that measures incorporation of a radioactively labeled nucleotide into acid-insoluble material in a polymerase reaction. The amount of incorporated radioactivity indicates the total number of nucleotides incorporated. See, e.g., Wu et al., Gene Biotechnology, 2nd Ed., CRC Press; Sambrook, J., Fritsch, E F, and Maniatis, T. (1989) Molecular Cloning A Laboratory Manual, 2nd ed., Cold Spring Harbor Laboratory Press, Cold Spring Harbor, N.Y.

In another exemplary embodiment, levels of primer extension activity in a sample can be measured by monitoring the fluorescence intensity change over time during extension of a fluorescein-labeled hairpin oligonucleotide. Exemplary assays are described in the Examples, herein.

In yet another exemplary embodiment, the primer extension activity can be quantified by quantifying the amount of pyrophosphate liberated after peforming primer extension under defined reaction conditions for 5 minutes.

In yet another exemplary embodiment, the primer extension activity can be quantified by measuring the fraction of extended primer within a population of primer-template duplexes. In this exemplary embodiment, the template can comprise a radioactive ($^{32}$P) moiety or fluorescent (TAMRA) label to permit visualization of polymerase reaction products (e.g., extended primer). The primer extension products can be resolved on a gel, and the primer extension activity can then quantified as the proportion (%) of extended primer relative to total starting primer, by adding the intensities of all bands observed within a single lane as measured by densitometric analysis.

When comparing the primer extension activites of conjugates comprising multiple polymerases per conjugate and free (unconjugated) polymerase, the primer extension activities can be normalized for relative polymerase concentration before comparing them against each other. One exemplary such assay is described herein in Example 9.

In some embodiments, the nucleotide comprises a nucleotide analog that is capable of acting as a reversible terminator of nucleic acid synthesis. Typically, reversible terminators can be incorporated by a polymerase onto the end of an extending nucleic acid molecule, but then "terminate" further synthesis by blocking further addition of nucleotides. In some embodiments, this "termination" capability can be manipulated by adjusting the reaction conditions and/or by suitable treatment. The ability to terminate can result from the presence of a moiety or group, typically named a "blocking" group, which is linked to the nucleotide. In some embodiments, the ability of the nucleotide to terminate nucleic acid synthesis can be eliminated through physical removal, cleavage, structural modification or disruption of the blocking group. The blocking group can be attached to any portion of the nucleotide including, for example, a base moiety, sugar moiety or phosphate moiety. The blocking group can be attached to the nucleotide via a linker. The linkage between the blocking group and the nucleotide can be a photocleavable, chemically cleavable, enzymatically cleavable, thermocleavable (i.e., cleavable upon adjustment of temperature) or pH-sensitive linkage. In some embodiments, the label (which is linked to the nucleotide) is the blocking group.

In some embodiments, the reversible terminator further comprises a label or tag that facilitates detection of nucleotide. The label can be a fluorescent label. In some embodiments, the label can also be removed via suitable treatment. In some embodiments, the label is released from the nucleotide during incorporation of the nucleotide into the extending nucleic acid molecule. Alternatively, the label becomes incorporated into the extending nucleic acid molecule and is then removed via suitable treatment. In some embodiments, the label is attached to the nucleotide via a cleavable linkage. The cleavable linkage can be a photocleavable, chemically cleavable, enzymatically cleavable, thermocleavable (i.e., cleavable upon adjustment of temperature) or pH-sensitive linkage.

The removal of the blocking group can be accomplished in a variety of ways. In some embodiments, the blocking group is attached to the nucleotide via a photocleavable linkage and can be removed from the nucleotide via exposure to photocleaving radiation. In some embodiments, the linkage is a chemically or enzymatically cleavable linkage. In some embodiments, the linkage can be disrupted by varying reaction conditions, e.g., pH, temperature, concentrations of divalent cations, etc.

Non-limiting examples of suitable reversible terminators include, inter alia, nucleotide base-labeled nucleotides comprising one or more blocking groups attached to 3' hydroxyl group, the base moiety or a phosphate group. For example, the nucleotide can comprise an azidomethyl group linked to the 3' hydroxyl group and a fluorescent label linked to the base of the nucleotide. In some embodiments, the reversible terminator can comprise one or more blocking groups attached to the phosphate group. In some embodiments, the nucleotide can comprise a blocking group and a label. In some embodiments, both the blocking group and the label can be linked to the base moiety, while the 3' hydroxyl group is not modified. In some embodiments, the blocking group can be a photocleavable group linked to the base of the nucleotide. See, e.g., U.S. Publication No. 2008/0132692, published Jun. 5, 2008. Further examples of nucleotides comprising extension blocking groups and methods of their use in polymerase-based applications can be found, for example, in U.S. Pat. No. 7,078,499 issued Jul. 18, 2006; as well as in U.S. Published Application Nos. 2004/0048300 published Mar. 11, 2004; 2008/0132692 published Jun. 5, 2008; 2009/0081686, published Mar. 26, 2009; and 2008/0131952, published Jun. 5, 2008; Tsien, WO/1991/006678; Stemple, U.S. Pat. No. 7,270,951, Balasubramanian, U.S. Pat. No. 7,427,673; Milton, U.S. Pat. No. 7,541,444.

In some embodiments, the nucleotide comprises a cleavable label linked to the base. In some embodiments, the blocking group and the label can be removed via the same cleavage treatment. See, e.g., U.S. Pat. No. 7,553,949, issued Jun. 30, 2009. Alternatively, different treatments can be required to remove the blocking group and the label. In some embodiments, the label of the reversible terminator correlates with the base identity of the nucleotide. In some embodiments, each reversible terminator is added sequentially to the polymerase reaction; alternatively, different kinds of reversible terminators can be present simultaneously in the reaction mixture.

In some embodiments, the blocking group is linked to the 2' hydroxyl group of the sugar moiety. See, e.g., U.S. Pat. No. 7,553,949, issued Jun. 30, 2009.

In some embodiments, the reversible terminator can comprise more than one blocking group. In some embodiments, these multiple blocking groups may function cooperatively by enhancing the termination efficiency of the nucleotide. In one exemplary embodiment, the nucleotide comprises a blocking group linked to the base moiety, while another group linked to the terminal phosphate group further suppresses the incorporation of a nucleotide onto the free 3' hydroxyl group. See, e.g., U.S. patent application Ser. No. 12/355,487, filed Jan. 16, 2009.

Typically, the labeled polymerase conjugates of the present disclosure can be used to sequence one or more nucleic acid molecules of interest. In an exemplary method, the reversible terminator is incorporated in a template-dependent manner onto the 3' end of an extending nucleic acid molecule by a labeled polymerase conjugate. The incorporated reversible terminator is detected and identified; and the blocking group of the reversible terminator is then removed. In some embodiments, the unincorporated reversible terminators can be washed away; in some embodiments, it is not necessary to wash or otherwise remove the unincorporated reversible terminators prior to detection, identification or subsequent extension of the extending nucleic acid molecule. In some embodiments, incorporation of the reversible terminator onto the end of a nucleic acid molecule can involve the formation of a covalent bond between the reversible terminator and the nucleotide moiety at the 3' end of the nucleic acid molecule. Alternatively, incorporation of reversible terminator onto the end of a nucleic acid molecule will not involve formation of any covalent bond between the reversible terminator and the nucleotide moiety at the 3' end of the nucleic acid molecule; instead, the reversible terminator is bound in a template-dependent fashion and positioned within the active site of the polymerase until the blocking group is cleaved or otherwise removed, following which the remaining portion of the reversible terminator can remain as a portion of the extending nucleic acid molecule or alternatively will also dissociate from the polymerase active site and diffuse away.

In some embodiments, the nucleic acid molecule, the polymerase, or both, may be isolated within a suitable nanostructure. In some embodiments, the nanostructure can be useful in elongating the nucleic acid molecule to permit visualization of nucleotide synthesis along some or all of the length of the nucleic acid molecule. In some embodiments, the nanostructure is also useful in limiting the amount of background signal ("noise") in the system by reducing the excitation or detection volume, and/or by reducing the amount of labeled moieties present within the reaction chamber. In some embodiments, the nanostructure is designed to admit only a single polymeric molecule and elongate it as it flows through the nanostructure. Suitable devices comprising nanostructures that may be used to practice the inventions disclosed herein are described, for example, in U.S. Pat. Nos. 6,635,163; 7,217,562, U.S. Pub. No. 2004/0197843 and U.S. Pub. No. 2007/0020772. In some embodiments, the nanostructures of the nanofluidic device will satisfy three requirements: (1) they will have a sufficiently small dimension to elongate and isolate macromolecules; (2) they will be sufficient length to permit instantaneous observation of the entire elongated macromolecule; and (3) the nanochannels or other nanostructures will be sufficiently numerous to permit simultaneous and parallel observation of a large population of macromolecules. In one embodiment, the radius of the component nanostructures of the nanofluidic device will be roughly equal to or less than the persistence length of the target DNA. Suitable methods of detecting nucleotide incorporations using nanostructures are disclosed, for example, in U.S. Provisional Application Nos. 61/077,090, filed Jun. 30, 2008; 61/089,497, filed Aug. 15, 2008; and 61/090,346, filed Aug. 20, 2008; and International Application No. PCT/US09/49324, filed Jun. 30, 2009.

Signal Detection

In some embodiments, the label of the disclosed labeled conjugates can emit, or cause to be emitted, a signal that permits visualization of the conjugate and/or provides an indication of biomolecular activity.

Particular disclosed herein are compositions, methods and systems relating to labeled polymerase conjugates, wherein the conjugate emits, or causes the emission of, a signal indicating a nucleotide incorporation by the polymerase of the conjugate.

In some embodiments, the signal is an optically detectable signal. Optionally, the optically detectable signal can be a fluorescent signal.

The signal emitted, or caused to be emitted by the labeled conjugates of the disclosed compositions, methods and systems can be detected and analyzed using any suitable methods and related devices. A wide variety of detectors are available in the art. Representative detectors include but are not limited to optical readers, high-efficiency photon detection systems, photodiodes (e.g. avalanche photo diodes (APD); APD arrays, etc.), cameras, charge couple devices (CCD), electron-multiplying charge-coupled device (EMCCD), intensified charge coupled device (ICCD), photomultiplier tubes (PMT), a multi-anode PMT, and a confocal microscope equipped with any of the foregoing detectors. Where desired, the subject arrays can contain various alignment aides or keys to facilitate a proper spatial placement of each spatially addressable array location and the excitation sources, the photon detectors, or the optical transmission element as described below.

The systems and methods can detect and/or measure a change or an amount of change of an optical or spectral characteristic of a signal (e.g., fluorescence or quenching) from a label. In some embodiments, the label can be the label of the conjugate or a nucleotide label. The change in the signal can include changes in the: intensity of the signal; duration of the signal; wavelength of the signal; amplitude of the signal; duration between the signals; and/or rate of the change in intensity, duration, wavelength or amplitude. The change in the signal can include a change in the ratio of the change of the energy transfer donor relative to change of the energy transfer acceptor signals.

In some embodiments, the detection system comprises: excitation illumination, optical transmission elements, detectors, and/or computers.

The detection system can comprise excitation illumination which can excite the energy transfer or reporter moieties which produce a detectable signal. The excitation illumination can be electromagnetic energy, such as radio waves, infrared, visible light, ultraviolet light, X-rays or gamma rays. The source of the electromagnetic radiation can be a laser, which possesses properties of mono-chromaticity, directionality, coherence, polarization, and/or intensity. The laser can produce a continuous output beam (e.g., continuous wave laser) or produce pulses of light (e.g., Q-switching or mode-locking). The laser can be used in a one-photon or multi-photon excitation mode. The laser can produce a focused laser beam. The wavelength of the excitation electromagnetic radiation can be between about 325-850 nm, or between about 325-752 nm, or between about 330-752 nm, or between about 405-752 nm. The laser can be generated by a mercury, xenon, halogen, or other lamps.

The wavelength and/or power of the excitation illumination can be selected to avoid interfering with or damaging the polymerase enzymatic activities. The excitation illumination can be focused on a stationary position or moved to a different field of view (FOV). The excitation illumination can be directed at a nucleotide incorporation reaction which is: in a liquid volume (e.g., aqueous or oil); on a surface; in or on a nanodevice; in a waveguide; or in an evanescent illumination system (e.g., total internal reflection illumination). The excitation illumination can pass through a transparent or partially transparent surface which is conjugated (covalently or non-covalently) with the components of the nucleotide incorporation reaction.

The energy transfer moiety (e.g., a FRET donor) can be excited by the excitation illumination at a particular wavelength, and transmit the excitation energy to an acceptor moiety which is excited and emits a signal at a longer wavelength. The energy transfer moiety or reporter moiety can undergo multi-photon excitation with a longer wavelength, typically using a pulsed laser.

The detection system comprises suitable optical transmission elements which are capable of transmitting light from one location to another with the desired refractive indices and geometries. The optical transmission elements transmit the excitation illumination and/or the emitted energy in an unaltered or altered form. The optical transmission elements include: lens, optical fibers, polarization filters (e.g., dichroic filters), diffraction gratings (e.g., etched diffraction grating), arrayed waveguide gratings (AWG), optical switches, mirrors, dichroic mirrors, dichroic beam splitter, lenses (e.g., microlens and nanolens), collimators, filters, prisms, optical attenuators, wavelength filters (low-pass, band-pass, or high-pass), wave-plates, and delay lines, or any combination thereof.

The detection system comprises suitable detectors which are capable of detecting and/or distinguishing the excitation illumination and/or the emitted energy. A wide variety of detectors are available in the art, including: single or multiple channel detectors, high-efficiency photon detection systems, optical readers, charge couple devices (CCD), photodiodes (e.g. avalanche photo diodes (APD)), APD arrays, cameras, electron-multiplying charge-coupled device (EMCCD), intensified charge coupled device (ICCD), photomultiplier tubes (PMT), multi-anode PMT, complementary metal oxide semiconductor (CMOS) chip(s), and a confocal microscope equipped with any of the foregoing detectors. The location of the nucleotide incorporation reaction can be aligned, with respect to the excitation illumination and/or detectors, to facilitate proper optical transmission.

Suitable detection methods can be used for detecting and/or distinguishing the excitation illumination (or change in excitation illumination) and/or the emitted energy (or change in emitted energy), including: confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, multi-foci multi-photon, or any combinations thereof.

The signals emitted from different energy transfer moieties can be resolved using suitable discrimination methods which are based on: fluorescence resonance energy transfer measurements; photoconversion; fluorescent lifetime measurements; polarization; fluorescent lifetime determination; correlation/anti-correlation analysis; Raman; intensity; ratiometric; time-resolved methods; anisotropy; near-field or far field microscopy; fluorescence recovery after photobleaching (FRAP); spectral wavelength discrimination; measurement and separation of fluorescence lifetimes; fluorophore identification; background suppression, parallel multi-color imaging, or any combination thereof. See, for example, J. R. Lakowitz 2006, in: "Principles of Fluorescence Spectroscopy", Third Edition. If the different nucleotides are labeled with different energy transfer or reporter moieties, then resolving the emitted signals can be used to distinguish between the different nucleotides which bind the polymerase and/or which are incorporated by the polymerase.

In one embodiment, a system and method for detecting radiation emitted by an excited energy transfer or reporter moiety comprises: an illumination source (e.g., a laser) which produces the excitation energy (e.g., one or multi-photon excitation radiation) which is directed, via a dichroic beam splitter, through a lens, and through a transparent surface or onto a surface, where the nucleotide binding reaction or the nucleotide incorporation reaction is attached to the surface or is in a solution. The excitation illumination excites the energy transfer or reporter moiety (e.g., fluorescent dye and/or nanoparticle) resulting in emitted radiation (or a change in radiation) which passes back through the dichroic beam splitter and is directed to the detector (or an array of detectors) which is capable of identifying and/or resolving the type of emission. Information about the detected emitted signals is directed to the computer where the information is registered and/or stored. The computer can process the registered and/or stored information to determine the identity of the nucleotide which bound the polymerase or the identity of the incorporated nucleotide.

In one aspect, the system and method for detecting radiation emitted by an excited energy transfer or reporter moiety includes a multifluorescence imaging system. For example, the different nucleotides may each be linked to different FRET acceptor moieties. The FRET acceptor moieties can be selected to have minimal overlap between the absorption and emission spectra, and the absorption and emission maxima. The multifluorescence imaging system can simultaneously (or substantially simultaneously) detect signals from the FRET acceptor moieties, and resolve the signals. Such multifluorescent imaging can be accomplished using suitable filters, including: band pass filters, image splitting prisms, band cutoff filters, wavelength dispersion prisms, dichroic mirrors, or diffraction gratings, or any combination thereof.

In another aspect, the multifluorescence imaging system is capable of detecting the signals emitted by the different energy transfer and reporter moieties attached to the different nucleotides. Such a system can include special filter combinations for each excitation line and/or each emission band. In one embodiment, the detection system includes tunable excitation and/or tunable emission fluorescence imaging. For tunable excitation, light from a light source can pass through a tuning section and condenser prior to irradiating the sample. For tunable emissions, emissions from the sample can be imaged onto a detector after passing through imaging optics and a tuning section. The tuning sections can be controlled to improve performance of the system.

In yet another aspect, the detection system comprises an optical train which directs signals emitted from an organized array onto different locations of an array-based detector to detect multiple optical signals from multiple locations. The optical trains typically include optical gratings and/or wedge prisms to simultaneously direct and separate signals having differing spectral characteristics from different addressable locations in an array to different locations on an array-based detector, e.g., a CCD.

In another aspect, the detection methods include detecting photon bursts from the labeled nucleotides during incorporation. The photon bursts can be the fluorescent signals emitted by the energy transfer moiety which is linked to the nucleotide. The photon bursts can be a FRET event. The methods can additionally include analyzing the time trace of the photon bursts. The methods can be practiced using time-resolved fluorescence correlation spectroscopy.

Nucleotide incorporation reactions using nucleotides labeled at the terminal phosphate with a fluorescent dye have been previously demonstrated (Sood, U.S. published patent application No. 2004/0152119; and Kumar, U.S. Pat. No. 7,393,640). Furthermore, fluorescence detection of single molecule nucleotide incorporation reactions has been routinely obtained (Kao, U.S. Pat. No. 6,399,335; and Fuller, U.S. Pat. No. 7,264,934).

The nucleotide labeling strategy can be used as a basis for selecting any suitable detection system for detecting and/or resolving signals emitted by the nucleotide binding reaction or the nucleotide incorporation reaction. Exemplary labeling and detection strategies include but are not limited to optical train and TIRF detection methods such as those disclosed by Harris in U.S. Pat. No. 6,423,551; and U.S. Pub. Nos. 2006/0176479, 2007/0109536, 2007/0111350, and 2007/0250274.

Once FRET events have been identified, they can be analyzed to determine the order and sequence of nucleotide incorporations, thereby determining some or all of the sequence of the nucleic acid template that is acted upon by the polymerase. In some embodiments, the FRET events are then computationally filtered to determine the nature of the underlying event and/or to identify the substrate. In another exemplary embodiment, detection events can be analyzed to determine sequence information using the procedure described in Example 6.

Also provided herein are kits for conducting the nucleotide binding reactions and/or the nucleotide incorporation reactions described herein. The kits can include, in one or more containers, the components of nucleotide binding and/or nucleotide incorporation disclosed herein, including: labeled biomolecule conjugates, labeled polymerase conjugates, nucleotides, target nucleic acid molecules (e.g., a control test target molecules), primers, and/or oligonucleotides.

In some embodiments, the kit comprises a labeled polymerase conjugate according to the present disclosure. Optionally, the kit can further include a nucleotide. The nucleotide can be a labeled nucleotide. In some embodiments, the nucleotide includes a polyphosphate chain. The nucleotide label can optionally be attached to the terminal phosphate group of the nucleotide.

In the kits, the solid surfaces, energy transfer moieties, reporter moieties, nanoparticles, polymerases, nucleotides, target nucleic acid molecules, primers, and/or oligonucleotides can be attached to each other in any combination, and/or be unattached. The kits can include positive and/or negative control samples.

Additional components can be included in the kit, such as buffers and reagents. For example, the buffers can include Tris, Tricine, HEPES, or MOPS, or chelating agents such as EDTA or EGTA. In another example, the reagents can include monovalent ions, such as KCl, K-acetate, NH$_4$-acetate, K-glutamate, NH$_4$Cl, or ammonium sulfate. In yet another example, the reagents can include divalent ions, such as Ca$^{2+}$, CaCl$_2$, Mg$^{2+}$, MgCl$_2$, Mg-acetate, Mn$^{2+}$, MnCl$_2$, and the like. The kits can include the components in pre-measured unit amounts. The kits can include instructions for performing the nucleotide binding reactions and/or the nucleotide incorporation reactions. Where the kit is intended for diagnostic applications, the kits may further include a label indicating regulatory approval for the diagnostic application.

All of the compositions and methods disclosed and claimed herein can be made and executed without undue experimentation in light of the present disclosure. While the compositions and methods of this invention have been described in terms of embodiments, these embodiments are in no way intended to limit the scope of the claims, and it will be apparent to those of skill in the art that variations can be applied to the compositions and/or methods and in the steps or in the sequence of steps of the methods described herein without departing from the concept, spirit and scope of the invention. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope and concept of the invention as defined by the appended claims.

EXAMPLES

Example 1: Preparation of Dye-Labeled Polymerase Using Biotin-Avidin Binding Pairs This Example illustrates the preparation of an exemplary labeled polymerase conjugate comprising streptavidin labeled with a Cy3B dye moiety linked to biotinylated Phi29 polymerase.

To prepare Cy3B labeled streptavidin, 25 mg of streptavidin were dissolved in 5 ml of water and the solution was filtered through a 0.2 micrometer filter. To this solution was added 2 ml of a freshly prepared 1M sodium bicarbonate, followed by 700 µl of a solution of 5 mg Cy3B NHS ester in DMSO. The solution was mixed and allowed to react at room temperature for 3 hours with occasional mixing. A small amount of precipitate formed and was removed by centrifugation and the resulting mixture was processed through multiple rounds of ultrafiltration using 10,000 MWCO ultrafiltration devices and PBS as the buffer. The ultrafiltration was continued until the filtrate did not show any traces of free dye by absorbance measurements. The resulting solution was characterized by measuring its UV absorbance and the degree of dye loading was determined from the known molar extinction coefficients of the Cy3B and streptavidin. The degree of loading thus calculated was 3.9 dyes/molecule of streptavidin. The product was stored at 4° C.

The Cy3B labeled streptavidin was conjugated to biotinylated Phi29 polymerase using biotin-avidin binding to generate a linkage comprising one or more biotin-avidin bonds. Briefly, biotinylated Phi29 was obtained by bacterial expression using the AviTag™ system. The resulting biotinylated Phi29 protein is modified by a single biotin residue located at a predetermined site close to the N-terminus of the protein. In addition, the expressed polymerase contains a hexahistidine tag. Conjugation was performed by mixing 150 µl of 85 µM of the biotinylated Phi29 with 250 µl of PBS buffer. To this was added 40 µl of 5M NaCl followed by 250 µl of 94 µM Cy3B labeled streptavidin. The mixture was mixed and allowed to react for 1 hour at 4° C. A small amount of precipitation was removed by centrifugation and then the mixture was loaded onto a 1 ml His-Trap cartridge, pre-equilibrated with PBS buffer. The cartridge was washed with PBS buffer until no more free, dye-labeled streptavidin was eluting, whereupon the desired reaction product was eluted from the column using a solution of 500 mM imidazole in PBS. The product thus obtained was dialyzed overnight against a buffer containing 50 mM TrisHCl pH 7.5, 150 mM NaCl, 5 mM DTT, 0.1% Tween 20, 0.2 mM EDTA and 50% glycerol.

Example 2: Evaluation of Nucleotide Binding and Discrimination Activity of Dye-Labeled Polymerase The ability of a dye-labeled polymerase prepared according to the method of Example 1, above, to discriminate between a "correct" and an "incorrect" incoming, dye-labeled nucleotide polyphosphate when bound to a primed template was evaluated. Solely in the context of this Example, the term "correct" is used to refer to a nucleotide that can undergo Watson-Crick base pairing with the nucleotide of the template that is immediately adjacent to the 3' end of the primer, whereas "incorrect" refers to any nucleotide that is not capable of undergoing such Watson-Crick base pairing with the nucleotide of the template. In this assay, the template and primers were selected such that a nucleotide polyphosphate comprising an adenosine as the nucleobase would be the "correct" nucleotide.

In a typical experiment, serial dilutions of AF647 labeled deoxyguanosine hexaphosphate, wherein the AF647 label is attached to the terminal phosphate group (referred to herein as "omega-labeled AF647-dG6P" or simply as "wAF647-dG6P") were prepared in the wells of a microtiter plate, in a buffer containing 50 mM TrisHCl pH 7.5, 50 mM NaCl and either 2 mM MnCl$_2$ or 10 mM CaCl$_2$. The highest final concentration of the labeled nucleotide was 4 µM. Aliquots of solutions of preformed complexes between a dye-labeled streptavidin-biotin Phi29 and different primer-template duplexes were added. (Note: The primer-template duplexes can be replaced by suitable hairpin-type oligonucleotides comprising a 5' single stranded overhang). In some experiments, the 3' ends of the primer strands included dideoxy-modified residues in order to prevent the enzymatic elongation of the primers by the polymerase.

Figure 4A:
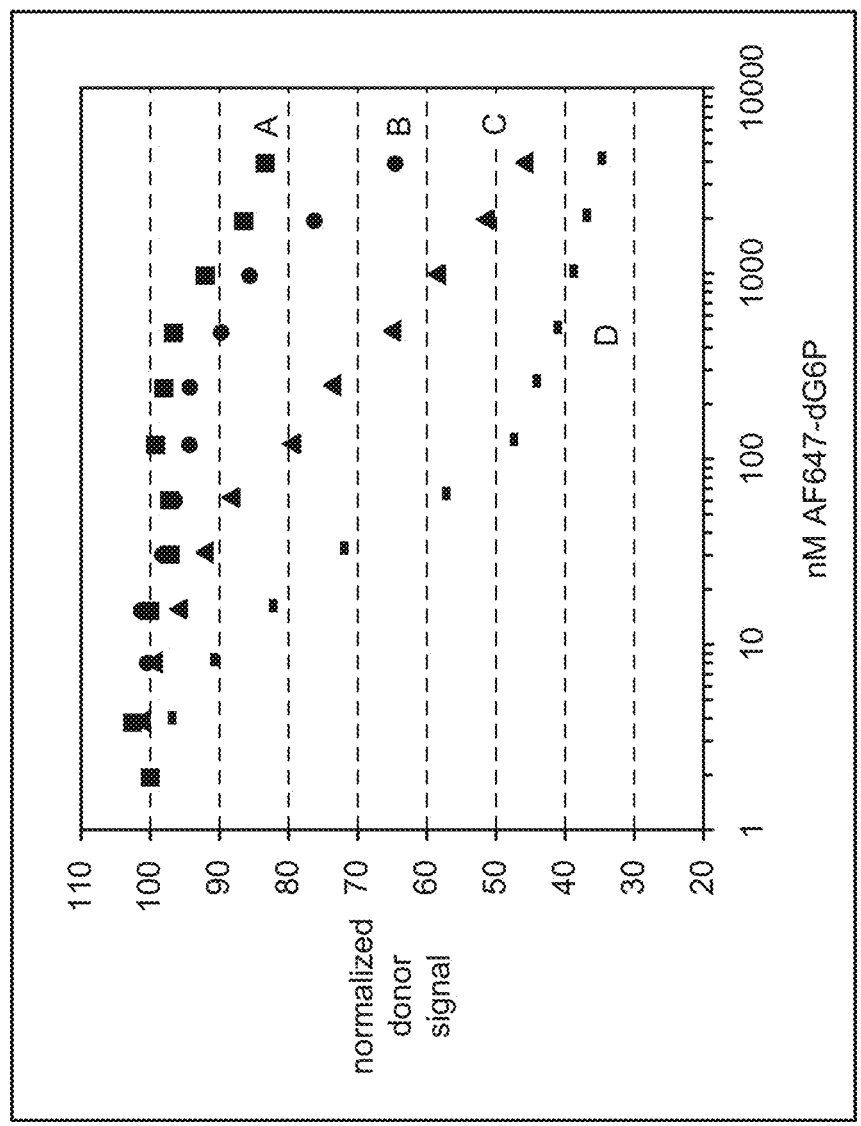
FIG. 4A depicts the results of a nucleotide binding assay using a labeled polymerase conjugate according to the methods described in Example 2, and shows normalized donor signal from the binding assay using a dye-labeled polymerase and a labeled nucleotide.
Figure 4B:
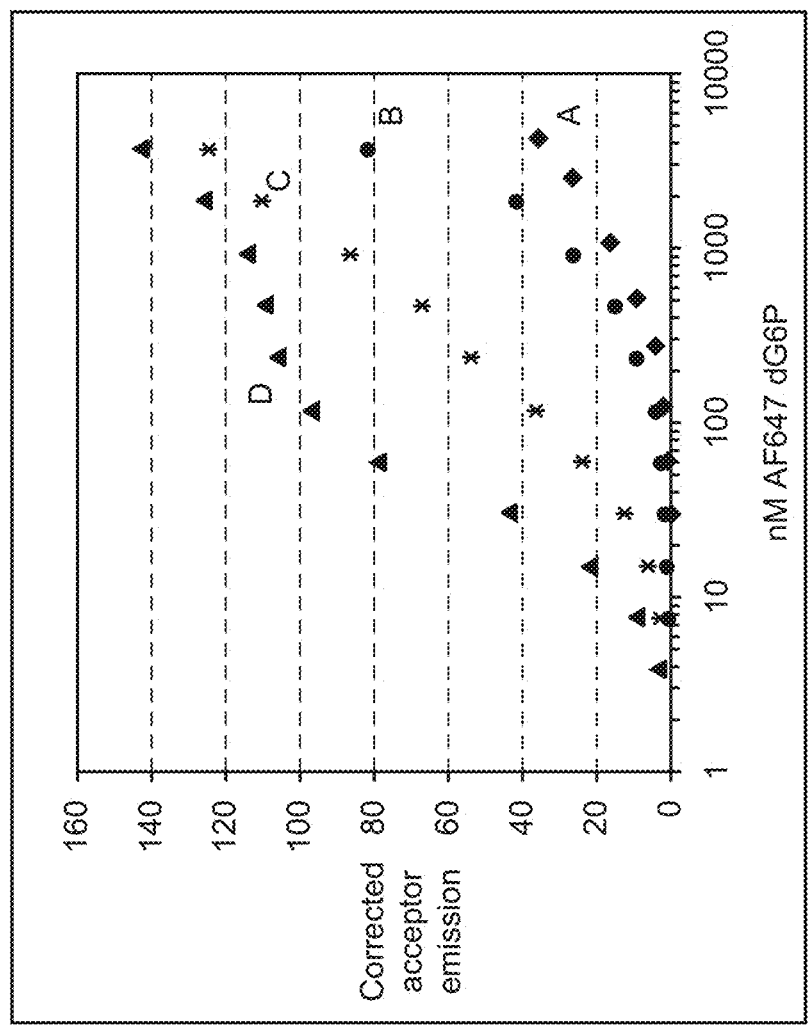
FIG. 4B depicts the results of a nucleotide binding assay using a labeled polymerase conjugate according to the methods described in Example 2, and shows corrected acceptor emission from the binding assay using a dye-labeled polymerase and a labeled nucleotide.

The resulting ternary complexes between the dye-labeled polymerase, the primer-template duplex (or alternatively the self-priming hairpin oligonucleotide) and the labeled nucleotide can be detected by measuring the fluorescence resonance energy transfer (FRET) signal between the dye of the dye-labeled polymerase (in this case, Cy3B) and the dye linked to the terminal phosphate group of the nucleotide (in this case AF647). The results from such a binding experiment are shown in FIGS. 4A and B. The individual curves depicted in FIGS. 4A and B are: Curve A: "incorrect" nucleotide, Mn$^{2+}$ buffer; Curve B: "incorrect" nucleotide, Ca$^{2+}$ buffer; Curve C: "correct' nucleotide, Mn$^{2+}$ buffer; Curve D: "correct" nucleotide, Ca$^{2+}$ buffer. These results indicate that the affinity of the polymerase for the correct incoming nucleotide is greater than the affinity for the incorrect nucleotide, and that the binding event can be detected by the resulting FRET between the donor and acceptor dyes. In addition, these results indicate that better discrimination can be achieved in a buffer containing $Ca^{2+}$ compared to a buffer containing $Mn^{2+}$.

Example 3: Preparation of a Dye-Labeled Polymerase Comprising Different Types of Labels A labeled polymerase conjugate comprising two different types of dye labels, Alexa Fluor 488 and Cy3B, linked to Phi-29 polymerase was prepared. To prepare the conjugate, 50 µl of an 85 µM solution of biotin Phi29 was added to 180 µl of 34 µM AF488 labeled streptavidin solution, followed by 150 ml of PBS buffer. The mixture was left at 40° C. for one hour and then loaded onto a His-Trap column. The excess free labeled streptavidin was removed by washing the column with PBS, whereupon a solution of 50 mM Cy3B-biotin was introduced into the column. The excess Cy3B-biotin was washed off with PBS buffer and the conjugate was eluted with 500 mM imidazole in PBS buffer. The resulting product was dialyzed against the same buffer described above. The presence of two different dyes in the final product was confirmed by UV absorbance measurements (data not shown).

Figure 5:
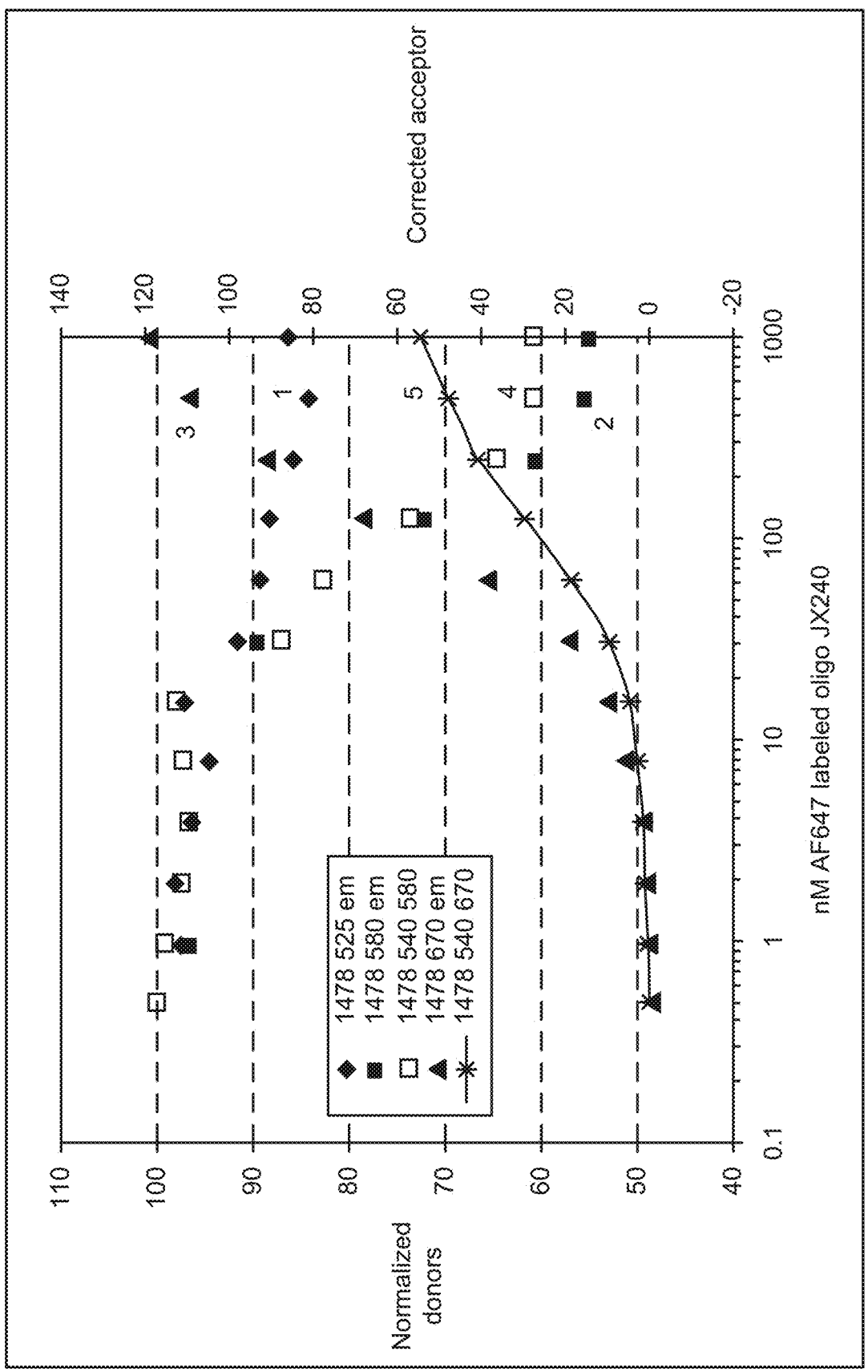
FIG. 5 depicts the results of a nucleic acid binding assay using a labeled polymerase conjugate according to the methods described in Example 3.

The polymerase activity of the resulting conjugate was evaluated in a nucleic acid binding assay using an AF647-labeled DNA molecule. Serial dilutions of the latter (starting at 1 µM) were mixed with 120 nM of the resulting AF488/Cy3B-streptavidin-biotin-Phi-29 conjugate. The resulting FRET was measured using two different excitation wavelengths: 490 and 540 nm, with the emission being measured at both 580 and 670 nm. The results are depicted in FIG. 5. The five binding curves depicted in FIG. 5 representing the following: Curve 1: Excitation at 490 nm and emission at 525 nm; Curve 2: Excitation at 490 nm and emission at 580 nm; Curve 3: Excitation at 490 nm and emission at 670 nm; Curve 4: Excitation at 540 nm, emission at 580 nm; and Curve 5: Excitation at 540 nm and emission at 670 nm. As depicted in FIG. 5, the use of an excitation wavelength of 490 nm results in substantially higher acceptor emission signals at 670 nm than use of an excitation wavelength at 540 nm, with reduced donor emission ("bleed-through") in the acceptor channel.

Example 4: Preparation of a Labeled Polymerase Conjugate Comprising a Single Label Covalently Attached to a Polymerase 80 µL of an 111 µM stock solution of His-tagged polymerase comprising the amino acid sequence of SEQ ID NO: 34 (referred to herein as "HP1-B104 exo-polymerase") in 10 mM Tris (pH 7.5), 100 mM NaCl, 4 mM DTT, 0.5% v/v Tween-20, 0.1 mM EDTA and 50% v/v glycerol) was buffer exchanged into 1× phosphate buffered saline (1×PBS) pH 7.4 with additional 200 mM NaCl using an NAP-5 column.

The buffer-exchanged His-tagged polymerase (150 µL, 18.9 µM in 1×PBS pH 7.4 with additional 200 mM NaCl) was mixed with 800 µL of a buffer comprising 1×PBS buffer, pH 7.4 and 200 mM NaCl. The mixture was added into a vial containing 6.5 µL of 1.3 mM Cy3B NHS ester in DMSO in a 3:1 dye to polymerase molar ratio. The reaction solution was mixed and rotated at 4° C. for 2 hour, and then centrifuged for 5 minutes at 16.8K rcf. The supernatant was loaded by a syringe onto a Ni-NTA cartridge that was previously washed by ~6 mL water and then by ~6 mL of 100 mM Tris buffer (pH 7.5) with 300 mM NaCl and 1 mM DTT. The column was continuously washed with 100 mM Tris buffer (pH 7.5) with 300 mM NaCl and 1 mM DTT to completely remove the unbound dye. The conjugate retained on the column during the wash was eluted from the cartridge by using 100 mM Tris buffer (pH 7.5) with 0.5 M imidazole, 300 mM NaCl and 1 mM DTT. The solution collected from the cartridge was centrifuged and transferred into a 10K MWCO dialysis cassette. The solution was then dialysized at 4° C. overnight into a buffer comprising 50 mM Tris buffer pH7.5, 150 mM NaCl, 0.2 mM EDTA, 0.1% v/v Tween-20, 5 mM DTT and 50% v/v glycerol. The dye:enzyme stochiometry of the resulting conjugate preparation was measured using UV absorbance to estimate the concentration of the protein (280 nm) and Cy3B dye (564 nm) and was determined to be about 1 Cy3B dye label per polymerase. This conjugate preparation was assayed to determine concentration, DNA extension activity, and DNA binding by FRET as described below.

Primer extension assays were performed to measure the primer extension activity of the labeled polymerase conjugates. Primer extension activity is quantified by monitoring the fluorescence intensity change over time during extension of a fluorescein-labeled hairpin oligonucleotide, comprising the following nucleotide sequence, known as "oligo 221" (SEQ ID NO: 43 below). The fluorescence intensity correlates with the level of primer extension activty in the sample.

The extension buffer used was 50 mM Tris buffer pH 7.5 with 50 mM NaCl, 10 mM $MgCl_2$ and 0.5 mM $MnCl_2$.

To reaction wells containing 100 µL of 150 nM of a fluorescein-labeled hairpin oligonucleotide, oligo221 (SEQ ID NO: 43), and 10 nM of the labeled polymerase conjugate in extension buffer, 2 µL of 1 mM dATP was added to initiate the extension reaction. Oligo 221 comprises the following sequence:

(SEQ ID NO: 43)
(5'-TTTTTTTGCAGGTGACAGGTTTTTCCTGTCACC(fluorescein-T)GC-3')

The fluorescence intensity in the wells was recorded at 525 nm fluorescence with 490 nm excitation for every 20 second in a 10 minutes period immediately after the addition of dATP. Assay control reaction wells contained the same components but no dATP was added.

To calculate the enzyme activity rate, reference polymerase reaction/control wells were included containing 150 nM fluorescein-labeled oligo-221 and 50 nM free polymerase with 20 µM dATP (for reaction wells) or without 20 µM dATP (for control wells) in the same extension buffer as above. The time course data for conjugate reaction/control and reference polymerase reaction/control is used to calculate the conjugate activity rate using the following equations:

$$\text{turnover\_rate(base/sec)} = \frac{\Delta RFU_{sample}\_\text{per\_sec}}{\Delta RFU_{max}\_\text{per\_nMsubs}} \times \frac{1}{10 \text{ nM}} \times 7(\text{base})$$

$$\text{and } \Delta RFU_{max}\_\text{per\_nMsubs} = \frac{RFU_{max} - RFU_{min}}{\text{substr\_conc.(nM)}}$$

Where: $RFU_{max}$ is the average maximal RFU in the reference polymerase reaction wells;
$RFU_{min}$ is the average minimal RFU in the reference polymerase control wells;
Substr_conc. (nM) is the oligo 221 concentration in assay, which is 150 nM.

$$\Delta RFU_{sample}\_per\_sec = \frac{RFU_t - RFU_0}{t(\sec)}$$

Where: t (sec) is the time period where the fluorescence intensity increases in the conjugate reaction well linearly from the start;

$RFU_t$ is the average RFU of the conjugate extension wells for the tested sample at t second point; and $RFU_0$ is the average RFU of the conjugate extension wells for the tested sample at the start point.

Figure 6:
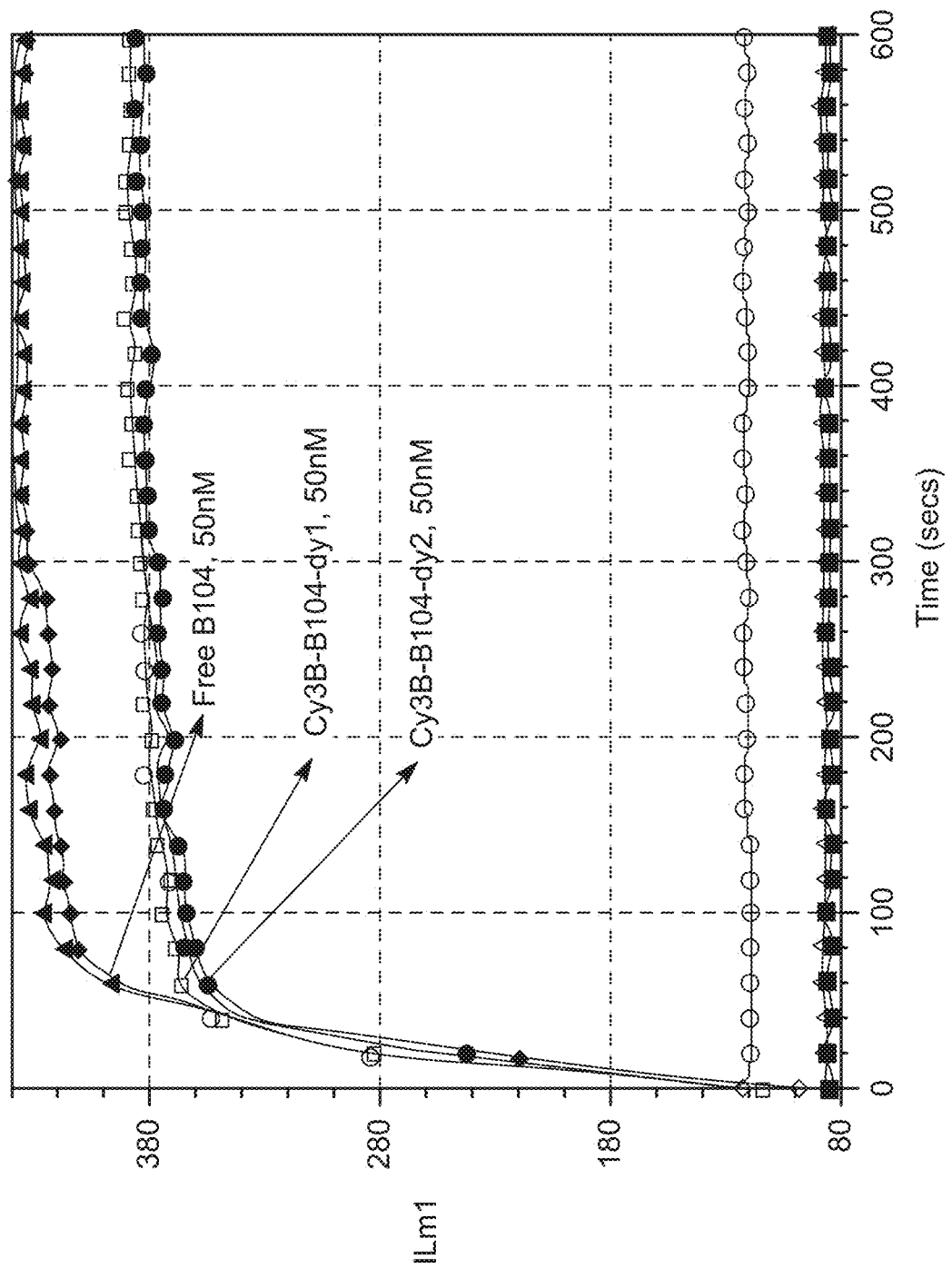
FIG. 6 depicts the results of a primer extension assays using labeled polymerase conjugates according to the methods described in Examples 4 and 5.

Representative results of extension assays comparing the extension observed using the conjugate of this Example and the conjugate of the next Example, as well as using a control (unconjugated) polymerase, are depicted in FIG. 6.

In addition, FRET-based binding assays were performed to evaluate the ability of the conjugates to bind to a nucleic acid template. The assay buffer is 50 mM Tris buffer pH 7.5 with 50 mM NaCl, 10 mM $MgCl_2$ and 0.5 mM $MnCl_2$. 50 µL of 20 nM conjugate was added into each well that contains either 50 µL of ALEXA FLUOR 647 labeled oligonucleotide 199 or 50 µL of ALEXA FLUOR 647 labeled oligonucleotide 192 at various concentrations (2-fold dilution series with concentrations ranging from 1000 nM to 0.49 nM). These oligonucleotides have the following sequences:

```
Oligonucleotide 199:
                                      (SEQ ID NO: 41)
5'-TTATCTTTGTGGGTGACAGGTTTTTCCTGTCACCC-3'-ALEXA
FLUOR 647

Oligonucleotide 192:
                                      (SEQ ID NO: 42)
5'-TTTTTTTGCCCCCAGGGTGACAGGTTTTTCCTGTCACCC-3'-
ALEXA FLUOR 647
```

Figure 7A:
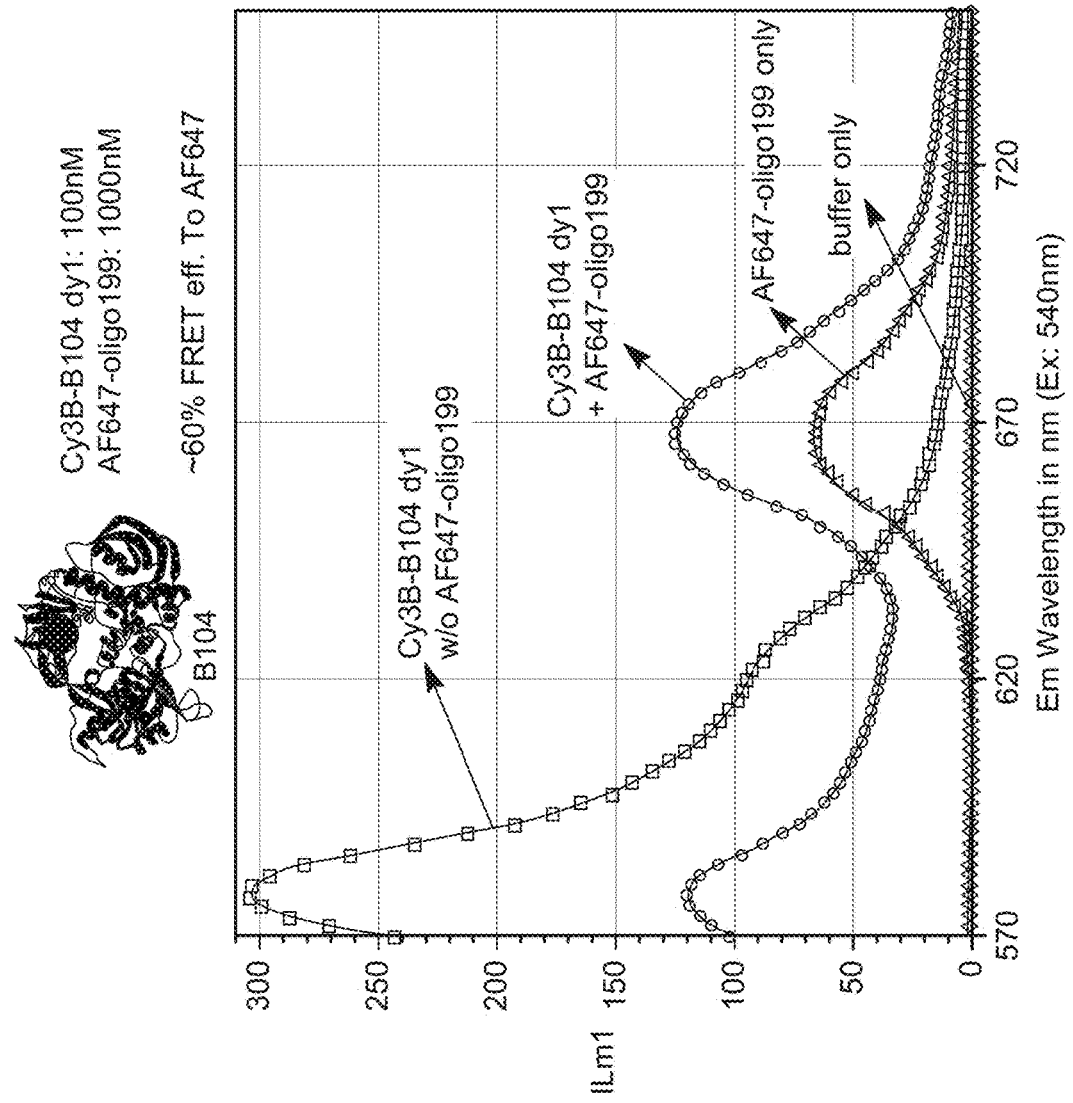
FIG. 7A depicts the results of a nucleic acid binding assay using a labeled polymerase conjugate according to the methods described in Example 4 and 5, and shows the results of a FRET assay using a conjugate carrying an average of one dye per polymerase.

The binding of conjugate to the dye-labeled oligonucleotide was measured by detecting the fluorescence intensity at 670 nm (AF647 acceptor wavelength) and 580 nm (Cy3B donor emission wavelength) with 540 nm excitation (FRET) at various oligonucleotide concentrations. The fluorescence intensity (FIGS. 7A and B, Y axis) was plotted against the fluorescence wavelength (FIGS. 7A and B, X axis). As indicated in FIG. 7A, the conjugate of Example 4 showed high emission at donor wavelengh; in the presence of the acceptor-labeled oligonucleotide, the acceptor fluorescence increased and donor fluorescence decreased. Negative control reactions included the AF-647 labeled oligonucleotide but with no conjugate included, as well as a second control comprising buffer alone. The FRET efficiency was calculated based on the decrease in donor signal after addition of dye-labeled oligonucleotide.

Example 5: Preparation of a Second Labeled Polymerase Conjugate

80 µL of an 111 µM stock solution of His-tagged polymerase comprising the amino acid sequence of SEQ ID NO: 34 (referred to herein as "HP1-B104 exo-polymerase") in 10 mM Tris (pH 7.5), 100 mM NaCl, 4 mM DTT, 0.5% v/v Tween-20, 0.1 mM EDTA and 50% v/v glycerol) was buffer exchanged into 1× phosphate buffered saline (1×PBS) pH 7.4 with additional 200 mM NaCl using an NAP-5 column.

The buffer-exchanged His-tagged polymerase (150 µL, 18.9 µM in 1×PBS pH 7.4 and 200 mM NaCl) was mixed with 800 µL of a buffer comprising 1×PBS pH 7.4 and 200 mM NaCl. The mixture was added into a vial containing 10.8 µL of 1.3 mM Cy3B NHS ester in DMSO in a 5:1 dye to polymerase molar ratio. The reaction solution was mixed and rotated at 4° C. for 2 hour, and then centrifuged for 5 minutes at 16.8K rcf. The supernatant of the conjugation solution was loaded by a syringe onto a Ni-NTA cartridge that was previously washed by ~6 mL water and then by ~6 mL of 100 mM Tris buffer (pH 7.5) with 300 mM NaCl and 1 mM DTT. The column was continuously washed with 100 mM Tris buffer (pH 7.5) with 300 mM NaCl and 1 mM DTT to completely remove the unbound dye. The conjugate retained on the column during the wash was eluted from the cartridge by using 100 mM Tris buffer (pH 7.5) with 0.5 M imidazole, 300 mM NaCl and 1 mM DTT. The solution collected from the cartridge was centrifuged and transferred into a 10K MWCO dialysis cassette. The solution was then dialysized at 4° C. overnight into 50 mM Tris buffer pH7.5 with 150 mM NaCl, 0.2 mM EDTA, 0.1% v/v Tween-20, 5 mM DTT and 50% v/v glycerol. The dye:enzyme stochiometry of the resulting conjugate preparation was measured using UV absorbance to estimate the concentration of the protein (280 nm) and Cy3B dye (564 nm) and was determined to be about 2 Cy3B dye label per polymerase. This conjugate preparation was assayed to determine concentration, DNA extension activity, and DNA binding by FRET as described in Example 4, above.

FIG. 6 shows the results of the extension assays to measure primer extension activity of conjugates prepared according to the method of Example 4 (referred to in FIG. 6 as "Cy3B-B104 dy1" and comprising an average of 1 dye per polymerase) and Example 5 (referred to in FIG. 6 as "Cy3B-B104 dy2" and comprising an average of 2 dyes per polymerase), as well as of a control unconjugated polymerase comprising the amino acid sequence of SEQ ID NO: 34 and further comprising a His-tag and the HP1 linker (referred to in FIG. 6 as "B104"). These results indicate that the negative control reaction wells (no nucleotide) exhibit steady baseline fluorescence level over time compared to conjugate reaction wells or positive control (unconjugated polymerase), which show increasing fluorescence level over time. Based on the fluorescence traces depicted in FIG. 6, the extension activity of the two conjugates was calculated and compared to the extension activity of the positive control (unconjugated polymerase). The results are shown in Table 1, below:

TABLE 1

Extension activity of labeled polymerase conjugates and unconjugated polymerase

| Conjugate | Activity |
|---|---|
| Cy3B-B104 dy1 | 0.41 base/sec/conj |
| Cy3B-B104 dy2 | 0.42 base/sec/conj |
| B104 stock | 0.34 base/sec/enz |

As indicated in Table 1, above, the two conjugates prepared according to the methods of Examples 4 and 5, respectively, exhibited comparable levels of extension activity as compared to the control (unconjugated) polymerase.

Figure 7B:
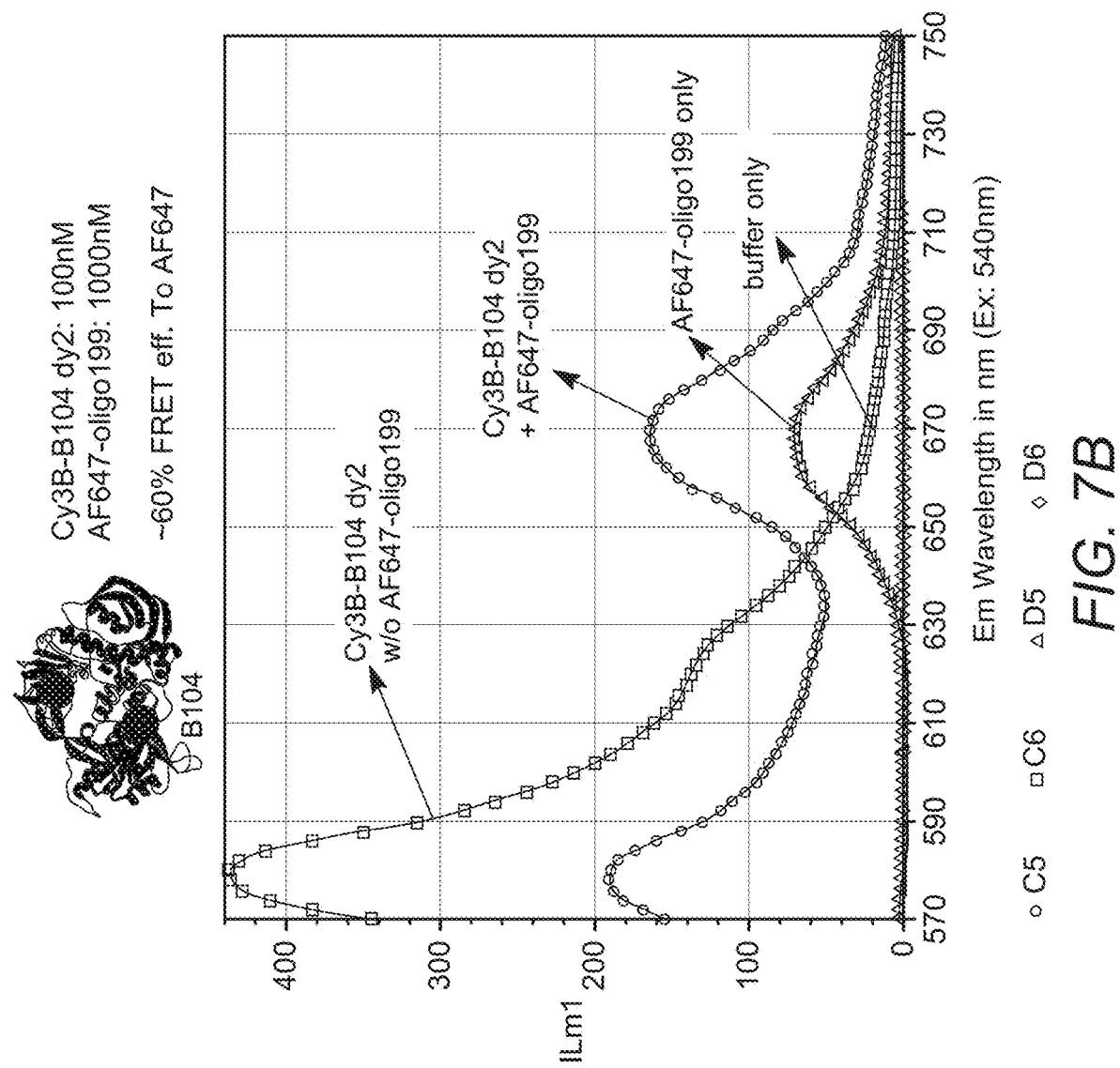
FIG. 7B depicts the results of a nucleic acid binding assay using a labeled polymerase conjugate according to the methods described in Example 4 and 5, and shows the results of a FRET assay using a conjugate carrying an average of two dyes per polymerase.

FIG. 7 depicts the results of the FRET assays to measure DNA binding on conjugates prepared according to the method of Example 4 (referred to in the Figure as "Cy3B-B104 dy1" and comprising an average of 1 dye per polymerase, left panel) and Example 5 (referred to in the Figure as "Cy3B-B104 dy2" and comprising an average of 2 dyes per polymerase, right panel). The binding of conjugate to the dye-labeled oligonucleotide was measured by detecting the fluorescence intensity at 670 nm (AF647 acceptor wavelength) and 580 nm (Cy3B donor emission wavelength) with 540 nm excitation (FRET) at various oligonucleotide concentrations. The fluorescence intensity (FIG. 7, Y axis) was plotted against the fluorescence wavelength (FIG. 7, X axis). As indicated in FIG. 7 (left panel), the conjugate of Example 4 showed high emission at donor wavelength; in the presence of the acceptor-labeled oligonucleotide, the acceptor fluorescence was increased and donor fluorescence decreased. Negative control reactions included the AF-647 labeled oligonucleotide but with no conjugate included, as well as a second control comprising buffer alone. The FRET efficiency was calculated based on the decrease in donor signal after addition of dye-labeled oligonucleotide according to the following formula:

$$\text{FRET\_eff}(\%) = \frac{I_0 - I}{I_0} \times 100$$

where:

$I_0$ is the conjugate's donor fluorescence intensity at the absence of AF647 labeled oligo199;

I is the conjugate's donor fluorescence intensity at the presence of AF647 labeled oligo199.

Using these procedures, the calculated FRET efficiency of each conjugate was approximately 60%. These results indicate that both conjugates comprise donor Cy3B dye linked to the the phi29 polymerase, and that the polymerase of both conjugates retains DNA binding activity with high FRET efficiency to the oligonucleotide acceptor label.

Example 6: Single Molecule Sequencing Using Labeled Polymerases Conjugates

PEG-Biotin Surfaces:

Glass coverslips surfaces were plasma cleaned and treated with a mixture of poly-ethyleneglycol (PEG) and biotin-PEG to produce a low density biotin surface with a PEG coating to prevent non-specific background of proteins and macromolecules.

Fluidic Chamber Assembly:

Fluidic cassettes were assembled with glass coverslips to create fluidic chambers capable of containing approximately 20 ul of fluid.

Attaching Biotinylated DNA to Low Density PEG-Biotin Surfaces:

Streptavidin protein was diluted to 200 pM in incubation buffer (50 mM NaCl; 50 mM Tris-Cl pH=7.5; 0.5% BSA). Diluted streptavidin was flowed into fluidic chamber and left to incubate for 10 minutes. Chambers were washed once with 1 ml incubation buffer. Biotinylated-DNA templates were diluted to 200 pM in incubation buffer and allowed to bind for 5 minutes. Surfaces were washed 1× with 1 ml incubation buffer.

Figure 8:
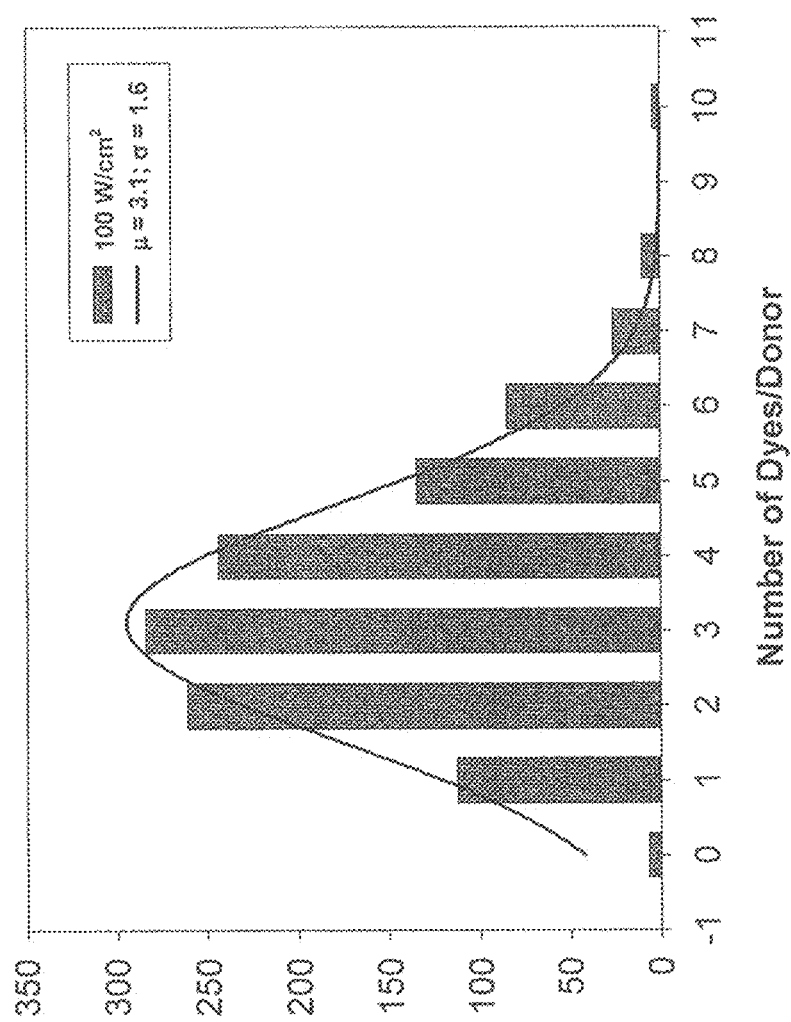
FIG. 8 depicts the dye loading distribution, as measured by UV absorbance, of an exemplary labeled polymerase conjugate.

SA-Polymerase Preparation:

Labeled polymerase conjugates comprising a Phi-29 polymerase comprising the amino acid sequence of SEQ ID NO: 40 was conjugated to Streptavidin-Cy3B according to the methods of Examples 1. Briefly, dye-labeled streptavidin (consisting of Cy3B dye labels linked to streptavidin according to the method of Example 1 and at a average ratio of about 3.1:1=dye:streptavidin) was mixed with biotinylated Phi29 polymerase comprising the amino acid sequence of SEQ ID NO: 3 at a 1:1 ratio in 1× PBS. The dye loading distribution (i.e., relative stochiometry of dye and protein) of the dye-labeled streptavidin preparation was measured using UV absorbance; the results are depicted in FIG. 8.

SA-Cy3B-bPhi29 Binding to Templates:

SA-Cy3B-b-Phi29 was diluted to 1 nM in binding buffer (150 mM NaCl; 50 mM MOPS pH=6.8; 0.3% BSA). Surfaces were incubated for 5 minutes with 1 nM SA-Cy3B-b-Phi29. Surfaces were washed with 1×1 ml incubation buffer.

Figure 9:
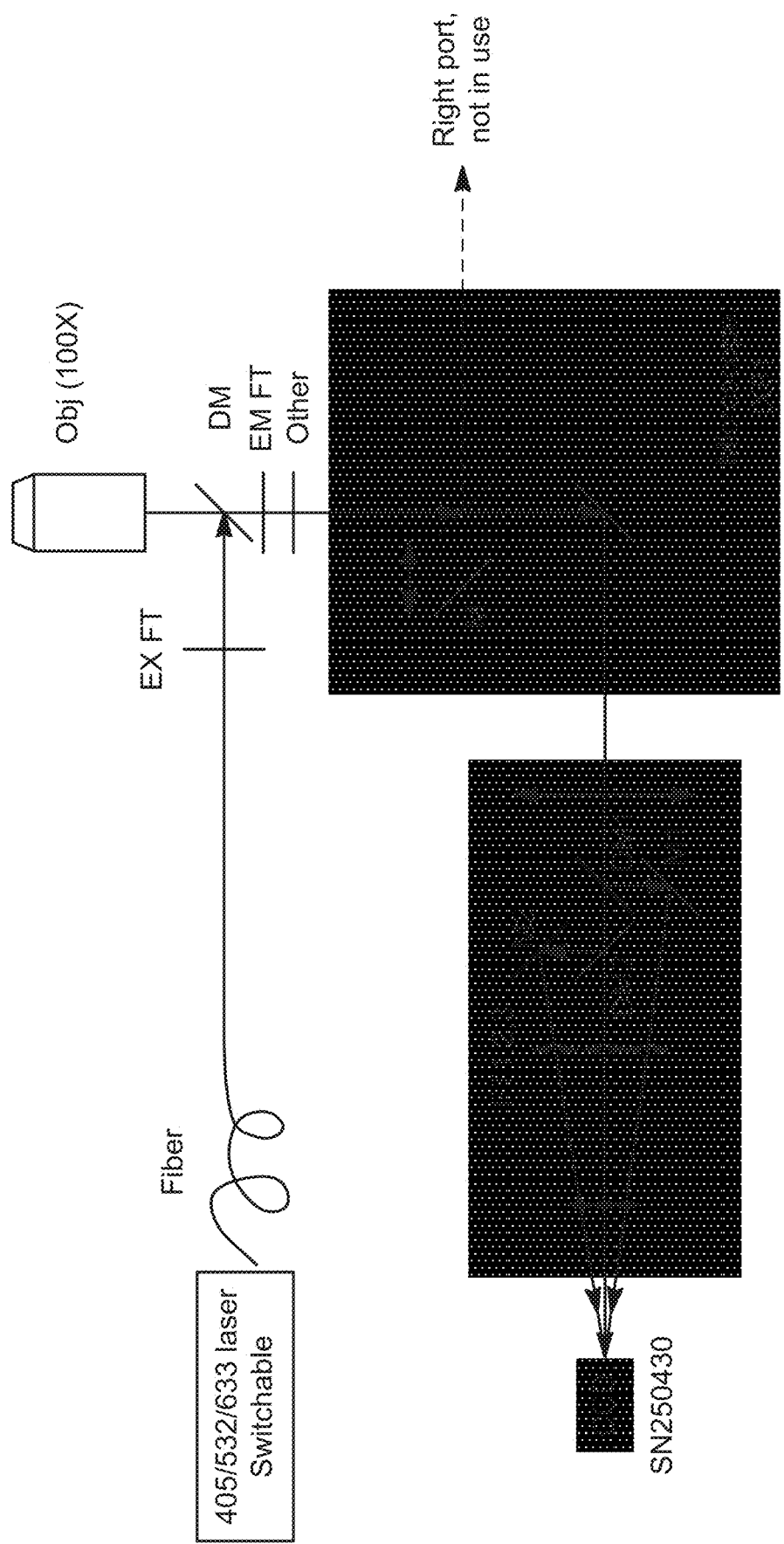
FIG. 9 depicts the detection apparatus used to monitor nucleotide incorporation using an exemplary labeled polymerase conjugate.

Fluorescence Imaging:

The microscope body was purchased from Olympus and was outfitted with a TIRF objective lens (100×; 1.45 NA). The excitation light passes through an excitation filter (EX FT—543/22), and dichroic mirror (DM—532) and the sample was epi-illuminated (Coherent) using TIR at approximately 100 W/cm². Upon excitation, resulting epifluorescence emission was passed through an emission filter (EM FT—540LP) and the resulting emission was split into three paths ("triview" format) using 2 dichroic mirrors and the appropriate bandpass filters for the dye sets of choice. The emission was imaged on a CCD camera. This detection setup is depicted in FIG. 9. Images were collected at a frame rate of approximately 30 ms. Images depict single DNA strands complexed with single SA-Cy3B-bPhi29 conjugates (donor molecules in this Example) and FRET signals from acceptor species (hexaphoshate 647 and/or 680 nucleotides) bound in the enzyme active (not shown).

Figure 10A:
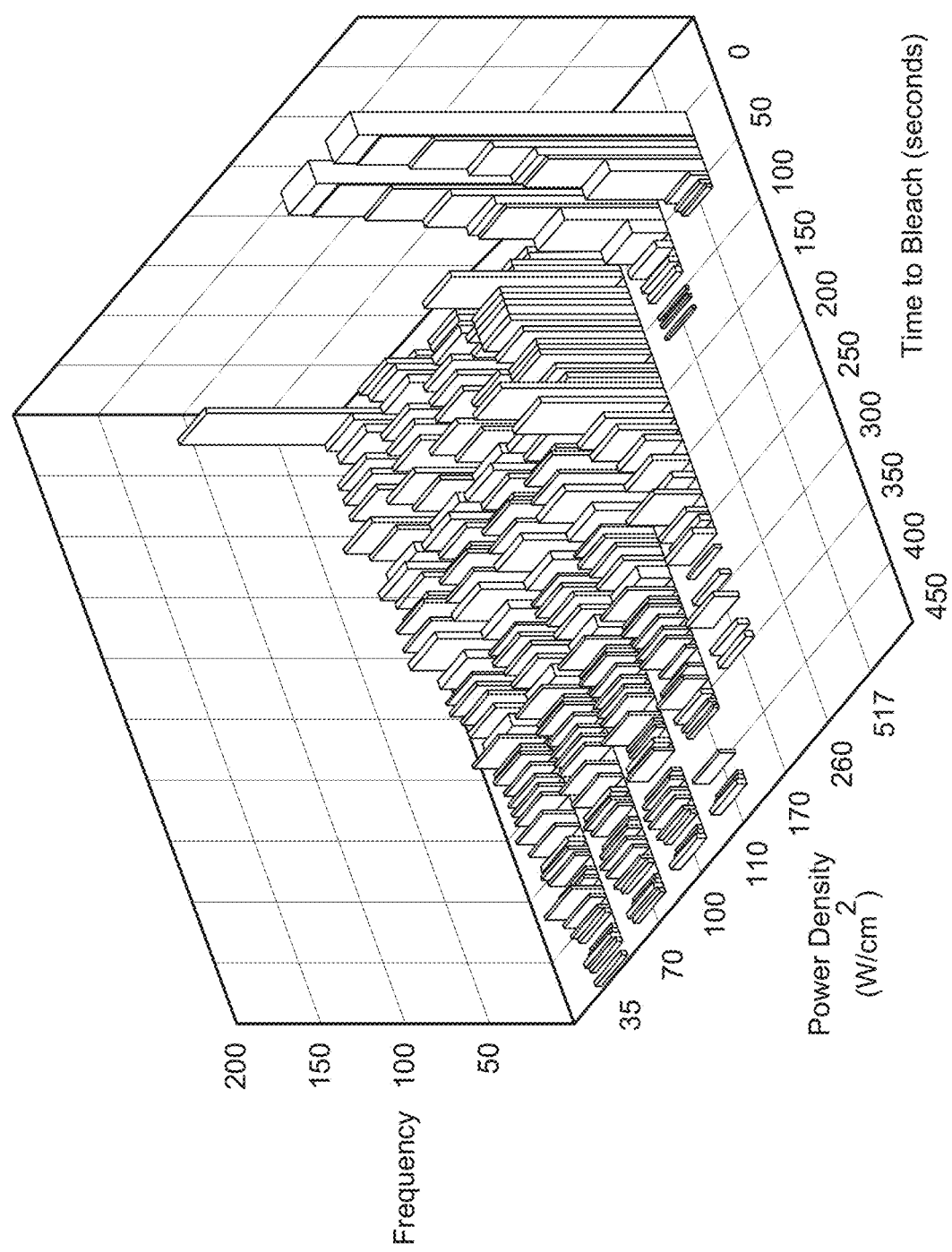
FIG. 10A depicts a graph showing the average donor lifetimes observed using an exemplary labeled polymerase conjugate which is a histogram showing donor lifetimes at different power densities.
Figure 10B:
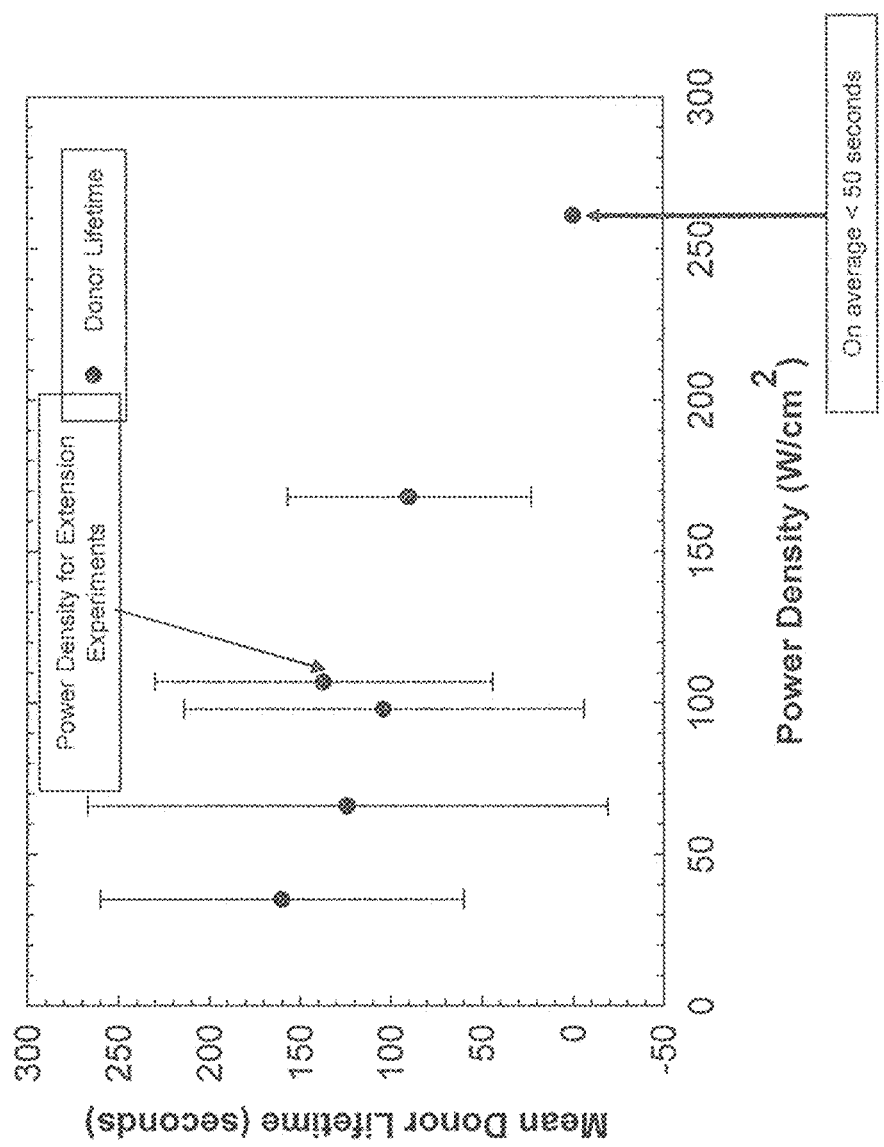
FIG. 10B depicts a graph showing the average donor lifetimes observed using an exemplary labeled polymerase conjugate, which shows a graph plotting power density against mean donor lifetime.

Characterization of Donor Lifetime for SA-Cy3B-Phi29 Conjugates:

The average donor lifetime for the SA-Cy3B-Phi29 at laser power densities relevant for pattern sequencing experiments was characterized. From an estimated 1000 donors per field of view (1000 donors/FOV) at each of the respective power densities, the donor lifetimes before photobleaching were histogrammed at various power densities (FIG. 10A). The average donor lifetime was estimated to be approximately 2 minutes at the power density used for these experiments, 100 W/cm² (FIG. 10B).

Figure 11A:
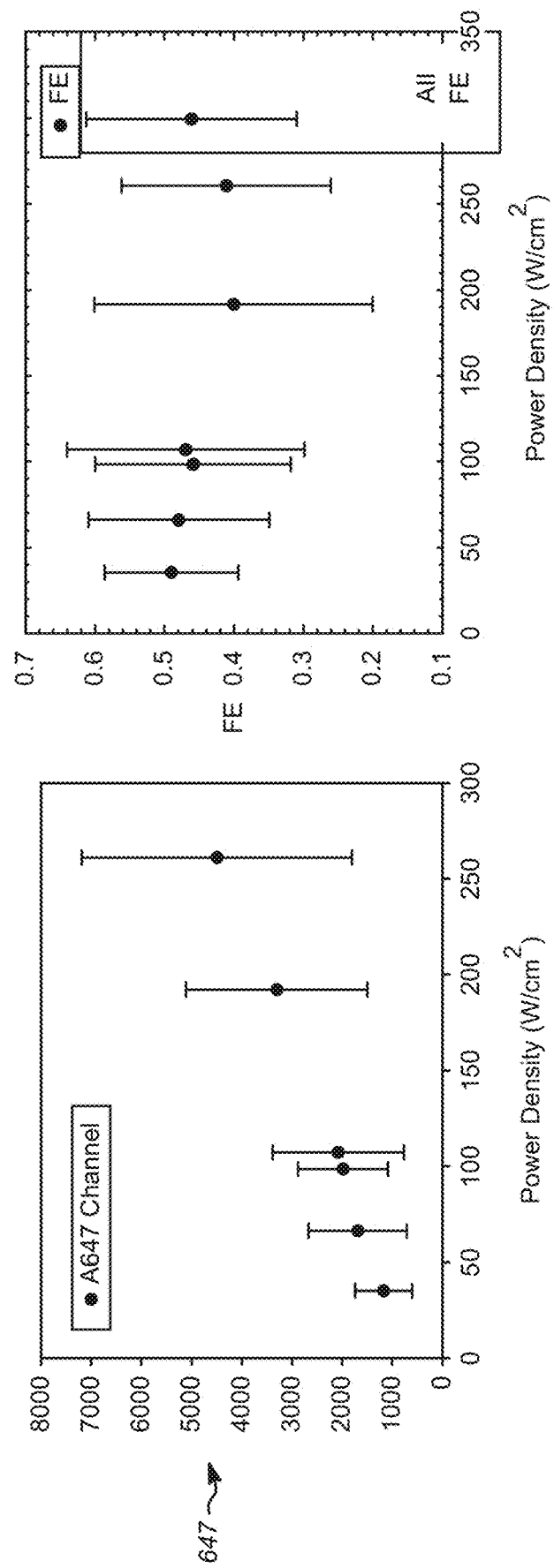
FIG. 11A depicts a graph showing the FRET efficiencies observed using an exemplary labeled polymerase conjugate, which shows a graph of the photon counts using AF647 dye.
Figure 11B:
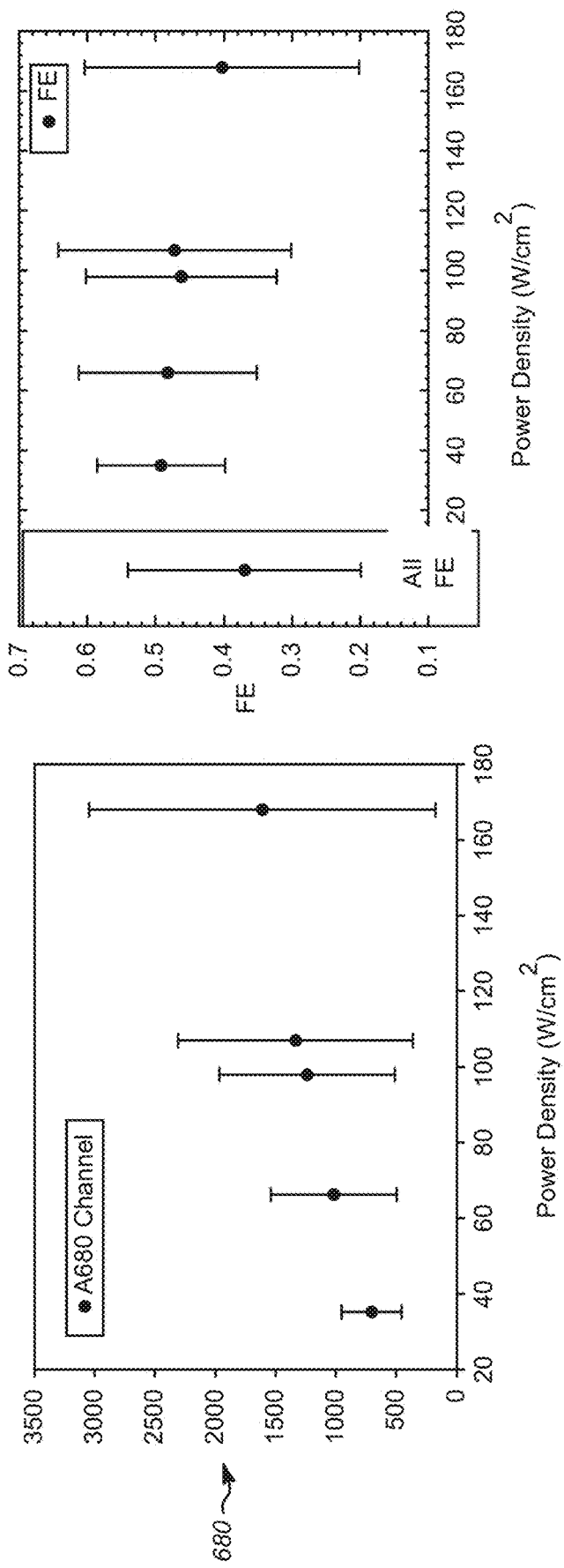
FIG. 11B depicts a graph showing the FRET efficiencies observed using an exemplary labeled polymerase conjugate, which shows a graph of the photon counts using AF680 dye.

In addition, the photon counts to both the 647 and 680 dyes at the relevant excitation powers and the average FRET efficiency for each of these respective dyes were characterized (FIG. 11A). This characterization was performed by trapping the next correct nucleotide in the active site of the enzyme complexed with a DNA strand using calcium. From this experiment, the approximate FRET efficiency for acceptor and donor dye combinations used in FRET based pattern sequencing was deduced (FIG. 11B). The boxed red rectangles in FRET efficiency curves (FIG. 11B) are the FRET efficiency distributions and means for FRET efficiency, calculated at all power densities.

Figure 12:
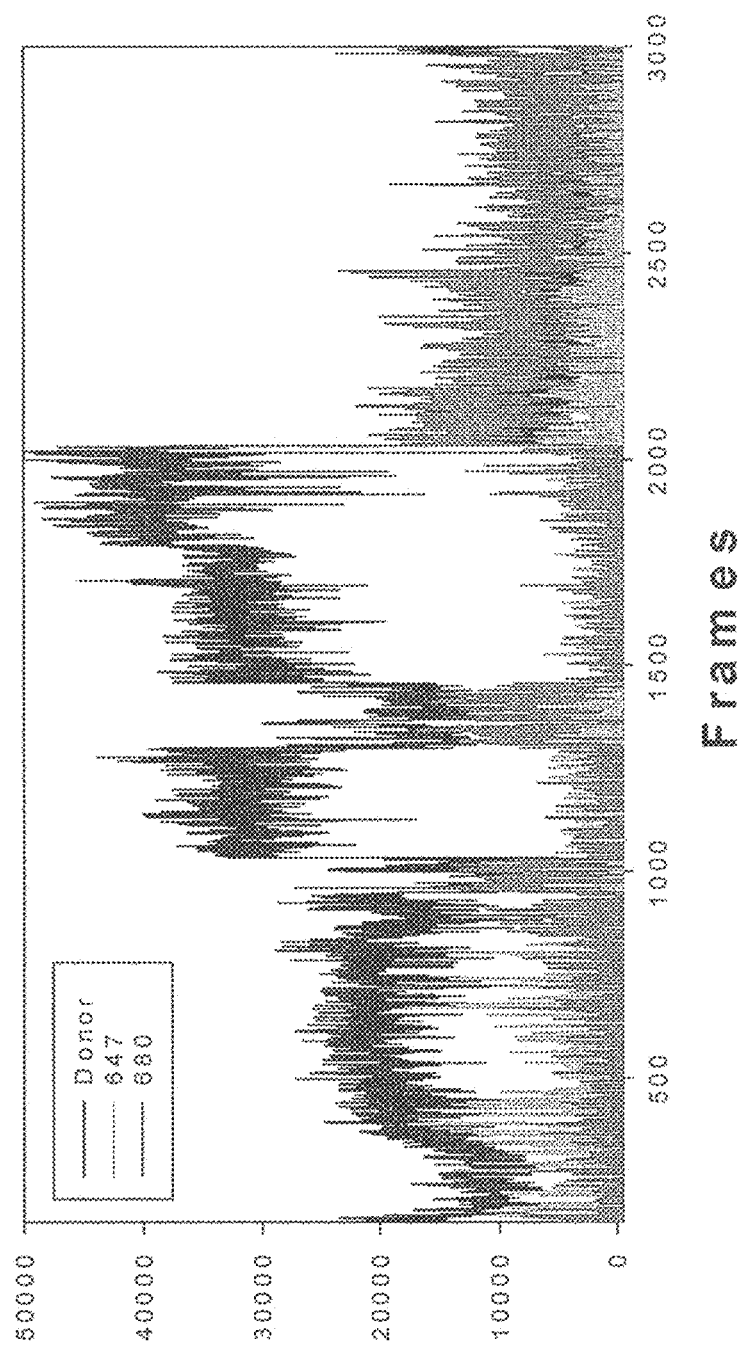
FIG. 12 depicts exemplary fluorescence traces observed during a single molecule nucleotide incorporation assay using an exemplary labeled polymerase conjugate.

Sequencing Reaction:

Hexa-phosphate dye-labeled nucleotides were diluted to 250 nM in extension buffer. (50 mM MOPS pH=6.8; 50 mM potassium acetate (pH=7.0); 0.3% BSA; 5 mM $CaCl_2$; Katalase 10,772 u/ml; Glucose oxidase 0.5 mg/ml; Glucose 0.2%). This mixture was flowed into a channel containing SA-Cy3B-bPhi29 bound to DNA template, and images were recorded for approximately 2 minutes at approximately 30 ms frame rates. In one representative example, the DNA template sequence comprised the following sequence $(G)_5$ $(A)_8$ (SEQ ID NO: 61) immediately following the primer annealing site. Using 250 nM hexaphosphate-647-dGTP, 250 nM hexaphosphate-680-dATP and 1 μM cold dTTP, patterns were identified with spectral signatures for 647 dye emission (G signal) preceding spectral signatures for 680 dye emission (A signal) that resulted from fluorescence resonance energy transfer (FRET) from the Cy3B molecule (donor) linked to the Phi-29 polymerase. Exemplary time traces observed in this assay are depicted in FIG. 12.

Figure 13:
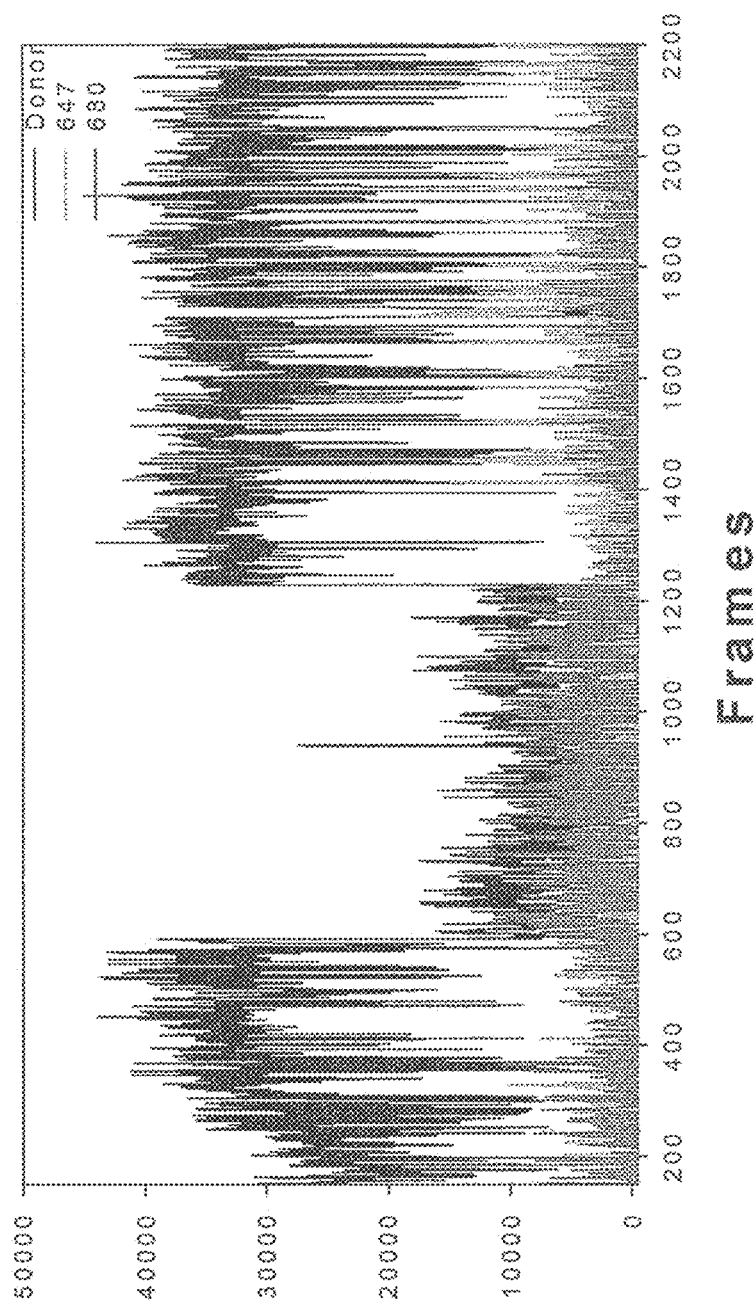
FIG. 13 depicts exemplary fluorescence traces observed during a single molecule nucleotide incorporation assay using an exemplary labeled polymerase conjugate.

The same sequencing pattern, using the same template and nucleotide combination, was also demonstrated by inverting the color sequencing, such that 250 nM hexaphosphate-680-dGTP and 250 nM hexaphosphate-647-dATP and cold dTTP at 1 µM were used. In this example, patterns were identified with spectral signatures for 680 dye emission (G signal, long grey spike) preceding spectral signatures for 647 dye (A signal, short grey spikes) emission that resulted from fluorescence resonance energy transfer (FRET) from the Cy3B molecule (donor) linked to the Phi-29 polymerase. Exemplary time traces observed in this assay are depicted in FIG. 13.

Analysis of Fluorescence Data to Extrapolate Sequence Information

To convert the observed fluorescence emissions detected during the sequencing reaction into nucleotide sequence information, the raw data comprising a movie of observed emissions was first processed by using a Hidden Markov Model (HMM)-based algorithm to detect and identify FRET events. The subsequent detected FRET events were filtered and filtered sequences were aligned. Each of these two steps, FRET event detection and sequence analysis, are described in more detail below.

Detection of FRET Events

The analysis underlying FRET event detection is designed to process spatially correlated movie(s) comprising real time sequence fluorescence emission data, and extract time-series of interest from those data. A movie typically contains one or more channels where each channel represents the same spatial location at different wavelengths. The analysis chain begins with the submission of one or more movies to the analysis machine via a comprehensive user interface. The user interface requires the user to input various parameters that describe the movie(s) (e.g. channel regions, dye emission properties, and the like). Once this data is submitted the movie(s) are then processed by the image analysis software where a sliding window of N frames propagates through the movie calculating a temporal local average of the frames within the window. At each position of the window in the movie, the local average image is then further processed and enhanced using well known image processing algorithms and a record of the maximum projection of all the local average images is recorded to produce a global image of the movie. This global image is the input into a spot identification algorithm which produces a set of spots identified by a unique spot id, its x and y location and its corresponding channel. Each set of spots for a given channel is then registered to the set of spots in every other channel. In this way a set of spot tuples is constructed. If a detected spot in one channel does not have a corresponding detected spot in another channel, then the position of the undetected spot using the transformation between the two channels and the location of the detected spot is inferred. Once a complete set of spot tuples is constructed the movie is iterated over and at each frame the amplitude of each spot is calculated and appended to the appropriate time-series.

The collection of time-series from a spot tuple consists of time-series from donor and corresponding acceptor channels. This collection is called a Vector Time-Series (VTS). The FRET detection process starts with a data segmentation step using a Markov Chain Monte-Carlo (MCMC) algorithm. Each segment of VTS is modeled by a multivariate Gaussian model, with each of the channel modeled by a mean and a standard deviation. This model establishes a baseline for each channel, from which quantities such as "Donor Down" and "Acceptor Up" can be calculated. A Hidden Markov Model (HMM) is used to model the observed data. The underlying states consist of a null state, a blink state and a number of FRET states (one for each acceptor channel). Each state has its emission probability, which reflects the state's corresponding physical concept. FRET states are characterized by significant "donor down" and "acceptor up" signals. Blink state is characterized by significant "donor down" with no "acceptor up". Null state is characterized by no "donor down" and no "acceptor up". Given the observed VTS signal, the emission matrix, and a state transition probability matrix, the most probable state path can be computed using the Viterbi algorithm. This state path assigns each of the frames to a state. Temporally neighboring FRET frames are grouped into FRET events. For each of the detected FRET events, a list of event features are calculated, including event duration, signal average, signal to noise ratio, FRET efficiency, probability of event, color calling and other features. This list of events and corresponding features are stored in a file.

The final stage of the automated analysis generates a report summarizing the results in the form of a web page containing summary image, statistics of the spots and FRET detection, together with line intensity plots and base call plots.

Using the above process, the movie data obtained from the sequencing reactions was analyzed to detect and identify FRET events according to the process described above. The FRET events were then processed to identify sequences as described below.

Sequence Analysis

Beginning with the set of detected Forster resonance energy transfer (FRET) events, a data overview was constructed in the form of a color image interpreted as a sequencing plot. To generate the plot, the original FRET event data was pre-processed using a set of filters constructed by a priori knowledge of the sequence. For each reaction site (each molecule) an ordered sequence of FRET events was constructed. The base call letters for each FRET event (e.g. "A", "C", "G" or "T") were concatenated to form a sequence ASCII string. The order of letters in the string reflects the temporal relationship of the events. Given that the expected sequence was known a priori, a regular expression was then constructed that represented the full or partial expected sequence or sequence pattern. Matching against the regular expression (expected sequence) was then computed for each sequence in the set and the start and stop indices of the match were recorded. A color plot image was then constructed where each row corresponds to a sequence in the set. The plot image was padded to accommodate sequences of different lengths. A color map of 2*N+1 colors was constructed, where N denotes the number of possible base calls in each sequence (N=2 for the plot of this Example). N colors were assigned to the base characters that fell within the pattern, N colors were assigned to the base characters that did not fall within the pattern (muted color), and finally a color was assigned to the padding (background) of the image. The rows of the image were then sorted according to the number of base calls in the first part of the sequence pattern. The rows of the image were also aligned such that the start of the expected sequence is in the same column for all rows of the plot.

Figure 14:
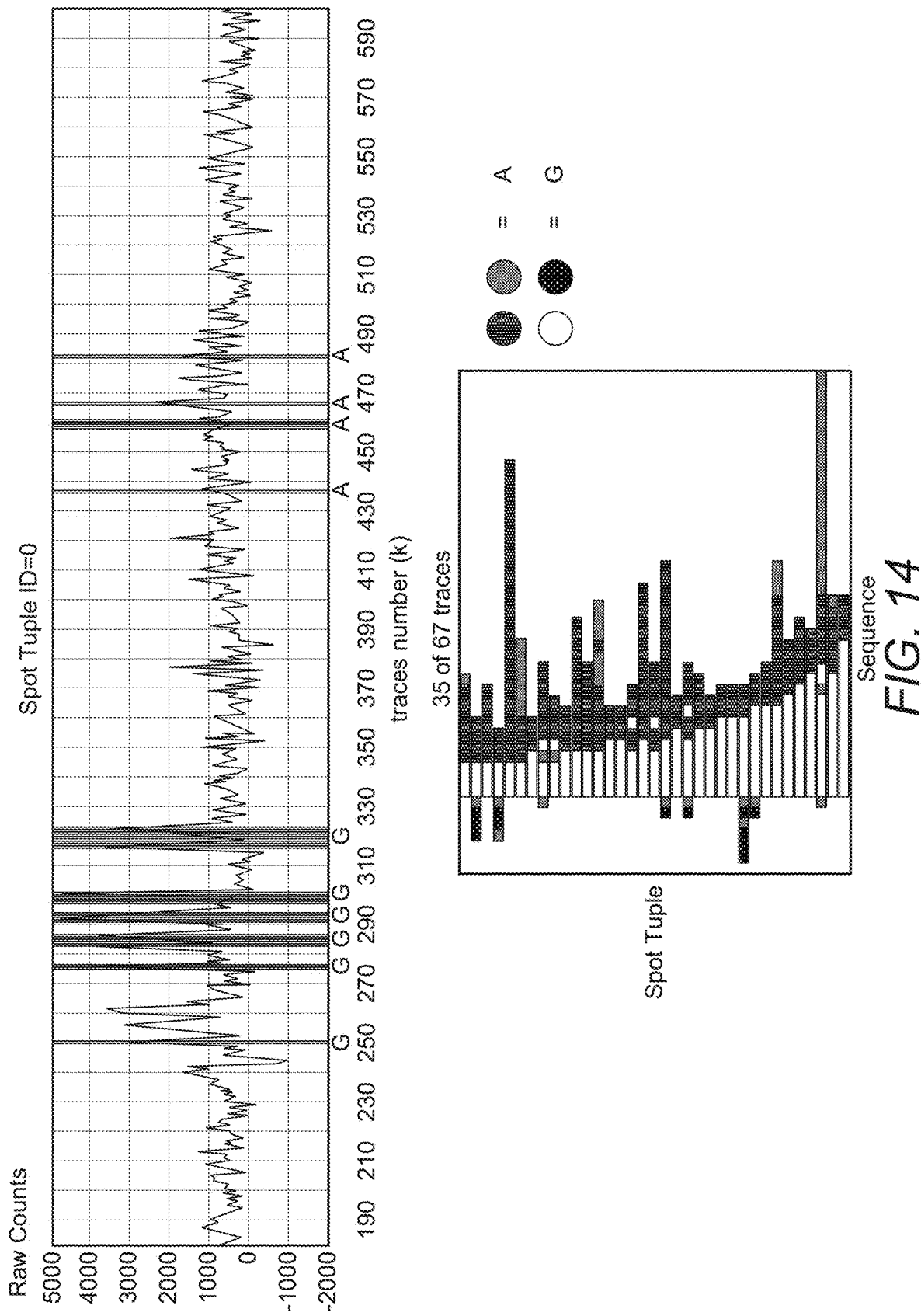
FIG. 14 depicts sequence data obtained using exemplary labeled polymerase conjugates according to the methods described in Example 6.

Representative results of the sequence analysis are depicted in FIG. 14. Pattern results are represented by the aligning the sequences, where bright yellow represents the initial onset of the G signal and sequence, and bright pink indicates the onset of the A signal and sequence. Greyed yellow and pink boxes represent outlier signals that were detected using HMM FRET detection which lie outside of the typical sequence onset (HMM detected FRET events shown with gray bars, FIG. 14, top).

In an exemplary assay that used 250 nM hexaphosphate-647-dGTP and 250 nM hexaphosphate-680-dATP and cold dTTP at 1 µM, approximately 50% of the total filtered donor spots (single molecule DNA/enzyme complexes) showed the correct pattern for 647 emission signals before 680 emission signals (FIG. 14, bottom).

Figure 15:
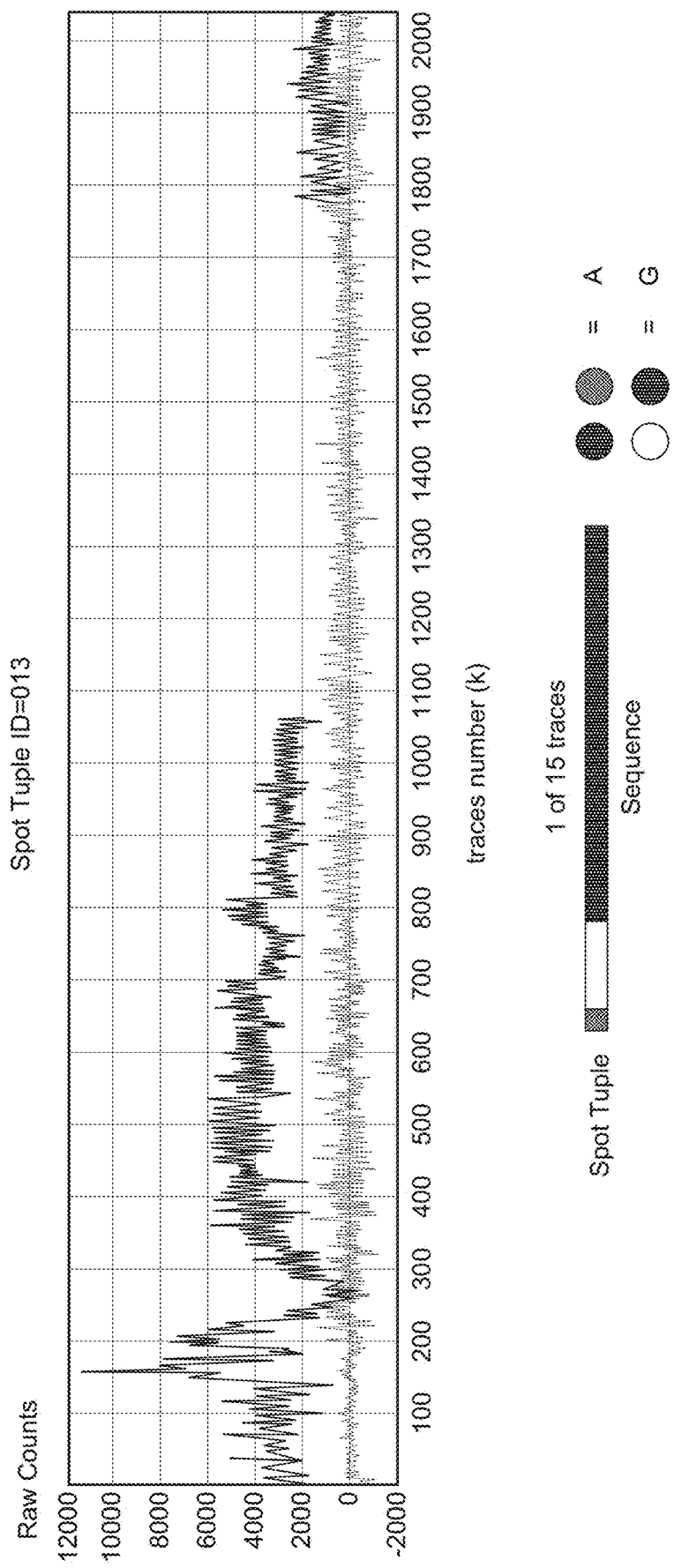
FIG. 15 depicts fluorescence data obtained during a nucleotide incorporation reaction using exemplary labeled polymerase conjugates according to the methods described in Example 6.

As a negative control, 250 nM hexaphosphate-647-dGTP and 250 nM hexaphosphate-680-dATP, cold dTTP at 1 µM, and cold dGTP at 20 µM were mixed. Representative results of this control sequence analysis are depicted in FIG. 15. One of the total filtered donor spots (single molecule DNA/enzyme complexes) showed a sequence that resembled the patterns found in the positive lane. (FIG. 15).

Example 7: Comparison of Photostability of Exemplary Polymerases and Labeled Polymerase Conjugates The photostability of an exemplary control (unconjugated) polymerase comprising a His-tagged version of Phi-29 polymerase ("HP1; see, e.g., U.S. Provisional Application No. 61/184,770, filed Jun. 5, 2009 for disclosure of HP1 sequence and purification) comprising the amino acid sequence of SEQ ID NO: 14, and an exemplary labeled polymerase conjugate comprising a Phi-29 polymerase including the amino acid sequence of SEQ ID NO: 3 conjugated to a dye label according to the methods of Example 1, were characterized and compared. The photostability was determined by measuring the amount of primer extension observed in each sample prior to and following exposure to excitation radiation at 405 nm. Reactions (100 µL) containing 50 mM Tris, pH 7.5, 50 mM NaCl, 1 mM DTT, 2 mM $MnCl_2$, 0.3% BSA, 10-200 nM polymerase, and 100 nM of 5'-TAMRA-labeled templates were prepared with and without the Oxygen Scavenging System (OSS). The OSS consists of 0.1 mg/ml Glucose Oxidase (Sigma, Catalog #G3660-1CAP), 2 units/µl Katalase (Fluka, Catalog #02071), 2 mM Trolox, and 0.5% glucose (added just prior to illuminations with 532 laser). Aliquots (4 µl) were added to a quartz cuvette having a path length of 1.5 mm and a height of 15 mm (Hellma, 105.252-QS) and illuminated with a 532 nm laser for a specified time and at specified power levels. After illumination, samples were removed and placed on ice until extensions were performed at 23° C. The extensions were performed by addition of 5 µM nucleotide hexaphosphates comprising a hexaphosphate moiety linked to the 3' carbon of the sugar moiety, and further comprising a 6-carbon linker attached to the terminal phosphate but without any fluorescent label. Extensions were performed for 30 seconds followed by termination with loading buffer (90% formamide, 10 mM EDTA). Samples were resolved on denaturing polyacrylamide gels (8M urea, 20% polyacrylamide) and exposed to phosphorimager screen. Representative results are provided in FIG. 16. An image of the gel is shown in the bottom left corner of the graph; the polymerase activity was quantified as the % of extended primer (as compared to the total starting amount of primer), as measured by densitometric analysis. Phototoxicity is quantified by measuring the percent decrease in polymerase activity that occurs when samples are illuminated compared to non-illuminated samples.

Figure 16:
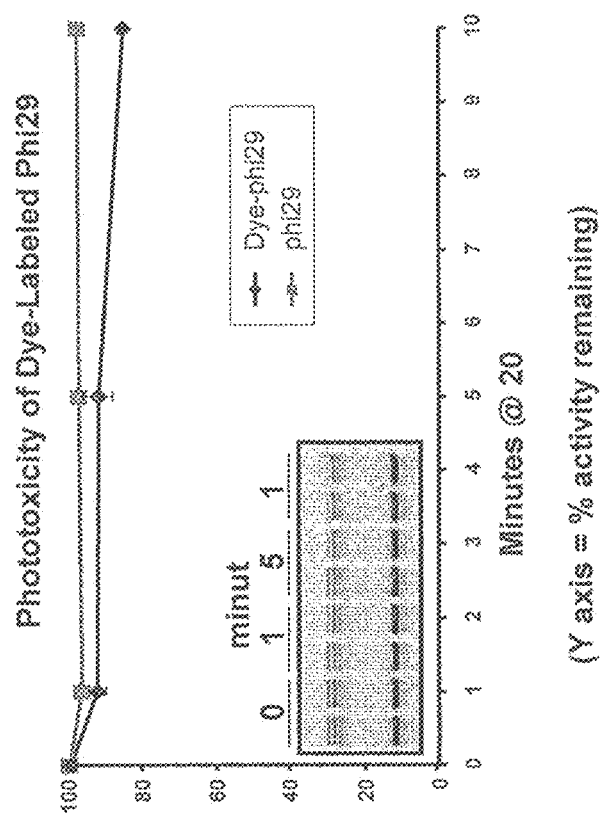
FIG. 16 depicts the results of an assay for polymerase activity using a primer extension assay.

FIG. 16 shows the % activity remaining (Y axis) after various durations of exposure (time, X axis) to radiation at 532 nm at 20 $W/cm^2$. As shown in FIG. 16, the labeled enzyme conjugate (diamonds) retained 80-90% activity following exposure at 20 $W/cm^2$ for up to 10 minutes, a level comparable to the activity retained by the control Phi-29 polymerase (squares).

Example 8: Nucleotide Incorporation with Labeled Biomolecule Conjugates Comprising a Mutant B103 Polymerase Linked to a Fluorescent Dye Label In this Example, a mutant B103 polymerase comprising the amino acid sequence of SEQ ID NO: 40, was prepared, biotinylated and labeled as outlined below. This modified B103 polymerase comprises the amino acid sequence of SEQ ID NO: 34 and further includes the mutation H370R as well as a biotinylation site and His tag fused to the N-terminus of the protein. The dye-labeled polymerase conjugate was then used to study nucleotide incorporations in single molecule format.

Preparation of Biotinylated Polymerase

The construct HB B104 (H370R) _pAN6 was transformed and expressed in CVB101 (for in vivo biotinylation) cells. The cells were grown at 30° C. to OD 0.6 and induced with 0.5 mM IPTG. Upon induction 200 uM D-Biotin was added and cultures were moved to 18° C. shaker and grown 0/N and harvested the following morning. Cell pellets were resuspended in Buffer B and sonicated to lyse. PEI (0.3%) was added to cell resuspension and incubated on ice for 30 min. Cell resuspension was centrifuged to remove cell debris and DNA Ammonium sulfate was added to cell lysate at final concentration of 55%. Lysate was centrifuged and pellets containing HB B104 (H370R) were resuspended in Buffer, loaded onto EMD-sulfate column and eluted with linear gradient 10-100% BufferB. Fractions containing HB B104 (H370R) were pooled and loaded onto a His Trap column, eluted with linear gradient from 5-100% Buffer C. Peak fractions were pooled and loaded onto a Heparin column, eluted with a linear gradient from 10-100% B. Fractions were then quantitated and analyzed for polymerase activity.

Buffer compositions were as follows:
Buffer A: 30 mM Tris pH 7.5, 100 mM NaCl, 2 mM DTT, 0.1 mM EDTA, 8% glycerol
Buffer B: 30 mM Tris pH 7.5, 1 M NaCl, 2 mM DTT, 0.1 mM EDTA, 8% glycerol
Buffer C: 30 mM Tris pH 7.5, 100 mM NaCl, 2 mM DTT, 0.5M Imidazole, 8% glycerol Preparing NHS-Ester Surfaces:

Glass coverslips surfaces were plasma cleaned and treated with a mixture of poly-ethyleneglycol (PEG) and NHS-ester to produce a low density NHS-ester surface with a PEG coating to prevent non-specific background of proteins and macromolecules.

Fluidic Chamber Assembly:

Fluidic cassettes were assembled with glass coverslips to create fluidic chambers capable of carrying approximately 2 µl of fluid.

Attaching Amine Terminated Hairpin DNA to Low Density NHS-Ester Surfaces:

```
Target DNA hairpin sequence:
5'-TTTTTTTTACCCCCGGGTGACAGGTTXTTCCTGTCACCC-3'

(SEQ ID NOS 48 and 60, respectively, in order of
appearance)
``` where "X" is an amine group.

The target DNA was diluted to 500 nM in 1 M $NaHCO_3$. The diluted target molecules were flowed into the fluidic chamber and incubated for 1 hour. Chambers were washed 1× with 1 ml deactivating buffer (ethanolamine). Surfaces were washed 1× with 1 ml incubation buffer (50 mM Tris-Cl, pH=7.5; 50 mM NaCl; 0.3% BSA).

SA-Polymerase Conjugate Preparation:

In this example, dye-labeled Streptavidin was mixed with biotinylated mutant B103 polymerase (b-B103-exo minus) comprising the amino acid sequence of SEQ ID NO: 40 at a 1:1 ratio of SA-protein: b-B103-exo minus in 1×PBS to produce conjugates comprising biotinylated mutant B103 polymerase linked to dye.

Dye-labeled Streptavidin was purchased from Invitrogen Corp. (Catalog #SA1010). The Cy3-streptavidin was estimated to contain approximately 7-8 Cy3 dyes per streptavidin based on UV absorbance studies (data not shown).

Briefly, 500 µl of a 3.4 µM solution of Cy3 dye-labeled Streptavidin (Invitrogen, SA1010) was mixed with 25 µl of 200 µM biotin-B104 H370R. Twenty five microliters of 5M NaCl were added to the mixture and it was left at 4 deg C. for 1 hour. To remove any free, unconjugated labeled streptavidin, the mixture was diluted with an equal volume of phosphate buffer saline buffer (PBS) and loaded onto a 1 ml HisTrap cartridge (GE Healthcare). Following the loading, the cartridge was washed with PBS until the initially colored eluate from the cartridge became completely colorless. Finally, the bound Cy3 streptavidin-biotin B104 H370R conjugate was eluted off the cartridge with a solution of 500 mM imidazole in PBS buffer containing 200 mM additional NaCl. To the eluted material was added 50 mM biocytin to a final concentration of 5 mM, and the mixture was dialyzed overnight against a solution containing 50% glycerol, 50 mM Tris-HCl pH 7.5, 200 mM NaCl, 5 mM DTT.

SA-Cy3-b-B103 Binding to Templates:

The conjugates were diluted to 1 nM in binding buffer (50 mM Tris-Cl; pH=7.5; 0.3% BSA; 100 mM NaCl). The conjugates were flowed into the fluidic chamber which were previously loaded with DNA templates on the surface. Surfaces were incubated for 5 minutes with conjugates. Surfaces were washed with 1×1 ml incubation buffer.

Fluorescence Imaging:

The microscope body was purchased from Olympus and was outfitted with a TIRF objective lens (100×; 1.45 NA). The excitation light passes through an excitation filter (EX FT—543/22), and dichroic mirror (DM—532) and the sample was epi-illuminated (Coherent) using TIR at typically 100 W/cm². Upon excitation, the resulting epifluorescence emission passed through an emission filter (EM FT—540LP) and the resulting emission was split into three paths (tri-view) using 2 dichroic mirrors and the appropriate bandpass filters for the dye sets of choice. Using this filter combination, we were able to spectrally resolve 1 donor dye and 3 acceptor dyes in 3 detection channels.

In separate experiments, 1 donor dye and 4 different acceptor dyes could be resolved in 4 detection channels. The optical detection scheme was as follows: DC1=635, F1 640LP; DC2=675, F2=688/31; DC3=705, F3=700 LP. The donor dye used in this case was CY3 and the 4 acceptor dyes are as follows DY634, AF647, AF676, AF700

The emissions resulting in each experiment were imaged on a CCD camera. Images were collected at a frame rate of approximately 20 ms.

Three-Color Nucleotide Incorporation Reaction:

Hexa-phosphate dye-labeled nucleotides were diluted to 200 nM in extension buffer (50 mM MOPS pH=7.1; 75 mM potassium acetate (pH=7.0); 0.3% BSA; 1 mM MnCl$_2$; 300 nM procatuate dioxygenase; 4 mM 3,4 dihydroxyl benzoic acid; 1 mM 2-nitrobenzoic acid; 400 µM 1,2 phenylenediamine; 100 µM ferrocene monocarboxylic acid; 0.02% cyclooctratetraene; 6 mM TROLOX). Nucleotide mix was flowed into channel with conjugate bound to DNA template and images are recorded for approximately 2 minutes at approximately 20 ms frame rates. In this example, the synthesized strand is expected to have the following sequence: $(G)_5T(A)_8$ (SEQ ID NO: 62). Terminal phosphate-labeled nucleotides and 125 nM cold dC6P were used for the nucleotide incorporation reaction. The labeled nucleotides included 125 nM 647-dT6P, 125 nM 676-dG6P, 125 nM 700-dA6P. The spectral signatures for the ALEXA FLUOR-676 G signal, AF-647 T signal, and AF-700 A signal were identified that resulted from fluorescence resonance energy transfer (FRET) from the Cy3 donor molecule, and corresponded to the correct insertion sequence pattern.

Analysis of Three-Color Sequencing Results

Resulting pattern sequencing data was processed using an alignment algorithm. The alignment algorithm found 100 molecules in the field of view, which demonstrated completion of the full 14-nucleotide sequence $((G)_5T(A)_8$ (SEQ ID NO: 62), which represented approximately 20% of the total single molecule donor population. The consensus sequence was determined using an HMM alignment algorithm (e.g., see Example 14). By plotting the accuracy definition (measured as a percentage value) against the HMM score (X axis), a linear relationship was detected (data not shown). Various measurements of accuracy can be devised that can be suitable for such analysis. In one exemplary experiment, the accuracy was estimated according to the following equation:

$$\alpha(T, A) = \frac{\beta - \delta - \eta + \lambda}{2\lambda}$$

The measurement of accuracy in the above equation is intended to provide some measure of similarity between some given template, T, and some alignment, A, of an observed sequence O. It should be noted that alphabet of T, A, and O are identical. The length of T is denoted by $\lambda$, the number of deletions in the alignment A by $\delta$, the number of insertions in the alignment by $\eta$, and the number of matches in the alignment by $\beta$. Equation (1) is normalized by $\lambda$ such that a an accuracy of 1 indicates a total agreement, and an accuracy of 0 indicates no agreement between T and A. The above definition of accuracy is provided as an example only and is in no way intended to limit the disclosure to any particular theory or definition of accuracy; alternative definitions of accuracy are also possible and it may be suitable to use such alternative definitions in some contexts.

The accuracy in this system using an HMM alignment threshold of 0 was estimated to be approximately 80% (data not shown).

Four-Color Nucleotide Incorporation Reaction:

Oligonucleotides

```
401 template molecule:
                                           (SEQ ID NO: 49)
TTTTTCCCCGACGATGCCTCCCC g ACA Cgg Agg TTC TAT CAT CgT CAT CgT CAT CgT CAT Cg-Biotin TEG-T-3

Primer for 401 template:
                                           (SEQ ID NO: 50)
5' TGA TAG AAC CTC CGT GTC 3'
```

In this example, the synthesized strand is expected to have the following sequence:

(SEQ ID NO: 51)
GGGGAGGCATCGTCGGGAAAA

Nucleotide Incorporation Reaction:

Hexa-phosphate dye-labeled nucleotides were diluted to 200 nM in extension buffer (50 mM MOPS pH=7.1; 75 mM potassium acetate (pH=7.0); 0.3% BSA; 1 mM MnCl$_2$; 300 nM procatuate dioxygenase; 4 mM 3,4 dihydroxyl benzoic acid; 1 mM 2-nitrobenzoic acid; 400 µM 1,2 phenylenediamine; 100 µM ferrocene monocarboxylic acid; 0.02% cyclooctratetraene; 6 mM TROLOX). Nucleotide mix was flowed into channel with SA-Cy3-b-B103 bound to DNA template and images are recorded for approximately 2 minutes at approximately 20 ms frame rates.

The terminal phosphate-labeled nucleotides used for the nucleotide incorporation reaction included 125 nM DY634-dA6P, 125 nM 647-dT6P, 125 nM 676-dG6P, 125 nM 700-dC6P. The spectral signatures for the DY-634 A signal, and the ALEXA FLUOR G, T and C signals (AF-676 G signal, AF-647 T signal, and AF-700 C signal) were identified that resulted from fluorescence resonance energy transfer (FRET) from the Cy3 donor molecule, and corresponded to the correct insertion sequence pattern. 4-color sequence alignment was obtained by visual inspection.

The observed FRET event durations for various SA-Cy3-b-B103 conjugates, the event count distributions, and the observed extension speeds of various SA-Cy3-b-B103 conjugates were calculated.

Example 9: Comparing the Primer Extension Activities of Conjugated and Unconjugated Polymerases This assay describes how to measure and compare the primer extension activity of a labeled polymerase conjugate comprising multiple polymerases per conjugate, with the primer extension activity of unconjugated (free) enzyme. Primer extension activity is quantified by monitoring the fluorescence intensity change over time during extension of a fluorescein-labeled hairpin oligonucleotide, comprising the following nucleotide sequence. The fluorescence intensity correlates with the level of primer extension activity in the sample.

Step 1: Measure the Primer Extension Activities of the Conjugate and the Free (Unconjugated) Enzyme Conjugate primer extension activity is measured by monitoring the fluorescence intensity change over time during extension of a fluorescein-labeled hairpin oligonucleotide, oligo 221 comprising the nucleotide sequence of SEQ ID NO: 43, below:

(SEQ ID NO: 43)
(5'-TTTTTTTGCAGGTGACAGGTTTTTCCTGTCA-

CC(fluorescein-T)GC-3')

The extension reactions are performed in 1× extension buffer (50 mM Tris buffer pH 7.5, 50 mM NaCl, 10 mM MgCl$_2$ and 0.5 mM MnCl$_2$). To reaction wells that contain 100 µL of 150 nM of a fluorescein-labeled hairpin oligonucleotide, oligo221 (SEQ ID NO: 43, above) and 10 nM of polymerase (or conjugated polymerase) in extension buffer, 2 µL of 1 mM dATP (final concentration: 20 µM) is added to initiate the enzymatic reaction and the fluorescence intensity in each well is recorded at 525 nm fluorescence with 490 nm excitation for every 20 seconds for the next 10 minutes. Control reaction wells include the same components without any addition of dATP. The fluorescence intensity at 525 nm (as measured in arbitrary fluorescence units, RFU, y axis) is plotted against time (seconds, X axis) for each sample, as well as the control wells (no nucleotide). The fluorescence time course data from each well is used to calculate the primer extension activity of each sample.

For conjugate activity (base/sec/conj), the activity is calculated according to the following equations:

$$\text{Activity(base/sec/}enz) = \frac{\Delta RFU_{sample\_per\_sec}}{\Delta RFU_{max\_per\_nMsubs}} \times \frac{1}{10 \text{ nM}} \times 7(\text{base})$$

$$\text{and } \Delta RFU_{max\_per\_nMsubs} = \frac{RFU_{max} - RFU_{min}}{\text{substr\_conc.(nM)}}$$

Where: $RFU_{max}$ is the average maximal RFU in the reference polymerase reaction wells; $RFU_{min}$ is the average minimal RFU in the reference polymerase control wells; Substr_conc. (nM) is the oligo 221 concentration in assay, which is 150 nM; and:

$$\Delta RFU_{sample\_per\_sec} = \frac{RFU_t - RFU_0}{t(\sec)}$$

Where: t (sec) is the time period where the fluorescence intensity increases in the reference enzyme reaction well linearly from the start; $RFU_t$ is the average RFU of the reference enzyme extension wells at t second point; and $RFU_0$ is the average RFU of the reference enzyme extension wells at the start point.

For activity of free enzyme (base/sec/enzyme), the activity is calculated according to the following equations:

$$\text{Free} - \text{enzyme\_activity(base/sec/}enz) =$$

$$\frac{\Delta RFU_{sample\_per\_sec}}{\Delta RFU_{max\_per\_nMsubs}} \times \frac{1}{50 \text{ nM}} \times 7(\text{base})$$

$$\text{and } \Delta RFU_{max\_per\_nMsubs} = \frac{RFU_{max} - RFU_{min}}{\text{substr\_conc.(nM)}}$$

Where: $RFU_{max}$ is the average maximal RFU in the reference polymerase reaction wells; $RFU_{min}$ is the average minimal RFU in the reference polymerase control wells; and Substr_conc. (nM) is the oligo 221 concentration in assay, which is 150 nM; and $$\Delta RFU_{sample\_per\_sec} = \frac{RFU_t - RFU_0}{t(\sec)}$$

Where: t (sec) is the time period where the fluorescence intensity increases in the reference enzyme reaction well linearly from the start; $RFU_t$ is the average RFU of the reference enzyme extension wells at t second point.; $RFU_0$ is the average RFU of the reference enzyme extension wells at the start point.

Step 2: Measure the Number of Active Enzyme Per Conjugate

This procedure describes a method to measure the active number of polymerase per conjugate based on the active polymerase binding to fluorescein-labeled template using FP as the readout. In this assay, the mP values of a conjugate at several concentrations are measured and a standard curve is also generated for the mP values at known concentrations of free polymerase. By fitting the mP values into the standard curve, the number of polymerase per conjugate can be calculated Extension buffer (50 mM Tris pH7.5 with 50 mM NaCl, 10 mM MgCl2 and 0.5 mM MnCl2) is added into the first two rows of a 96-well microtiter plate for 50 µL per well. To the first well of the above each row, 50 µL of 4000 nM free polymerase (polymerase used in the tested conjugate) in extension buffer is added, mixed and transferred 50 µL per well into the second well of the above each row. A 2-fold dilution (concentration from 4000 nM to 1.95 nM) of the free polymerase is then prepared in the above two rows by sub-sequentially transferring and mixing as described. 50 µL of solution is removed from the last well of each row to make 50 µL volume for each well. These two rows are served as the free polymerase standard wells.

For the wells containing conjugate, 50 µL of conjugate is added to each well with various concentrations (e.g. 20 nM, 40 nM, 60 nM, 80 nM) that are prepared by diluting conjugate into the extension buffer.

To all wells including either free enzyme or or conjugated enzyme, 50 µL of 300 nM oligo221 in 1× extension buffer is added. The plate is then mixed and the mP value of each well is measured using a plate reader.

To calculate the active number of polymerase per conjugate, the standard curve is fitted into a non-linear regression equation:

$$Y = b + \frac{a-b}{1+10^{(\log EC50-X)*c}}$$

Where Y is the mP value;
X is the log [phi29(nM)];
a is the top value of the standard curve;
b is the bottom value of the standard curve;
c is the slope of the curve
EC50 is the concentration that gives 50% of the total response.

Based on the standard curve fitting results, the active polymerase concentration at certain conjugate concentration can be calculated by inputting the mP value at particular conjugate concentration into the equation. The actual number of active polymerase per conjugate is then determined by dividing the calculated active polymerase concentration by the corresponding conjugate concentration.

Step 3: Calculate the "Ratio of Activity for Conjugated-Enzyme to Free-Enzyme"

Based on the results of the measurements for "conjugate_activity", "Free-enzyme _activity" and the "Nn active polymerase per conjugate", the ratio of activity of conjugated enzyme to free enzyme ("Ratio of Activity for Conj-enzyme to Free-enzyme") can be calculated as follows:

$$\text{Ratio\_Activity\_of\_Conj-Enzyme-to-FreeEnzyme} = \frac{\text{Conjugate\_activity}}{\text{Nn\_active-Pol-per-Conjugate}} \times \frac{1}{\text{Free-polymerase\_activity}}$$

Example 10: Measurement of $t_{-1}$ and $t_{pol}$ Values of Modified Phi-29 and B103 Polymerases In this example, the $t_{-1}$ and $t_{pol}$ values of a Phi-29 polymerase comprising the amino acid sequence of SEQ ID NO: 3 and a B103 polymerase comprising the amino acid sequence of SEQ ID NO: 34 (referred to as "mB103" in the table below) and including amino acid substitutions at various positions were measured using a stopped-flow procedure. The stopped-flow techniques for measuring $t_{pol}$ ($1/k_{pol}$) followed the techniques described by MP Roettger (2008 Biochemistry 47:9718-9727; M. Bakhtina 2009 Biochemistry 48:3197-320).

Stopped-Flow Measurements of $t_{pol}$

Template C sequence:
(SEQ ID NO: 44)
5'-CGTTAA<u>C</u>CGCCCGCTCCTTTGCAAC-3'

Primer sequence:
(SEQ ID NO: 45)
5 -GTTGCAAAGGAGCGGGCG-3'

The template sequence (SEQ ID NO: 44) further included an Alexa Fluor 546 dye moiety bonded to the 5' position of the template.

The kinetics of nucleotide incorporation by each polymerase was measured in an Applied Photophysics SX20 stopped-flow spectrometer by monitoring changes in fluorescence from the dye-labeled primer-template duplex complexed to enzyme, following the mixing of the enzyme-DNA complex with dye-labeled nucleotides. These dye-labeled nucleotides comprise terminal-phosphate-labeled nucleotides having an alkyl linker with a functional amine group attached to the dye, and have the general structure shown in FIG. 21. This structure includes a sugar bonded to a hexaphosphate chain at the 5' carbon position, and to a nucleotide base (denoted as "N"). The terminal phosphate group of the hexaphosphate is linked to a 6-carbon linker, and the other end of the 6-carbon linker is attached to a dye moiety (denoted as "dye"), typically through an amide bond. In this example, the particular dye-labeled nucleotide added was a labeled nucleotide hexaphosphate comprising a guanine base at the N (base) position and an Alexa Fluor 647 (AF647) at the dye position, and is referred to herein as "AF647-C6-dG6P".

The primer and template were annealed to form a dye-labeled primer-template duplex using standard methods. This duplex was preincubated with polymerase. The mixture included 330 nM recombinant DNA polymerase, 100 nM template/primer duplex in buffer ("reaction buffer") comprising 50 mM Tris-HCl, pH 7.5, 50 mM NaCl, 4 mM DTT, 0.2% BSA, and 2 mM MnCl$_2$. The dye-labeled nucleotide AF647-C6-dG6P was then added to a final concentration of 7 µM, and the resulting fluorescence was monitored over time.

The averaged (5 traces) stopped-flow fluorescence traces (>1.5 ms) were fitted with a double exponential equation (1) to extrapolate the rates of the nucleotide binding and product release, $$\text{Fluorescence} = A_1 * e^{-k1*t} + A_2 * e^{-kpol*t} + C \quad \text{(equation 1)}$$

where $A_1$ and $A_2$ represent corresponding fluorescence amplitudes, C is an offset constant, and k1 and kpol are the observed rate constants for the fast and slow phases of the fluorescence transition, respectively.

Stopped-Flow Measurements of $t_{-1}$

The stopped-flow techniques for measuring $t_{-1}$ ($1/k_{-1}$) followed the techniques described by M. Bakhtina (2009 Biochemistry 48:3197-3208).

Template C sequence:
(SEQ ID NO: 46)
5'-CAGTAACGG AGT TGG TTG GAC GGC TGC GAG GC-3'

Dideoxy-primer sequence:
(SEQ ID NO: 47)
5'-GCC TCG CAG CCG TCC AAC CAA CTC ddC-3

The rate of the nucleotide dissociation ($k_{-1}$) from the ternary complex of [enzyme•DNA•nucleotide] was measured in an Applied Photophysics SX20 stopped-flow spectrometer by monitoring changes in fluorescence from in fluorescence from a duplex Alexa fluor 546 dye-labeled-DNA template following the mixing of the [enzyme•DNA•labeled nucleotide] ternary complex with 50 µM cognate non-labeled deoxynucleoside triphosphate in a buffer containing 50 mM Tris-HCl (pH 7.5), 50 mM NaCl, 4 mM DTT, 0.2% BSA, and 2 mM $MnCl_2$.

The ternary complexes were prepared using: 330 nM polymerase, 100 nM template/primer duplex, and 7 µM terminal phosphate-labeled nucleotides (AF647-C6-dG6P).

The averaged stopped-flow fluorescence traces (>1.5 msec) were fitted with a single exponential equation (2) to extrapolate the rate of the nucleotide dissociation ($k_{-1}$) from the [enzyme•DNA•nucleotide] ternary complex.

$$\text{Fluorescence} = A_1 * e^{-k-1*t} + C \quad \text{(equation 2)}$$

where $A_1$ represents the corresponding fluorescence amplitude, C is an offset constant, and $k_{-1}$ and the observed rate constants for the fluorescence transition.

Some representative results of the stopped flow data are shown below.

Some representative results of the stopped flow data are shown in the Table below:

TABLE

Summary of $t_{pol}$ and $t_{-1}$ measurements for various exemplary modified Phi-29 and B103 polymerases

| Protein | $t_{pol}$ | $t_{-1}$ |
| --- | --- | --- |
| mB103 (SEQ ID: 8) | 14 | 16 |
| mB103 + H370R | 17 | 43 |
| mB103 + H370Y | 15 | 12 |
| mB103 + E371R | 11 | 17 |
| mB103 + E371Y | 11 | 7 |
| K372R | 14 | 12 |
| K380R | 783 | 17 |
| mB103 + D507G | 11 | 13 |
| mB103 + D507H | 7 | 16 |
| mB103 + K509Y | 10 | 20 |
| Phi-29 (exo-) | 11 | 27 |
| Phi-29 (exo-) + T373R | 15 | 81 |
| Phi-29 (exo-) + T373Y | 14 | 45 |

What is claimed is:

1. A labeled polymerase conjugate, comprising:
a polymerase linked to at least two fluorescent dye labels to form a labeled polymerase conjugate,
wherein the polymerase comprises one or more biotin acceptor peptide sequences, and the two or more fluorescent dye labels are linked to the one or more biotin acceptor peptide sequences;
wherein the conjugate has polymerase activity, wherein the polymerase activity is at least about 80% relative to the polymerase activity of the unconjugated polymerase and the conjugate emits upon continuous excitation a total photon count of at least $10^4$ photons before irreversibly photobleaching; and
wherein the labeled polymerase conjugate does not comprise a labeled nucleotide, however, the polymerase conjugate is capable of binding a labeled nucleotide under conditions where the polymerase conjugate catalyzes incorporation of the labeled nucleotide into a nucleic acid, and the labeled polymerase emits, or induces the emission of, a signal with a labeled nucleotide bound to an active site of the polymerase indicative of such nucleotide incorporation.

2. The conjugate of claim 1, wherein the conjugate comprises at least three labels.

3. The conjugate of claim 2, wherein the at least three labels are linked to a single biotin acceptor peptide sequence.

4. The conjugate of claim 2, wherein the polymerase comprises at least three biotin acceptor peptide sequences and each of the at least three labels are linked to a different biotin acceptor peptide sequence.

5. The conjugate of claim 2, wherein the polymerase further comprises a protein kinase modification site or a transglutaminase modification site.

6. A labeled polymerase conjugate, comprising:
a polymerase linked to a plurality of labels including two or more fluorescent dye labels to form a labeled polymerase conjugate,
wherein the polymerase comprises one or more biotin acceptor peptide sequences, and the two or more fluorescent dye labels are linked to the one or more biotin acceptor peptide sequences,
where the conjugate has polymerase activity, wherein the polymerase activity is at least about 80% relative to the polymerase activity of the unconjugated polymerase and where the conjugate emits upon continuous excitation a total photon count of at least $10^4$ photons before irreversibly photobleaching, and
wherein the labeled polymerase conjugate does not comprise a labeled nucleotide, however, the polymerase conjugate is capable of binding a labeled nucleotide under conditions where the polymerase conjugate catalyzes incorporation of the labeled nucleotide into a nucleic acid, and the where at least one label of the labeled polymerase undergoes energy transfer with a labeled nucleotide bound to an active site of the polymerase indicative of such nucleotide incorporation.

7. The conjugate of claim 6, wherein the labeled nucleotide comprises a polyphosphate and wherein the nucleotide label is linked to the terminal phosphate of the polyphosphate.

8. The conjugate of claim 6, wherein the energy transfer produces a signal in a single molecule reaction.

9. The conjugate of claim 6, wherein the plurality of labels are linked to a single biotin acceptor peptide sequence.

10. The conjugate of claim 6, wherein the polymerase comprises a plurality of biotin acceptor peptide sequences and each of the plurality of labels are linked to a different biotin acceptor peptide sequence.

11. The conjugate of claim 6, wherein the polymerase further comprises a protein kinase modification site or a transglutaminase modification site.

* * * * *